(12) United States Patent
Ting et al.

(10) Patent No.: US 10,900,083 B2
(45) Date of Patent: Jan. 26, 2021

(54) METHODS AND ASSAYS RELATING TO CIRCULATING TUMOR CELLS

(71) Applicant: THE GENERAL HOSPITAL CORPORATION, Boston, MA (US)

(72) Inventors: David T. Ting, Dover, MA (US); Daniel A. Haber, Newton, MA (US); Shyamala Maheswaran, Lexington, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/105,137

(22) PCT Filed: Dec. 18, 2014

(86) PCT No.: PCT/US2014/071169
§ 371 (c)(1),
(2) Date: Jun. 16, 2016

(87) PCT Pub. No.: WO2015/095527
PCT Pub. Date: Jun. 25, 2015

(65) Prior Publication Data
US 2016/0312298 A1 Oct. 27, 2016

Related U.S. Application Data

(60) Provisional application No. 61/937,883, filed on Feb. 10, 2014, provisional application No. 61/918,816, filed on Dec. 20, 2013.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57438* (2013.01); *G01N 33/57484* (2013.01); *C12Q 2600/158* (2013.01); *G01N 2333/47* (2013.01); *G01N 2333/90* (2013.01); *G01N 2800/52* (2013.01); *G01N 2800/56* (2013.01)

(58) Field of Classification Search
CPC ............ C12Q 1/6886; C12Q 2600/158; C12Q 2600/178; G01N 2800/52; G01N 33/57484
See application file for complete search history.

(56) References Cited

U.S. PATENT DOCUMENTS

| | | |
|---|---|---|
| 2007/0026398 A1 | 2/2007 | Farnsworth et al. |
| 2012/0009582 A1 | 1/2012 | Hayes |

FOREIGN PATENT DOCUMENTS

| | | | |
|---|---|---|---|
| WO | | 2003/006029 A1 | 1/2003 |
| WO | WO 2006089091 | * | 8/2006 |
| WO | | 2009/051734 A1 | 4/2009 |
| WO | | 2011/112903 A2 | 9/2011 |
| WO | | 2013/109944 A1 | 7/2013 |
| WO | WO 2013/117705 A1 | * | 8/2013 |
| WO | | 2013/134649 A1 | 9/2013 |

OTHER PUBLICATIONS

Sergeant et al. Pancreatic cancer circulating tumour cells express a cell motility gene signature that predicts survival after surgery. BioMed Central Cancer 12 (527): 1-9 and additional file 2, published online Nov. 16, 2012.*
Sieuwerts et al. mRNA and microRNA expression profiles in circulating tumor cells and primary tumors of metastatic breast cancer patients and Supplemental Table 3. Clin. Cancer Res. 17(11): 3600-3618, published online Apr. 19, 2011.*
Sun et al. Size-based hydrodynamic rare tumor cell separation in curved microfluidic channels. Biomicrofluidics 7, 011802-1 to 011802-11 (published online Jan. 7, 2013).*
Lin et al. (Critical Reviews in Oncology/ Hematology 77: 1-11, 2011).*
Cann et al., "mRna-Seq of Single Prostate Cancer Circulating Tumor Cell Reveals Recapitulation of Gene Expression and Pathways Found in Prostate Cancer", PLOS One 7(11):e49144 (2012).
Chen et al., "Single-cell Analysis of Circulating Tumor Cells Identifies Cumulative Expression Patterns of EMT-related Genes in Metastatic Prostate Cancer", Prostate 73(8):813-826 (2013).
Powell et al., "Single Cell Profiling of Circulating Tumor Cells: Transcriptional Heterogeneity and Diversity from Breast Cancer Cell Lines", PLoS One 7(5):e33788 (2012).
Ramskold et al., "Full-Length mRna-Seq from single cell levels of RNA and individual circulating tumor cells", Nat Biotechnol. 30(8):777-782 (2012).
Welty et al., "Single cell transcriptomic analysis of prostate cancer cells", BMC Molecular Biology 14:6 (2013).
Seung Bae Rho et al. "Insulin-like growth factor-binding protein-5 (IGFBP-5) acts as a tumor suppressor by inhibiting angiogenesis." Carcinogenesis 29(11): 2106-2111 (2008).
Barczak et al., "UCSF 4 Hs version 2 human long oligo array" GEO (Gene Exression) Jan. 18, 2013.
Johnson et al., "Insulin-like growth factor binding protein-5 influences pancreatic cancer cell growth" World Journal of Gastroenterology: WJG 15(27):3355 (2009).
Rho et al., "Insulin-like growth factor-binding protein-5 (IGFBP-5) acts as a tumor suppressor by inhibiting angiogenesis." Carcinogenesis 29(11):2106-2111 (2008).
Sun et al., "Circulating tumor cells: advances in detection methods, biological issues, and clinical relevance." Journal of Cancer Research and Clinical Oncology 137(8):1151-1173 (2011).

(Continued)

*Primary Examiner* — Alana Harris Dent
(74) *Attorney, Agent, or Firm* — Nixon Peabody LLP; David S. Resnick; Nicole D. Kling

(57) ABSTRACT

The technology described herein relates to methods of detecting circulating tumor cells (CTCs), e.g. by detecting changes in the expression of certain CTC marker genes. Aberrant expression of CTC marker genes, e.g. changes in expression indicative of CTCs can also be targeted in order to treat cancer.

9 Claims, 24 Drawing Sheets

(56) References Cited

OTHER PUBLICATIONS

Ting et al., "Single-cell RNA sequencing identifies extracellular matrix gene expression by pancreatic circulating tumor cells." Cell Reports 8(6):1905-1918 (2014).
Zalatnai et al., "Molecular background of chemoresistance in pancreatic cancer." In Vivo 21(2):339-347 (2007).
De Albuquerque et al. "Multimarker gene analysis of circulating tumor cells in pancreatic cancer patients: a feasibility study." Oncology 82(1): 3-10 (2012).
Khoja et al. "A pilot study to explore circulating tumour cells in pancreatic cancer as a novel biomarker." British Journal of Cancer 106(3): 508-516 (2012).
Portela-Gomes et al. "Synaptic vesicle protein 2, a new neuroendocrine cell marker." The American Journal of Pathology 157(4): 1299-1309 (2000).
Yu et al. "RNA sequencing of pancreatic circulating tumour cells implicates WNT signalling in metastasis." Nature 487 (7408): 510-513 (2012).

* cited by examiner

| MOUSE ID | Kras | Cre | Trp53 | GENDER | AGE (WEEKS) | GROSS METASTASES | IF CK+ CTC/mL BLOOD | CELLS PICKED | CELLS SEQUENCED |
|---|---|---|---|---|---|---|---|---|---|
| MP1 | G12D | Pdx1 | L/L | M | 5.86 | NO | 118 | 3 | N/A |
| MP2 | G12D | Pdx1 | L/L | M | 5.00 | NO | 1684 | 36 | 16 |
| MP3 | G12D | Pdx1 | L/L | M | 6.14 | NO | 0 | 24 | 8 |
| MP4 | G12D | Pdx1 | L/L | F | 8.00 | YES | 28 | 42 | 15 |
| MP5 | G12D | Pdx1 | L/L | M | 6.00 | NO | 240 | 3 | N/A |
| MP6 | G12D | Pdx1 | L/L | F | 6.43 | NO | 861 | 24 | 16 |
| MP7 | G12D | Pdx1 | L/+ | F | 16.71 | YES | 63 | 42 | 22 |

*FIG. 5A*

METHODS AND ASSAYS RELATING TO CIRCULATING TUMOR CELLS

CROSS-REFERENCE TO RELATED APPLICATIONS

This application is a 35 U.S.C. § 371 National Phase Entry Application of International Application No. PCT/US2014/071169 filed Dec. 18, 2014, which designates the U.S. and claims benefit under 35 U.S.C. § 119(e) of U.S. Provisional Application Nos. 61/918,816 filed Dec. 20, 2013 and 61/937,883 filed Feb. 10, 2014, the contents of which are incorporated herein by reference in their entirety.

GOVERNMENT SUPPORT

This invention was made with federal funding under Grant Nos. 2R01CA129933 awarded by the National Institutes of Health. The U.S. government has certain rights in the invention.

TECHNICAL FIELD

The technology described herein relates to the diagnosis and treatment of cancer.

BACKGROUND

Circulating Tumor Cells (CTCs) are shed from primary tumors into the bloodstream, mediating the spread of cancer to distant organs (metastasis). Thus, the presence of circulating tumor cells (CTCs) in the bloodstream ultimately leads to spread of cancer to distant organs. However, CTCs are rare, estimated at one to ten tumor cells among ten billion normal blood cells in a milliliter of blood. As such, their isolation and molecular analysis has posed a significant technological challenge (Pantel et al., Nat Rev Cancer 2008 8:329-340; Yu et al., J Cell Biol 2011 192:373-382).

SUMMARY

As described herein, the inventors have identified a number of genes, the expression of which is characteristic of CTCs. In particular, the expression of these genes differentiates CTCs from primary tumor cells Accordingly, provided herein are methods and assays relating to the detection of CTCs, including diagnostic and prognostic methods and assays. Further, provided herein are treatments for cancer that target these markers of CTCs, e.g., to inhibit metastasis.

In one aspect, described herein is a method of detecting circulating tumor cells (CTCs) in a sample, the method comprising: measuring the level of a PC-CTC marker gene expression product in the sample; and determining that PC-CTCs are present if the detected level of the marker gene expression product is greater than a reference level. In some embodiments, the CTCs are pancreatic cancer CTCs. In some embodiments, the method further comprises a first step of isolating the CTCs from the sample. In some embodiments, the expression product is a nucleic acid. In some embodiments, the level of the expression product is determined using a method selected from the group consisting of RT-PCR; quantitative RT-PCR; Northern blot; microarray based expression analysis; next-generation sequencing; and RNA in situ hybridization. In some embodiments, the expression product is a polypeptide. In some embodiments, the level of the expression product is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the CTC marker gene is selected from Table 7 or Table 8. In some embodiments, the CTC marker gene is selected from the group consisting of: ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4. In some embodiments, the CTC marker gene is selected from the group consisting of: ALDH1A1; ALDH1A2; IGFBP5; KLF4; DCN; SPARC; WNT; TGFB2; VEGF; COL1A2; COL3A1; and TIMP2. In some embodiments, the CTC marker gene is selected from the group consisting of: ALDH1A2; IGFBP5; KLF4; DCN; and SPARC.

In one aspect, described herein is a method of treating cancer in a subject, the method comprising administering a therapeutically effective amount of a CTC marker gene-targeted therapy to the subject. In some embodiments, the cancer is pancreatic cancer. In some embodiments, the CTC marker gene-targeted therapy comprises an inhibitor of a CTC marker gene. In some embodiments, the inhibitor is an antibody reagent. In some embodiments, the inhibitor is an inhibitory nucleic acid reagent. In some embodiments, the CTC marker gene-targeted therapy comprises a CTC marker gene-binding antibody reagent and a chemotherapeutic agent. In some embodiments, the subject is a subject determined to have an elevated level of CTCs and/or an elevated level of a CTC marker gene present in the blood and/or stroma of the cancer.

In one aspect, described herein is a method of determining if a subject is likely to respond to treatment with a CTC marker gene-targeted therapy, the method comprising measuring the level of a CTC marker gene expression product present in the blood and/or stroma of a cancer; and determining that the subject is likely to respond to the treatment if the level of the expression product is increased relative to a reference level. In some embodiments, the method further comprises a first step of isolating the CTCs from the sample. In some embodiments, the cancer is pancreatic cancer. In some embodiments, the expression product is a nucleic acid. In some embodiments, the level of the expression product is determined using a method selected from the group consisting of RT-PCR; quantitative RT-PCR; Northern blot; microarray based expression analysis; next-generation sequencing; and RNA in situ hybridization. In some embodiments, the expression product is a polypeptide. In some embodiments, the level of the expression product is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the PC-CTC marker gene is selected from Table 7 or Table 8. In some embodiments, the CTC marker gene is selected from the group consisting of: ABI3BP; ADAMTS5;

ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4. In some embodiments, the CTC marker gene is selected from the group consisting of: ALDH1A1; ALDH1A2; IGFBP5; KLF4; DCN; SPARC; WNT; TGFB2; VEGF; COL1A2; COL3A1; and TIMP2. In some embodiments, the CTC marker gene is selected from the group consisting of: ALDH1A2; IGFBP5; KLF4; DCN; and SPARC.

In one aspect, described herein is a method of monitoring the treatment of a subject, the method comprising: administering a cancer therapy to a subject in need thereof; measuring the level of a CTC marker gene expression product present in the blood and/or stroma of a cancer; and determining that the subject is responding if the level of the CTC marker gene expression product is decreased relative to the reference level and determining that the subject is not responding to the treatment if the CTC marker gene expression product is not decreased relative to the reference level. In some embodiments, the cancer is pancreatic cancer. In some embodiments, the reference level is the level of the gene expression product in the patient prior to the administering step. In some embodiments, the method further comprises a first step of isolating the CTCs from the sample. In some embodiments, the expression product is a nucleic acid. In some embodiments, the level of the expression product is determined using a method selected from the group consisting of RT-PCR; quantitative RT-PCR; Northern blot; microarray based expression analysis; next-generation sequencing; and RNA in situ hybridization. In some embodiments, the expression product is a polypeptide. In some embodiments, the level of the expression product is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the PC-CTC marker gene is selected from Table 7 or Table 8. In some embodiments, the CTC marker gene is selected from the group consisting of: ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4. In some embodiments, the CTC marker gene is selected from the group consisting of: ALDH1A1; ALDH1A2; IGFBP5; KLF4; DCN; SPARC; WNT; TGFB2; VEGF; COL1A2; COL3A1; and TIMP2. In some embodiments, the CTC marker gene is selected from the group consisting of: ALDH1A2; IGFBP5; KLF4; DCN; and SPARC.

BRIEF DESCRIPTION OF THE DRAWINGS

FIG. 1A depicts a schematic of CTC-iChip negative IFD system. FIG. 1B depicts a graph of mouse WBC depletion consistency between normal and cancer mouse models. WBC depletion shown in log 10. FIG. 1C depicts a graph of CTC enumeration by immunofluorescent staining (CK+/CD45−/DAPI+) from normal and KPC mice.

FIG. 4A depicts a graph of the percent of WBC deflected (y-axis) as a function of the number of anti-CD45 beads per WBC (x-axis). FIG. 4B depicts a graph of the recovery of mouse PDAC cell line NB508 spiked into normal mouse blood (4 independent experiments shown). FIG. 4C depicts a graph of the captured CTCs/mL of blood from syngeneic orthotopic PDAC tumors using NB508 cell line.

FIG. 5A depicts a table of KPC mouse genotype and characteristics.

FIG. 14A depicts a graph of proliferation of PDAC3 cell lines determined by MTT. FIG. 14B depicts a graph of tumor spheres in PDAC3 shNT versus shSPARC counted per 43 field (error bars represent SD). FIG. 14C depicts a graph of invasion of shSPARC and shNT cell lines quantitated by number of nuclei/203 field. p value<0.01 (), 0.001 (*), 0.0001 (****). Error bars represent SD. FIG. 14D depicts a graph of Percentage of detectable lung metastases by in vivo luciferase imaging after 3 weeks after tail vein inoculation of PDAC3 cell lines. Fisher's exact test p value is shown. FIG. 14E depicts a graph of normalized metastasis burden in mice with orthotopic pancreatic tumors from PDAC3 cell lines. Error bars represent SD (*p<0.05).

DETAILED DESCRIPTION

Figure 1A:
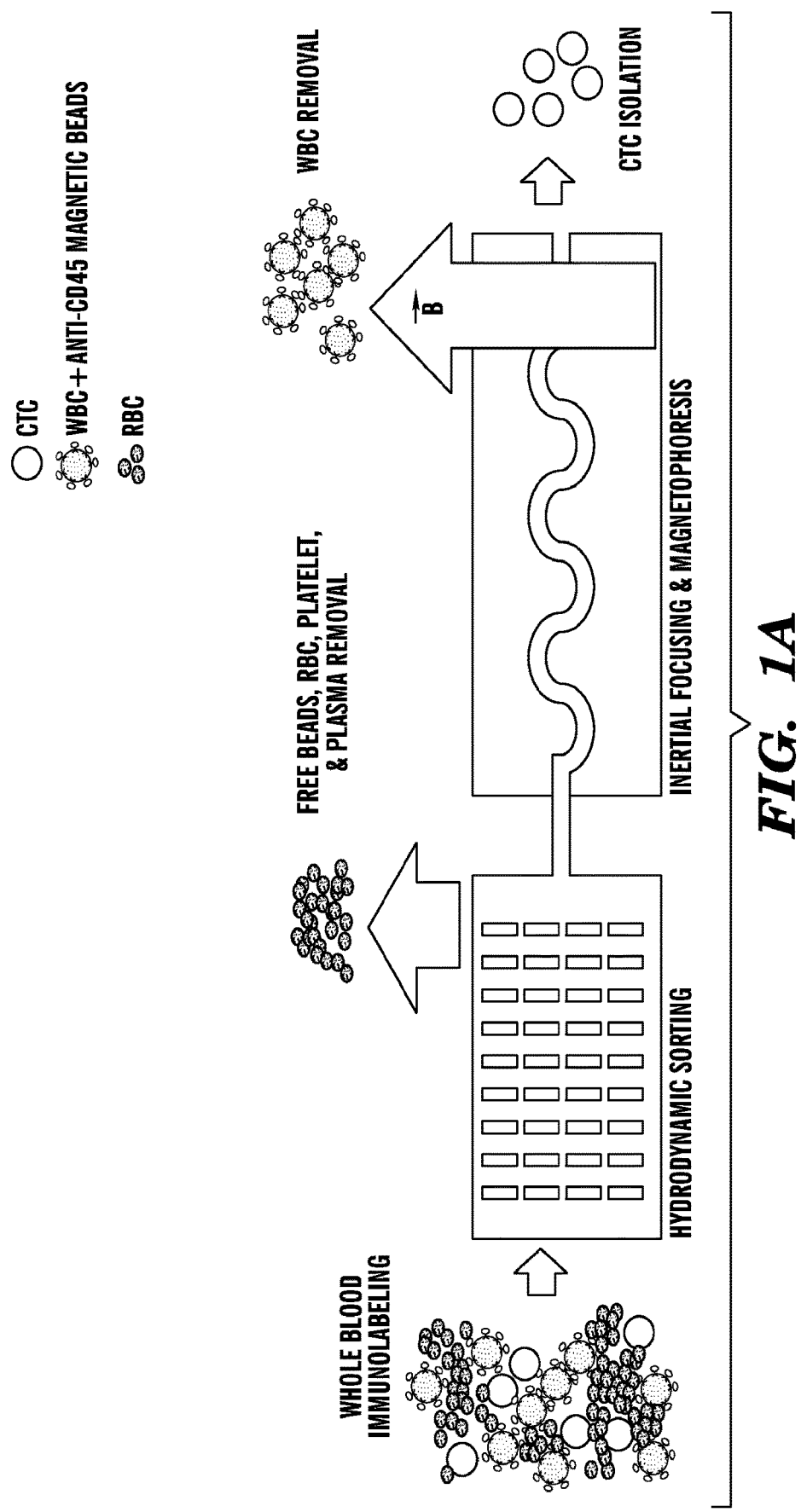
FIGS. 1A-1C demonstrate the isolation and characterization of CTCs.
Figure 1B:
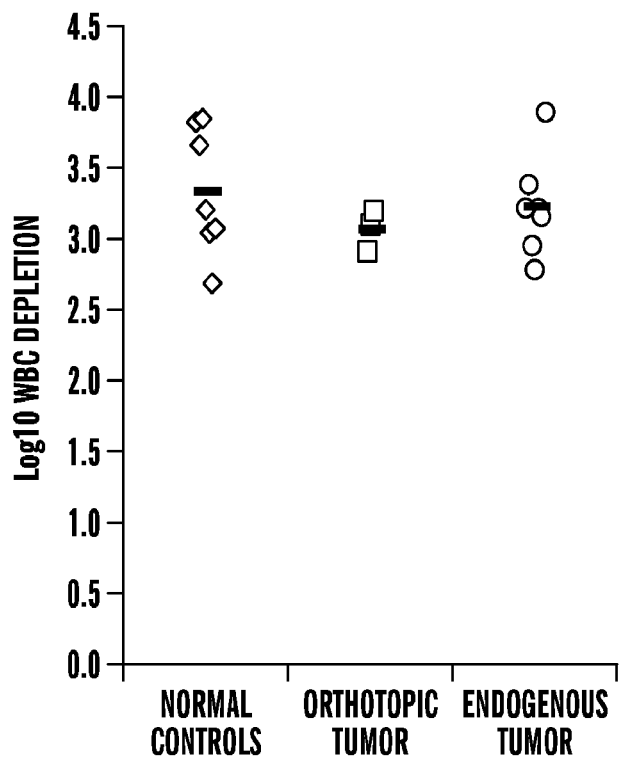

As described herein, the inventors have discovered that circulating tumor cells (CTCs) are characterized by the expression of certain genes, i.e. CTC marker genes. The discovery of these CTC marker genes permit methods and assays for the detection and/or measurement of CTC levels, e.g. CTC levels in a sample from a subject. These methods and assays can provide improved speed and accuracy in the measurement of CTC levels. Furthermore, because the expression of these marker genes distinguishes CTCs from other cells, e.g., other circulating cells and/or normal tumor cells, therapies can be targeted against CTCs by binding to and/or inhibiting these marker gene expression products to reduce the level and/or metastatic potential of CTCs.

As used herein, "circulating tumor cell" or "CTC" refers to tumor cells which are shed from a tumor and present in the blood, i.e. in circulation. Cell markers (e.g. marker genes) that can be used to identify and/or isolate CTCs from other components of the blood are described below herein. In some embodiments, a CTC can be a pancreatic cancer CTC.

In one aspect, described herein is a method of detecting circulating tumor cells (CTCs) in a sample, the method comprising measuring the level of a CTC marker gene expression product in the sample; and determining that CTCs are present if the detected level of the marker gene expression product is greater than a reference level.

As described herein, the inventors have discovered that a number of genes are differentially regulated in CTCs, e.g. as compared to non-circulating tumor cells. Accordingly, there are provided herein methods and assays relating to the measurement of CTC levels. Elevated CTC levels can indicate a poor prognosis, e.g. an increased risk of metastatsis. Accordingly, provided herein are methods and assays related to the prognosis, risk assessment, and treatment of subjects having cancer. In certain embodiments, the assays and methods are directed to determination and/or measurement of the expression level of a gene product (e.g. protein and/or gene transcript such as mRNA) in a biological sample of a subject. In certain embodiments the assays and methods are directed to determination of the expression level of a gene product of at least two genes in a biological sample of a subject, i.e. at least two genes, at least three genes, at least four genes, at least five genes, at least six genes, at least seven genes, at least eight genes, at least nine genes, at least 10 genes . . . at least 15 genes, . . . at least 25 genes, . . . at least 30 genes, or more genes, or any number of genes selected from Table 7, Table 8, and/or Table 14 as described herein.

In some embodiments, the marker gene(s) is selected from the group consisting of ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4.

In some embodiments, the marker gene(s) is selected from the group consisting of ALDH1A1; ALDH1A2; IGFBP5; KLF4; DCN; SPARC; WNT; TGFB2; VEGF; COL1A2; COL3A1; and TIMP2. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: ALDH1A1; ALDH1A2; IGFBP5; KLF4; DCN; SPARC; WNT; TGFB2; VEGF; COL1A2; COL3A1; and TIMP2.

In some embodiments, the marker gene(s) is selected from the group consisting of ALDH1A2; IGFBP5; KLF4; DCN; and SPARC. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: ALDH1A2; IGFBP5; KLF4; DCN; and SPARC.

In some embodiments, the marker gene(s) is selected from the group consisting of ALDH1A2; IGFBP5; KLF4; and DCN. In some embodiments, the assays, methods, and systems described herein are directed to determination of the expression level of a gene product of at least two genes in a biological sample of a subject, e.g. at least two genes, or at least three genes, or e.g. all of the following genes: ALDH1A2; IGFBP5; KLF4; and DCN.

In some embodiments, the marker gene(s) is selected from the group consisting of TPT1; HMGB1; SPON 2;

SPARC; and ARSA. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: TPT1; HMGB1; SPON 2; SPARC; and ARSA.

In some embodiments, the marker gene(s) is selected from the group consisting of IL6ST; ARSA; TIMP2; CD55; SULF2; ITGA6; SDC4; CDON; and SV2A. In some embodiments, the assays, methods, and systems described herein are directed to determination of the expression level of a gene product of at least two genes in a biological sample of a subject, e.g. at least two genes, or at least three genes, or at least four genes, or at least five genes, or at least six genes, or at least seven genes, or at least eight genes or, e.g. all of the following genes: IL6ST; ARSA; TIMP2; CD55; SULF2; ITGA6; SDC4; CDON; and SV2A. In some embodiments, the level of polypeptide expression products are determined for the marker gene(s) is selected from the group consisting of IL6ST; ARSA; TIMP2; CD55; SULF2; ITGA6; SDC4; CDON; and SV2A, e.g. because, as described herein, RNA levels of cell surface proteins are lower than polypeptide levels.

TABLE 7

Exemplary mouse marker genes

| MOUSE GENE SYMBOL | Gene Name |
|---|---|
| Abcb1b | ATP-binding cassette, sub-family B (MDR/TAP), member 1B |
| Abi3bp | ABI gene family, member 3 (NESH) binding protein |
| Ablim3 | actin binding LIM protein family, member 3 |
| Acad9 | acyl-Coenzyme A dehydrogenase family, member 9 |
| Acbd3 | acyl-Coenzyme A binding domain containing 3 |
| Acin1 | apoptotic chromatin condensation inducer 1 |
| Actb | actin, beta |
| Actg1 | predicted gene 8543; actin-like 8; predicted gene 7505; predicted gene 12715; predicted gene 12003; predicted gene 8399; predicted gene 6375; actin, gamma, cytoplasmic 1; similar to gamma-actin; predicted gene 4667; similar to cytoplasmic beta-actin; predicted gene 16385 |
| Adamts5 | similar to a disintegrin-like and metalloprotease (reprolysin type) with thrombospondin type 1 motif, 5 (aggrecanase-2); a disintegrin-like and metallopeptidase (reprolysin type) with thrombospondin type 1 motif, 5 (aggrecanase-2) |
| Adamtsl1 | ADAMTS-like 1 |
| Add3 | adducin 3 (gamma) |
| Aebp1 | AE binding protein 1 |
| Agap1 | ArfGAP with GTPase domain, ankyrin repeat and PH domain 1 |
| Akap13 | A kinase (PRKA) anchor protein 13 |
| Akap2 | A kinase (PRKA) anchor protein 2; paralemmin 2 |
| Akr1b3 | aldo-keto reductase family 1, member B3 (aldose reductase) |
| Akt2 | similar to RAC-beta serine/threonine-protein kinase (RAC-PK-beta) (Protein kinase Akt-2) (Protein kinase B, beta) (PKB beta); thymoma viral proto-oncogene 2; similar to serine/threonine kinase |
| Aldh1a1 | aldehyde dehydrogenase family 1, subfamily A1 |
| Aldh1a2 | aldehyde dehydrogenase family 1, subfamily A2 |
| Alox12 | arachidonate 12-lipoxygenase |
| Amfr | autocrine motility factor receptor |
| Amhr2 | anti-Mullerian hormone type 2 receptor |
| Ang | angiogenin, ribonuclease, RNase A family, 5 |
| Ankrd11 | ankyrin repeat domain 11 |
| Ankrd12 | ankyrin repeat domain 12; similar to Ankrd12 protein |
| Ankrd17 | ankyrin repeat domain 17 |
| Ano6 | anoctamin 6 |
| Anp32a | acidic (leucine-rich) nuclear phosphoprotein 32 family, member A |
| Anxa7 | annexin A7 |
| Ap1s3 | predicted gene 8532; similar to adaptor-related protein complex AP-1, sigma 3; adaptor-related protein complex AP-1, sigma 3 |
| Ap3s1 | predicted gene 7603; adaptor-related protein complex 3, sigma 1 subunit; predicted gene 5610 |
| Ap4e1 | adaptor-related protein complex AP-4, epsilon 1 |
| Aplp1 | amyloid beta (A4) precursor-like protein 1 |
| Apol9a | apolipoprotein L 9b; apolipoprotein L 9a |
| App | amyloid beta (A4) precursor protein |
| Aqp1 | aquaporin 1 |
| Arap2 | predicted gene 336; ArfGAP with RhoGAP domain, ankyrin repeat and PH domain 2 |
| Arf2 | ADP-ribosylation factor 2 |
| Arf3 | ADP-ribosylation factor 3 |
| Arf5 | similar to ADP-ribosylation factor; ADP-ribosylation factor 5 |
| Arhgap28 | Rho GTPase activating protein 28 |
| Arhgap29 | Rho GTPase activating protein 29 |
| Arhgap5 | Rho GTPase activating protein 5 |
| Arhgef12 | predicted gene 7281; predicted gene 5831; similar to SP140 nuclear body protein (predicted); Rho guanine nucleotide exchange factor (GEF) 12 |
| Arid1a | similar to AT rich interactive domain 1A isoform a; AT rich interactive domain 1A (SWI-like) |

TABLE 7-continued

Exemplary mouse marker genes

| MOUSE GENE SYMBOL | Gene Name |
|---|---|
| Arid4a | AT rich interactive domain 4A (RBP1-like) |
| Arid4b | AT rich interactive domain 4B (RBP1-like) |
| Arid5b | similar to modulator recognition factor 2; AT rich interactive domain 5B (MRF1-like) |
| Arl3 | ADP-ribosylation factor-like 3 |
| Arl4d | ADP-ribosylation factor-like 4D; hypothetical protein LOC100044157 |
| Arl6ip5 | ADP-ribosylation factor-like 6 interacting protein 5 |
| Armcx3 | armadillo repeat containing, X-linked 3; hypothetical protein LOC100044266; predicted gene 9299 |
| Arpc2 | predicted gene 5492; actin related protein 2/3 complex, subunit 2 |
| Arsa | arylsulfatase A |
| Arsb | arylsulfatase B |
| Ascc3 | activating signal cointegrator 1 complex subunit 3 |
| Atf3 | activating transcription factor 3 |
| Atg3 | autophagy-related 3 (yeast) |
| Atp1a1 | ATPase, Na+/K+ transporting, alpha 1 polypeptide |
| Atp1b1 | ATPase, Na+/K+ transporting, beta 1 polypeptide |
| Atp2b1 | ATPase, Ca++ transporting, plasma membrane 1 |
| Atp6v1a | ATPase, H+ transporting, lysosomal V1 subunit A |
| Atxn2 | ataxin 2 |
| B230120H23Rik | RIKEN cDNA B230120H23 gene |
| B2m | beta-2 microglobulin |
| BC003331 | similar to odorant response abnormal 4; cDNA sequence BC003331 |
| BC005537 | cDNA sequence BC005537 |
| BC005561 | THO complex 2; cDNA sequence BC005561 |
| BC013529 | cDNA sequence BC013529 |
| Baz2a | bromodomain adjacent to zinc finger domain, 2A |
| Bbs4 | Bardet-Biedl syndrome 4 (human) |
| Bbx | bobby sox homolog (*Drosophila*) |
| Bcam | basal cell adhesion molecule |
| Bcl10 | B-cell leukemia/lymphoma 10; predicted gene 6141 |
| Bdp1 | B double prime 1, subunit of RNA polymerase III transcription initiation factor IIIB |
| Bicc1 | bicaudal C homolog 1 (*Drosophila*) |
| Bicd1 | bicaudal D homolog 1 (*Drosophila*) |
| Birc6 | baculoviral IAP repeat-containing 6 |
| Blvrb | biliverdin reductase B (flavin reductase (NADPH)) |
| Bnc1 | basonuclin 1 |
| Bnc2 | basonuclin 2 |
| Bod1l | biorientation of chromosomes in cell division 1-like |
| Bptf | bromodomain PHD finger transcription factor |
| Braf | Braf transforming gene |
| Brd2 | similar to mKIAA4005 protein; bromodomain containing 2 |
| Brd4 | bromodomain containing 4 |
| Brp44l | similar to brain protein 44-like protein; brain protein 44-like; predicted gene 3452; predicted gene 8219 |
| Bst2 | bone marrow stromal cell antigen 2 |
| Btbd2 | BTB (POZ) domain containing 2 |
| Btbd7 | BTB (POZ) domain containing 7 |
| Btf3 | predicted gene 9308; basic transcription factor 3; predicted gene 3531; predicted gene 7973 |
| Btg2 | B-cell translocation gene 2, anti-proliferative |
| Bzw1 | predicted gene 11652; predicted gene 5191; basic leucine zipper and W2 domains 1 |
| C1d | C1D nuclear receptor co-repressor |
| C1ra | complement component 1, r subcomponent; predicted gene 8551 |
| C1rl | complement component 1, r subcomponent-like |
| C1s | similar to Complement component 1, s subcomponent; complement component 1, s subcomponent |
| C2 | complement component 2 (within H-2S) |
| C3 | complement component 3; similar to complement component C3 prepropeptide, last |
| C4a | similar to Complement C4 precursor; complement component 4A (Rodgers blood group); similar to complement C4; complement component 4B (Childo blood group) |
| C4b | similar to Complement C4 precursor; complement component 4A (Rodgers blood group); similar to complement C4; complement component 4B (Childo blood group) |
| Calm1 | predicted gene 7743; calmodulin 3; calmodulin 2; calmodulin 1; predicted gene 7308 |
| Calm2 | predicted gene 7743; calmodulin 3; calmodulin 2; calmodulin 1; predicted gene 7308 |
| Cap1 | CAP, adenylate cyclase-associated protein 1 (yeast) |
| Cast | calpastatin |

TABLE 7-continued

Exemplary mouse marker genes

| MOUSE GENE SYMBOL | Gene Name |
|---|---|
| Cav1 | caveolin 1, caveolae protein |
| Ccdc109b | coiled-coil domain containing 109B |
| Ccdc34 | coiled-coil domain containing 34 |
| Ccdc80 | coiled-coil domain containing 80 |
| Ccdc88a | coiled coil domain containing 88A |
| Ccdc90a | coiled-coil domain containing 90A |
| Ccnl1 | cyclin L1 |
| Cd109 | CD109 antigen |
| Cd200 | CD200 antigen; similar to MRC OX-2 antigen homolog |
| Cd248 | CD248 antigen, endosialin |
| Cd34 | CD34 antigen |
| Cd55 | CD55 antigen |
| Cd81 | CD81 antigen |
| Cd82 | CD82 antigen |
| Cd9 | CD9 antigen |
| Cdc42ep3 | CDC42 effector protein (Rho GTPase binding) 3 |
| Cdh11 | cadherin 11 |
| Cdh3 | cadherin 3 |
| Cdk13 | cell division cycle 2-like 5 (cholinesterase-related cell division controller) |
| Cdon | cell adhesion molecule-related/down-regulated by oncogenes |
| Celf2 | CUG triplet repeat, RNA binding protein 2 |
| Cep164 | centrosomal protein 164 |
| Cep57 | centrosomal protein 57 |
| Cfh | complement component factor h; similar to complement component factor H |
| Cfl1 | cofilin 1, non-muscle; similar to Cofilin-1 (Cofilin, non-muscle isoform); predicted gene 6180 |
| Cfl2 | cofilin 2, muscle |
| Chd1 | chromodomain helicase DNA binding protein 1 |
| Chd2 | chromodomain helicase DNA binding protein 2 |
| Chi3l1 | chitinase 3-like 1 |
| Chst4 | carbohydrate (chondroitin 6/keratan) sulfotransferase 4 |
| Cish | cytokine inducible SH2-containing protein |
| Clcn3 | chloride channel 3 |
| Cldn15 | claudin 15 |
| Cldn25 | predicted gene 16492 |
| Clec1b | C-type lectin domain family 1, member b |
| Clec3b | C-type lectin domain family 3, member b |
| Clic4 | chloride intracellular channel 4 (mitochondrial) |
| Clip1 | CAP-GLY domain containing linker protein 1 |
| Clip3 | CAP-GLY domain containing linker protein 3 |
| Cln8 | ceroid-lipofuscinosis, neuronal 8 |
| Cmah | cytidine monophospho-N-acetylneuraminic acid hydroxylase |
| Cmtm3 | CKLF-like MARVEL transmembrane domain containing 3 |
| Cmtm7 | CKLF-like MARVEL transmembrane domain containing 7 |
| Cnot6l | CCR4-NOT transcription complex, subunit 6-like |
| Cobl | cordon-bleu |
| Cobll1 | Cobl-like 1 |
| Col14a1 | collagen, type XIV, alpha 1 |
| Col1a2 | collagen, type I, alpha 2 |
| Col3a1 | collagen, type III, alpha 1 |
| Col4a6 | collagen, type IV, alpha 6 |
| Colec12 | collectin sub-family member 12 |
| Coq10b | hypothetical protein LOC675736; coenzyme Q10 homolog B (S. cerevisiae); predicted gene 4899 |
| Creb3l1 | cAMP responsive element binding protein 3-like 1 |
| Creb5 | RIKEN cDNA 9430076C15 gene; cAMP responsive element binding protein 5 |
| Crebbp | CREB binding protein |
| Creg1 | cellular repressor of E1A-stimulated genes 1 |
| Crim1 | cysteine rich transmembrane BMP regulator 1 (chordin like) |
| Crls1 | cardiolipin synthase 1 |
| Cryab | crystallin, alpha B |
| Cryl1 | crystallin, lambda 1 |
| Crym | crystallin, mu |
| Csda | cold shock domain protein A |
| Csf1 | colony stimulating factor 1 (macrophage) |
| Csnk1a1 | casein kinase 1, alpha 1 |
| Csrnp1 | cysteine-serine-rich nuclear protein 1 |
| Csrp1 | cysteine and glycine-rich protein 1 |
| Cuedc1 | CUE domain containing 1 |
| Cyb5 | cytochrome b-5 |
| Cybrd1 | cytochrome b reductase 1 |
| Cyp2d22 | cytochrome P450, family 2, subfamily d, polypeptide 22 |

TABLE 7-continued

Exemplary mouse marker genes

| MOUSE GENE SYMBOL | Gene Name |
|---|---|
| Cyp2s1 | cytochrome P450, family 2, subfamily s, polypeptide 1 |
| Cyr61 | cysteine rich protein 61 |
| Dab2 | disabled homolog 2 (*Drosophila*) |
| Dag1 | dystroglycan 1 |
| Daglb | diacylglycerol lipase, beta |
| Dapk1 | death associated protein kinase 1 |
| Dcn | decorin |
| Ddr1 | discoidin domain receptor family, member 1 |
| Ddr2 | discoidin domain receptor family, member 2 |
| Ddx3x | DEAD/H (Asp-Glu-Ala-Asp/His) box polypeptide 3, X-linked |
| Ddx5 | DEAD (Asp-Glu-Ala-Asp) box polypeptide 5; predicted gene 12183 |
| Dennd5a | DENN/MADD domain containing 5A; similar to Rab6 interacting protein 1 |
| Dhx15 | DEAH (Asp-Glu-Ala-His) box polypeptide 15 |
| Diap1 | diaphanous homolog 1 (*Drosophila*) |
| Dlgap4 | discs, large homolog-associated protein 4 (*Drosophila*) |
| Dmkn | dermokine |
| Dnaja2 | DnaJ (Hsp40) homolog, subfamily A, member 2 |
| Dnajb9 | predicted gene 6568; DnaJ (Hsp40) homolog, subfamily B, member 9 |
| Dnajc1 | DnaJ (Hsp40) homolog, subfamily C, member 1 |
| Dnmt1 | DNA methyltransferase (cytosine-5) 1 |
| Dpp4 | dipeptidylpeptidase 4 |
| Dpysl2 | dihydropyrimidinase-like 2 |
| Dpysl3 | dihydropyrimidinase-like 3 |
| Dst | dystonin; hypothetical protein LOC100047109 |
| Dtx2 | deltex 2 homolog (*Drosophila*) |
| Dusp1 | dual specificity phosphatase 1 |
| Dusp14 | dual specificity phosphatase 14 |
| Dusp3 | dual specificity phosphatase 3 (vaccinia virus phosphatase VH1-related) |
| Dync1i2 | dynein cytoplasmic 1 intermediate chain 2 |
| Ecd | ecdysoneless homolog (*Drosophila*) |
| Eea1 | early endosome antigen 1 |
| Eef1a1 | predicted gene 5869; predicted gene 7161; predicted gene 7105; predicted gene 5822; similar to eukaryotic translation elongation factor 1 alpha 1; predicted gene 6192; predicted gene 6392; predicted gene 6767; predicted gene 6170; predicted gene 6548; predicted gene 6789; eukaryotic translation elongation factor 1 alpha 1 |
| Efemp1 | epidermal growth factor-containing fibulin-like extracellular matrix protein 1 |
| Efhd2 | similar to EF hand domain containing 2; EF hand domain containing 2 |
| Efna5 | ephrin A5 |
| Egr1 | early growth response 1 |
| Ehd2 | EH-domain containing 2 |
| Eif2s3x | eukaryotic translation initiation factor 2, subunit 3, structural gene X-linked; similar to translation initiation factor eIF-2 gamma subunit; predicted gene 2223 |
| Eif3a | eukaryotic translation initiation factor 3, subunit A |
| Elf1 | E74-like factor 1 |
| Elovl6 | predicted gene 11295; ELOVL family member 6, elongation of long chain fatty acids (yeast) |
| Emp2 | epithelial membrane protein 2 |
| Enpp2 | ectonucleotide pyrophosphatase/phosphodiesterase 2 |
| Enpp4 | ectonucleotide pyrophosphatase/phosphodiesterase 4 |
| Esam | endothelial cell-specific adhesion molecule |
| Esf1 | ESF1, nucleolar pre-rRNA processing protein, homolog (*S. cerevisiae*) |
| Espn | espin |
| Esyt3 | family with sequence similarity 62 (C2 domain containing), member C |
| Etfa | predicted gene 2893; electron transferring flavoprotein, alpha polypeptide |
| Evpl | envoplakin |
| Exoc4 | exocyst complex component 4 |
| F11r | F11 receptor |
| Faim2 | Fas apoptotic inhibitory molecule 2 |
| Fam117a | family with sequence similarity 117, memberA |
| Fam134b | family with sequence similarity 134, member B |
| Fam53b | family with sequence similarity 53, member B |
| Fam63b | RIKEN cDNA B230380D07 gene |
| Fam76a | predicted gene 7527; family with sequence similarity 76, member A |
| Fam84b | RIKEN cDNA D330050I23 gene |
| Fas | Fas (TNF receptor superfamily member 6) |
| Fbln1 | fibulin 1 |
| Fermt2 | fermitin family homolog 2 (*Drosophila*) |
| Fgf1 | fibroblast growth factor 1 |
| Fhl1 | four and a half LIM domains 1 |
| Filip1l | filamin A interacting protein 1-like |
| Fkbp5 | FK506 binding protein 5 |

TABLE 7-continued

Exemplary mouse marker genes

| MOUSE GENE SYMBOL | Gene Name |
|---|---|
| Flii | flightless I homolog (*Drosophila*); similar to cytoskeletal actin-modulating protein |
| Flnc | filamin C, gamma |
| Flrt2 | fibronectin leucine rich transmembrane protein 2 |
| Fmo2 | flavin containing monooxygenase 2 |
| Fmod | fibromodulin |
| Fndc1 | fibronectin type III domain containing 1; similar to fibronectin type III domain containing 1 |
| Fos | FBJ osteosarcoma oncogene |
| Foxn3 | forkhead box N3 |
| Frmd4b | FERM domain containing 4B |
| Fth1 | ferritin heavy chain 1 |
| Fxyd1 | FXYD domain-containing ion transport regulator 1 |
| G3bp1 | Ras-GTPase-activating protein SH3-domain binding protein 1 |
| Gabarapl1 | gamma-aminobutyric acid (GABA) A receptor-associated protein-like 1 |
| Gadd45b | growth arrest and DNA-damage-inducible 45 beta |
| Ganab | alpha glucosidase 2 alpha neutral subunit |
| Gas1 | growth arrest specific 1 |
| Gas6 | growth arrest specific 6 |
| Gata6 | GATA binding protein 6 |
| Gbp2 | guanylate binding protein 2 |
| Gbp3 | guanylate binding protein 3 |
| Gcap14 | granule cell antiserum positive 14 |
| Gcsh | predicted gene 3672; similar to Glycine cleavage system H protein, mitochondrial precursor; glycine cleavage system protein H (aminomethyl carrier) |
| Gda | guanine deaminase |
| Gem | GTP binding protein (gene overexpressed in skeletal muscle) |
| Gfm2 | G elongation factor, mitochondrial 2 |
| Gfpt2 | glutamine fructose-6-phosphate transaminase 2 |
| Gja1 | gap junction protein, alpha 1 |
| Gjb5 | gap junction protein, beta 5 |
| Gm10052 | predicted gene 10052 |
| Gm13251 | predicted gene 13251; predicted gene, OTTMUSG00000010657; RIKEN cDNA 1700029I01 gene |
| Gm3893 | similar to 4933409K07Rik protein; predicted gene, 665845; predicted gene 2490; predicted gene 10601; predicted gene 2163; predicted gene 3892; RIKEN cDNA 4933409K07 gene; predicted gene 3893 |
| Gm6548 | predicted gene 5869; predicted gene 7161; predicted gene 7105; predicted gene 5822; similar to eukaryotic translation elongation factor 1 alpha 1; predicted gene 6192; predicted gene 6392; predicted gene 6767; predicted gene 6170; predicted gene 6548; predicted gene 6789; eukaryotic translation elongation factor 1 alpha 1 |
| Gm6578 | predicted gene 6578 |
| Gm6644 | predicted gene 6644 |
| Gm9199 | predicted gene 9199 |
| Gnb2 | guanine nucleotide binding protein (G protein), beta 2 |
| Golga4 | golgi autoantigen, golgin subfamily a, 4 |
| Golgb1 | golgi autoantigen, golgin subfamily b, macrogolgin 1 |
| Gpc3 | glypican 3 |
| Gpc4 | glypican 4; similar to Glypican 4 |
| Gpcpd1 | preimplantation protein 4 |
| Gpm6a | glycoprotein m6a |
| Gpr116 | G protein-coupled receptor 116 |
| Gpr133 | G protein-coupled receptor 133 |
| Gpr64 | G protein-coupled receptor 64 |
| Gprc5b | G protein-coupled receptor, family C, group 5, member B |
| Gpx8 | glutathione peroxidase 8 (putative) |
| Gsr | similar to Glutathione reductase, mitochondrial precursor (GR) (GRase); glutathione reductase |
| Gsta3 | glutathione S-transferase, alpha 3 |
| Gstm1 | similar to Glutathione S-transferase Mu 1 (GST class-mu 1) (Glutathione S-transferase GT8.7) (pmGT10) (GST 1-1); predicted gene 5562; glutathione S-transferase, mu 1 |
| Gstm4 | glutathione S-transferase, mu 4 |
| Gucy1a3 | guanylate cyclase 1, soluble, alpha 3 |
| H2-D1 | histocompatibility 2, D region; histocompatibility 2, D region locus 1 |
| H2-K1 | histocompatibility 2, K1, K region; similar to H-2K(d) antigen |
| H2-Q6 | histocompatibility 2, Q region locus 1; histocompatibility 2, Q region locus 9; similar to H-2 class I histocompatibility antigen, L-D alpha chain precursor; histocompatibility 2, Q region locus 8; histocompatibility 2, Q region locus 2; similar to MHC class Ib antigen; histocompatibility 2, Q region locus 7; histocompatibility 2, Q region locus 6; hypothetical protein |

TABLE 7-continued

Exemplary mouse marker genes

| MOUSE GENE SYMBOL | Gene Name |
|---|---|
| | LOC100044307; similar to H-2 class I histocompatibility antigen, Q7 alpha chain precursor (QA-2 antigen); RIKEN cDNA 0610037M15 gene |
| H3f3a | predicted gene 14383; predicted gene 3835; predicted gene 14384; predicted gene 12950; predicted gene, 670915; H3 histone, family 3A; predicted gene 12657; predicted gene 6132; predicted gene 10257; predicted gene 7227; H3 histone, family 3B; predicted gene 6128; similar to histone; predicted gene 1986; predicted gene 6186; hypothetical protein LOC676337; predicted gene 6421; predicted gene 2198; predicted gene 6817; predicted gene 8095; predicted gene 12271; predicted gene 13529; predicted gene 8029; predicted gene 4938; predicted gene 7100; predicted gene 9014; similar to Histone H3.4 (Embryonic); predicted gene 7179; similar to H3 histone, family 3B; predicted gene 7900; predicted gene 2099; similar to H3 histone, family 3A; predicted gene 6749; predicted gene 6485; predicted gene 4028; predicted gene 7194 |
| Hdac3 | histone deacetylase 3 |
| Hdac5 | histone deacetylase 5 |
| Heg1 | HEG homolog 1 (zebrafish) |
| Herpud2 | HERPUD family member 2 |
| Hes1 | hairy and enhancer of split 1 (Drosophila) |
| Hexb | hexosaminidase B |
| Hist1h1c | histone cluster 1, H1c |
| Hmgb1 | predicted gene 13121; predicted gene 3160; high-mobility group (nonhistone chromosomal) protein 1-like 1; predicted gene 6090; predicted gene 3851; predicted gene 8967; predicted gene 7782; predicted gene 4587; predicted gene 4689; predicted gene 3307; predicted gene 13932; predicted gene 15059; predicted gene 3565; predicted gene 15447; predicted gene 12587; predicted gene 9012; predicted gene 6115; predicted gene 9480; high mobility group box 1; predicted gene 8423; predicted gene 5853; predicted gene 8288; predicted gene 7888; predicted gene 8594; predicted gene 15387; predicted gene 5473; predicted gene 8807; similar to high mobility group box 1; similar to 2810416G20Rik protein; predicted gene 8390; predicted gene, OTTMUSG00000005439; predicted gene 5842; predicted gene 5527; predicted gene 8563; predicted gene 2710; predicted gene 12331; predicted gene 5937; predicted gene 5504; similar to high-mobility group box 1; predicted gene 10361; predicted gene 2607; predicted gene 7422; predicted gene 10075; predicted gene 12568; predicted gene 6589; predicted gene 4383; predicted gene 8031; similar to High mobility group protein 1 (HMG-1) (High mobility group protein B1) (Amphoterin) (Heparin-binding protein p30); predicted gene 7468; predicted gene 8554 |
| Hnrnph1 | heterogeneous nuclear ribonucleoprotein H1 |
| Hnrnph2 | heterogeneous nuclear ribonucleoprotein H2 |
| Hnrnpl | heterogeneous nuclear ribonucleoprotein L |
| Hnrnpm | heterogeneous nuclear ribonucleoprotein M |
| Hnrnpr | predicted gene 6159; heterogeneous nuclear ribonucleoprotein R |
| Hook3 | hook homolog 3 (Drosophila) |
| Hoxa5 | homeo box A5 |
| Hp1bp3 | heterochromatin protein 1, binding protein 3 |
| Hsp90aa1 | predicted gene 5511; heat shock protein 90, alpha (cytosolic), class A member 1 |
| Hsp90ab1 | heat shock protein 90 alpha (cytosolic), class B member 1 |
| Hsp90b1 | heat shock protein 90, beta (Grp94), member 1 |
| Hspa12a | heat shock protein 12A |
| Hspa2 | heat shock protein 2 |
| Hspb1 | heat shock protein 1 |
| Hspb8 | heat shock protein 8 |
| Id1 | inhibitor of DNA binding 1 |
| Id2 | inhibitor of DNA binding 2 |
| Ier2 | immediate early response 2 |
| Ifi204 | interferon activated gene 204 |
| Ifi205 | interferon activated gene 205 |
| Ifi27l2a | interferon, alpha-inducible protein 27 like 2A |
| Ifi35 | interferon-induced protein 35 |
| Ifit3 | interferon-induced protein with tetratricopeptide repeats 3 |
| Ifitm3 | interferon induced transmembrane protein 3 |
| Ifnar2 | interferon (alpha and beta) receptor 2 |
| Ifngr1 | interferon gamma receptor 1 |
| Ifrd1 | interferon-related developmental regulator 1 |
| Ift74 | intraflagellar transport 74 homolog (Chlamydomonas) |
| Igf1r | insulin-like growth factor I receptor |
| Igfbp5 | insulin-like growth factor binding protein 5 |
| Igfbp6 | insulin-like growth factor binding protein 6 |
| Il16 | interleukin 16 |
| Il17re | interleukin 17 receptor E |

TABLE 7-continued

Exemplary mouse marker genes

| MOUSE GENE SYMBOL | Gene Name |
|---|---|
| Il6ra | interleukin 6 receptor, alpha |
| Il6st | interleukin 6 signal transducer |
| Ildr2 | immunoglobulin-like domain containing receptor 2 |
| Ilf3 | interleukin enhancer binding factor 3 |
| Impad1 | inositol monophosphatase domain containing 1 |
| Ints10 | integrator complex subunit 10; similar to integrator complex subunit 10 |
| Iqsec1 | IQ motif and Sec7 domain 1 |
| Irak4 | interleukin-1 receptor-associated kinase 4 |
| Irf2bp2 | interferon regulatory factor 2 binding protein 2 |
| Irf7 | interferon regulatory factor 7 |
| Irs2 | insulin receptor substrate 2 |
| Itch | itchy, E3 ubiquitin protein ligase |
| Itga6 | integrin alpha 6 |
| Itpr2 | inositol 1,4,5-triphosphate receptor 2 |
| Jmjd1c | jumonji domain containing 1C |
| Jun | Jun oncogene |
| Junb | Jun-B oncogene |
| Jund | Jun proto-oncogene related gene d |
| Jup | junction plakoglobin |
| Kank1 | KN motif and ankyrin repeat domains 1 |
| Kcnab1 | potassium voltage-gated channel, shaker-related subfamily, beta member 1 |
| Kdelr1 | KDEL (Lys-Asp-Glu-Leu) endoplasmic reticulum protein retention receptor 1 |
| Kdm5a | lysine (K)-specific demethylase 5A |
| Kdm6b | KDM1 lysine (K)-specific demethylase 6B |
| Kdr | kinase insert domain protein receptor |
| Keap1 | kelch-like ECH-associated protein 1 |
| Kif1b | kinesin family member 1B |
| Kif5b | kinesin family member 5B |
| Klf10 | Kruppel-like factor 10 |
| Klf2 | Kruppel-like factor 2 (lung) |
| Klf4 | Kruppel-like factor 4 (gut) |
| Klf6 | Kruppel-like factor 6 |
| Klf7 | Kruppel-like factor 7 (ubiquitous) |
| Klf9 | Kruppel-like factor 9 |
| Kpna1 | karyopherin (importin) alpha 1 |
| Kpna3 | karyopherin (importin) alpha 3 |
| Krcc1 | lysine-rich coiled-coil 1 |
| Krt14 | keratin 14 |
| Ktn1 | kinectin 1 |
| Lama4 | laminin, alpha 4 |
| Lamp2 | lysosomal-associated membrane protein 2 |
| Lars2 | leucyl-tRNA synthetase, mitochondrial |
| Lass2 | LAG1 homolog, ceramide synthase 2 |
| Lass4 | LAG1 homolog, ceramide synthase 4 |
| Lgals7 | lectin, galactose binding, soluble 7 |
| Limch1 | LIM and calponin homology domains 1 |
| Lims2 | LIM and senescent cell antigen like domains 2 |
| Lman1 | lectin, mannose-binding, 1 |
| Lpar2 | lysophosphatidic acid receptor 2 |
| Lrrc20 | leucine rich repeat containing 20 |
| Lrrc58 | leucine rich repeat containing 58; predicted gene, OTTMUSG00000025724 |
| Lrrc61 | leucine rich repeat containing 61 |
| Lrrn4 | leucine rich repeat neuronal 4 |
| Lrrn4cl | LRRN4 C-terminal like |
| Ltbp4 | latent transforming growth factor beta binding protein 4 |
| Luc7l3 | RIKEN cDNA 3300001P08 gene |
| Maf | similar to c-Maf long form; avian musculoaponeurotic fibrosarcoma (v-maf) AS42 oncogene homolog |
| Maged1 | melanoma antigen, family D, 1 |
| Magt1 | magnesium transporter 1 |
| Malat1 | metastasis associated lung adenocarcinoma transcript 1 (non-coding RNA) |
| Man1a | mannosidase 1, alpha |
| Manf | mesencephalic astrocyte-derived neurotrophic factor |
| Maoa | monoamine oxidase A |
| Map3k3 | mitogen-activated protein kinase kinase kinase 3 |
| Mapk1 | mitogen-activated protein kinase 1 |
| Mapkapk3 | mitogen-activated protein kinase-activated protein kinase 3 |
| Mapre2 | microtubule-associated protein, RP/EB family, member 2 |
| Marcksl1 | MARCKS-like 1; predicted gene 9106 |
| Mat2a | methionine adenosyltransferase II, alpha |
| Mat2b | methionine adenosyltransferase II, beta |
| Matr3 | matrin 3; similar to Matrin 3 |

TABLE 7-continued

Exemplary mouse marker genes

| MOUSE GENE SYMBOL | Gene Name |
|---|---|
| Med13l | mediator complex subunit 13-like |
| Med21 | mediator complex subunit 21 |
| Mef2c | myocyte enhancer factor 2C |
| Meis2 | Meis homeobox 2 |
| Mesdc1 | mesoderm development candidate 1 |
| Metap2 | methionine aminopeptidase 2 |
| Mettl2 | methyltransferase like 2 |
| Mettl7a1 | methyltransferase like 7A1 |
| Mfap1a | similar to microfibrillar-associated protein 1A; microfibrillar-associated protein 1A; microfibrillar-associated protein 1B |
| Mfhas1 | malignant fibrous histiocytoma amplified sequence 1 |
| Mgll | monoglyceride lipase |
| Mgst1 | microsomal glutathione S-transferase 1 |
| Mll1 | myeloid/lymphoid or mixed-lineage leukemia 1 |
| Mll3 | myeloid/lymphoid or mixed-lineage leukemia 3 |
| Morf4l2 | predicted gene 5521; similar to mortality factor 4 like 2; mortality factor 4 like 2 |
| Mpdz | multiple PDZ domain protein |
| Mphosph8 | M-phase phosphoprotein 8 |
| Mras | muscle and microspikes RAS |
| Mrgprf | MAS-related GPR, member F |
| Msn | moesin |
| Mtap1a | microtubule-associated protein 1 A |
| Mtdh | metadherin |
| Mtmr6 | myotubularin related protein 6 |
| Mut | methylmalonyl-Coenzyme A mutase |
| Mxd4 | Max dimerization protein 4 |
| Myh10 | myosin, heavy polypeptide 10, non-muscle |
| Myl7 | myosin, light polypeptide 7, regulatory |
| Mylip | myosin regulatory light chain interacting protein |
| Myst4 | MYST histone acetyltransferase monocytic leukemia 4 |
| Naa25 | RIKEN cDNA C330023M02 gene |
| Naga | N-acetyl galactosaminidase, alpha |
| Nckap1 | NCK-associated protein 1 |
| Ncoa1 | similar to Nuclear receptor coactivator 1 (NCoA-1) (Steroid receptor coactivator 1) (SRC-1) (Nuclear receptor coactivator protein 1) (mNRC-1); nuclear receptor coactivator 1 |
| Ncoa4 | predicted gene 6768; nuclear receptor coactivator 4 |
| Ncor1 | nuclear receptor co-repressor 1 |
| Ndn | necdin |
| Ndst1 | N-deacetylase/N-sulfotransferase (heparan glucosaminyl) 1 |
| Ndufa4 | NADH dehydrogenase (ubiquinone) 1 alpha subcomplex, 4 |
| Nedd4 | neural precursor cell expressed, developmentally down-regulated 4 |
| Nf1 | neurofibromatosis 1 |
| Nfe2l1 | nuclear factor, erythroid derived 2, -like 1 |
| Nfia | nuclear factor I/A |
| Nfic | nuclear factor I/C |
| Nfix | nuclear factor I/X |
| Nfkb2 | nuclear factor of kappa light polypeptide gene enhancer in B-cells 2, p49/p100 |
| Nfkbia | nuclear factor of kappa light polypeptide gene enhancer in B-cells inhibitor, alpha |
| Nfkbiz | nuclear factor of kappa light polypeptide gene enhancer in B-cells inhibitor, zeta |
| Nfyc | nuclear transcription factor-Y gamma |
| Nid2 | nidogen 2 |
| Ninl | ninein-like |
| Nipal3 | NIPA-like domain containing 3; similar to NIPA-like domain containing 3 |
| Nipbl | Nipped-B homolog (Drosophila) |
| Nkain4 | Na+/K+ transporting ATPase interacting 4 |
| Nkd1 | naked cuticle 1 homolog (Drosophila); similar to naked cuticle 1 homolog |
| Nnmt | nicotinamide N-methyltransferase |
| Nod1 | nucleotide-binding oligomerization domain containing 1 |
| Npr1 | natriuretic peptide receptor 1 |
| Nr1d1 | nuclear receptor subfamily 1, group D, member 1 |
| Nr3c1 | nuclear receptor subfamily 3, group C, member 1 |
| Nr4a1 | nuclear receptor subfamily 4, group A, member 1 |
| Nrgn | neurogranin |
| Nucks1 | nuclear casein kinase and cyclin-dependent kinase substrate 1 |
| Oasl2 | 2'-5' oligoadenylate synthetase-like 2 |
| Oat | ornithine aminotransferase |
| Ogdh | oxoglutarate dehydrogenase (lipoamide) |
| Ogn | osteoglycin |
| Olfr1033 | olfactory receptor 1033 |

TABLE 7-continued

Exemplary mouse marker genes

| MOUSE GENE SYMBOL | Gene Name |
|---|---|
| Olfr613 | olfactory receptor 614; hypothetical protein LOC100044261; olfactory receptor 613 |
| Opa3 | optic atrophy 3 (human) |
| Orai3 | ORAI calcium release-activated calcium modulator 3 |
| Osr1 | odd-skipped related 1 (*Drosophila*) |
| Oxct1 | 3-oxoacid CoA transferase 1 |
| Oxnad1 | oxidoreductase NAD-binding domain containing 1 |
| Pard3b | par-3 partitioning defective 3 homolog B (*C. elegans*) |
| Parp14 | poly (ADP-ribose) polymerase family, member 14 |
| Parp4 | poly (ADP-ribose) polymerase family, member 4 |
| Parvb | parvin, beta; similar to parvin, beta |
| Pbx1 | pre B-cell leukemia transcription factor 1; region containing RIKEN cDNA 2310056B04gene; pre B-cell leukemia transcription factor 1 |
| Pcdh15 | protocadherin 15 |
| Pcdhgb5 | protocadherin gamma subfamily B, 5 |
| Pcm1 | pericentriolar material 1 |
| Pdap1 | PDGFA associated protein 1 |
| Pdcd6ip | programmed cell death 6 interacting protein |
| Pde4dip | phosphodiesterase 4D interacting protein (myomegalin) |
| Pdia3 | protein disulfide isomerase associated 3 |
| Pdia4 | protein disulfide isomerase associated 4 |
| Pdpn | podoplanin |
| Pef1 | penta-EF hand domain containing 1 |
| Peli1 | pellino 1 |
| Per1 | period homolog 1 (*Drosophila*) |
| Pf4 | platelet factor 4 |
| Pfn1 | profilin 1 |
| Pgcp | plasma glutamate carboxypeptidase |
| Pgrmc1 | progesterone receptor membrane component 1 |
| Phf21a | PHD finger protein 21A |
| Phf3 | PHD finger protein 3 |
| Phip | pleckstrin homology domain interacting protein |
| Pigt | phosphatidylinositol glycan anchor biosynthesis, class T; similar to GPI transamidase component PIG-T precursor (Phosphatidylinositol-glycan biosynthesis class T protein) (Neuronal development-associated protein 7) |
| Pik3c2a | phosphatidylinositol 3-kinase, C2 domain containing, alpha polypeptide |
| Pim1 | proviral integration site 1 |
| Pitpnm2 | phosphatidylinositol transfer protein, membrane-associated 2 |
| Pkhd1l1 | polycystic kidney and hepatic disease 1-like 1 |
| Pknox1 | Pbx/knotted 1 homeobox |
| Pla2g4a | phospholipase A2, group IVA (cytosolic, calcium-dependent) |
| Plat | plasminogen activator, tissue |
| Plce1 | phospholipase C, epsilon 1 |
| Plk1s1 | non-protein coding RNA 153 |
| Plk2 | polo-like kinase 2 (*Drosophila*) |
| Plod2 | procollagen lysine, 2-oxoglutarate 5-dioxygenase 2 |
| Plxdc1 | plexin domain containing 1 |
| Plxdc2 | plexin domain containing 2 |
| Plxna4 | plexin A4 |
| Pmp22 | peripheral myelin protein 22 |
| Pnrc1 | proline-rich nuclear receptor coactivator 1 |
| Podn | podocan |
| Ppap2a | phosphatidic acid phosphatase type 2A |
| Ppbp | pro-platelet basic protein |
| Ppfibp2 | protein tyrosine phosphatase, receptor-type, F interacting protein, binding protein 2 |
| Ppig | peptidyl-prolyl isomerase G (cyclophilin G) |
| Ppl | periplakin |
| Ppp1cb | protein phosphatase 1, catalytic subunit, beta isoform |
| Ppp1r12a | protein phosphatase 1, regulatory (inhibitor) subunit 12A |
| Ppp1r15a | protein phosphatase 1, regulatory (inhibitor) subunit 15A; myeloid differentiation primary response gene 116 |
| Ppp3ca | protein phosphatase 3, catalytic subunit, alpha isoform |
| Pppde1 | PPPDE peptidase domain containing 1 |
| Pqlc3 | PQ loop repeat containing |
| Prelp | proline arginine-rich end leucine-rich repeat |
| Prg4 | proteoglycan 4 (megakaryocyte stimulating factor, articular superficial zone protein) |
| Prkar2a | protein kinase, cAMP dependent regulatory, type II alpha |
| Prpf40a | PRP40 pre-mRNA processing factor 40 homolog A (yeast) |
| Prr13 | proline rich 13 |
| Prss23 | protease, serine, 23 |
| Psd | pleckstrin and Sec7 domain containing |
| Psip1 | PC4 and SFRS1 interacting protein 1 |

TABLE 7-continued

Exemplary mouse marker genes

| MOUSE GENE SYMBOL | Gene Name |
|---|---|
| Psmb2 | proteasome (prosome, macropain) subunit, beta type 2 |
| Psmd11 | predicted gene 14048; proteasome (prosome, macropain) 26S subunit, non-ATPase, 11 |
| Psmd7 | proteasome (prosome, macropain) 26S subunit, non-ATPase, 7 |
| Ptges3 | predicted gene 9769; prostaglandin E synthase 3 (cytosolic); similar to Sid3177p; predicted gene 11893 |
| Ptgis | prostaglandin I2 (prostacyclin) synthase |
| Ptgs1 | prostaglandin-endoperoxide synthase 1 |
| Ptma | predicted gene 12504; predicted gene 9800; predicted gene 4617; predicted gene 6625; predicted gene 7614; similar to prothymosin alpha; prothymosin alpha; predicted gene 9009 |
| Ptp4a2 | predicted gene 13422; protein tyrosine phosphatase 4a2 |
| Ptplad2 | protein tyrosine phosphatase-like A domain containing 2 |
| Ptprd | protein tyrosine phosphatase, receptor type, D |
| Ptprf | protein tyrosine phosphatase, receptor type, F |
| Ptrf | polymerase 1 and transcript release factor |
| Qrich1 | glutamine-rich 1 |
| Qser1 | glutamine and serine rich 1 |
| R74862 | expressed sequence R74862 |
| Rab11fip1 | RAB11 family interacting protein 1 (class I) |
| Rab1b | RAB1B, member RAS oncogene family |
| Rab5c | RAB5C, member RAS oncogene family |
| Rab6b | RAB6B, member RAS oncogene family |
| Rab7 | RAB7, member RAS oncogene family |
| Rabgap1l | RAB GTPase activating protein 1-like |
| Ralbp1 | ralA binding protein 1 |
| Raly | RIKEN cDNA C130057N11 gene; hnRNP-associated with lethal yellow |
| Rarres2 | retinoic acid receptor responder (tazarotene induced) 2 |
| Rb1cc1 | RB1-inducible coiled-coil 1 |
| Rbbp6 | retinoblastoma binding protein 6 |
| Rbbp8 | retinoblastoma binding protein 8 |
| Rbm25 | RNA binding motif protein 25 |
| Rbm27 | RNA binding motif protein 27 |
| Rbm3 | predicted gene 15453; RNA binding motif protein 3 |
| Rbpms | RNA binding protein gene with multiple splicing |
| Rdx | radixin |
| Rest | RE1-silencing transcription factor |
| Rgma | RGM domain family, member A |
| Rgs10 | regulator of G-protein signalling 10 |
| Rhob | ras homolog gene family, member B |
| Rhoj | ras homolog gene family, member J |
| Rhou | ras homolog gene family, member U |
| Rnase4 | ribonuclease, RNase A family 4 |
| Rnd3 | Rho family GTPase 3 |
| Rnf167 | ring finger protein 167 |
| Rnf20 | ring finger protein 20 |
| Rock1 | Rho-associated coiled-coil containing protein kinase 1 |
| Rock2 | Rho-associated coiled-coil containing protein kinase 2 |
| Rpp25 | ribonuclease P 25 subunit (human) |
| Rras2 | related RAS viral (r-ras) oncogene homolog 2 |
| Rspo1 | R-spondin homolog (*Xenopus laevis*) |
| Rtf1 | Rtf1, Paf1/RNA polymerase II complex component, homolog (*S. cerevisiae*) |
| Rtn1 | reticulon 1 |
| Ryk | receptor-like tyrosine kinase |
| Sarnp | predicted gene 6563; SAP domain containing ribonucleoprotein |
| Sat1 | similar to spermidine/spermine N1-acetyltransferase; predicted gene 5552; spermidine/spermine N1-acetyl transferase 1 |
| Sbsn | suprabasin |
| Scd1 | stearoyl-Coenzyme A desaturase 1 |
| Sdc4 | syndecan 4 |
| Sdpr | serum deprivation response |
| Sec62 | SEC62 homolog (*S. cerevisiae*) |
| Secisbp2 | SECIS binding protein 2 |
| Sema5a | sema domain, seven thrombospondin repeats (type 1 and type 1-like), transmembrane domain (TM) and short cytoplasmic domain, (semaphorin) 5A |
| Senp6 | similar to Sentrin-specific protease 6 (Sentrin/SUMO-specific protease SENP6) (SUMO-1-specific protease 1); SUMO/sentrin specific peptidase 6 |
| Sep15 | selenoprotein |
| Sept9 | septin 9 |
| Serinc5 | serine incorporator 5 |
| Serpinb6b | serine (or cysteine) peptidase inhibitor, clade B, member 6b |
| Serping1 | serine (or cysteine) peptidase inhibitor, clade G, member 1 |
| Serpinh1 | serine (or cysteine) peptidase inhibitor, clade H, member 1 |

TABLE 7-continued

Exemplary mouse marker genes

| MOUSE GENE SYMBOL | Gene Name |
|---|---|
| Sesn1 | sestrin 1 |
| Setd2 | SET domain containing 2 |
| Sf3b1 | splicing factor 3b, subunit 1 |
| Sf3b4 | predicted gene 7935; splicing factor 3b, subunit 4 |
| Sfrs18 | splicing factor, arginine/serine-rich 18 |
| Shc1 | predicted gene 5500; src homology 2 domain-containing transforming protein C1 |
| Shfm1 | split hand/foot malformation (ectrodactyly) type 1 |
| Siae | sialic acid acetylesterase |
| Siah1a | seven in absentia 1A |
| Sirt2 | sirtuin 2 (silent mating type information regulation 2, homolog) 2 (*S. cerevisiae*) |
| Slc10a3 | solute carrier family 10 (sodium/bile acid cotransporter family), member 3 |
| Slc16a1 | solute carrier family 16 (monocarboxylic acid transporters), member 1 |
| Slc1a5 | solute carrier family 1 (neutral amino acid transporter), member 5 |
| Slc26a3 | solute carrier family 26, member 3 |
| Slc27a3 | solute carrier family 27 (fatty acid transporter), member 3 |
| Slc38a1 | solute carrier family 38, member 1 |
| Slc39a8 | solute carrier family 39 (metal ion transporter), member 8 |
| Slc43a3 | solute carrier family 43, member 3 |
| Slc4a4 | solute carrier family 4 (anion exchanger), member 4 |
| Slc6a4 | solute carrier family 6 (neurotransmitter transporter, serotonin), member 4 |
| Slc6a6 | solute carrier family 6 (neurotransmitter transporter, taurine), member 6 |
| Slc8a1 | solute carrier family 8 (sodium/calcium exchanger), member 1 |
| Slc9a3r1 | solute carrier family 9 (sodium/hydrogen exchanger), member 3 regulator 1 |
| Slpi | secretory leukocyte peptidase inhibitor |
| Sltm | SAFB-like, transcription modulator |
| Slu7 | SLU7 splicing factor homolog (*S. cerevisiae*) |
| Slurp1 | secreted Ly6/Plaur domain containing 1 |
| Smad4 | similar to MAD homolog 4 (*Drosophila*); MAD homolog 4 (*Drosophila*) |
| Smarca2 | SWI/SNF related, matrix associated, actin dependent regulator of chromatin, subfamily a, member 2 |
| Smarca5 | predicted gene 13034; SWI/SNF related, matrix associated, actin dependent regulator of chromatin, subfamily a, member 5 |
| Smc2 | structural maintenance of chromosomes 2 |
| Smc3 | predicted gene 8892; structural maintenace of chromosomes 3 |
| Smc4 | structural maintenance of chromosomes 4 |
| Smc6 | structural maintenance of chromosomes 6 |
| Smchd1 | SMC hinge domain containing 1 |
| Smpd3 | sphingomyelin phosphodiesterase 3, neutral |
| Snrnp70 | small nuclear ribonucleoprotein 70 (U1) |
| Sntb2 | similar to beta-2-syntrophin; syntrophin, basic 2 |
| Soat1 | sterol O-acyltransferase 1 |
| Socs3 | suppressor of cytokine signaling 3 |
| Sod3 | superoxide dismutase 3, extracellular |
| Sorbs1 | sorbin and SH3 domain containing 1 |
| Sorbs3 | sorbin and SH3 domain containing 3 |
| Sox6 | SRY-box containing gene 6 |
| Sp100 | nuclear antigen Sp100 |
| Spag9 | sperm associated antigen 9 |
| Sparc | secreted acidic cysteine rich glycoprotein; similar to Secreted acidic cysteine rich glycoprotein |
| Spen | SPEN homolog, transcriptional regulator (*Drosophila*) |
| Spint2 | serine protease inhibitor, Kunitz type 2 |
| Spnb2 | spectrin beta 2 |
| Spock2 | sparc/osteonectin, cwcv and kazal-like domains proteoglycan 2 |
| Spon2 | spondin 2, extracellular matrix protein |
| Spop | speckle-type POZ protein |
| Src | Rous sarcoma oncogene |
| Srrm1 | serine/arginine repetitive matrix 1 |
| Ssh2 | slingshot homolog 2 (*Drosophila*) |
| Ssr3 | signal sequence receptor, gamma |
| St3gal1 | ST3 beta-galactoside alpha-2,3-sialyltransferase 1 |
| Stag1 | stromal antigen 1 |
| Star | steroidogenic acute regulatory protein |
| Stard5 | StAR-related lipid transfer (START) domain containing 5 |
| Stat3 | similar to Stat3B; signal transducer and activator of transcription 3 |
| Stim1 | similar to Stromal interaction molecule 1; stromal interaction molecule 1 |
| Stk10 | serine/threonine kinase 10 |
| Stk40 | serine/threonine kinase 40 |
| Stmn2 | stathmin-like 2 |
| Stra6 | stimulated by retinoic acid gene 6 |
| Strn3 | striatin, calmodulin binding protein 3 |
| Sulf1 | sulfatase 1 |

TABLE 7-continued

Exemplary mouse marker genes

| MOUSE GENE SYMBOL | Gene Name |
|---|---|
| Sulf2 | sulfatase 2 |
| Supt16h | suppressor of Ty 16 homolog (*S. cerevisiae*) |
| Sv2a | synaptic vesicle glycoprotein 2 a |
| Syne1 | synaptic nuclear envelope 1 |
| Syne2 | synaptic nuclear envelope 2 |
| Syt11 | synaptotagmin XI; similar to synaptotagmin XI |
| Sytl1 | synaptotagmin-like 1; similar to synaptotagmin-like 1 |
| Taf3 | TAF3 RNA polymerase II, TATA box binding protein (TBP)-associated factor |
| Taf7 | TAF7 RNA polymerase II, TATA box binding protein (TBP)-associated factor |
| Tapbp | TAP binding protein |
| Tbc1d15 | TBC1 domain family, member 15 |
| Tbcel | tubulin folding cofactor E-like |
| Tbl1x | transducin (beta)-like 1 X-linked |
| Tbx18 | T-box18 |
| Tceal8 | transcription elongation factor A (SII)-like 8; similar to transcription elongation factor A (SII)-like 8 |
| Tcf7l1 | transcription factor 3 |
| Tfdp2 | transcription factor Dp 2 |
| Tgfb1i1 | transforming growth factor beta 1 induced transcript 1 |
| Tgfb2 | transforming growth factor, beta 2 |
| Tgfbr2 | transforming growth factor, beta receptor II |
| Tgm2 | transglutaminase 2, C polypeptide |
| Thbd | thrombomodulin |
| Thbs1 | thrombospondin 1; similar to thrombospondin 1 |
| Thoc2 | THO complex 2; cDNA sequence BC005561 |
| Thrap3 | thyroid hormone receptor associated protein 3; predicted gene 5898 |
| Thsd4 | thrombospondin, type I, domain containing 4 |
| Timp2 | tissue inhibitor of metalloproteinase 2 |
| Tirap | toll-interleukin 1 receptor (TIR) domain-containing adaptor protein |
| Tlr2 | toll-like receptor 2 |
| Tm4sf1 | transmembrane 4 superfamily member 1 |
| Tm4sf5 | transmembrane 4 superfamily member 5 |
| Tmcc3 | transmembrane and coiled coil domains 3 |
| Tmco1 | transmembrane and coiled-coil domains 1 |
| Tmco7 | transmembrane and coiled-coil domains 7 |
| Tmed2 | transmembrane emp24 domain trafficking protein 2; predicted gene 10698; predicted gene 7318 |
| Tmem119 | transmembrane protein 119 |
| Tmem140 | transmembrane protein 140 |
| Tmem151a | transmembrane protein 151A |
| Tmem221 | transmembrane protein 221 |
| Tmem50a | transmembrane protein 50A |
| Tmem98 | transmembrane protein 98 |
| Tmod3 | tropomodulin 3 |
| Tmpo | thymopoietin |
| Tmsb4x | thymosin, beta 4, X chromosome; similar to thymosin beta-4 |
| Tnxb | tenascin XB |
| Tob2 | transducer of ERBB2, 2 |
| Topors | topoisomerase 1 binding, arginine/serine-rich |
| Tpm3 | predicted gene 7848; predicted gene 7839; predicted gene 4157; similar to tropomyosin 3, gamma; tropomyosin 3, gamma; predicted gene 4903 |
| Tppp3 | tubulin polymerization-promoting protein family member 3 |
| Tpt1 | predicted gene 1974; tumor protein, translationally-controlled 1 pseudogene; tumor protein, translationally-controlled 1; predicted gene 14456 |
| Trafd1 | TRAF type zinc finger domain containing 1 |
| Trib1 | tribbles homolog 1 (*Drosophila*) |
| Trim8 | tripartite motif protein 8 |
| Trpm7 | transient receptor potential cation channel, subfamily M, member 7 |
| Tsc22d3 | TSC22 domain family, member 3 |
| Tshz1 | teashirt zinc finger family member 1 |
| Tsix | X (inactive)-specific transcript, antisense |
| Tspan31 | tetraspanin 31 |
| Tspan5 | tetraspanin 5 |
| Ttc28 | tetratricopeptide repeat domain 28 |
| Ttc38 | tetratricopeptide repeat domain 38 |
| Tuba1a | predicted gene 7172; similar to tubulin, alpha 1; tubulin, alpha 1A |
| Tubb2a | tubulin, beta 2A |
| Twsg1 | twisted gastrulation homolog 1 (*Drosophila*) |
| Txndc5 | thioredoxin domain containing 5 |
| Txnrd1 | thioredoxin reductase 1 |
| Uap1 | UDP-N-acetylglucosamine pyrophosphorylase 1 |
| Uba7 | ubiquitin-activating enzyme E1-like; RIKEN cDNA D330022A01 gene |
| Ube2d1 | ubiquitin-conjugating enzyme E2D 1, UBC4/5 homolog (yeast) |

TABLE 7-continued

Exemplary mouse marker genes

| MOUSE GENE SYMBOL | Gene Name |
|---|---|
| Ube2l6 | ubiquitin-conjugating enzyme E2L 6 |
| Ube2n | ubiquitin-conjugating enzyme E2N; similar to ubiquitin-conjugating enzyme E2 UbcH-ben; similar to ubiquitin-conjugating enzyme E2N; predicted gene 5943 |
| Ube2v1 | ubiquitin-conjugating enzyme E2 variant 1; predicted gene 7181; predicted gene 12502; similar to ubiquitin-conjugating enzyme E2 variant 1 |
| Ubqln2 | ubiquilin 2 |
| Ubxn2a | UBX domain protein 2A; predicted gene 6245 |
| Ubxn4 | UBX domain protein 4 |
| Ugdh | UDP-glucose dehydrogenase |
| Upk1b | uroplakin 1B |
| Upk3b | uroplakin 3B |
| Usp16 | ubiquitin specific peptidase 16 |
| Usp2 | ubiquitin specific peptidase 2 |
| Usp25 | ubiquitin specific peptidase 25 |
| Usp54 | ubiquitin specific peptidase 54 |
| Usp8 | ubiquitin specific peptidase 8 |
| Utp20 | UTP20, small subunit (SSU) processome component, homolog (yeast) |
| Vat1 | vesicle amine transport protein 1 homolog (*T californica*) |
| Vim | vimentin |
| Vps13a | vacuolar protein sorting 13A (yeast) |
| Vwa5a | von Willebrand factor A domain containing 5A |
| Wac | similar to WW domain-containing adapter protein with coiled-coil; WW domain containing adaptor with coiled-coil |
| Wasf2 | WAS protein family, member 2 |
| Wdr26 | WD repeat domain 26; similar to myocardial ischemic preconditioning upregulated protein 2 |
| Wdr92 | WD repeat domain 92 |
| Wfdc1 | WAP four-disulfide core domain 1 |
| Wls | G protein-coupled receptor 177 |
| Wnt4 | wingless-related MMTV integration site 4 |
| Wrnip1 | Werner helicase interacting protein 1 |
| Wt1 | similar to Wilms tumor homolog; Wilms tumor 1 homolog |
| Wwc2 | WW, C2 and coiled-coil domain containing 2 |
| Xdh | xanthine dehydrogenase |
| Xist | inactive X specific transcripts |
| Yipf5 | Yip1 domain family, member 5; predicted gene 5738 |
| Ywhaz | tyrosine 3-monooxygenase/tryptophan 5-monooxygenase activation protein, zeta polypeptide; predicted gene 4202 |
| Zbed6 | similar to Zinc finger BED domain containing protein 4 |
| Zbtb16 | zinc finger and BTB domain containing 16 |
| Zbtb20 | zinc finger and BTB domain containing 20 |
| Zbtb4 | zinc finger and BTB domain containing 4 |
| Zbtb7c | zinc finger and BTB domain containing 7C |
| Zc3h13 | zinc finger CCCH type containing 13 |
| Zc3h18 | predicted gene 5939; zinc finger CCCH-type containing 18 |
| Zcchc11 | zinc finger, CCHC domain containing 11 |
| Zcchc3 | zinc finger, CCHC domain containing 3 |
| Zfand6 | zinc finger, AN1-type domain 6 |
| Zfhx4 | zinc finger homeodomain 4 |
| Zfp148 | zinc finger protein 148 |
| Zfp277 | zinc finger protein 277 |
| Zfp281 | zinc finger protein 281 |
| Zfp318 | zinc finger protein 318 |
| Zfp353 | zinc finger protein 353 |
| Zfp36 | zinc finger protein 36 |
| Zfp385a | zinc finger protein 385A |
| Zfp488 | zinc finger protein 488 |
| Zfp672 | zinc finger protein 672 |
| Zfp704 | zinc finger protein 704 |
| Zmat1 | zinc finger, matrin type 1 |
| Zrsr1 | zinc finger (CCCH type), RNA binding motif and serine/arginine rich 1 |
| Zzef1 | zinc finger, ZZ-type with EF hand domain 1 |
| 1110002B05Rik | RIKEN cDNA 1110002B05 gene |
| 1110003E01Rik | RIKEN cDNA 1110003E01 gene |
| 1110004F10Rik | predicted gene 9169; RIKEN cDNA 1110004F10 gene; similar to small acidic protein |
| 1500003O03Rik | RIKEN cDNA 1500003O03 gene; similar to EF-hand Ca2+ binding protein p22 |
| 1600029D21Rik | RIKEN cDNA 1600029D21 gene |
| 1810014B01Rik | RIKEN cDNA 1810014B01 gene |
| 1810041L15Rik | RIKEN cDNA 1810041L15 gene |
| 1810074P20Rik | RIKEN cDNA 1810074P20 gene |
| 2010107G12Rik | RIKEN cDNA 2010107G12 gene |

TABLE 7-continued

Exemplary mouse marker genes

| MOUSE GENE SYMBOL | Gene Name |
|---|---|
| 2210403K04Rik | hypothetical protein LOC100042498 |
| 2310030G06Rik | RIKEN cDNA 2310030G06 gene |
| 2510002D24Rik | RIKEN cDNA 2510002D24 gene |
| 2610034B18Rik | RIKEN cDNA 2610034B18 gene |
| 2610101N10Rik | RIKEN cDNA 2610101N10 gene |
| 2810474O19Rik | RIKEN cDNA 2810474O19 gene |
| 2900002K06Rik | RIKEN cDNA 2900002K06 gene |
| 3110062M04Rik | RIKEN cDNA 3110062M04 gene |
| 4930402H24Rik | RIKEN cDNA 4930402H24 gene |
| 4930523C07Rik | RIKEN cDNA 4930523C07 gene |
| 5430435G22Rik | RIKEN cDNA 5430435G22 gene |
| 6330406I15Rik | RIKEN cDNA 6330406I15 gene |
| A130040M12Rik | RIKEN cDNA A130040M12 gene |
| AI848100 | expressed sequence AI848100 |
| Gm16897 | |
| kg:uc009lxf.1 | |
| Prrc2c | |
| kg:uc007won.1 | |
| kg:uc009ogv.1 | |
| kg:uc009iln.1 | |
| kg:uc007qca.1 | |
| Atxn7l3b | |
| kg:uc008ewj.2 | |
| kg:uc008wkn.1 | |
| kg:uc007bgn.1 | |
| Ces2g | |
| kg:uc009cvm.1 | |
| kg:uc008ehr.1 | |
| Tmem234 | |
| kg:uc012hdk.1 | |
| kg:uc008ajk.1 | |
| eg:245190:chr7:m | |
| kg:uc007qse.1 | |
| kg:uc007bvx.1 | |
| Mob3c | |
| kg:uc008dzh.1 | |
| kg:uc009okn.1 | |
| kg:uc007zts.1 | |
| kg:uc008jup.1 | |
| kg:uc008tkz.1 | |
| kg:uc007zwh.1 | |
| kg:uc008znh.1 | |
| Mau2 | |
| kg:uc009mng.1 | |
| kg:uc007ded.1 | |
| kg:uc007ctp.1 | |
| kg:uc007zak.1 | |
| eg:497210:chr14:m | |
| kg:uc007vsr.1 | |
| Mir3064 | |
| kg:uc009ize.1 | |
| Kansl1 | |
| eg:320169:chr9:p | |
| kg:uc009vev.1 | |
| kg:uc009acs.1 | |
| kg:uc009tuw.1 | |
| kg:uc007pff.1 | |
| kg:uc007vnc.1 | |
| kg:uc009igb.1 | |
| kg:uc008oki.1 | |
| kg:uc008tky.1 | |

TABLE 8

Exemplary human marker genes

| HUMAN GENE SYMBOL | Gene Name |
|---|---|
| ABI3BP | ABI family, member 3 (NESH) binding protein |
| ABLIM3 | actin binding LIM protein family, member 3 |
| ACAD9 | acyl-Coenzyme A dehydrogenase family, member 9 |
| ACBD3 | acyl-Coenzyme A binding domain containing 3 |
| ACIN1 | apoptotic chromatin condensation inducer 1 |
| ACTB | actin, beta |
| ACTG1 | actin, gamma 1 |
| ADAMTS5 | ADAM metallopeptidase with thrombospondin type 1 motif, 5 |
| ADAMTSL1 | ADAMTS-like 1 |
| ADD3 | adducin 3 (gamma) |
| AEBP1 | AE binding protein 1 |
| AGAP1 | ArfGAP with GTPase domain, ankyrin repeat and PH domain 1 |
| AKAP13 | A kinase (PRKA) anchor protein 13 |
| AKAP2 | A kinase (PRKA) anchor protein 2; paralemmin 2; PALM2-AKAP2 readthrough transcript |
| AKT2 | v-akt murine thymoma viral oncogene homolog 2 |
| ALDH1A1 | aldehyde dehydrogenase 1 family, member A1 |
| ALDH1A2 | aldehyde dehydrogenase 1 family, member A2 |
| ALOX12 | arachidonate 12-lipoxygenase |
| AMFR | autocrine motility factor receptor |
| AMHR2 | anti-Mullerian hormone receptor, type II |
| ANG | angiogenin, ribonuclease, RNase A family, 5 |
| ANKRD11 | ankyrin repeat domain 11; hypothetical protein LOC100128265 |
| ANKRD12 | ankyrin repeat domain 12 |
| ANKRD17 | ankyrin repeat domain 17 |
| ANO6 | anoctamin 6 |
| ANP32A | hepatopoietin PCn127; acidic (leucine-rich) nuclear phosphoprotein 32 family, member A |
| ANXA7 | annexin A7 |
| AP1S3 | adaptor-related protein complex 1, sigma 3 subunit |
| AP3S1 | adaptor-related protein complex 3, sigma 1 subunit |
| AP4E1 | adaptor-related protein complex 4, epsilon 1 subunit |
| APLP1 | amyloid beta (A4) precursor-like protein 1 |
| APP | amyloid beta (A4) precursor protein |
| AQP1 | aquaporin 1 (Colton blood group) |
| ARAP2 | ArfGAP with RhoGAP domain, ankyrin repeat and PH domain 2 |
| ARF3 | ADP-ribosylation factor 3 |
| ARF5 | ADP-ribosylation factor 5 |
| ARHGAP28 | Rho GTPase activating protein 28 |
| ARHGAP29 | Rho GTPase activating protein 29 |
| ARHGAP5 | Rho GTPase activating protein 5 |
| ARHGEF12 | Rho guanine nucleotide exchange factor (GEF) 12 |
| ARID1A | AT rich interactive domain 1A (SWI-like) |
| ARID4A | AT rich interactive domain 4A (RBP1-like) |
| ARID4B | AT rich interactive domain 4B (RBP1-like) |
| ARID5B | AT rich interactive domain 5B (MRF1-like) |
| ARL3 | ADP-ribosylation factor-like 3 |
| ARL4D | ADP-ribosylation factor-like 4D |
| ARL6IP5 | ADP-ribosylation-like factor 6 interacting protein 5 |
| ARMCX3 | armadillo repeat containing, X-linked 3 |
| ARPC2 | actin related protein 2/3 complex, subunit 2, 34 kDa |
| ARSA | arylsulfatase A |
| ARSB | arylsulfatase B |
| ASCC3 | activating signal cointegrator 1 complex subunit 3 |
| ATF3 | activating transcription factor 3 |
| ATG3 | ATG3 autophagy related 3 homolog (*S. cerevisiae*) |
| ATP1A1 | ATPase, Na+/K+ transporting, alpha 1 polypeptide |
| ATP1B1 | ATPase, Na+/K+ transporting, beta 1 polypeptide |
| ATP2B1 | ATPase, Ca++ transporting, plasma membrane 1 |
| ATP6V1A | ATPase, H+ transporting, lysosomal 70 kDa, V1 subunit A |
| ATXN2 | ataxin 2 |
| B2M | beta-2-microglobulin |
| BAZ2A | bromodomain adjacent to zinc finger domain, 2A |
| BBS4 | Bardet-Biedl syndrome 4 |
| BBX | bobby sox homolog (*Drosophila*) |
| BCAM | basal cell adhesion molecule (Lutheran blood group) |
| BCL10 | B-cell CLL/lymphoma 10; hypothetical LOC646626 |
| BDP1 | B double prime 1, subunit of RNA polymerase III transcription initiation factor IIIB |
| BICC1 | bicaudal C homolog 1 (*Drosophila*) |
| BICD1 | bicaudal D homolog 1 (*Drosophila*) |
| BIRC6 | baculoviral IAP repeat-containing 6 |
| BLVRB | biliverdin reductase B (flavin reductase (NADPH)) |
| BNC1 | basonuclin 1 |

TABLE 8-continued

Exemplary human marker genes

| HUMAN GENE SYMBOL | Gene Name |
|---|---|
| BNC2 | basonuclin 2 |
| BOD1L | biorientation of chromosomes in cell division 1-like |
| BPTF | bromodomain PHD finger transcription factor |
| BRAF | v-raf murine sarcoma viral oncogene homolog B1 |
| BRD2 | bromodomain containing 2 |
| BRD4 | bromodomain containing 4 |
| BRP44L | brain protein 44-like |
| BST2 | NPC-A-7; bone marrow stromal cell antigen 2 |
| BTBD2 | BTB (POZ) domain containing 2 |
| BTBD7 | BTB (POZ) domain containing 7 |
| BTF3 | basic transcription factor 3; basic transcription factor 3, like 1 pseudogene |
| BTG2 | BTG family, member 2 |
| BZW1 | basic leucine zipper and W2 domains 1 pseudogene 1; basic leucine zipper and W2 domains 1 like 1; basic leucine zipper and W2 domains 1 |
| C1D | C1D nuclear receptor co-repressor; similar to nuclear DNA-binding protein; similar to hCG1791993 |
| C1RL | complement component 1, r subcomponent-like |
| C1S | complement component 1, s subcomponent |
| C2 | complement component 2 |
| C3 | similar to Complement C3 precursor; complement component 3; hypothetical protein LOC100133511 |
| C4A | complement component 4A (Rodgers blood group) |
| C4B | complement component 4B (Chido blood group) |
| CALM1 | calmodulin 3 (phosphorylase kinase, delta); calmodulin 2 (phosphorylase kinase, delta); calmodulin 1 (phosphorylase kinase, delta) |
| CALM2 | calmodulin 3 (phosphorylase kinase, delta); calmodulin 2 (phosphorylase kinase, delta); calmodulin 1 (phosphorylase kinase, delta) |
| CAP1 | CAP, adenylate cyclase-associated protein 1 (yeast) |
| CAST | calpastatin |
| CAV1 | caveolin 1, caveolae protein, 22 kDa |
| CCDC109B | coiled-coil domain containing 109B |
| CCDC34 | coiled-coil domain containing 34 |
| CCDC80 | coiled-coil domain containing 80 |
| CCDC88A | coiled-coil domain containing 88A |
| CCDC90A | coiled-coil domain containing 90A |
| CCNL1 | cyclin L1 |
| CD109 | CD109 molecule |
| CD200 | CD200 molecule |
| CD248 | CD248 molecule, endosialin |
| CD34 | CD34 molecule |
| CD55 | CD55 molecule, decay accelerating factor for complement (Cromer blood group) |
| CD81 | CD81 molecule |
| CD82 | CD82 molecule |
| CD9 | CD9 molecule |
| CDC42EP3 | CDC42 effector protein (Rho GTPase binding) 3 |
| CDH11 | cadherin 11, type 2, OB-cadherin (osteoblast) |
| CDH3 | cadherin 3, type 1, P-cadherin (placental) |
| CDK13 | cell division cycle 2-like 5 (cholinesterase-related cell division controller) |
| CDON | Cdon homolog (mouse) |
| CELF2 | CUG triplet repeat, RNA binding protein 2 |
| CEP164 | centrosomal protein 164 kDa |
| CEP57 | centrosomal protein 57 kDa |
| CFH | complement factor H |
| CFL1 | cofilin 1 (non-muscle) |
| CFL2 | cofilin 2 (muscle) |
| CHD1 | chromodomain helicase DNA binding protein 1 |
| CHD2 | chromodomain helicase DNA binding protein 2 |
| CHI3L1 | chitinase 3-like 1 (cartilage glycoprotein-39) |
| CHST4 | carbohydrate (N-acetylglucosamine 6-O) sulfotransferase 4 |
| CISH | cytokine inducible SH2-containing protein |
| CLCN3 | chloride channel 3 |
| CLDN10 | claudin 10 |
| CLDN15 | claudin 15 |
| CLDN25 | claudin-like |
| CLEC1B | C-type lectin domain family 1, member B |
| CLEC3B | C-type lectin domain family 3, member B |
| CLIC4 | chloride intracellular channel 4 |
| CLIP1 | CAP-GLY domain containing linker protein 1 |

TABLE 8-continued

Exemplary human marker genes

| HUMAN GENE SYMBOL | Gene Name |
|---|---|
| CLIP3 | CAP-GLY domain containing linker protein 3 |
| CLN8 | ceroid-lipofuscinosis, neuronal 8 (epilepsy, progressive with mental retardation) |
| CMAH | cytidine monophosphate-N-acetylneuraminic acid hydroxylase (CMP-N-acetylneuraminate monooxygenase) pseudogene |
| CMTM3 | CKLF-like MARVEL transmembrane domain containing 3 |
| CMTM7 | CKLF-like MARVEL transmembrane domain containing 7 |
| CNOT6L | CCR4-NOT transcription complex, subunit 6-like |
| COBL | cordon-bleu homolog (mouse) |
| COBLL1 | COBL-like 1 |
| COL14A1 | collagen, type XIV, alpha 1 |
| COL1A2 | collagen, type I, alpha 2 |
| COL3A1 | collagen, type III, alpha 1 |
| COL4A6 | collagen, type IV, alpha 6 |
| COLEC12 | collectin sub-family member 12 |
| COQ10B | coenzyme Q10 homolog B (*S. cerevisiae*) |
| CREB3L1 | cAMP responsive element binding protein 3-like 1 |
| CREB5 | cAMP responsive element binding protein 5 |
| CREBBP | CREB binding protein |
| CREG1 | cellular repressor of E1A-stimulated genes 1 |
| CRIM1 | cysteine rich transmembrane BMP regulator 1 (chordin-like) |
| CRLS1 | cardiolipin synthase 1 |
| CRYAB | crystallin, alpha B |
| CRYL1 | crystallin, lambda 1 |
| CRYM | crystallin, mu |
| CSDA | cold shock domain protein A; cold shock domain protein A pseudogene 1 |
| CSF1 | colony stimulating factor 1 (macrophage) |
| CSNK1A1 | casein kinase 1, alpha 1 |
| CSRNP1 | cysteine-serine-rich nuclear protein 1 |
| CSRP1 | cysteine and glycine-rich protein 1 |
| CUEDC1 | CUE domain containing 1 |
| CYBRD1 | cytochrome b reductase 1 |
| CYP2S1 | cytochrome P450, family 2, subfamily S, polypeptide 1 |
| CYR61 | cysteine-rich, angiogenic inducer, 61 |
| DAB2 | disabled homolog 2, mitogen-responsive phosphoprotein (*Drosophila*) |
| DAG1 | dystroglycan 1 (dystrophin-associated glycoprotein 1) |
| DAGLB | diacylglycerol lipase, beta |
| DAPK1 | death-associated protein kinase 1 |
| DCN | decorin |
| DDR1 | discoidin domain receptor tyrosine kinase 1 |
| DDR2 | discoidin domain receptor tyrosine kinase 2 |
| DDX3X | DEAD (Asp-Glu-Ala-Asp) box polypeptide 3, X-linked |
| DDX5 | DEAD (Asp-Glu-Ala-Asp) box polypeptide 5 |
| DENND5A | DENN/MADD domain containing 5A |
| DHX15 | DEAH (Asp-Glu-Ala-His) box polypeptide 15 |
| DLGAP4 | discs, large (*Drosophila*) homolog-associated protein 4 |
| DMKN | dermokine |
| DNAJA2 | DnaJ (Hsp40) homolog, subfamily A, member 2 |
| DNAJB9 | DnaJ (Hsp40) homolog, subfamily B, member 9 |
| DNAJC1 | DnaJ (Hsp40) homolog, subfamily C, member 1 |
| DNMT1 | DNA (cytosine-5-)-methyltransferase 1 |
| DPP4 | dipeptidyl-peptidase 4 |
| DPYSL2 | dihydropyrimidinase-like 2 |
| DPYSL3 | dihydropyrimidinase-like 3 |
| DST | dystonin |
| DTX2 | deltex homolog 2 (*Drosophila*) |
| DUSP1 | dual specificity phosphatase 1 |
| DUSP14 | dual specificity phosphatase 14 |
| DUSP3 | dual specificity phosphatase 3 |
| DYNC1I2 | similar to dynein cytoplasmic 1 intermediate chain 2; dynein, cytoplasmic 1, intermediate chain 2 |
| ECD | ecdysoneless homolog (*Drosophila*) |
| EEA1 | early endosome antigen 1 |
| EEF1A1 | eukaryotic translation elongation factor 1 alpha-like 7; eukaryotic translation elongation factor 1 alpha-like 3; similar to eukaryotic translation elongation factor 1 alpha 1; eukaryotic translation elongation factor 1 alpha 1 |
| EFEMP1 | EGF-containing fibulin-like extracellular matrix protein 1 |
| EFHD2 | EF-hand domain family, member D2 |
| EFNA5 | ephrin-A5 |
| EGR1 | early growth response 1 |
| EHD2 | EH-domain containing 2 |
| EIF3A | eukaryotic translation initiation factor 3, subunit A |

TABLE 8-continued

Exemplary human marker genes

| HUMAN GENE SYMBOL | Gene Name |
|---|---|
| ELF1 | E74-like factor 1 (ets domain transcription factor) |
| ELOVL6 | ELOVL family member 6, elongation of long chain fatty acids (FEN1/Elo2, SUR4/Elo3-like, yeast) |
| EMP2 | epithelial membrane protein 2 |
| ENPP2 | ectonucleotide pyrophosphatase/phosphodiesterase 2 |
| ENPP4 | ectonucleotide pyrophosphatase/phosphodiesterase 4 (putative function) |
| ESAM | endothelial cell adhesion molecule |
| ESF1 | similar to ABT1-associated protein; ESF1, nucleolar pre-rRNA processing protein, homolog (S. cerevisiae) |
| ESPN | espin |
| ESYT3 | family with sequence similarity 62 (C2 domain containing), member C |
| ETFA | electron-transfer-flavoprotein, alpha polypeptide |
| EVPL | envoplakin |
| EXOC4 | exocyst complex component 4 |
| F11R | F11 receptor |
| FAIM2 | Fas apoptotic inhibitory molecule 2 |
| FAM117A | family with sequence similarity 117, member A |
| FAM134B | family with sequence similarity 134, member B |
| FAM53B | family with sequence similarity 53, member B |
| FAM63B | family with sequence similarity 63, member B |
| FAM76A | family with sequence similarity 76, member A |
| FAM84B | family with sequence similarity 84, member B |
| FAS | Fas (TNF receptor superfamily, member 6) |
| FBLN1 | fibulin 1 |
| FERMT2 | fermitin family homolog 2 (Drosophila) |
| FGF1 | fibroblast growth factor 1 (acidic) |
| FHL1 | four and a half LIM domains 1 |
| FILIP1L | filamin A interacting protein 1-like |
| FKBP5 | FK506 binding protein 5 |
| FLII | flightless I homolog (Drosophila) |
| FLNC | filamin C, gamma (actin binding protein 280) |
| FLRT2 | fibronectin leucine rich transmembrane protein 2 |
| FMO2 | flavin containing monooxygenase 2 (non-functional) |
| FMOD | fibromodulin |
| FNDC1 | fibronectin type III domain containing 1 |
| FOS | v-fos FBJ murine osteosarcoma viral oncogene homolog |
| FOXN3 | forkhead box N3 |
| FRMD4B | FERM domain containing 4B |
| FTH1 | ferritin, heavy polypeptide 1; ferritin, heavy polypeptide-like 16; similar to ferritin, heavy polypeptide 1; ferritin, heavy polypeptide-like 3 pseudogene |
| FXYD1 | FXYD domain containing ion transport regulator 1 |
| G3BP1 | GTPase activating protein (SH3 domain) binding protein 1 |
| GABARAPL1 | GABA(A) receptors associated protein like 3 (pseudogene); GABA(A) receptor-associated protein like 1 |
| GADD45B | growth arrest and DNA-damage-inducible, beta |
| GANAB | glucosidase, alpha; neutral AB |
| GAS1 | growth arrest-specific 1 |
| GAS6 | similar to growth arrest-specific 6; growth arrest-specific 6 |
| GATA6 | GATA binding protein 6 |
| GBP2 | guanylate binding protein 2, interferon-inducible |
| GBP3 | guanylate binding protein 3 |
| GBP7 | guanylate binding protein 7 |
| GCSH | similar to Glycine cleavage system H protein, mitochondrial precursor; glycine cleavage system protein H (aminomethyl carrier); similar to Glycine cleavage system H protein, mitochondrial |
| GDA | guanine deaminase |
| GEM | GTP binding protein overexpressed in skeletal muscle |
| GFM2 | G elongation factor, mitochondrial 2 |
| GFPT2 | glutamine-fructose-6-phosphate transaminase 2 |
| GJA1 | gap junction protein, alpha 1, 43 kDa |
| GJB5 | gap junction protein, beta 5, 31.1 kDa |
| GNB2 | guanine nucleotide binding protein (G protein), beta polypeptide 2 |
| GOLGA4 | golgi autoantigen, golgin subfamily a, 4 |
| GOLGB1 | golgin B1, golgi integral membrane protein |
| GPC3 | glypican 3 |
| GPC4 | glypican 4 |
| GPCPD1 | hypothetical protein KIAA1434 |
| GPM6A | glycoprotein M6A |
| GPR116 | G protein-coupled receptor 116 |
| GPR133 | G protein-coupled receptor 133 |
| GPR64 | G protein-coupled receptor 64 |
| GPRC5B | G protein-coupled receptor, family C, group 5, member B |

TABLE 8-continued

Exemplary human marker genes

| HUMAN GENE SYMBOL | Gene Name |
|---|---|
| GPX8 | glutathione peroxidase 8 (putative) |
| GSR | glutathione reductase |
| GSTA3 | glutathione S-transferase alpha 3 |
| GSTM1 | glutathione S-transferase mu 1 |
| GSTM4 | glutathione S-transferase mu 4 |
| GUCY1A3 | guanylate cyclase 1, soluble, alpha 3 |
| H3F3A | H3 histone, family 3B (H3.3B); H3 histone, family 3A pseudogene; H3 histone, family 3A; similar to H3 histone, family 3B; similar to histone H3.3B |
| HDAC3 | histone deacetylase 3 |
| HDAC5 | histone deacetylase 5 |
| HEG1 | HEG homolog 1 (zebrafish) |
| HERPUD2 | HERPUD family member 2 |
| HES1 | hairy and enhancer of split 1, (Drosophila) |
| HEXB | hexosaminidase B (beta polypeptide) |
| HIST1H1C | histone cluster 1, H1c |
| HMGB1 | high-mobility group box 1; high-mobility group box 1-like 10 |
| HNRNPH1 | heterogeneous nuclear ribonucleoprotein H1 (H) |
| HNRNPH2 | ribosomal protein L36a pseudogene 51; ribosomal protein L36a pseudogene 37; ribosomal protein L36a pseudogene 49; heterogeneous nuclear ribonucleoprotein H2 (H'); ribosomal protein L36a |
| HNRNPL | similar to heterogeneous nuclear ribonucleoprotein L-like; heterogeneous nuclear ribonucleoprotein L |
| HNRNPM | heterogeneous nuclear ribonucleoprotein M |
| HNRNPR | heterogeneous nuclear ribonucleoprotein R |
| HOOK3 | hook homolog 3 (Drosophila) |
| HOXA5 | homeobox A5 |
| HP1BP3 | heterochromatin protein 1, binding protein 3 |
| HSP90AA1 | heat shock protein 90 kDa alpha (cytosolic), class A member 2; heat shock protein 90 kDa alpha (cytosolic), class A member 1 |
| HSP90AB1 | heat shock protein 90 kDa alpha (cytosolic), class B member 1 |
| HSP90B1 | heat shock protein 90 kDa beta (Grp94), member 1 |
| HSPA12A | heat shock 70 kDa protein 12A |
| HSPA2 | heat shock 70 kDa protein 2 |
| HSPB1 | heat shock 27 kDa protein-like 2 pseudogene; heat shock 27 kDa protein 1 |
| HSPB8 | heat shock 22 kDa protein 8 |
| ID1 | inhibitor of DNA binding 1, dominant negative helix-loop-helix protein |
| ID2 | inhibitor of DNA binding 2, dominant negative helix-loop-helix protein |
| IER2 | immediate early response 2 |
| IFI35 | interferon-induced protein 35 |
| IFIT3 | interferon-induced protein with tetratricopeptide repeats 3 |
| IFITM3 | interferon induced transmembrane protein 3 (1-8 U) |
| IFNAR2 | interferon (alpha, beta and omega) receptor 2 |
| IFNGR1 | interferon gamma receptor 1 |
| IFRD1 | interferon-related developmental regulator 1 |
| IFT74 | intraflagellar transport 74 homolog (Chlamydomonas) |
| IGF1R | insulin-like growth factor 1 receptor |
| IGFBP5 | insulin-like growth factor binding protein 5 |
| IGFBP6 | insulin-like growth factor binding protein 6 |
| IL16 | interleukin 16 (lymphocyte chemoattractant factor) |
| IL17RE | interleukin 17 receptor E |
| IL6ST | interleukin 6 signal transducer (gp130, oncostatin M receptor) |
| ILDR2 | immunoglobulin-like domain containing receptor 2 |
| ILF3 | interleukin enhancer binding factor 3, 90 kDa |
| IMPAD1 | inositol monophosphatase domain containing 1 |
| INTS10 | integrator complex subunit 10 |
| IQSEC1 | IQ motif and Sec7 domain 1 |
| IRAK4 | interleukin-1 receptor-associated kinase 4 |
| IRF2BP2 | interferon regulatory factor 2 binding protein 2 |
| IRF7 | interferon regulatory factor 7 |
| IRS2 | insulin receptor substrate 2 |
| ITCH | itchy E3 ubiquitin protein ligase homolog (mouse) |
| ITGA6 | integrin, alpha 6 |
| ITPR2 | inositol 1,4,5-triphosphate receptor, type 2 |
| JMJD1C | jumonji domain containing 1C |
| JUN | jun oncogene |
| JUNB | jun B proto-oncogene |
| JUND | jun D proto-oncogene |
| JUP | junction plakoglobin |
| KANK1 | KN motif and ankyrin repeat domains 1; similar to ankyrin repeat domain protein 15 isoform b |

TABLE 8-continued

Exemplary human marker genes

| HUMAN GENE SYMBOL | Gene Name |
|---|---|
| KCNAB1 | potassium voltage-gated channel, shaker-related subfamily, beta member 1 |
| KDELR1 | KDEL (Lys-Asp-Glu-Leu) endoplasmic reticulum protein retention receptor 1 |
| KDM5A | lysine (K)-specific demethylase 5A |
| KDM6B | lysine (K)-specific demethylase 6B |
| KDR | kinase insert domain receptor (a type III receptor tyrosine kinase) |
| KEAP1 | kelch-like ECH-associated protein 1 |
| KIF1B | kinesin family member 1B |
| KIF5B | kinesin family member 5B |
| KLF10 | Kruppel-like factor 10 |
| KLF2 | Kruppel-like factor 2 (lung) |
| KLF4 | Kruppel-like factor 4 (gut) |
| KLF6 | Kruppel-like factor 6 |
| KLF7 | Kruppel-like factor 7 (ubiquitous) |
| KLF9 | Kruppel-like factor 9 |
| KPNA1 | karyopherin alpha 1 (importin alpha 5) |
| KPNA3 | karyopherin alpha 3 (importin alpha 4) |
| KRCC1 | lysine-rich coiled-coil 1 |
| KRT14 | keratin 14 |
| KTN1 | kinectin 1 (kinesin receptor) |
| LAMA4 | laminin, alpha 4 |
| LAMP2 | lysosomal-associated membrane protein 2 |
| LARS2 | leucyl-tRNA synthetase 2, mitochondrial |
| LASS2 | LAG1 homolog, ceramide synthase 2 |
| LASS4 | LAG1 homolog, ceramide synthase 4 |
| LGALS7 | lectin, galactoside-binding, soluble, 7; lectin, galactoside-binding, soluble, 7B |
| LIMCH1 | LIM and calponin homology domains 1 |
| LIMS2 | LIM and senescent cell antigen-like domains 2 |
| LMAN1 | lectin, mannose-binding, 1 |
| LPAR2 | lysophosphatidic acid receptor 2 |
| LRRC20 | leucine rich repeat containing 20 |
| LRRC58 | leucine rich repeat containing 58 |
| LRRC61 | leucine rich repeat containing 61 |
| LRRN4 | leucine rich repeat neuronal 4 |
| LRRN4CL | LRRN4C-terminal like |
| LTBP4 | latent transforming growth factor beta binding protein 4 |
| LUC7L3 | cisplatin resistance-associated overexpressed protein |
| MAF | v-maf musculoaponeurotic fibrosarcoma oncogene homolog (avian) |
| MAGED1 | melanoma antigen family D, 1 |
| MAGT1 | magnesium transporter 1 |
| MALAT1 | metastasis associated lung adenocarcinoma transcript 1 (non-protein coding) |
| MANF | mesencephalic astrocyte-derived neurotrophic factor |
| MAOA | monoamine oxidase A |
| MAP3K3 | mitogen-activated protein kinase kinase kinase 3 |
| MAPK1 | mitogen-activated protein kinase 1 |
| MAPKAPK3 | mitogen-activated protein kinase-activated protein kinase 3 |
| MAPRE2 | microtubule-associated protein, RP/EB family, member 2 |
| MARCKSL1 | MARCKS-like 1 |
| MAT2A | methionine adenosyltransferase II, alpha |
| MAT2B | methionine adenosyltransferase II, beta |
| MATR3 | matrin 3 |
| MED13L | mediator complex subunit 13-like |
| MED21 | mediator complex subunit 21 |
| MEF2C | myocyte enhancer factor 2C |
| MEIS2 | Meis homeobox 2 |
| MESDC1 | mesoderm development candidate 1 |
| METAP2 | methionyl aminopeptidase 2 |
| MFHAS1 | malignant fibrous histiocytoma amplified sequence 1 |
| MGLL | monoglyceride lipase |
| MGST1 | microsomal glutathione S-transferase 1 |
| MLL3 | myeloid/lymphoid or mixed-lineage leukemia 3 |
| MORF4L2 | mortality factor 4 like 2 |
| MPDZ | multiple PDZ domain protein |
| MPHOSPH8 | M-phase phosphoprotein 8 |
| MRAS | muscle RAS oncogene homolog |
| MRGPRF | MAS-related GPR, member F |
| MSN | moesin |
| MTDH | metadherin |
| MTMR6 | myotubularin related protein 6 |
| MUT | methylmalonyl Coenzyme A mutase |
| MXD4 | MAX dimerization protein 4 |

TABLE 8-continued

Exemplary human marker genes

| HUMAN GENE SYMBOL | Gene Name |
|---|---|
| MYH10 | myosin, heavy chain 10, non-muscle |
| MYL12A | myosin, light chain 12A, regulatory, non-sarcomeric |
| MYL7 | myosin, light chain 7, regulatory |
| MYLIP | myosin regulatory light chain interacting protein |
| MYST4 | MYST histone acetyltransferase (monocytic leukemia) 4 |
| NAA25 | chromosome 12 open reading frame 30 |
| NAGA | N-acetylgalactosaminidase, alpha- |
| NCKAP1 | NCK-associated protein 1 |
| NCOA1 | nuclear receptor coactivator 1 |
| NCOA4 | nuclear receptor coactivator 4 |
| NCOR1 | nuclear receptor co-repressor 1 |
| NDN | necdin homolog (mouse) |
| NDST1 | N-deacetylase/N-sulfotransferase (heparan glucosaminyl) 1 |
| NDUFA4 | NADH dehydrogenase (ubiquinone) 1 alpha subcomplex, 4, 9 kDa |
| NEDD4 | neural precursor cell expressed, developmentally down-regulated 4 |
| NF1 | neurofibromin 1 |
| NFE2L1 | nuclear factor (erythroid-derived 2)-like 1 |
| NFIA | nuclear factor I/A |
| NFIC | nuclear factor I/C (CCAAT-binding transcription factor) |
| NFIX | nuclear factor I/X (CCAAT-binding transcription factor) |
| NFKB2 | nuclear factor of kappa light polypeptide gene enhancer in B-cells 2 (p49/p100) |
| NFKBIA | nuclear factor of kappa light polypeptide gene enhancer in B-cells inhibitor, alpha |
| NFKBIZ | nuclear factor of kappa light polypeptide gene enhancer in B-cells inhibitor, zeta |
| NFYC | nuclear transcription factor Y, gamma |
| NID2 | nidogen 2 (osteonidogen) |
| NINL | ninein-like |
| NIPAL3 | NIPA-like domain containing 3 |
| NIPBL | Nipped-B homolog (Drosophila) |
| NKAIN4 | Na+/K+ transporting ATPase interacting 4 |
| NKD1 | naked cuticle homolog 1 (Drosophila) |
| NNMT | nicotinamide N-methyltransferase |
| NOD1 | nucleotide-binding oligomerization domain containing 1 |
| NPR1 | natriuretic peptide receptor A/guanylate cyclase A (atrionatriuretic peptide receptor A) |
| NR1D1 | nuclear receptor subfamily 1, group D, member 1 |
| NR3C1 | nuclear receptor subfamily 3, group C, member 1 (glucocorticoid receptor) |
| NR4A1 | nuclear receptor subfamily 4, group A, member 1 |
| NRGN | neurogranin (protein kinase C substrate, RC3) |
| NUCKS1 | nuclear casein kinase and cyclin-dependent kinase substrate 1 |
| OAT | ornithine aminotransferase (gyrate atrophy) |
| OGDH | oxoglutarate (alpha-ketoglutarate) dehydrogenase (lipoamide) |
| OGN | osteoglycin |
| OPA3 | optic atrophy 3 (autosomal recessive, with chorea and spastic paraplegia) |
| ORAI3 | ORAI calcium release-activated calcium modulator 3 |
| OSR1 | odd-skipped related 1 (Drosophila) |
| OXCT1 | 3-oxoacid CoA transferase 1 |
| OXNAD1 | oxidoreductase NAD-binding domain containing 1 |
| PARD3B | par-3 partitioning defective 3 homolog B (C. elegans) |
| PARP14 | poly (ADP-ribose) polymerase family, member 14 |
| PARP4 | poly (ADP-ribose) polymerase family, member 4 |
| PARVB | parvin, beta |
| PBX1 | pre-B-cell leukemia homeobox 1 |
| PCDH15 | protocadherin 15 |
| PCDHGB5 | protocadherin gamma subfamily B, 5 |
| PCM1 | pericentriolar material 1 |
| PDAP1 | PDGFA associated protein 1; similar to PDGFA associated protein 1 |
| PDCD6IP | programmed cell death 6 interacting protein |
| PDE4DIP | hypothetical protein LOC100134230; similar to KIAA0454 protein; similar to phosphodiesterase 4D interacting protein isoform 2; phosphodiesterase 4D interacting protein |
| PDIA3 | protein disulfide isomerase family A, member 3 |
| PDIA4 | protein disulfide isomerase family A, member 4 |
| PDPN | podoplanin |
| PEF1 | penta-EF-hand domain containing 1 |
| PELI1 | pellino homolog 1 (Drosophila) |
| PER1 | period homolog 1 (Drosophila) |
| PF4 | platelet factor 4 |
| PFN1 | profilin 1 |
| PGCP | plasma glutamate carboxypeptidase |

TABLE 8-continued

Exemplary human marker genes

| HUMAN GENE SYMBOL | Gene Name |
|---|---|
| PGRMC1 | progesterone receptor membrane component 1 |
| PHF21A | PHD finger protein 21A |
| PHF3 | PHD finger protein 3 |
| PHIP | pleckstrin homology domain interacting protein |
| PIGT | phosphatidylinositol glycan anchor biosynthesis, class T |
| PIK3C2A | phosphoinositide-3-kinase, class 2, alpha polypeptide |
| PIM1 | pim-1 oncogene |
| PITPNM2 | phosphatidylinositol transfer protein, membrane-associated 2 |
| PKHD1L1 | polycystic kidney and hepatic disease 1 (autosomal recessive)-like 1 |
| PKNOX1 | PBX/knotted 1 homeobox 1 |
| PLA2G4A | phospholipase A2, group IVA (cytosolic, calcium-dependent) |
| PLAT | plasminogen activator, tissue |
| PLCE1 | phospholipase C, epsilon 1 |
| PLK1S1 | non-protein coding RNA 153 |
| PLK2 | polo-like kinase 2 (Drosophila) |
| PLOD2 | procollagen-lysine, 2-oxoglutarate 5-dioxygenase 2 |
| PLXDC1 | plexin domain containing 1 |
| PLXDC2 | plexin domain containing 2 |
| PLXNA4 | plexin A4 |
| PMP22 | peripheral myelin protein 22 |
| PNRC1 | proline-rich nuclear receptor coactivator 1 |
| PODN | podocan |
| PPAP2A | phosphatidic acid phosphatase type 2A |
| PPBP | pro-platelet basic protein (chemokine (C-X-C motif) ligand 7) |
| PPFIBP2 | PTPRF interacting protein, binding protein 2 (liprin beta 2) |
| PPIG | peptidylprolyl isomerase G (cyclophilin G) |
| PPL | periplakin |
| PPP1CB | protein phosphatase 1, catalytic subunit, beta isoform; speedy homolog A (Xenopus laevis) |
| PPP1R12A | protein phosphatase 1, regulatory (inhibitor) subunit 12A |
| PPP1R15A | protein phosphatase 1, regulatory (inhibitor) subunit 15A |
| PPP3CA | protein phosphatase 3 (formerly 2B), catalytic subunit, alpha isoform |
| PPPDE1 | PPPDE peptidase domain containing 1 |
| PQLC3 | PQ loop repeat containing 3 |
| PRELP | proline/arginine-rich end leucine-rich repeat protein |
| PRG4 | proteoglycan 4 |
| PRKAR2A | protein kinase, cAMP-dependent, regulatory, type II, alpha |
| PRPF40A | PRP40 pre-mRNA processing factor 40 homolog A (S. cerevisiae) |
| PRR13 | proline rich 13 |
| PRSS23 | protease, serine, 23 |
| PSD | pleckstrin and Sec7 domain containing |
| PSIP1 | PC4 and SFRS1 interacting protein 1 |
| PSMB2 | proteasome (prosome, macropain) subunit, beta type, 2 |
| PSMD11 | proteasome (prosome, macropain) 26S subunit, non-ATPase, 11 |
| PSMD7 | proteasome (prosome, macropain) 26S subunit, non-ATPase, 7 |
| PTGES3 | prostaglandin E synthase 3 (cytosolic) |
| PTGIS | prostaglandin I2 (prostacyclin) synthase |
| PTGS1 | prostaglandin-endoperoxide synthase 1 (prostaglandin G/H synthase and cyclooxygenase) |
| PTMA | hypothetical LOC728026; prothymosin, alpha; hypothetical gene supported by BC013859; prothymosin, alpha pseudogene 4 (gene sequence 112) |
| PTP4A2 | protein tyrosine phosphatase type IVA, member 2 |
| PTPLAD2 | protein tyrosine phosphatase-like A domain containing 2 |
| PTPRD | protein tyrosine phosphatase, receptor type, D |
| PTPRF | protein tyrosine phosphatase, receptor type, F |
| PTRF | polymerase 1 and transcript release factor |
| QRICH1 | glutamine-rich 1 |
| QSER1 | glutamine and serine rich 1 |
| RAB11FIP1 | RAB11 family interacting protein 1 (class I) |
| RAB1B | RAB1B, member RAS oncogene family |
| RAB5C | RAB5C, member RAS oncogene family |
| RAB6B | RAB6B, member RAS oncogene family |
| RABGAP1L | RAB GTPase activating protein 1-like |
| RALBP1 | hypothetical LOC100129773; ralA binding protein 1 |
| RALY | RNA binding protein, autoantigenic (hnRNP-associated with lethal yellow homolog (mouse)) |
| RARRES2 | retinoic acid receptor responder (tazarotene induced) 2 |
| RB1CC1 | RB1-inducible coiled-coil 1 |
| RBBP6 | retinoblastoma binding protein 6 |
| RBBP8 | retinoblastoma binding protein 8 |
| RBM25 | RNA binding motif protein 25 |
| RBM27 | RNA binding motif protein 27 |
| RBM3 | RNA binding motif (RNP1, RRM) protein 3 |

TABLE 8-continued

Exemplary human marker genes

| HUMAN GENE SYMBOL | Gene Name |
|---|---|
| RBPMS | RNA binding protein with multiple splicing |
| RDX | radixin |
| REST | RE1-silencing transcription factor |
| RGMA | RGM domain family, member A |
| RGS10 | regulator of G-protein signaling 10 |
| RHOB | ras homolog gene family, member B |
| RHOJ | ras homolog gene family, member J |
| RHOU | ras homolog gene family, member U |
| RNASE4 | ribonuclease, RNase A family, 4 |
| RND3 | Rho family GTPase 3 |
| RNF167 | ring finger protein 167 |
| RNF20 | ring finger protein 20 |
| ROCK1 | similar to Rho-associated, coiled-coil containing protein kinase 1; Rho-associated, coiled-coil containing protein kinase 1 |
| ROCK2 | Rho-associated, coiled-coil containing protein kinase 2 |
| RPP25 | ribonuclease P/MRP 25 kDa subunit |
| RRAS2 | related RAS viral (r-ras) oncogene homolog 2; similar to related RAS viral (r-ras) oncogene homolog 2 |
| RSPO1 | R-spondin homolog (*Xenopus laevis*) |
| RTF1 | Rtf1, Paf1/RNA polymerase II complex component, homolog (*S. cerevisiae*) |
| RTN1 | reticulon 1 |
| RYK | RYK receptor-like tyrosine kinase |
| SARNP | SAP domain containing ribonucleoprotein |
| SAT1 | spermidine/spermine N1-acetyltransferase 1 |
| SBSN | suprabasin |
| SDC4 | syndecan 4 |
| SDPR | serum deprivation response (phosphatidylserine binding protein) |
| SEC62 | SEC62 homolog (*S. cerevisiae*) |
| SECISBP2 | SECIS binding protein 2 |
| SEMA5A | sema domain, seven thrombospondin repeats (type 1 and type 1-like), transmembrane domain (TM) and short cytoplasmic domain, (semaphorin) 5A |
| SENP6 | SUMO1/sentrin specific peptidase 6 |
| SEP15 | 15 kDa selenoprotein |
| SEPT9 | septin 9 |
| SERINC5 | serine incorporator 5 |
| SERPING1 | serpin peptidase inhibitor, clade G (C1 inhibitor), member 1 |
| SERPINH1 | serpin peptidase inhibitor, clade H (heat shock protein 47), member 1, (collagen binding protein 1) |
| SESN1 | sestrin 1 |
| SETD2 | SET domain containing 2 |
| SF3B1 | splicing factor 3b, subunit 1, 155 kDa |
| SF3B4 | splicing factor 3b, subunit 4, 49 kDa |
| SFRS18 | splicing factor, arginine/serine-rich 18 |
| SHC1 | SHC (Src homology 2 domain containing) transforming protein 1 |
| SHFM1 | split hand/foot malformation (ectrodactyly) type 1 |
| SIAE | sialic acid acetylesterase |
| SIRT2 | sirtuin (silent mating type information regulation 2 homolog) 2 (*S. cerevisiae*) |
| SLC10A3 | solute carrier family 10 (sodium/bile acid cotransporter family), member 3 |
| SLC16A1 | solute carrier family 16, member 1 (monocarboxylic acid transporter 1) |
| SLC1A5 | solute carrier family 1 (neutral amino acid transporter), member 5 |
| SLC26A3 | solute carrier family 26, member 3 |
| SLC27A3 | solute carrier family 27 (fatty acid transporter), member 3 |
| SLC38A1 | solute carrier family 38, member 1 |
| SLC39A8 | solute carrier family 39 (zinc transporter), member 8 |
| SLC43A3 | solute carrier family 43, member 3 |
| SLC4A4 | solute carrier family 4, sodium bicarbonate cotransporter, member 4 |
| SLC6A4 | solute carrier family 6 (neurotransmitter transporter, serotonin), member 4 |
| SLC6A6 | solute carrier family 6 (neurotransmitter transporter, taurine), member 6 |
| SLC8A1 | solute carrier family 8 (sodium/calcium exchanger), member 1 |
| SLC9A3R1 | solute carrier family 9 (sodium/hydrogen exchanger), member 3 regulator 1 |
| SLPI | secretory leukocyte peptidase inhibitor |
| SLTM | SAFB-like, transcription modulator |
| SLU7 | SLU7 splicing factor homolog (*S. cerevisiae*) |
| SLURP1 | secreted LY6/PLAUR domain containing 1 |
| SMAD4 | SMAD family member 4 |
| SMARCA2 | SWI/SNF related, matrix associated, actin dependent regulator of chromatin, subfamily a, member 2 |

TABLE 8-continued

Exemplary human marker genes

| HUMAN GENE SYMBOL | Gene Name |
|---|---|
| SMARCA5 | SWI/SNF related, matrix associated, actin dependent regulator of chromatin, subfamily a, member 5 |
| SMC2 | structural maintenance of chromosomes 2 |
| SMC3 | structural maintenance of chromosomes 3 |
| SMC4 | structural maintenance of chromosomes 4 |
| SMC6 | structural maintenance of chromosomes 6 |
| SMCHD1 | structural maintenance of chromosomes flexible hinge domain containing 1 |
| SMPD3 | sphingomyelin phosphodiesterase 3, neutral membrane (neutral sphingomyelinase II) |
| SNRNP70 | small nuclear ribonucleoprotein 70 kDa (U1) |
| SNTB2 | syntrophin, beta 2 (dystrophin-associated protein A1, 59 kDa, basic component 2) |
| SOAT1 | sterol O-acyltransferase 1 |
| SOCS3 | suppressor of cytokine signaling 3 |
| SOD3 | superoxide dismutase 3, extracellular |
| SORBS1 | sorbin and SH3 domain containing 1 |
| SORBS3 | sorbin and SH3 domain containing 3 |
| SOX6 | SRY (sex determining region Y)-box 6 |
| SP100 | SP100 nuclear antigen |
| SPAG9 | sperm associated antigen 9 |
| SPARC | secreted protein, acidic, cysteine-rich (osteonectin) |
| SPEN | spen homolog, transcriptional regulator (*Drosophila*) |
| SPINT2 | serine peptidase inhibitor, Kunitz type, 2 |
| SPOCK2 | sparc/osteonectin, cwcv and kazal-like domains proteoglycan (testican) 2 |
| SPON2 | spondin 2, extracellular matrix protein |
| SPOP | speckle-type POZ protein |
| SRC | v-src sarcoma (Schmidt-Ruppin A-2) viral oncogene homolog (avian) |
| SRRM1 | serine/arginine repetitive matrix 1 |
| SSH2 | slingshot homolog 2 (*Drosophila*) |
| SSR3 | signal sequence receptor, gamma (translocon-associated protein gamma) |
| ST3GAL1 | ST3 beta-galactoside alpha-2,3-sialyltransferase 1 |
| STAG1 | stromal antigen 1 |
| STAR | steroidogenic acute regulatory protein |
| STARD5 | StAR-related lipid transfer (START) domain containing 5 |
| STAT3 | signal transducer and activator of transcription 3 (acute-phase response factor) |
| STIM1 | stromal interaction molecule 1 |
| STK10 | serine/threonine kinase 10 |
| STK40 | serine/threonine kinase 40 |
| STMN2 | stathmin-like 2 |
| STRA6 | stimulated by retinoic acid gene 6 homolog (mouse) |
| STRN3 | striatin, calmodulin binding protein 3 |
| SULF1 | sulfatase 1 |
| SULF2 | sulfatase 2 |
| SUPT16H | suppressor of Ty 16 homolog (*S. cerevisiae*); suppressor of Ty 16 homolog (*S. cerevisiae*) pseudogene |
| SV2A | synaptic vesicle glycoprotein 2A |
| SYNE1 | spectrin repeat containing, nuclear envelope 1 |
| SYNE2 | spectrin repeat containing, nuclear envelope 2 |
| SYT11 | synaptotagmin XI |
| SYTL1 | synaptotagmin-like 1 |
| TAF3 | TAF3 RNA polymerase II, TATA box binding protein (TBP)-associated factor, 140 kDa |
| TAF7 | TAF7 RNA polymerase II, TATA box binding protein (TBP)-associated factor, 55 kDa |
| TAPBP | TAP binding protein (tapasin) |
| TBC1D15 | TBC1 domain family, member 15 |
| TBCEL | tubulin folding cofactor E-like |
| TBL1X | transducin (beta)-like 1X-linked |
| TBX18 | T-box 18 |
| TCEAL8 | transcription elongation factor A (SII)-like 8 |
| TCF7L1 | transcription factor 7-like 1 (T-cell specific, HMG-box) |
| TFDP2 | transcription factor Dp-2 (E2F dimerization partner 2) |
| TGFB1I1 | transforming growth factor beta 1 induced transcript 1 |
| TGFB2 | transforming growth factor, beta 2 |
| TGFBR2 | transforming growth factor, beta receptor II (70/80 kDa) |
| TGM2 | transglutaminase 2 (C polypeptide, protein-glutamine-gamma-glutamyltransferase) |
| THBD | thrombomodulin |
| THBS1 | thrombospondin 1 |
| THOC2 | THO complex 2 |

TABLE 8-continued

Exemplary human marker genes

| HUMAN GENE SYMBOL | Gene Name |
|---|---|
| THRAP3 | thyroid hormone receptor associated protein 3 |
| THSD4 | thrombospondin, type I, domain containing 4 |
| TIMP2 | TIMP metallopeptidase inhibitor 2 |
| TIRAP | toll-interleukin 1 receptor (TIR) domain containing adaptor protein |
| TLR2 | toll-like receptor 2 |
| TM4SF1 | transmembrane 4 L six family member 1 |
| TM4SF5 | transmembrane 4 L six family member 5 |
| TMCC3 | transmembrane and coiled-coil domain family 3 |
| TMCO1 | transmembrane and coiled-coil domains 1 |
| TMCO7 | transmembrane and coiled-coil domains 7 |
| TMED2 | transmembrane emp24 domain trafficking protein 2 |
| TMEM119 | transmembrane protein 119 |
| TMEM140 | transmembrane protein 140 |
| TMEM151A | transmembrane protein 151A |
| TMEM221 | transmembrane protein 221 |
| TMEM50A | transmembrane protein 50A |
| TMEM98 | similar to transmembrane protein 98; transmembrane protein 98 |
| TMOD3 | tropomodulin 3 (ubiquitous) |
| TMPO | thymopoietin |
| TMSB4X | thymosin-like 2 (pseudogene); thymosin-like 1 (pseudogene); thymosin beta 4, X-linked |
| TNXB | tenascin XB; tenascin XA pseudogene |
| TOB2 | transducer of ERBB2, 2 |
| TOPORS | topoisomerase 1 binding, arginine/serine-rich |
| TPM3 | tropomyosin 3 |
| TPPP3 | tubulin polymerization-promoting protein family member 3 |
| TPT1 | similar to tumor protein, translationally-controlled 1; tumor protein, translationally-controlled 1 |
| TRAFD1 | TRAF-type zinc finger domain containing 1 |
| TRIB1 | tribbles homolog 1 (*Drosophila*) |
| TRIM8 | tripartite motif-containing 8 |
| TRPM7 | transient receptor potential cation channel, subfamily M, member 7 |
| TSC22D3 | TSC22 domain family, member 3; GRAM domain containing 4 |
| TSHZ1 | teashirt zinc finger homeobox 1 |
| TSIX | XIST antisense RNA (non-protein coding) |
| TSPAN31 | tetraspanin 31 |
| TSPAN5 | tetraspanin 5 |
| TTC28 | chromosome 6 open reading frame 35; hCG1820764; tetratricopeptide repeat domain 28 |
| TTC38 | tetratricopeptide repeat domain 38 |
| TUBA1A | tubulin, alpha 1a |
| TUBB2A | tubulin, beta 2A |
| TWSG1 | twisted gastrulation homolog 1 (*Drosophila*) |
| TXNDC5 | thioredoxin domain containing 5 (endoplasmic reticulum); muted homolog (mouse) |
| TXNRD1 | thioredoxin reductase 1; hypothetical LOC100130902 |
| UAP1 | UDP-N-acetylglucosamine pyrophosphorylase 1 |
| UBA7 | ubiquitin-like modifier activating enzyme 7 |
| UBE2D1 | ubiquitin-conjugating enzyme E2D 1 (UBC4/5 homolog, yeast) |
| UBE2L6 | ubiquitin-conjugating enzyme E2L 6 |
| UBE2N | ubiquitin-conjugating enzyme E2N (UBC13 homolog, yeast) |
| UBE2V1 | ubiquitin-conjugating enzyme E2 variant 1; ubiquitin-conjugating enzyme E2 variant 1 pseudogene 2; transmembrane protein 189; TMEM189-UBE2V1 readthrough transcript |
| UBQLN2 | ubiquilin 2 |
| UBXN2A | UBX domain protein 2A |
| UBXN4 | UBX domain protein 4 |
| UGDH | UDP-glucose dehydrogenase |
| UPK1B | uroplakin 1B |
| UPK3B | uroplakin 3B |
| USP16 | ubiquitin specific peptidase 16 |
| USP2 | ubiquitin specific peptidase 2 |
| USP25 | ubiquitin specific peptidase 25 |
| USP54 | ubiquitin specific peptidase 54 |
| USP8 | ubiquitin specific peptidase 8 |
| UTP20 | similar to Down-regulated in metastasis protein (Key-1A6 protein) (Novel nucleolar protein 73) (NNP73); UTP20, small subunit (SSU) processome component, homolog (yeast) |
| VAT1 | vesicle amine transport protein 1 homolog (*T. californica*) |
| VIM | vimentin |
| VPS13A | vacuolar protein sorting 13 homolog A (*S. cerevisiae*) |
| VWA5A | von Willebrand factor A domain containing 5A |
| WAC | WW domain containing adaptor with coiled-coil |
| WASF2 | WAS protein family, member 2 |

TABLE 8-continued

Exemplary human marker genes

| HUMAN GENE SYMBOL | Gene Name |
|---|---|
| WDR26 | WD repeat domain 26 |
| WDR92 | WD repeat domain 92 |
| WFDC1 | WAP four-disulfide core domain 1 |
| WLS | G protein-coupled receptor 177 |
| WNT4 | wingless-type MMTV integration site family, member 4 |
| WRNIP1 | Werner helicase interacting protein 1 |
| WT1 | Wilms tumor 1 |
| WWC2 | WW and C2 domain containing 2 |
| XDH | xanthine dehydrogenase |
| XIST | X (inactive)-specific transcript (non-protein coding) |
| YIPF5 | Yip1 domain family, member 5 |
| YWHAZ | tyrosine 3-monooxygenase/tryptophan 5-monooxygenase activation protein, zeta polypeptide |
| ZBTB16 | zinc finger and BTB domain containing 16 |
| ZBTB20 | zinc finger and BTB domain containing 20 |
| ZBTB4 | zinc finger and BTB domain containing 4 |
| ZBTB7C | zinc finger and BTB domain containing 7C |
| ZC3H13 | zinc finger CCCH-type containing 13 |
| ZC3H18 | zinc finger CCCH-type containing 18 |
| ZCCHC11 | zinc finger, CCHC domain containing 11 |
| ZCCHC3 | zinc finger, CCHC domain containing 3 |
| ZFAND6 | zinc finger, AN1-type domain 6 |
| ZFHX4 | zinc finger homeobox 4 |
| ZFP36 | zinc finger protein 36, C3H type, homolog (mouse) |
| ZMAT1 | zinc finger, matrin type 1 |
| ZRSR1 | zinc finger (CCCH type), RNA-binding motif and serine/arginine rich 1 |
| ZZEF1 | zinc finger, ZZ-type with EF-hand domain 1 |

The gene names listed in Table 7 and Table 8 are common names. NCBI Gene ID numbers for each of the genes listed in Table 7 or Table 8 can be obtained by searching the "Gene" Database of the NCBI (available on the World Wide Web at http://www.ncbi.nlm.nih.gov/) using the common name as the query and selecting the first returned *Homo sapiens* (for the genes in Table 8) or *Mus musculus* gene (for the genes in Table 7). Other genes may be obtained using the UCSC genome browser (available on the World Wide Web at http://genome.ucsc.edu) using the Gene Sorter function. Human homologs of mouse genes can be readily identified, e.g. the identified homologs in the NCBI database, or by querying databases such as BLAST. In certain embodiments, the marker gene(s) are selected from the genes listed in Table 7, Table 8, or Table 14.

In a CTC, the marker genes listed in Table 7, Table 8, or Table 14 can be upregulated, e.g. for marker genes listed in Table 7, Table 8, or Table 14, if the measured marker gene expression in a cell or sample is higher as compared to a reference level of that marker gene's expression, then the cell is identified as a CTC and/or the sample is identified as comprising CTCs. Preferably, once looks at a statistically significant change. However, even if a few genes in a group do not differ from normal, a sample can be identified as comprising CTCs if the overall change of the group shows a significant change, preferably a statistically significant change. All possible combinations of 2 or more of the indicated markers are contemplated herein.

The level of a gene expression product of a marker gene in Table 7, Table 8, or Table 14 which is higher than a reference level of that marker gene by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative of the presence of a CTC.

In some embodiments, the reference can be a level of expression of the marker gene product in a cell or population of cells which are not CTCs, e.g. the average level in non-circulating tumor cells and/or circulating cells which are not cancer cells. In some embodiments, the reference can also be a level of expression of the marker gene product in a control sample, a pooled sample of control individuals or a numeric value or range of values based on the same.

In some embodiments, the methods and assays described herein include (a) transforming the gene expression product into a detectable gene target; (b) measuring the amount of the detectable gene target; and (c) comparing the amount of the detectable gene target to an amount of a reference, wherein if the amount of the detectable gene target is statistically significantly different than the amount of the reference level, the presence and/or level of CTCs is determined. In some embodiments, if the amount of the detectable gene target is not statistically significantly different than the amount of the reference level, the sample is identified as not comprising CTCs.

As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Methods to measure gene expression products associated with the marker genes described herein are well known to a skilled artisan. Such methods to measure gene expression products, e.g., protein level, include ELISA (enzyme linked immunosorbent assay), western blot, FACS, radioimmunological assay; (RIA); sandwich assay; fluorescent in situ hybridization (FISH); immunohistological staining; immunoelectrophoresis; immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques.

For example, antibodies for the polypeptide expression products of the marker genes described herein are commercially available and can be used for the purposes of the invention to measure protein expression levels, e.g. anti-IGFBP5 (Cat. No. 4255; Abcam; Cambridge, Mass.). Alternatively, since the amino acid sequences for the marker genes described herein are known and publically available at NCBI website, one of skill in the art can raise their own antibodies against these proteins of interest for the purpose of the invention. The amino acid sequences of the marker genes described herein have been assigned NCBI accession numbers for different species such as human, mouse and rat.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as serum, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (i.e. a marker gene polypeptide as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., tumor, blood, serum or urine) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tumor samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622, 871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444, 880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, an adaptation of Western blotting (Towbin et al., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

Flow cytometry is a well-known technique for analyzing and sorting cells (or other small particles) suspended in a fluid stream. This technique allows simultaneous analysis of the physical and/or chemical characteristics of single cells flowing through an optical, electronic, or magnetic detection apparatus. As applied to FACS, the flow cytometer consists of a flow cell which carries the cells in a fluid stream in single file through a light source with excites the fluorescently labeled detection marker(s) (for example, antibody reagents) and measures the fluorescent character of the cell. The fluid stream is then ejected through a nozzle and a charging ring, under pressure, which breaks the fluid into droplets. The flow cell device and fluid stream is calibrated such that there is a relatively large distance between individual cells or bound groups of cells, resulting in a low probability that any droplet contains more than a single cell or bound group of cells. The charging ring charges the droplets based on the fluorescence characteristic of the cell which is contained therein. The charged droplets are then deflected by an electrostatically-charged deflection system which diverts the droplets into various containers based upon their charge (related to the fluorescence intensity of the cell). A FACS system (e.g. the FACSARIA™ flow cytometer (BD Biosciences) and FLOWJO™ Version 7.6.4 (TreeStar)) can detect and record the number of total cells as well as the number of cells which display one or more fluorescent characteristics, e.g. the total number of cells bound by one or more antibody reagents specific for a CTC marker gene.

In certain embodiments, the gene expression products as described herein can be instead determined by determining the level of messenger RNA (mRNA) expression of genes associated with the marker genes described herein. Such molecules can be isolated, derived, or amplified from a biological sample, such as a tumor biopsy. Detection of mRNA expression is known by persons skilled in the art, and comprise, for example but not limited to, PCR procedures, RT-PCR, quantitative PCR or RT-PCR, Northern blot analysis, differential gene expression, RNA protection assay, microarray analysis, hybridization methods, next-generation sequencing etc. Non-limiting examples of next-generation sequencing technologies can include Ion Torrent, Illumina, SOLiD, 454; Massively Parallel Signature Sequencing solid-phase, reversible dye-terminator sequencing; and DNA nanoball sequencing.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art. The nucleic acid sequences of the marker genes described herein have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the nucleic acid molecule to be amplified.

In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocyante (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3H$, $^{125}I$, $^{35}S$, $^{14}C$, $^{32}P$, and $^{33}P$. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}Eu$, or others of the lanthanide series. These metals can be attached to the reagent using such metal chelating groups as diethylenetriaminepentaacetic acid (DTPA) or ethylenediaminetetraacetic acid (EDTA).

In some embodiments of any of the aspects described herein, the level of expression products of more than one gene can be determined simultaneously (e.g. a multiplex assay) or in parallel. In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

The term "sample" or "test sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, a test sample can be a tumor cell test sample, e.g. the sample can comprise cancerous cells, cells from a tumor, and/or a tumor biopsy. In some embodiments, the test sample can be a blood sample.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the methods, assays, and systems described herein can further comprise a step of obtaining a test sample from a subject. In some embodiments, the subject can be a human subject.

In some embodiments, the methods and assays described herein can further comprise a step of isolating CTCs or potential CTCs from a sample prior to measuring the level the expression product of one or more of the marker genes described herein. By way of non-limitng example, CTCs can be isolated from, e.g. a blood sample by hydrodynamic size-based separation and/or immunodepletion of other cell types present in blood samples. The CTC-iChip, described in the Examples herein combines these two approaches to isolate CTCs.

Subjects with high, or at least detectable, levels of CTCs are most likely to benefit from treatment with therapies that specifically target CTCs. Accordingly, provided herein is a method of determining if a subject is likely to respond to treatment with a CTC marker gene-targeted therapy, the method comprising: measuring the level of a CTC marker gene expression product present in the blood and/or stroma of a cancer; and determining that the subject is likely to respond to the treatment if the level of the expression product is increased relative to a reference level. CTC marker gene-targeted therapies are discussed below herein.

Decreased levels of CTCs after administration of a therapy can be indicative of an improvement in the condition of the subject, e.g. the cancer is reduced in size, growth, and/or metastatic potential. Accordingly, provided herein is a method of monitoring the treatment of a subject, the method comprising administering a cancer therapy to a subject in need thereof; measuring the level of a CTC marker gene expression product present in the blood and/or stroma of a cancer; and determining that the subject is responding if the level of the CTC marker gene expression product is decreased relative to the reference level and determining that the subject is not responding to the treatment if the CTC marker gene expression product is not decreased relative to the reference level. In some embodiments the therapy is a chemotherapy, surgical therapy, and/or radiation therapy. In some embodiments, the therapy is a CTC marker gene-targeted therapy. In some embodiments, the reference level is the level of the gene expression product in the patient prior to the administering step.

The CTC marker genes described herein can be targeted directly and/or used to physically target a chemotherapeutic agent to reduce the levels and/or pathogenic activity of CTCs (e.g. metastatic activity). Accordingly, described herein is a method of treating cancer in a subject, the method comprising administering a therapeutically effective amount of a CTC marker gene-targeted therapy to the subject. In some embodiments, the subject is a subject determined to have an elevated level of CTCs and/or an elevated level of a CTC marker gene present in the blood and/or stroma of the cancer.

In some embodiments, the CTC marker gene-targeted therapy can comprise an inhibitor of a CTC marker gene, e.g. the CTC marker gene-targeted therapy can inhibit the level and/or activity of a CTC marker gene. As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of a CTC marker gene, e.g. its ability to decrease the level and/or activity of the CTC marker gene can be determined, e.g. by measuring the level of an expression product and/or the activity of the CTC marker gene. Methods for measuring the level of a given mRNA and/or polypeptide are known to one of skill in the art, e.g. RTPCR with primers can be used to determine the level of RNA and Western blotting with an antibody can be used to determine the level of a polypeptide. The activity of, e.g. a CTC marker gene can be determined, e.g. by measuring the levels and/or survival of CTCs using methods known in the art and described elsewhere herein. In some embodiments, the inhibitor of a CTC marker gene can be an inhibitory nucleic acid; an aptamer; an antibody reagent; an antibody; or a small molecule.

In some embodiments, the inhibitor of a CTC marker gene can be an antibody reagent. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to a given CTC marker gene.

In some embodiments, the inhibitor of a CTC marker gene can be an inhibitory nucleic acid reagent. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of the target mRNA. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,835, 826; 6,858,715; 6,867,289; 6,867,294; 6,878,805; 7,015,315; 7,041,816; 7,273,933; 7,321,029; 7,834,171; 7,919,612; 7,960,360; 7,989,603; 8,309,707; 6,524,681; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216, 141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677, 439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,700,920; 8,084,600; 8,124,745; 8,377,644 each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In some embodiments the CTC marker gene-targeted therapy can comprise an agent that binds to the CTC marker gene expression product and an agent that is chemotherapeutic. In some embodiments, the CTC marker gene-targeted therapy comprises a CTC marker gene-binding antibody reagent and a chemotherapeutic agent. A CTC marker gene-binding antibody reagent can be an antibody reagent that binds, e.g. a CTC marker gene polypeptide. The binding antibody reagent can be an inhibitor or can exhibit no inhibitory effect on its own. By binding to the CTC marker gene, and thereby a CTC, it concentrates and localizes the chemotherapeutic agent at CTC cells in the circulation and/or stroma of the tumor—increasing efficacy and reducing side effects.

In some embodiments, the CTC marker gene-targeted therapy comprises a CTC marker gene-binding antibody reagent that binds a marker gene selected from Table 14. In some embodiments, the CTC marker gene-targeted therapy comprises a CTC marker gene-binding antibody reagent that binds a marker gene selected from the group consisting of: IL6ST, SULF2, and SV2A.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I1131, I1125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

Non-limiting examples of chemotherapeutic agents can include gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE.™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In some embodiments, the binding antibody reagent and the chemotherapeutic agent can be directly conjugated and/or bound to each other, e.g. an antibody-drug conjugate. In some embodiments, binding can be non-covalent, e.g., by hydrogen, electrostatic, or van der waals interactions, however, binding may also be covalent. By "conjugated" is meant the covalent linkage of at least two molecules. In some embodiments, the composition can be an antibody-drug conjugate.

In some embodiments, the binding antibody reagent can be bound to and/or conjugated to multiple chemotherapeutic molecules. In some embodiments, the ratio of a given chemotherapeutic molecule to the binding antibody reagent molecule can be from about 1:1 to about 1,000:1, e.g. a single antibody binding reagent molecule can be linked to, conjugated to, etc. from about 1 to about 1,000 individual chemotherapeutic molecules.

In some embodiments, the binding antibody reagent and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one billionth of a meter. The term "nanoparticle" includes nanospheres; nanorods; nanoshells; and nanoprisms; and these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g. a binding reagent, kinase inhibitor, and/or EGFR inhibitor). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g. Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g. electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, the methods described herein relate to treating a subject having or diagnosed as having cancer with a CTC marker-gene targeted therapy. In some embodiments, the cancer can be pancreatic cancer. Subjects having cancer can be identified by a physician using current methods of diagnosing cancer. Symptoms and/or complications of cancer, e.g. pancreatic cancer, which characterize these conditions and aid in diagnosis are well known in the art and include but are not limited to, pain in the upper abdomen, heartburn, nausea, vomiting, diarrhea, cachexia, jaundice, pulmonary embolism, Trousseau syndrome, and diabetes mellitus. Tests that may aid in a diagnosis of, e.g. pancreatic cancer include, but are not limited to, liver function tests, CA19-9 tests, CT and endoscopic ultrasound. A family history of pancreatic cancer or exposure to risk factors for pancreatic cancer (e.g. smoking or drinking) can also aid in determining if a subject is likely to have cancer or in making a diagnosis of cancer.

The compositions and methods described herein can be administered to a subject having or diagnosed as having cancer, e.g. pancreatic cancer. In some embodiments, the methods described herein comprise administering an effective amount of compositions described herein, e.g. a CTC marker-gene targeted therapy to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a CTC marker-gene targeted therapy needed to alleviate at least one or more symptom of the disease or disorder, and relates to a sufficient amount of pharmacological composition to provide the desired effect. The term "therapeutically effective amount" therefore refers to an amount of CTC marker-gene targeted therapy that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a CTC marker-gene targeted therapy, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for CTC levels, among others.

The dosage can be determined by a physician and adjusted, as necessary, to suit observed effects of the treatment.

In some embodiments, the technology described herein relates to a pharmaceutical composition comprising a CTC marker-gene targeted therapy as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a CTC marker-gene targeted therapy as described herein.

In some embodiments, the pharmaceutical composition comprising a CTC marker-gene targeted therapy as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a CTC marker-gene targeted therapy as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a CTC marker-gene targeted therapy as disclosed herein can also be incorporated into the parenteral dosage forms of the disclosure, including conventional and controlled-release parenteral dosage forms.

Pharmaceutical compositions comprising a CTC marker-gene targeted therapy can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the CTC marker-gene targeted therapy can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, and chemotherapeutic agents as described above herein.

In certain embodiments, an effective dose of a composition comprising a CTC marker gene-targeted therapy as described herein can be administered to a patient once. In certain embodiments, an effective dose of a composition comprising a CTC marker gene-targeted therapy can be administered to a patient repeatedly. For systemic administration, subjects can be administered a therapeutic amount of a composition comprising a CTC marker gene-targeted therapy, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. CTC levels by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the CTC marker gene-targeted therapy. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a CTC marker gene-targeted therapy can be administered over a period of time, such as over a 5 minute, 10 minute, 15 minute, 20 minute, or 25 minute period.

The dosage ranges for the administration of a CTC marker gene-targeted therapy, according to the methods described herein depend upon, for example, the form of the CTC marker gene-targeted therapy, its potency, and the extent to which symptoms, markers, or indicators of a condition described herein are desired to be reduced, for example the percentage reduction desired for CTC levels. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a CTC marker gene-targeted therapy in, e.g. the treatment of a condition described herein, or to induce a response as described herein (e.g. reduction of CTC levels) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. CTC levels). It is well within the ability of one skilled in the art to monitor efficacy of administration and/or treatment by measuring any one of such parameters, or any combination of parameters. Efficacy can be assessed in animal models of a condition described herein, for example treatment of cancer, e.g. pancreatic cancer. When using an experimental animal model, efficacy of treatment is evidenced when a statistically significant change in a marker is observed, e.g. a change in CTC levels.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the term "cancer" or "tumor" refers to an uncontrolled growth of cells which interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510; Ni et al., Curr Med Chem. 2011; 18(27):4206-14; which are incorporated by reference herein in their entireties). Methods of generating an apatmer for any given target are well known in the art. Preclinical studies using, e.g. aptamer-siRNA chimeras and aptamer targeted nanoparticle therapeutics have been very successful in mouse models of cancer and HIV (Ni et al., Curr Med Chem. 2011; 18(27): 4206-14).

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of detecting circulating tumor cells (CTCs) in a sample, the method comprising:
   measuring the level of a PC-CTC marker gene expression product in the sample; and determining that PC-CTCs are present if the detected level of the marker gene expression product is greater than a reference level.
2. The method of paragraph 1, wherein the CTCs are pancreatic cancer CTCs.
3. The method of any of paragraphs 1-2, wherein the method further comprises a first step of isolating the CTCs from the sample.
4. The method of any of paragraphs 1-3, wherein the expression product is a nucleic acid.
5. The method of paragraph 4, wherein the level of the expression product is determined using a method selected from the group consisting of:
   RT-PCR; quantitative RT-PCR; Northern blot; microarray based expression analysis; next-generation sequencing; and RNA in situ hybridization.
6. The method of any of paragraphs 1-3, wherein the expression product is a polypeptide.
7. The method of paragraph 6, wherein the level of the expression product is determined using a method selected from the group consisting of:
   Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.
8. The method of any of paragraphs 1-7, wherein the CTC marker gene is selected from Table 7; Table 8; or Table 14.
9. The method of any of paragraphs 1-8, wherein the CTC marker gene is selected from the group consisting of: ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4.
10. The method of any of paragraphs 1-8, wherein the CTC marker gene is selected from the group consisting of:
    ALDH1A1; ALDH1A2; IGFBP5; KLF4; DCN; SPARC; WNT; TGFB2; VEGF; COL1A2; COL3A1; and TIMP2.
11. The method of any of paragraphs 1-9, wherein the CTC marker gene is selected from the group consisting of:
    ALDH1A2; IGFBP5; KLF4; DCN; and SPARC.
12. The method of any of paragraphs 1-9, wherein the CTC marker gene is selected from the group consisting of:
    ALDH1A2; IGFBP5; KLF4; and DCN.
13. The method of any of paragraphs 1-9, wherein the CTC marker gene is selected from the group consisting of:
    TPT1; HMGB1; SPON 2; SPARC; and ARSA.
14. The method of any of paragraphs 1-9, wherein the CTC marker gene is selected from the group consisting of:
    IL6ST; ARSA; TIMP2; CD55; SULF2; ITGA6; SDC4; CDON; and SV2A.
15. A method of treating cancer in a subject, the method comprising administering a therapeutically effective amount of a CTC marker gene-targeted therapy to the subject.
16. The method of paragraph 15, wherein the cancer is pancreatic cancer.
17. The method of any of paragraphs 15-16, wherein the CTC marker gene-targeted therapy comprises an inhibitor of a CTC marker gene.
18. The method of paragraph 17, wherein the inhibitor is an antibody reagent.
19. The method of paragraph 17, wherein the inhibitor is an inhibitory nucleic acid reagent.
20. The method of any of paragraphs 15-19, wherein the CTC marker gene-targeted therapy comprises a CTC marker gene-binding antibody reagent and a chemotherapeutic agent.
21. The method of any of paragraphs 15-20, wherein the subject is a subject determined to have an elevated level of CTCs and/or an elevated level of a CTC marker gene present in the blood and/or stroma of the cancer.
22. The method of any of paragraphs 15-21, wherein the CTC marker gene-targeted therapy comprises a CTC marker gene-binding antibody reagent that binds a marker gene selected from the group consisting of:
    IL6ST, SULF2, and SV2A.
23. A method of determining if a subject is likely to respond to treatment with a CTC marker gene-targeted therapy, the method comprising:
    measuring the level of a CTC marker gene expression product present in the blood and/or stroma of a cancer; and
    determining that the subject is likely to respond to the treatment if the level of the expression product is increased relative to a reference level.
24. The method of paragraph 23, wherein the method further comprises a first step of isolating the CTCs from the sample.
25. The method of any of paragraphs 23-24, wherein the cancer is pancreatic cancer.
26. The method of any of paragraphs 23-25, wherein the expression product is a nucleic acid.
27. The method of paragraph 26, wherein the level of the expression product is determined using a method selected from the group consisting of:
    RT-PCR; quantitative RT-PCR; Northern blot; microarray based expression analysis; next-generation sequencing; and RNA in situ hybridization.
28. The method of any of paragraphs 23-26, wherein the expression product is a polypeptide.

29. The method of paragraph 28, wherein the level of the expression product is determined using a method selected from the group consisting of:
Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

30. The method of any of paragraphs 23-29, wherein the PC-CTC marker gene is selected from Table 7; Table 8; or Table 14.

31. The method of any of paragraphs 23-30, wherein the CTC marker gene is selected from the group consisting of:
ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4.

32. The method of any of paragraphs 23-31, wherein the CTC marker gene is selected from the group consisting of:
ALDH1A1; ALDH1A2; IGFBP5; KLF4; DCN; SPARC; WNT; TGFB2; VEGF; COL1A2; COL3A1; and TIMP2.

33. The method of any of paragraphs 23-31, wherein the CTC marker gene is selected from the group consisting of:
ALDH1A2; IGFBP5; KLF4; DCN; and SPARC.

34. The method of any of paragraphs 23-31, wherein the CTC marker gene is selected from the group consisting of:
ALDH1A2; IGFBP5; KLF4; and DCN.

35. The method of any of paragraphs 23-31, wherein the CTC marker gene is selected from the group consisting of:
TPT1; HMGB1; SPON 2; SPARC; and ARSA.

36. The method of any of paragraphs 23-31, wherein the CTC marker gene is selected from the group consisting of:
IL6ST; ARSA; TIMP2; CD55; SULF2; ITGA6; SDC4; CDON; and SV2A.

37. A method of monitoring the treatment of a subject, the method comprising:
administering a cancer therapy to a subject in need thereof;
measuring the level of a CTC marker gene expression product present in the blood and/or stroma of a cancer; and
determining that the subject is responding if the level of the CTC marker gene expression product is decreased relative to the reference level and determining that the subject is not responding to the treatment if the CTC marker gene expression product is not decreased relative to the reference level.

38. The method of paragraph 37, wherein the cancer is pancreatic cancer.

39. The method of any of paragraphs 37-38, wherein the reference level is the level of the gene expression product in the patient prior to the administering step.

40. The method of any of paragraphs 37-39, wherein the method further comprises a first step of isolating the CTCs from the sample.

41. The method of any of paragraphs 37-40, wherein the expression product is a nucleic acid.

42. The method of paragraph 41, wherein the level of the expression product is determined using a method selected from the group consisting of:
RT-PCR; quantitative RT-PCR; Northern blot; microarray based expression analysis; next-generation sequencing; and RNA in situ hybridization.

43. The method of any of paragraphs 37-40, wherein the expression product is a polypeptide.

44. The method of paragraph 43, wherein the level of the expression product is determined using a method selected from the group consisting of:
Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

45. The method of any of paragraphs 37-44, wherein the PC-CTC marker gene is selected from Table 7; Table 8; or Table 14.

46. The method of any of paragraphs 37-45, wherein the CTC marker gene is selected from the group consisting of:
ABI3BP; ADAMTS5; ADAMTSL1; ANG; ARSA; C1RL; C3; C4A; C4B; CCDC80; CD109; CHI3L1; CLEC3B; CMTM3; CMTM7; COL14A1; COL1A2; COL3A1; COL4A6; CSF1; DAG1; DCN; DMKN; FBLN1; FGF1; FMOD; GPC3; GPC4; HMGB1; IFNAR2; IGFBP5; IL16; LAMA4; LTBP4; MFAP1A; NID2; OGN; PDAP1; PF4; PLAT; PODN; PRELP; RSPO1; SERPING1; SLURP1; SOD3; SPARC; SPOCK2; SPON2; SULF1; SULF2; TGFB2; TGM2; THBD; THBS1; THSD4; TIMP2; TNXB; TPT1; TWSG1 and WNT4.

47. The method of any of paragraphs 37-46, wherein the CTC marker gene is selected from the group consisting of:
ALDH1A1; ALDH1A2; IGFBP5; KLF4; DCN; SPARC; WNT; TGFB2; VEGF; COL1A2; COL3A1; and TIMP2.

48. The method of any of paragraphs 37-46, wherein the CTC marker gene is selected from the group consisting of:
ALDH1A2; IGFBP5; KLF4; DCN; and SPARC.

49. The method of any of paragraphs 37-46, wherein the CTC marker gene is selected from the group consisting of:
ALDH1A2; IGFBP5; KLF4; and DCN.

50. The method of any of paragraphs 37-46, wherein the CTC marker gene is selected from the group consisting of:
TPT1; HMGB1; SPON 2; SPARC; and ARSA.

51. The method of any of paragraphs 37-46, wherein the CTC marker gene is selected from the group consisting of:

IL6ST; ARSA; TIMP2; CD55; SULF2; ITGA6; SDC4; CDON; and SV2A.

EXAMPLES

Example 1

Single Cell RNA-Sequencing of Mouse Pancreatic Circulating Tumor Cells Reveals their Expression of ECM Proteins Circulating Tumor Cells (CTCs) are shed from primary tumors into the bloodstream, mediating the hematogenous spread of cancer to distant organs. Using a pancreatic cancer mouse model, a microfluidic device was applied to isolate CTCs independently of tumor epitopes, subjecting these to single cell RNA-sequencing. CTCs clustered into multiple subsets, distinct from primary tumors and cancer cell lines. While proliferative signatures were generally low, CTCs were enriched for MAPK, as well as WNT, TGF-β, Neurotrophin, Toll-like receptor, and B-cell receptor signaling pathways. CTCs were highly enriched for expression of the stem-cell associated gene Aldh1a2. Their virtually universal expression of Igfbp5 and Klf4 was correlated with a subset of primary tumor cells localized to the epithelial/stromal boundary, consistent with the presence of both epithelial and mesenchymal markers in CTCs. The very high CTC expression of stromal-derived extracellular matrix proteins, including Dcn and Sparc, indicates microenvironmental contributions to metastasis and identifies unexpected therapeutic targets.

Introduction

Pancreatic ductal adenocarcinoma (PDAC) is the fourth leading cause of cancer deaths in the US, with a 6% overall survival at 5 years (Society, 2013). The high mortality of this cancer stems from the rapid dissemination of tumor cells leading to widespread metastasis. While local tissue and lymphatic invasion are evident even in early PDAC, the presence of circulating tumor cells (CTCs) in the bloodstream ultimately leads to spread of cancer to distant organs. CTCs are rare, estimated at one to ten tumor cells among ten billion normal blood cells in a milliliter of blood. As such, their isolation and molecular analysis has posed a significant technological challenge (Pantel et al., 2008; Yu et al., 2011). Given their role in blood-borne metastasis, CTC populations are likely to be enriched for metastatic precursors, and their analysis may identify potential therapeutic targets, as well as providing opportunities for early detection of pancreatic cancer.

Genetically engineered mouse pancreatic cancer models have provided important insight into the progression of this disease. Specifically, the genetically engineered LSL-Kras$^{G12D}$, Trp53$^{flox/flox\ or\ +}$, Pdx1-Cre (KPC) mouse model recapitulates the histological progression from preneoplastic pancreatic intraepithelial neoplasia (PanIN) lesions to invasive carcinoma (Bardeesy et al., 2006). Recent studies have suggested that epithelial-to-mesenchymal transition (EMT) occurs early in this model potentially enhancing tumor invasiveness (Rhim et al., 2012). In an initial molecular characterization of mouse pancreatic CTCs, RNA sequencing of CTC-enriched populations was performed, thereby identifying activation of non-canonical WNT signaling as a recurrent event, potentially contributing to the anoikis resistance of circulating epithelial cells (Yu et al., 2012). In that study, analysis of purified CTC populations was accomplished using single molecule RNA sequencing, combined with digital subtraction of matched leukocyte RNA reads, so as to derive a CTC-enriched expression signature. However, transcriptomic analysis of such partially purified cell populations is limited by depth of coverage to the most highly differentially expressed genes, and such studies of bulk CTC populations cannot resolve the degree of heterogeneity across these poorly understood cell populations To achieve a deep RNA sequencing profile of CTCs at the single cell level, a novel inertial focusing-enhanced device, the CTC-iChip, which allows high efficiency negative depletion of normal blood cells, leaving unattached CTCs in solution where they can be selected and analyzed as single cells (Ozkumur et al., 2013) was used. By avoiding tumor epitope-specific capture, such as targeting the epithelial marker EpCAM, the CTC-iChip is unbiased in isolating cancer cells with both epithelial and mesenchymal characteristics. Further, the high quality of RNA purified from viable, untagged CTCs is particularly well suited for detailed transcriptomic analysis. Finally, the use of a mouse model of pancreatic cancer allows for simultaneous analysis of primary tumor and CTCs, while the shared driver mutations across different animals facilitates the identification of CTC-specific heterogeneity. Described herein is a comprehensive transcriptome analysis of CTCs at the single cell level, pointing to distinct cell subsets within CTC populations, signaling pathways that are enriched in CTCs, and identifying unique CTC markers and therapeutic targets.

Results

Isolation of Mouse Pancreatic CTCs.

The CTC-iChip, an integrated microfluidic cell separation platform applied directly to whole blood specimens for isolation of CTCs (Ozkumur et al., 2013) was used in the experiments described herein. It combines initial hydrodynamic size-based separation of all nucleated cells (leukocytes (WBC) and CTCs) away from red blood cells, platelets and plasma, with subsequent inertial focusing of the nucleated cells within a single streamline to achieve high efficiency in-line magnetic sorting. While tumor epitopes are highly variable, WBC cell surface markers are well established; applying magnetic-conjugated anti-WBC antibodies to this very high throughput microfluidic cell separation device can thus exclude the vast majority of WBCs to reveal a small number of untagged CTCs (FIG. 1A). The CTC-iChip was adapted for depletion of murine hematopoietic cells and applied to the KPC pancreatic cancer mouse model. This PDAC model generates significant numbers of CTCs (Rhim et al., 2012; Yu et al., 2012). Whole blood labeling using 100 anti-CD45 beads per WBC achieved>$10^3$ depletion in normal mice, mice bearing orthotopic tumors, and the genetically engineered KPC mice (FIGS. 1B and 4A-4C).

Figure 1C:
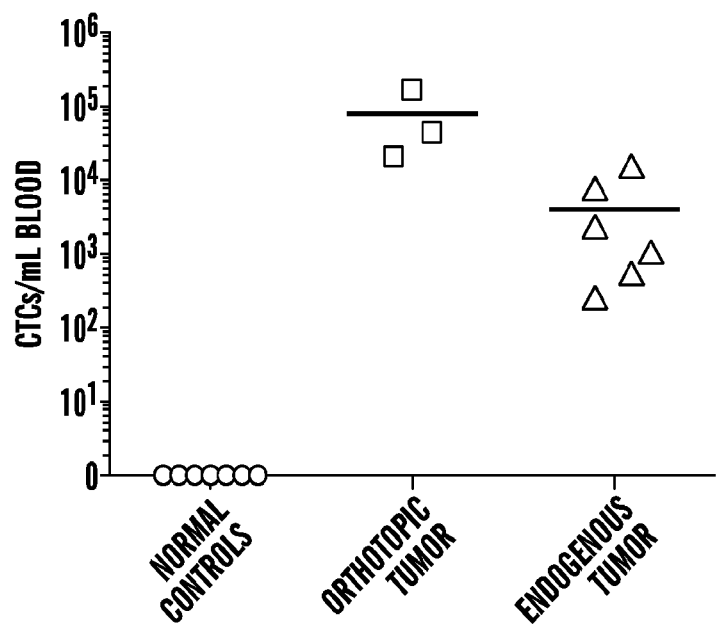
Figure 4A:
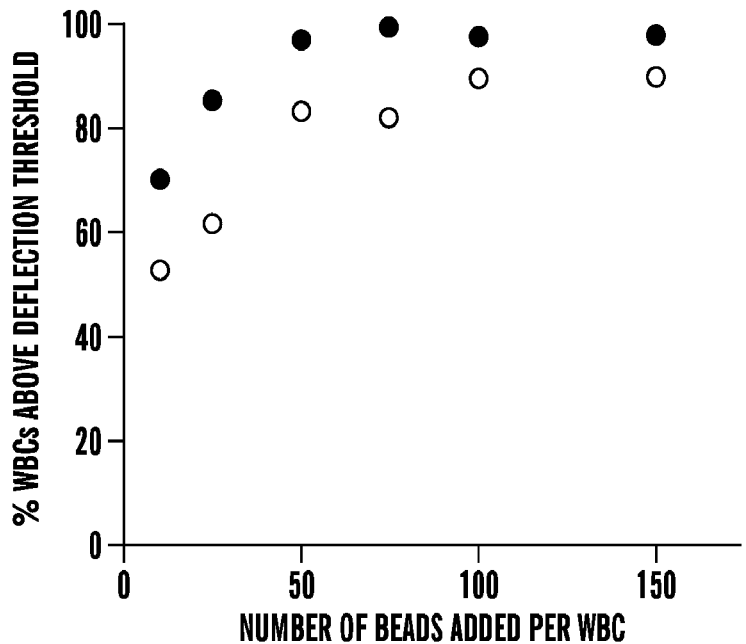
FIGS. 4A-4C demonstrate CTC-iChip characterization.
Figure 4B:
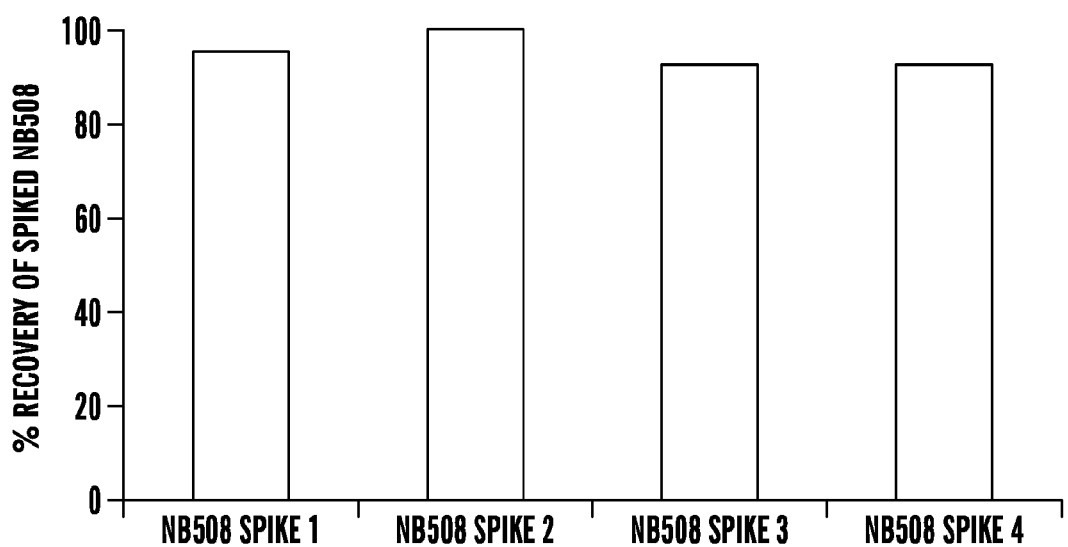
Figure 4C:
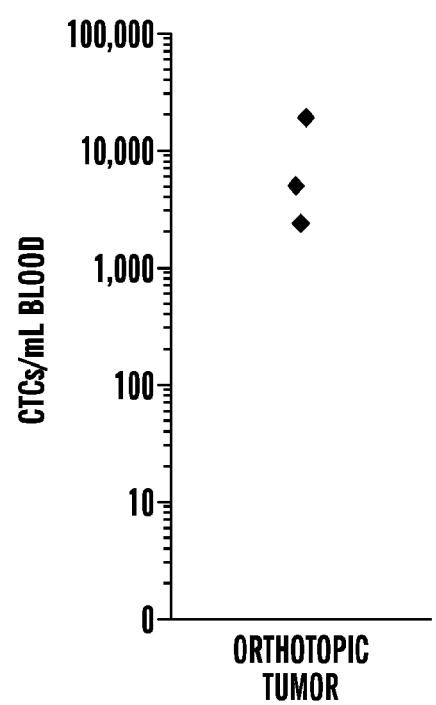

CTC recovery was measured as a mean of 95% (+/−3% std), using GFP-tagged NB508 mouse pancreatic cancer cells spiked into whole mouse blood and processed through the CTC-iChip (FIGS. 4A-4C). NB508 cells were previously generated from a pancreatic tumor arising in the same Kras/Trp53-driven KPC mouse model (Bardeesy et al., 2006). In comparison, only 35% recovery of the same cells was achieved using an alternative microfluidic platform based on anti-EpCAM capture of mouse CTCs (Yu et al., 2012). Applying the CTC-iChip to orthotopic tumors derived from pancreatic inoculation of GFP-tagged NB508 cells generated>1000 CTCs/mL in all three mice tested (FIGS. 4A-4C). Finally, testing the CTC-iChip with the genetically engineered KPC model, followed by dual immunofluorescence staining of isolated cells for the epithelial marker pan-cytokeratin (CK) versus the leukocyte marker CD45, revealed a median 118 CTCs/mL (mean 429 CTCs/ mL; range 0-1694) (FIG. 1C). No CK positive cells were isolated from 7 healthy control mice. The vast majority of CD45 positive cells that failed to be deflected in the microfluidic device retained some immunomagnetic beads on their surface. Thus, CTCs were readily distinguished from WBCs in the CTC-iChip product, enabling single cell manipulation without requiring staining for epithelial-specific cell surface epitopes, such as EpCAM.

Single CTC RNA-Sequencing.

Figure 5B:
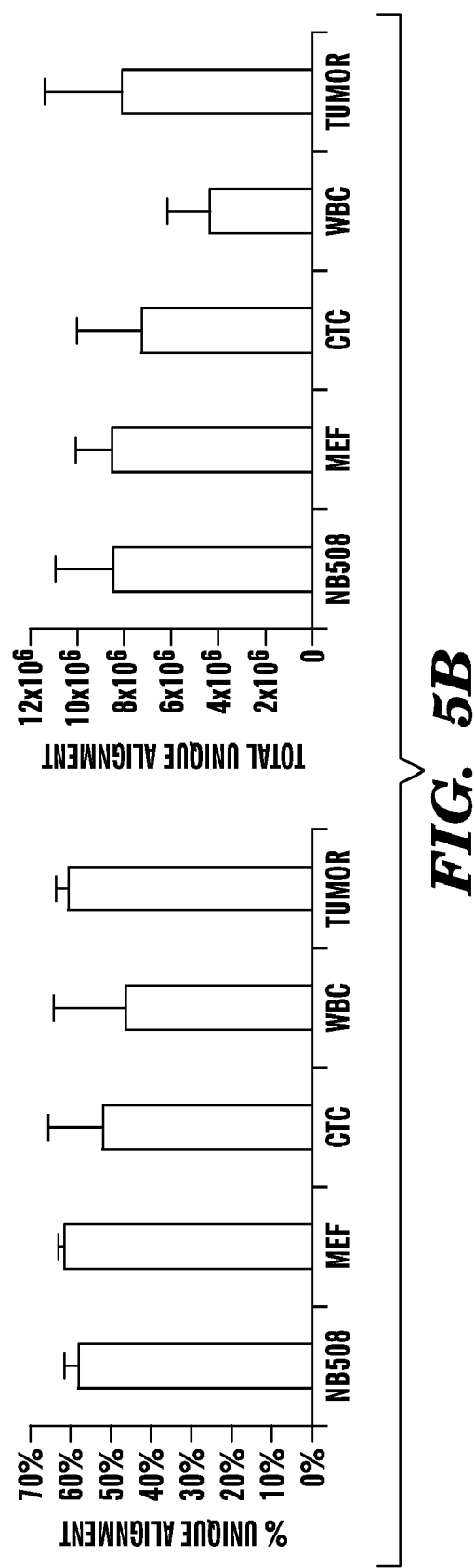
FIG. 5B depicts graphs of quality metrics of single cell sequencing with % of reads aligned and total unique alignments for cell lines (NB508, MEF), CTCs, WBC, and diluted bulk RNA from matched primary tumors.
Figure 5C:
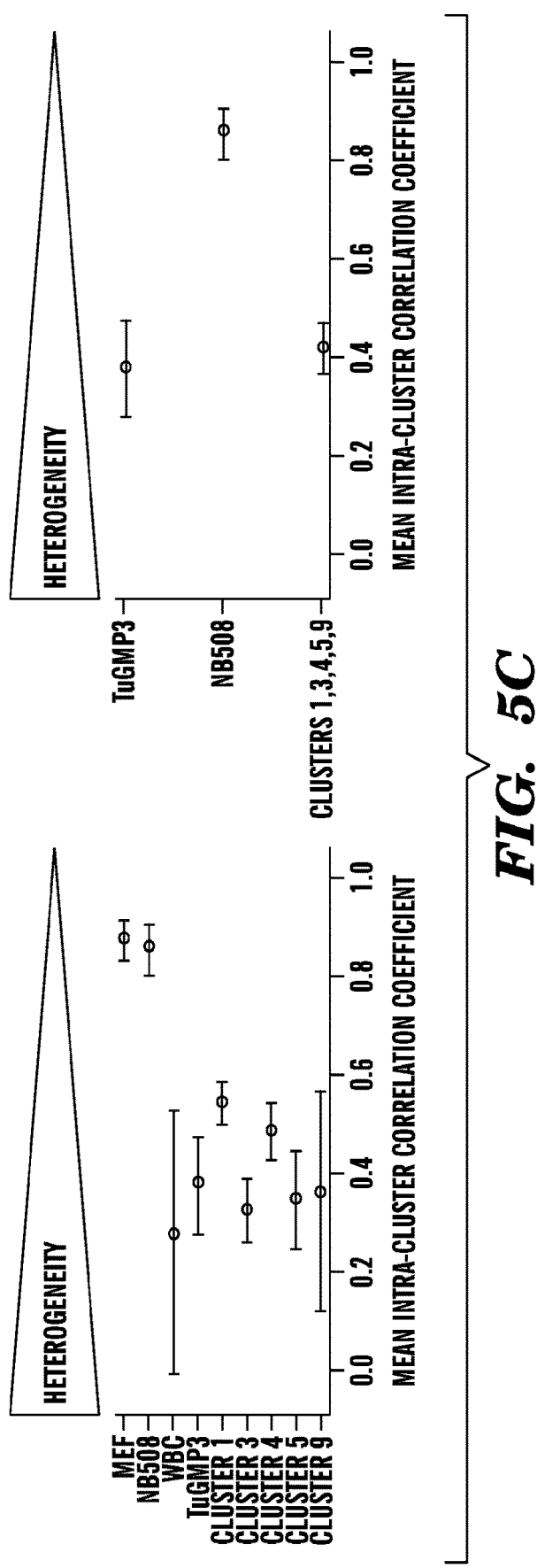
FIG. 5C depicts graphs of single cell heterogeneity using mean intra-cluster correlation coefficient for each cluster (rights) and between single cell primary tumor (TuGMP3), cancer cell line (NB508), and all CTCs (Cluster 1, 3, 4, 5, 9). Circle=mean, Range=95% CI.

Five tumor-bearing KPC mice generated a total of 168 single CTCs that were subjected to a modified initial cDNA amplification and library protocol (Tang et al., 2010), and screened for RNA quality (Gapdh, Actb), presence of pancreatic markers (Krt8, Krt18, Krt19, Pdx1), and absence of WBC markers (Cd45/Ptprc) (FIGS. 5A-5C). Of these, 75 (45%) were of sufficient quality to proceed to further amplification and library construction for next generation sequencing. It is noteworthy that a majority of candidate CTCs (55%) appeared morphologically intact but had degraded RNA. These cells likely represent tumor cells that have lost viability in the bloodstream. Given the rapid processing of blood samples from mouse models, the minimal shear condition in the microfluidic device, and the preserved RNA quality of control cells processed identically, it is unlikely that cells underwent such damage during in vitro purification. For comparison with pancreatic CTCs, single cell RNA-sequencing was also performed on 12 WBCs from a control mouse, 12 mouse embryonic fibroblasts (MEFs), and 16 single cells from the mouse NB508 pancreatic cancer cell line. Over 90% of single cells from NB508 and MEF cultures met criteria for sequencing quality, highlighting the high frequency of CTCs with compromised RNA templates under the same conditions. To compare CTC profiles to that of matched parental tumors harvested at the time of CTC isolation, bulk RNA from each primary tumor was diluted to 1 or 10 cell equivalents (10 or 100 pg RNA) and subjected to the same amplification and RNA-sequencing protocol (n=34; min 8 replicates from 4 matched tumors).

Figure 2:
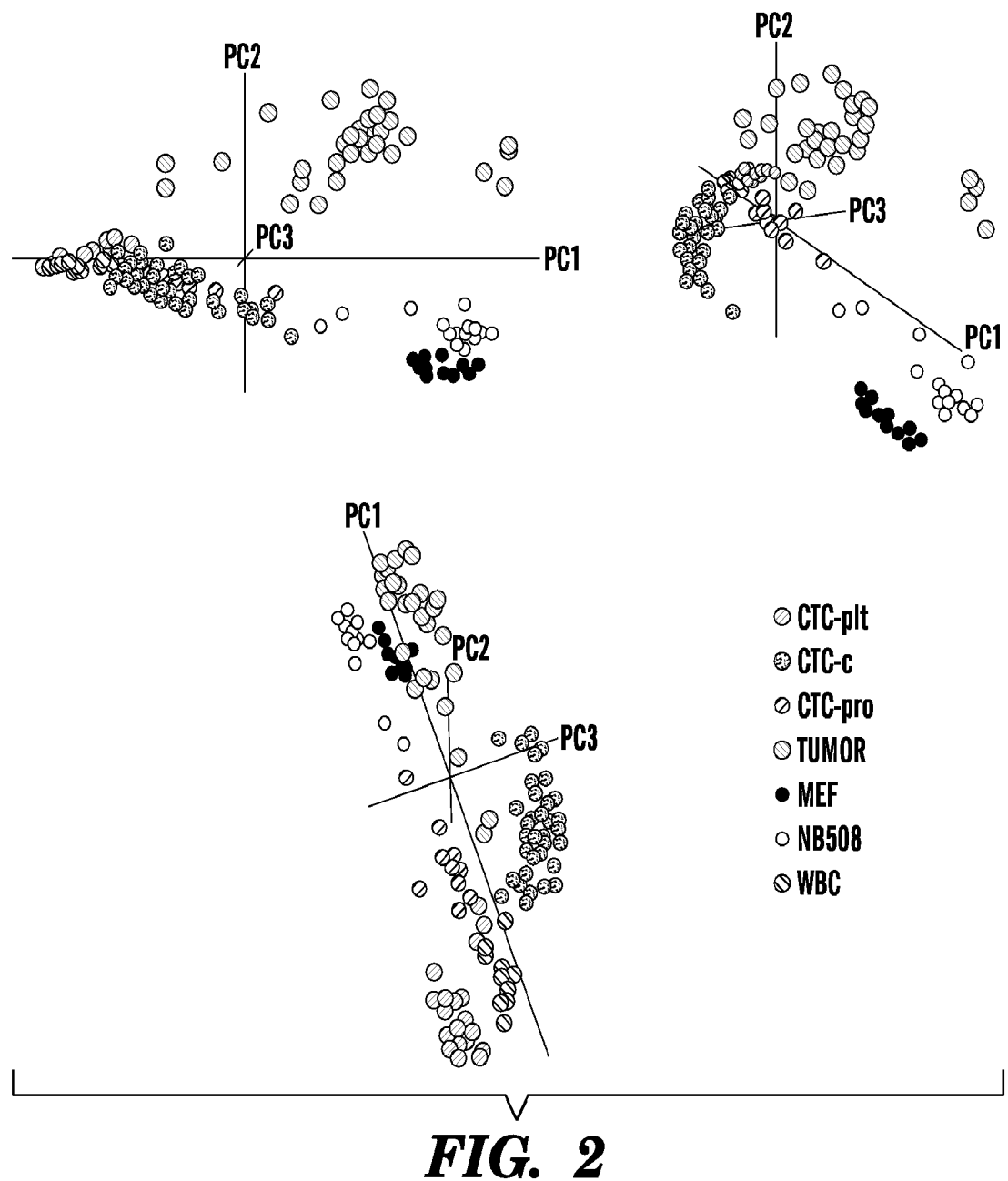
FIG. 2 depicts schematics of principal component analysis of single cell samples.

Single cell RNA sequencing performance was comparable for all samples analyzed, with a mean 4.4-8.5 million reads, of which a mean 46-61% were uniquely aligned to the genome (FIGS. 5A-5C). Genome aligned reads were annotated and counted using UCSC Known Gene transcriptome reference and normalized in reads per million (RPM). Normalized reads were then analyzed by unsupervised hierarchical clustering (data not shown). Single cell transcriptomes from MEFs, the NB508 pancreatic cancer cell line and normal WBCs were tightly clustered, supporting the analytic reliability of the RNA sequencing strategy. Five distinct clusters of candidate CTCs were identified, all of which were distinct from matched primary tumor sequences, as well as from cancer-derived cell lines. Principal component analysis demonstrates the clustering and inter-relationships of these different groups (FIG. 2).

The uniform genetic drivers of PDAC in the KPC mouse model made it possible to quantify measures of cellular heterogeneity in CTCs derived from individual mice and across different mice. Single cell heterogeneity within each CTC cluster was assessed by calculating the intra-cluster correlation coefficients, where lower correlation coefficients reflect higher heterogeneity (FIGS. 5A-5C). As expected, CTC clusters showed considerably more heterogeneity (mean 0.42, 95% CI 0.36-0.47) than single cells derived from the NB508 cancer cell line (mean 0.86, 95% CI 0.80-0.91, p-value $1.2 \times 10^{-15}$). To assess heterogeneity of cells within a primary PDAC, a conditional Tomato/EGFP (mT/mG) expression marker (Muzumdar et al., 2007) was crossed with the KPC mouse to generate a lineage-tagged mouse tumor (KPC-mT/mG), which could be used to isolate individual EGFP positive primary tumor cells away from contaminating stromal cells. A primary tumor (TuGMP3) was disaggregated into single cell suspension and 20 EGFP positive cells were subjected to RNA sequencing. The single primary tumor cells clustered well within the previously analyzed bulk tumor material (data not shown), with a heterogeneity score (mean 0.38, 95% CI 0.28-0.47) similar to that of CTCs (p-value 0.49).

In summary, described herein is the single cell RNA-sequencing of mouse pancreatic CTCs isolated without positive selection bias, along with parental tumors, an established genotype-matched cancer cell line, MEFs and WBCs. CTCs clustered separately from the primary tumor (both bulk tumor and isolated single cells) and from the tumor-derived cell line, with comparable degrees of intercellular heterogeneity between CTCs and primary tumor cells.

Defining Subsets of Pancreatic CTCs.

To identify and classify candidate CTCs, gene sets for known epithelial, hematopoietic, and endothelial markers were applied across all clustered samples. As expected, epithelial markers (Krt7, Krt8, Krt18, Krt19, Epcam, Egfr, Cdh1) were highly expressed in primary pancreatic tumors and in the cancer cell line NB508, and nearly absent in the non-epithelial MEFs and in normal WBCs (data not shown). In contrast, hematopoietic markers (Ptprc/Cd45, Csf3r/Cd114, Cd14, Fcgr3/Cd16, Itga2b/Cd41, Itgb3/Cd61) were present in normal WBCs, and absent in NB508 and MEFs. Some expression of hematopoietic markers was detectable in the bulk primary tumor samples, consistent with varying degrees of leukocytic infiltrates. No specific cluster of endothelial cells was identified, based on expression of characteristic markers (Cdh5/Cd144, Vwf Thbd/Cd141, Pecam1/Cd31, Mcam/Cd146, Sele/E-selectin, Cd34) and absence of epithelial and hematopoietic markers.

Interrogation of single cells isolated by CD45-depletion from tumor-bearing mice, using the epithelial, hematopoietic and endothelial markers, revealed five major candidate CTC groupings (Clusters 1, 3, 4, 5 and 9; data not shown). Clusters 3, 4, and 5 were all part of a larger grouping, showing strong expression of epithelial markers, consistent with "classical" CTCs (denoted CTC-c). A subset of these cells expressed Cd34, an endothelial progenitor marker that is also found in mesenchymal cells including MEFs (data not shown) and stromal cells (Krause et al., 1994), but other characteristic endothelial lineage markers were absent. Clusters 1 and 9 were more complex, with the former noteworthy for enrichment of platelet markers CD41 (Itga2b) and CD61 (Itgb3) (hence denoted CTC-plt), and the latter having a prominent cellular proliferation signature (CTC-pro).

To better define the characteristics of each candidate CTC cluster, a non-parametric differential gene expression analysis including a rank product (RP) methodology adapted to variations in absolute transcript levels and differences in transcriptome representation from cell to cell was used (Breitling et al., 2004). Setting very stringent parameters (FDR≤0.01), the control comparison of primary tumors versus WBCs identified 927 genes relatively overexpressed in tumors and 293 genes high in WBCs, including the expected differential expression of epithelial tumor markers keratin 7, 8, 18, and 19, versus the leukocyte specific CD45 (data not shown). Comparing the "classical" CTC-c cluster to WBCs also showed enrichment for cytokeratin 18 and 19 in CTCs versus CD45 in WBCs, validating the RP methodology to identify relevant differentially expressed genes between single cell populations.

The most abundant CTC cluster, CTC-c, comprised 41 of 75 cells (55%) meeting established criteria for epithelial tumor cells (versus CTC-plt: 32%; CTC-pro: 13%). Of note, the only mouse with multiple gross metastases (MP7) had large numbers of CTCs within this class. Compared with matched primary tumors CTC-c cells had 878 transcripts increased in expression and 774 genes with reduced expression (Table 2). Gene Ontology (GO) analysis of CTC-c enriched genes (Table 3) indicated enrichment for signatures associated with cellular interactions with environmental signals (GO:0045785—positive regulation of cell adhesion; GO:0048584—positive regulation of response to stimulus), cell shape and structure (GO: 0030036—actin cytoskeleton organization; GO:0060429—epithelium development), and transcriptional states (GO:0045449—regulation of transcription; GO:0051276—chromosome organization). To evaluate the contribution of signaling pathways activated by external stimuli in CTC-c cells, the enriched genes were annotated using the KEGG database (Table 1). Kyoto Encyclopedia of Genes and Genomes (KEGG) pathway analysis similarly showed enrichment for focal adhesion (odds ratio [OR]2.7, q-value 6.7 3 10.4) and regulation of actin cytoskeleton (OR 2.4, q-value 0.005). Notably, of the KEGG signaling pathways annotated, the mitogen-activated protein kinase (MAPK) pathway was most highly enriched Most highly represented was the MAPK pathway (OR 2.2, q-value 0.006); MAPK signaling is already activated in the $Kras^{G12D}$ driven primary tumor. However, while MSigDB Kras dependency signatures were enriched in primary tumors compared with CTCs, the latter had increased expression of Braf, Mras and Rras2, pointing to alternative paths to further activate MAPK in CTCs. This finding is consistent with another study that identified the MAPK pathway as being the most highly enriched in pancreatic CTCs using microarray based methodologies (Sergeant et al., 2012).

CTC enriched genes also had representation of well established signaling pathways involved with metastasis, including TGF-β (Ikushima and Miyazono, 2010; Siegel and Massague, 2003), WNT (Anastas and Moon, 2013; Clevers and Nusse, 2012; Katoh and Katoh, 2007), and VEGF (Carmeliet and Jain, 2011; Folkman, 1995). In this cohort of pancreatic cancer CTCs, Wnt4 and Tgfb2 were most highly enriched in CTCs relative to primary tumor, implicating autocrine signaling involving these major pathways. In addition to these well defined contributors to metastasis, CTC expression analyses also revealed activation of unexpected signaling pathways, including the neurotrophin, toll-like receptor, and B-cell receptor pathways. Neurotrophin pathway activation has been reported in pancreatic cancer, particularly in association with increased perineural invasion (Miknyoczki et al., 1996; Miknyoczki et al., 1999; Ohta et al., 1997; Wang et al., 2009; Zhang et al., 2005). Toll-like receptor and B-cell receptor pathways had less representation among CTC reads, but they suggest aberrant activation of immunomodulatory signaling components. Ultimately, the establishment of CTC-derived cultures will be required to test the functional significance of these activated signaling pathways.

While single cells within the CTC-c cluster fulfilled characteristic criteria for tumor cells, defining the identity of the non-classical CTC clusters, CTC-plt and CTC-pro, required additional analyses. Compared with CTC-c, single cells within the CTC-plt cluster had a high enrichment for wound healing and hemostasis signatures, as well as MSigDB platelet and megakaryocyte expression profiles (Table 4). This indicates that these cells are either circulating megakaryocytes/giant platelets or CTCs covered with adherent platelets. Tumor cell specific lineage tagging supports the identification of CTC-plt cells being of tumor origin. Eighteen EGFP lineage-tagged single CTCs from two KPC-mT/mG mice were subjected to single cell RNA sequencing: a total of 9 CTCs from the two mice (7/7 CTCs from mouse GMP1 and 2/11 from mouse GMP2) were included within CTC-plt, using unsupervised hierarchical clustering (data not shown). Thus, the CTC-plt cluster includes CTCs that exhibit strong platelet markers, most likely derived from transcripts encoded by adherent platelets. Interestingly, CTC-plt cells maintained their distinct segregation from CTC-c even after digital removal of all annotated platelet transcripts (data not shown). It is therefore possible that the adherence of abundant platelets may modulate the intrinsic CTC expression profile, as recently suggested by in vitro modeling experiments (Labelle et al., 2011).

The CTC-pro cluster was most similar to both the NB508 pancreatic cancer cell line and MEFs, and it was enriched for the cellular proliferation marker Mki67 when compared to CTC-c. Multiple lineages are likely to have contributed to this complex grouping: CTCs from KPC mice with tumor-restricted, lineage-tagged EGFP expression clustered with CTC-pro (data not shown), noteworthy for abundant expression of Mki67 and an annotated cell cycle signature in MSigDB (Whitfield et al., 2002) (data not shown). One single cell within the CTC-pro cluster was derived from the pancreatic cancer cell line NB508, while another (MP3-2) had high keratin/high E-cadherin expression characteristic of classical CTCs (data not shown). Nonetheless, another sub-cluster contained immune and dendritic cells, identified by their expression of antigen processing and presentation genes (GO:0019886—antigen processing and presentation of exogenous peptide antigen via MHC class II; Table 5). Taken together, the CTC-pro cluster appears to represent a grouping of highly proliferative cells, of which a subset are tumor-derived.

Together, unbiased isolation and RNA sequencing evaluation of single pancreatic CTCs indicate that over half of these are nonviable with RNA at various stages of degradation. Among the remaining viable CTCs, three major classes are distinguishable by unsupervised clustering: the classical subset (CTC-c) accounts for 55%, with a second platelet adherent group (CTC-plt; 32%) and a third heterogeneous cluster marked by proliferative signatures (CTC-pro; 13%). Given their most clearly defined tumor-derived characteristics, we selected the CTC-c cluster for detailed analysis of metastasis-associated pathways.

Pancreatic CTCs Co-Express Epithelial, Mesenchymal, and Stem Cell Markers.

Figure 3A:
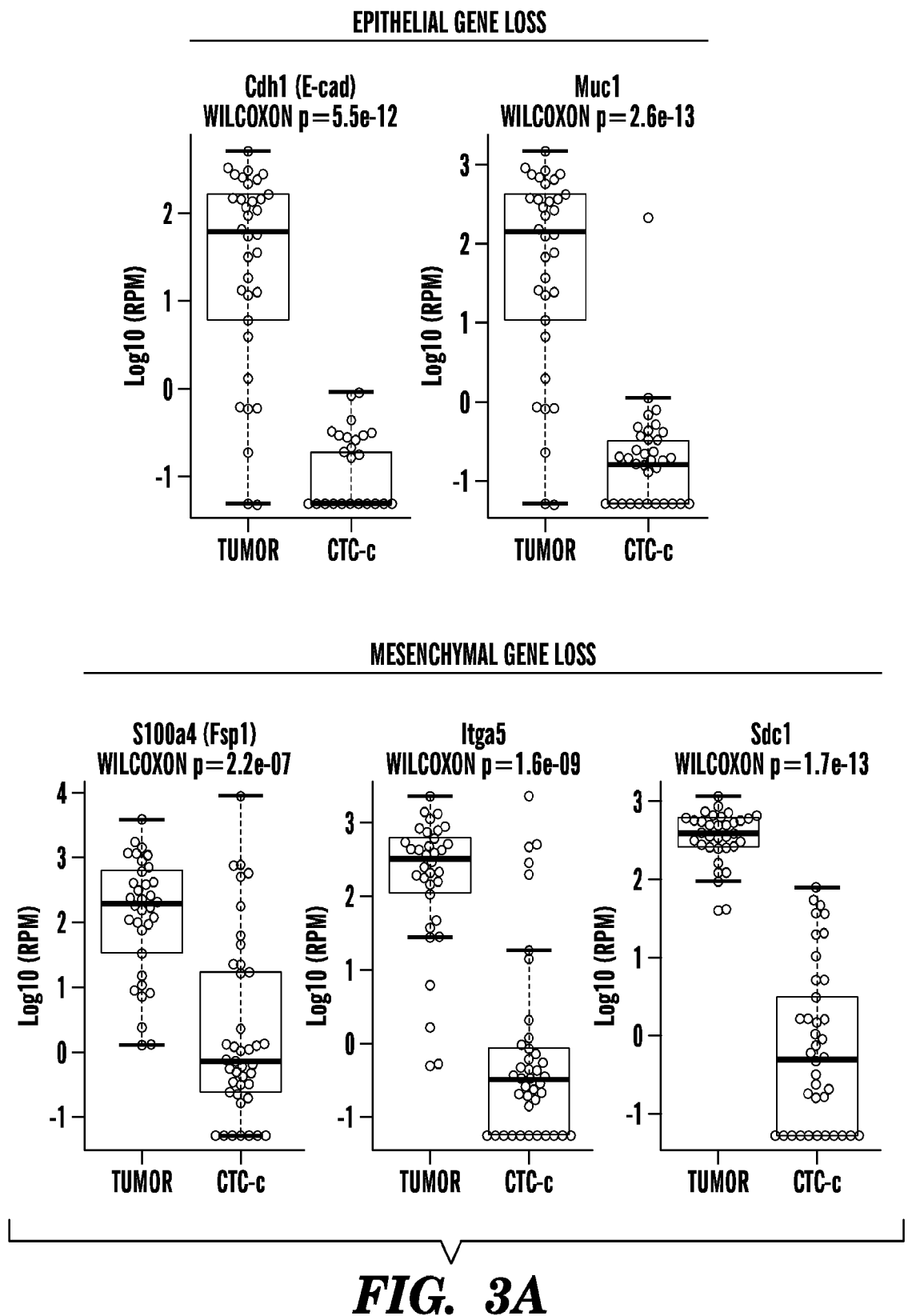
FIGS. 3A-3B demonstrate that epithelial, mesenchymal, and stem cell genes are differentially expressed in CTC-c cells vs Tumors. Depicted are boxplot of genes that are A) downregulated (FIG. 3A) and upregulated (FIG. 3B) in CTC-c cells vs Tumors. Bar=median, box plot=quartiles, scale in log 10 (rpm).
Figure 3B:
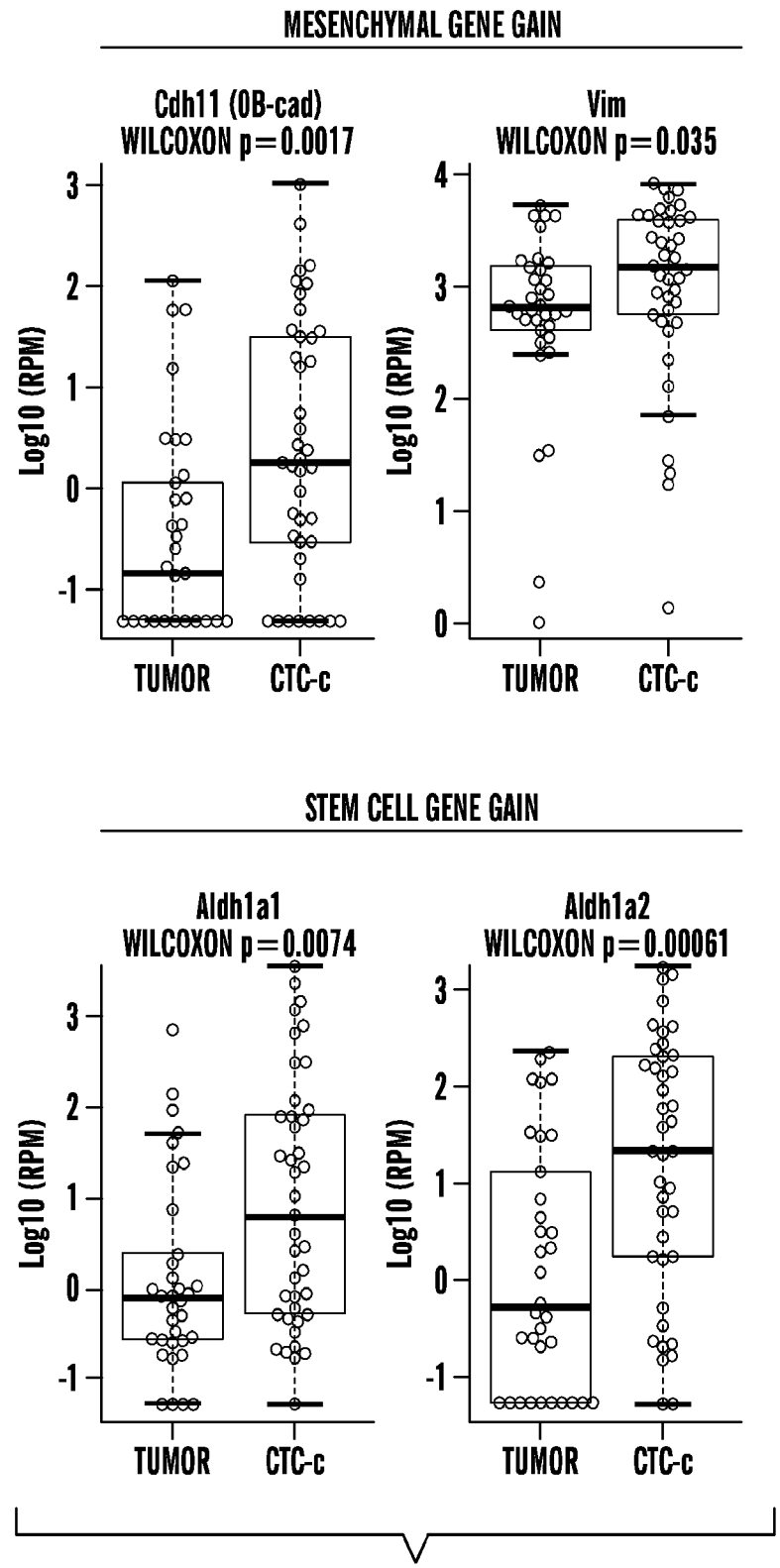

The relevance of EMT to early metastasis in pancreatic cancer has been supported by lineage tracing studies in the KPC mouse model (Rhim et al., 2012). In human breast cancer CTCs, a distribution of epithelial and mesenchymal markers within individual CTCs was recently reported by the inventors, reflecting both tumor histology and response or resistance to diverse therapies (Yu et al., 2013). To directly test for EMT in the mouse pancreatic CTCs, established epithelial (E) and mesenchymal (M) markers (Kalluri and Weinberg, 2009) were used to evaluate each cell within the CTC-c cluster (data not shown). Compared with the primary tumor, CTC-c cells demonstrated clear loss of the epithelial markers E-cadherin (Cdh1) and Muc1, whereas mesenchymal transcripts were mixed, with some showing increased expression (Cdh11, Vim) and others with reduced levels (S100a4, Itga5, Sdc1) (FIGS. 3A and 3B). Notably, even the mesenchymal genes that were upregulated in CTCs showed a high degree of heterogeneous expression across single cells (data not shown). In contrast, loss of epithelial marks, including E-cadherin (Cdh1) was nearly universal across all classical CTCs.

CTCs are also thought to be enriched for metastatic precursors, capable of initiating metastatic tumor deposits. The relationship between such precursor cells and postulated cancer stem cells is uncertain, as is the relevance of established stem cell markers in identifying these cells. Proposed pancreatic cancer stem cell genes (Rasheed and Matsui, 2012; Rasheed et al., 2010) were evaluated in the single cell RNA sequencing reads (FIG. 3B). Among all candidate markers tested (Aldh1a1, Aldh1a2, Prom1/Cd133, Cd44, Met, EpCAM), only Aldh1a1 and Aldh1a2 were enriched in CTCs. Classical CTCs expressed predominantly the Aldh1a2 isoform, while CTC-plt cells were enriched for Aldh1a1, but these isoforms were also co-expressed within some single CTCs. MEFs, NB508 pancreatic cancer cells and normal WBCs also expressed Aldh1a1, but not Aldh1a2 (data not shown). Within single CTCs, there was no correlation between expression of Aldh1 isoforms and enrichment for the mesenchymal genes Cdh11 or Vim, suggesting that these two biomarkers are not intrinsically linked.

Given the identification of Aldh1a2 as a potential stem-like marker expressed by CTCs, its expression within matched primary tumors was tested using RNA in situ hybridization (RNA-ISH). Expression patterns within tumors were heterogeneous: Aldh1a2 expressing cells were primarily localized within the "stromal" or non-epithelial (i.e. keratin low) compartment of the tumor (data not shown). The origin of these non-epithelial cells, which are particularly abundant in pancreatic cancer, is likely to be mixed. Both histological evaluation and negative KRAS mutational analysis (Biankin et al., 2012; Ogino et al., 2005) in human pancreatic cancer have indicated that most of these cells represent reactive fibroblasts or stroma, rather than being of tumor origin. However, lineage tracing in KPC mice has recently shown that a small fraction of these supposedly stromal cells are in fact tumor-derived, presumably having undergone EMT to appear fibroblastic (Rhim et al., 2012). Interestingly, the mouse with the most metastases and the highest number of Aldh1a2 positive CTCs, MP7, also had the primary tumor with the highest levels of Aldh1a2. In that case, Aldh1a2-positive cells were present diffusely in the stromal compartment, as well as comprising a small subpopulation of the epithelial (keratin high) component (data not shown). Thus, classical CTCs, which are keratin-high, express the stem cell-associated gene Aldh1a2, whose expression in primary tumors is restricted to the stromal (keratin low) compartment and only a small subpopulation of epithelial cells.

Classical CTCs Share Expression of Stromal Enriched Genes.

Figure 6:
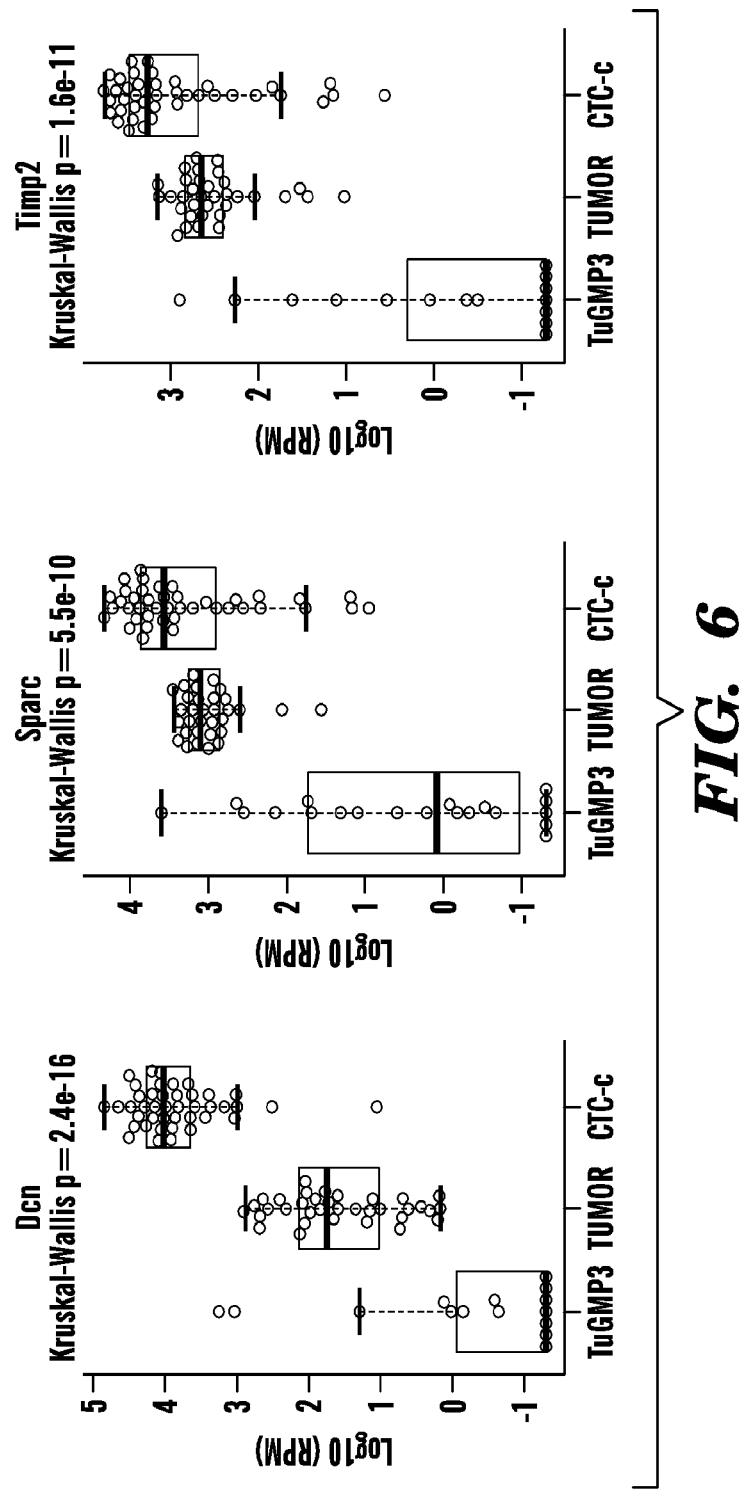
FIG. 6 depicts boxplot graphs of ECM protein gene enriched in CTC-c compared to bulk primary tumors and single cell primary tumors. Bar=median, boxplot—quartiles, scale in log 10 (rpm).
Figure 6:
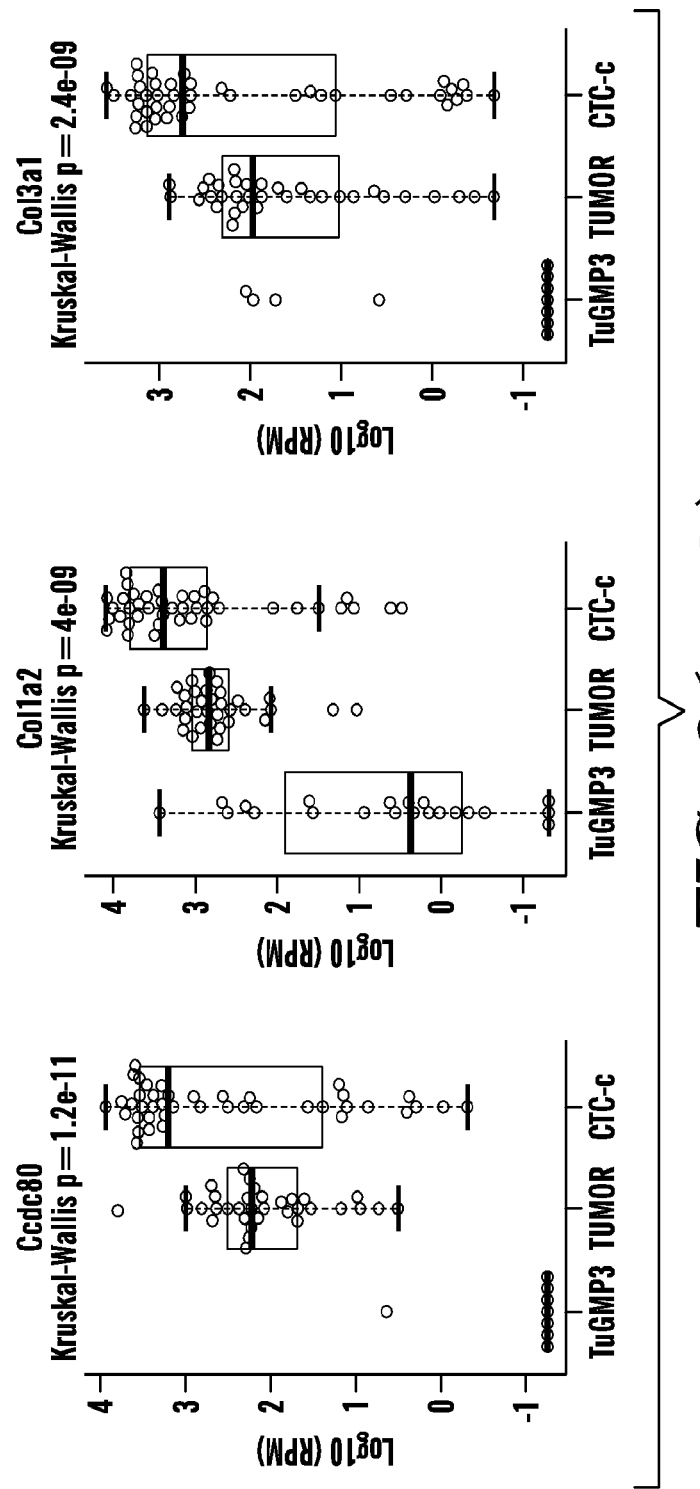

Beside the evident diversity of CTCs, shared transcripts were sought that might provide further insight into their cell of origin within the primary tumor, the mechanisms by which they invade and survive within the bloodstream, and ultimately identify potential CTC-specific therapeutic targets. Rigorous criteria were selected to identify the most highly enriched CTC transcripts (RP score<300), expressed at very high levels (>100 RPM) in ≥90% of all classical CTCs. Three genes met these criteria: Decorin (Dcn), a extracellular matrix proteoglycan expressed in tumor stroma across a variety of different cancers (Adany et al., 1990; Bostrom et al., 2013; Henke et al., 2012; Hunzelmann et al., 1995; Iozzo and Cohen, 1994; Mu et al., 2013; Nash et al., 2002); Insulin-like growth factor binding protein 5 (Igfbp5), an extracellular growth factor binding protein expressed in human PDAC reported to have both pro and anti-proliferative properties (Johnson et al., 2006; Johnson and Haun, 2009); and Kruppel-like factor 4 (Klf4), one of the key stem cell (iPS) reprogramming factors (Takahashi and Yamanaka, 2006), which has been implicated in pancreatic cancer development (Brembeck and Rustgi, 2000; Prasad et al., 2005; Wei et al., 2010). By RNA-ISH, Dcn was expressed diffusely in the stromal elements of the tumor (FIG. 6). Remarkably, both Igfbp5 and Klf4 were expressed focally, predominantly within stromal-appearing cells that border the epithelial compartments of the tumor (data not shown). RNA-ISH of EGFP lineage restricted primary tumors confirmed that the Igfbp5 positive cells at the epithelial/stromal interface are of tumor origin (data not shown). In addition to this transitional region, analysis of Klf4 in this EGFP-tagged tumor also found expression in a subset of epithelial ducts (data not shown). Of note, while they are expressed in only a small subset of primary tumor cells, both Igfbp5 and Klf4 are highly co-expressed in 85% of all classical CTCs. Together with the mixed epithelial/mesenchymal markers evident in CTCs, these observations raise the possibility that many CTCs are derived from foci at the epithelial/stromal interface, that may be defined by Igfbp5 and Klf4 expression.

In addition to the three most highly expressed transcripts, CTCs were noteworthy for high level expression of genes implicated in stromal cell matrix. Gene ontology analysis of all CTC-enriched genes (Table 3) identified 60 extracellular proteins (GO:0044421, OR 1.7, q-value $6.4 \times 10^{-3}$), of which 32 are found in proteinaceous extracellular matrix (ECM) (GO:0005578, OR 2.4, q-value $4.8 \times 10^{-3}$). Recent studies have highlighted the importance of the reactive stroma to pancreatic cancer pathogenesis and metastasis (Feig et al., 2012; Neesse et al., 2013; Neesse et al., 2011; Olive et al., 2009; Provenzano et al., 2012), however, the expression of these stroma-associated ECM genes within tumor cells in circulation was unexpected. To identify the predominant stromal enriched genes in the mouse pancreatic tumor model, we performed RP differential expression analysis between the bulk tumor samples representing tumor cells mixed with reactive stromal cells versus purified EGFP-tagged single cells from the primary tumor (TuGMP3). A total of 51 proteinaceous ECM genes were enriched in bulk tumors versus single primary tumor cells (GO:0005578, OR 4.8, q-value $3.4 \times 10^{-18}$). Of these, 6 genes (Ccdc80, Col1a2, Col3a1, Dcn, Sparc, Timp2) were shared with the previously identified CTC-enriched gene set (data not shown). Decorin (Dcn), as noted above, was identified as the most highly enriched (median 10,686 rpm) in CTCs with high level expression (>100 rpm) in 98% of CTCs. The second most abundant gene was Sparc (median 3,913 rpm) with high expression in 88% of CTCs. These two genes were co-expressed at high levels in 88% of classical CTCs. RNA-ISH of primary tumors for both Dcn (FIG. 6) and Sparc (data not shown) confirmed that these genes are expressed throughout the reactive stroma and are not present in the epithelial keratin-rich regions of primary tumors.

The expression of stromal-derived ECM genes is a common feature of all classical CTCs, yet a mouse-specific bias in distribution among these genes was evident, despite their identical Kras/p53 genetic drivers. This mouse-specific clustering was evident in the unsupervised analysis (p-value<$2.2 \times 10^{-16}$). For instance, sub-cluster 3 was over-represented with single CTCs from mouse MP6, while sub-cluster 4 was enriched for mouse MP7, and sub-cluster 5 for mouse MP2. Of 68 transcripts differentially expressed between the CTCs of mice MP2 and MP7 by RP analysis, gene ontology indicated significant enrichment for 11 extracellular proteins (GO:0044421, OR 3.8, q-value 0.06), 7 of which are found in proteinaceous ECM (GO:0005578, OR 6.3, q-value 0.05) (data not shown). Together, these data indicate that most CTCs derived from a mouse pancreatic cancer model express at high levels a set of ECM genes normally found in the stromal, rather than the epithelial compartment of the primary tumor. This may reflect the origin of many CTCs at the epithelial/stromal interface, consistent with their expression of uniquely restricted markers such as Igfbp5 and Klf4. The fact that individual genetically matched mouse tumors generate CTCs with both shared and unique patterns of ECM gene expression suggests tumor-specific invasion pathways that are superimposed upon fundamental characteristics of CTCs. The high levels of extracellular proteins expressed by CTCs provide unexpected opportunities for targeting these metastatic precursors.

Human Pancreatic CTCs Express the ECM Protein SPARC.

Figure 7:
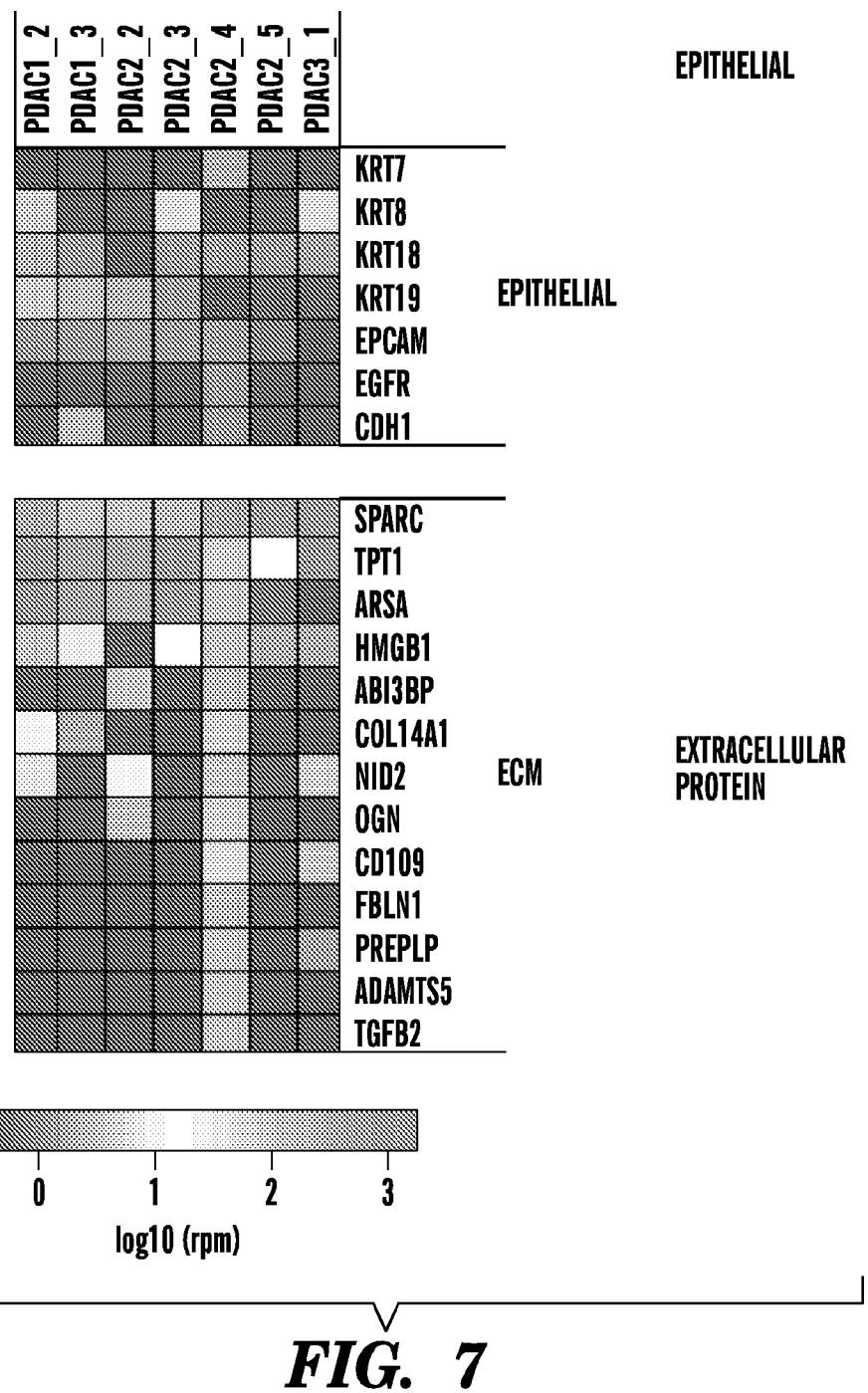
FIG. 7 depicts a heatmap expression profile of human pancreatic CTCs from 3 patients. Epithelial genes used to define CTCs and enriched extracellular proteins shown. Expression shown in log 10 scale.

To determine the relevance of ECM protein expression to human disease, CTCs were isolated from the blood of metastatic PDAC patients and subjected to single cell RNA-sequencing. Analysis of 7 pancreatic CTCs from 3 patients revealed that the majority expressed keratins defining their epithelial origins and a total of 13 of 60 extracellular protein genes enriched in mouse CTCs were expressed at high levels (>100 rpm) in at least one human pancreatic CTC (FIG. 7). Human SPARC was the only gene found at high levels in all human pancreatic CTCs. Analysis of human prostate and breast CTCs also show significant expression of extracellular proteins including SPARC highlighting that these targets are commonly shared in metastatic epithelial cancer cells (data not shown). RNA-ISH of Sparc/SPARC in both mouse and human PDAC found expression confined primarily to the stromal compartment of tumors (data not shown). SPARC expression was found in 196/198 (99%) human primary PDAC tumors and 36% of positive tumors had some detectable SPARC in epithelial tumor cells albeit the minority of the overall signal. The presence of SPARC as an extracellular protein permits antibody directed therapies that target SPARC. Together these data indicate that findings in mouse pancreatic CTCs can be found in human disease and offer both novel biomarkers and therapeutic targets.

Discussion

Described herein is a detailed analysis of CTC composition and diversity, using single cell RNA sequencing. In total, high quality transcriptomes were achieved in 93 single mouse pancreatic CTCs, which were compared with 20 single cells from matched primary tumors, as well as bulk tumor preparations, and with 16 cells from an immortalized cell line established from the same mouse pancreatic tumor model. The use of a mouse model, which closely matches human PDAC, made it possible to compare primary tumor specimens isolated simultaneously with the CTCs. Given the shared Kras/Trp53 genetic drivers in the KPC mouse model, it was also possible to examine CTC heterogeneity within individual mice and across different animals. Finally, the use of the CTC-iChip technology enabled the selection of untagged CTCs, irrespective of their cell surface epitopes, thus avoiding any bias associated with tumor marker-specific cell purification. Together, these observations include the following: 1. CTCs cluster into multiple subsets, including a major "classical CTC" group, and others that are marked by platelet-derived markers or proliferative signatures; 2. While individual mouse tumors may produce CTCs that fit into each of these clusters, there are unique patterns to CTCs derived from individual mice, despite their shared genetic drivers; 3. Common markers shared by virtually all classical CTCs include both epithelial and mesenchymal markers, the Aldh1a2 stem cell marker, and two highly expressed transcripts (Igfbp5 and Klf4) that identify foci localized to the epithelial/stromal boundary of primary tumors; and 4. The most highly enriched CTC-specific transcripts shared by almost all classical CTCs encode extracellular matrix proteins associated with the tumor stromal compartment.

Compared with previous RNA sequencing of partially purified, bulk CTC populations, the single cell analysis reported here provides considerably more depth of tumor cell-specific reads. As such, the detailed analysis of classical CTCs from the mouse pancreatic cancer model is unprecedented. It is demonstrated herein that pancreatic cancer CTCs uniformly lose expression of the epithelial marker E-cadherin (Cdh1), a key feature of epithelial-to-mesenchymal transition. However, the cells do not lose expression of other epithelial markers, such as cytokeratins, nor is there a consistent increase in classical EMT mesenchymal markers such as vimentin. As such, most classical CTCs appear arrested in a biphenotypic state. Despite their expression of cytokeratins (present in the epithelial components of the primary tumor), most other highly expressed markers in CTCs were shared with the non-epithelial or "stromal" component of the primary tumor. Among these stromal genes expressed in classical CTCs is Aldh1a2, a putative pancreatic cancer stem cell marker (Rasheed and Matsui, 2012; Rasheed et al., 2010). Whether Aldh1a2 is a functionally significant marker of cellular plasticity in metastatic precursors remains to be determined.

A provocative observation relating to the shared epithelial and mesenchymal state of classical CTCs is their virtually uniform (>85%) high level co-expression of Igfbp5 and Klf4, two genes that are only expressed in a small subpopulation of cells at the epithelial/stromal interface within primary tumors. This raises the intriguing possibility that this critical location within the tumor generates a disproportionate fraction of viable CTCs. Indeed, tumor cells that are actively undergoing EMT are presumably enriched at the epithelial-stromal function, contributing to the mixed lineage of the tumor stroma, with both tumor-derived and non-malignant reactive cell types. The potential roles of both IGF signaling and Klf4 transcriptional regulation in embryonic development and pancreatic malignancy make their unique expression pattern in both tumors and CTCs particularly noteworthy.

Finally, the most unexpected observation from this single CTC RNA sequencing study is the very high level abundance of ECM proteins on the vast majority of classical CTCs. Notably, prior evaluation of matched primary and metastatic breast tumors identified the most prevalent gene expression difference as enrichment for ECM molecules in the metastases, comprising some 18% of differentially expressed genes (Weigelt et al., 2005). While this has been interpreted as reflecting differences in the local environment of the metastatic site, the present data indicate that ECM proteins are highly expressed by CTCs themselves. By analogy with the classical "seed versus soil" debate (Fidler, 2003), CTCs may in fact be seeds carrying some of their own soil.

The ultimate goal of detailed molecular analysis of CTCs is to understand the process by which they are generated and their therapeutic vulnerabilities. In this regard, an important observation derived from the present single CTC RNA sequencing analysis is the unexpected expression of extracellular proteins with a preponderance of proteins found in ECM. Two of the most abundant and commonly shared ECM proteins in CTCs are Dcn and Sparc, both of which are established tumor stromal genes. Notably, Sparc expressing stroma appears to bind albumin-conjugated chemotherapy-containing nanoparticles (nab-paclitaxel) allowing for increased cytotoxicity and efficacy in human PDAC (Neuzillet et al., 2013; Von Hoff et al., 2011; Yardley, 2013). Indeed, considerable effort has been directed to targeting pancreatic cancer stroma as a means of improving delivery of chemotherapeutics and stripping tumor cells of their supportive microenvironment (Neesse et al., 2011; Olive et al., 2009; Provenzano et al., 2012; Rasheed et al., 2012). The finding that these gene products are also expressed by CTCs indicates that antibody-directed therapies can be used not only against primary tumor stroma, but also to target tumor cells as they transit in the blood.

As described herein, the present CTC analyses to extend from matching them to known tumor-defining markers to interrogating them for unique properties that distinguish them from most primary tumor cells and may underlie their ability to survive in the bloodstream and generate distant metastases. Such insights into the cellular process of human cancer metastasis are critical to the goal of ultimately preventing the spread of a primary tumor to distant organs.

Experimental Procedures

Mice and cell lines. Mice with pancreatic cancer used in these experiments express Cre driven by Pdx1, LSL-$Kras^{G12D}$, and $Trp53^{lox/+}$ or $Trp53^{lox/lox}$ as previously described (Bardeesy et al., 2006). EGFP pancreatic lineage tagged KPC mice were generated by breeding the mT/mG mouse (Jackson Laboratory—Gt(ROSA)26Sortm4(ACTB-tdTomato,-EGFP)Luo/J) into the breeder pairs used for KPC mouse generation. Normal FVB mice were purchased from Jackson Laboratory. All mice care and procedures were done under MGH SRAC approved protocols.

Adaptation of CTC Enrichment Technology.

Given the desire for an unbiased enrichment system, the previously presented negative depletion technology was selected for this application (Ozkumur et al., 2013). All processing protocols were identical to those previously identified, except a rat anti-mouse CD45 antibody (BAM114, R&D Systems, USA) was conjugated to MyOne beads.

Single Cell Micromanipulation, Amplification, and Sequencing.

After whole blood anti-CD45 negative depletion, the product containing enriched cells was collected in a 35 mm petri dish and viewed using a Nikon Eclipse Ti™ inverted fluorescent microscope. Cells of interest were identified based on intact cellular morphology and lack of labeling with anti-CD45 magnetic beads. These target cells were individually micromanipulated with a 10 μm transfer tip on an Eppendorf TransferMan® NK 2 micromanipulator and ejected into PCR tubes containing RNA protective lysis buffer and immediately flash frozen in liquid nitrogen. Single cells were amplified with a modified protocol (Tang et al., 2010) and sequenced on the ABI 5500XL™ system.

RNA In Situ Hybridization (RNA-ISH).

RNA-ISH was performed according to the Affymetrix QuantiGene ViewRNA ISH Tissue-2 Plex Assay™.

REFERENCES

Adany, R., Heimer, R., Caterson, B., Sorrell, J. M., and Iozzo, R. V. (1990). Altered expression of chondroitin sulfate proteoglycan in the stroma of human colon carcinoma. Hypomethylation of PG-40 gene correlates with increased PG-40 content and mRNA levels. The Journal of biological chemistry 265, 11389-11396.

Anastas, J. N., and Moon, R. T. (2013). WNT signalling pathways as therapeutic targets in cancer. Nat Rev Cancer 13, 11-26.

Bardeesy, N., Aguirre, A. J., Chu, G. C., Cheng, K. H., Lopez, L. V., Hezel, A. F., Feng, B., Brennan, C., Weissleder, R., Mahmood, U., et al. (2006). Both p16 (Ink4a) and the p19(Arf)-p53 pathway constrain progression of pancreatic adenocarcinoma in the mouse. Proc Natl Acad Sci USA 103, 5947-5952.

Biankin, A. V., Waddell, N., Kassahn, K. S., Gingras, M. C., Muthuswamy, L. B., Johns, A. L., Miller, D. K., Wilson, P. J., Patch, A. M., Wu, J., et al. (2012). Pancreatic cancer genomes reveal aberrations in axon guidance pathway genes. Nature 491, 399-405.

Bostrom, P., Sainio, A., Kakko, T., Savontaus, M., Soderstrom, M., and Jarvelainen, H. (2013). Localization of decorin gene expression in normal human breast tissue and in benign and malignant tumors of the human breast. Histochemistry and cell biology 139, 161-171.

Breitling, R., Armengaud, P., Amtmann, A., and Herzyk, P. (2004). Rank products: a simple, yet powerful, new method to detect differentially regulated genes in replicated microarray experiments. FEBS letters 573, 83-92.

Brembeck, F. H., and Rustgi, A. K. (2000). The tissue-dependent keratin 19 gene transcription is regulated by GKLF/KLF4 and Sp. The Journal of biological chemistry 275, 28230-28239.

Cann, G. M., Gulzar, Z. G., Cooper, S., Li, R., Luo, S., Tat, M., Stuart, S., Schroth, G., Srinivas, S., Ronaghi, M., et al. (2012). mRNA-Seq of single prostate cancer circulating tumor cells reveals recapitulation of gene expression and pathways found in prostate cancer. PLoS One 7, e49144.

Carmeliet, P., and Jain, R. K. (2011). Molecular mechanisms and clinical applications of angiogenesis. Nature 473, 298-307.

Chen, C. L., Mahalingam, D., Osmulski, P., Jadhav, R. R., Wang, C. M., Leach, R. J., Chang, T. C., Weitman, S. D., Kumar, A. P., Sun, L., et al. (2013). Single-cell analysis of circulating tumor cells identifies cumulative expression patterns of EMT-related genes in metastatic prostate cancer. The Prostate 73, 813-826.

Clevers, H., and Nusse, R. (2012). Wnt/beta-catenin signaling and disease. Cell 149, 1192-1205.

Feig, C., Gopinathan, A., Neesse, A., Chan, D. S., Cook, N., and Tuveson, D. A. (2012). The pancreas cancer microenvironment. Clin Cancer Res 18, 4266-4276.

Fidler, I. J. (2003). The pathogenesis of cancer metastasis: the 'seed and soil' hypothesis revisited. Nat Rev Cancer 3, 453-458.

Folkman, J. (1995). Angiogenesis in cancer, vascular, rheumatoid and other disease. Nature medicine 1, 27-31.

Henke, A., Grace, O. C., Ashley, G. R., Stewart, G. D., Riddick, A. C., Yeun, H., O'Donnell, M., Anderson, R. A., and Thomson, A. A. (2012). Stromal expression of decorin, Semaphorin6D, SPARC, Sprouty1 and Tsukushi in developing prostate and decreased levels of decorin in prostate cancer. PLoS One 7, e42516.

Hunzelmann, N., Schonherr, E., Bonnekoh, B., Hartmann, C., Kresse, H., and Krieg, T. (1995). Altered immunohistochemical expression of small proteoglycans in the tumor tissue and stroma of basal cell carcinoma. The Journal of investigative dermatology 104, 509-513.

Ikushima, H., and Miyazono, K. (2010). TGFbeta signalling: a complex web in cancer progression. Nat Rev Cancer 10, 415-424.

Iozzo, R. V., and Cohen, I. (1994). Altered proteoglycan gene expression and the tumor stroma. Exs 70, 199-214.

Johnson, S. K., Dennis, R. A., Barone, G. W., Lamps, L. W., and Haun, R. S. (2006). Differential expression of insulin-like growth factor binding protein-5 in pancreatic adenocarcinomas: identification using DNA microarray. Molecular carcinogenesis 45, 814-827.

Johnson, S. K., and Haun, R. S. (2009). Insulin-like growth factor binding protein-5 influences pancreatic cancer cell growth. World journal of gastroenterology: WJG 15, 3355-3366.

Kalluri, R., and Weinberg, R. A. (2009). The basics of epithelial-mesenchymal transition. J Clin Invest 119, 1420-1428.

Katoh, M., and Katoh, M. (2007). WNT signaling pathway and stem cell signaling network. Clin Cancer Res 13, 4042-4045.

Krause, D. S., Ito, T., Fackler, M. J., Smith, O. M., Collector, M. I., Sharkis, S. J., and May, W. S. (1994). Characterization of murine CD34, a marker for hematopoietic progenitor and stem cells. Blood 84, 691-701.

Labelle, M., Begum, S., and Hynes, R. O. (2011). Direct signaling between platelets and cancer cells induces an epithelial-mesenchymal-like transition and promotes metastasis. Cancer Cell 20, 576-590.

Miknyoczki, S. J., Klein-Szanto, A. J., and Ruggeri, B. A. (1996). Neurotrophin-Trk receptor interactions in neoplasia: a possible role in interstitial and perineural invasion in ductal pancreatic cancer. Critical reviews in oncogenesis 7, 89-100.

Miknyoczki, S. J., Lang, D., Huang, L., Klein-Szanto, A. J., Dionne, C. A., and Ruggeri, B. A. (1999). Neurotrophins and Trk receptors in human pancreatic ductal adenocarcinoma: expression patterns and effects on in vitro invasive behavior. International journal of cancer Journal international du cancer 81, 417-427.

Mu, Y., Chen, Y., Zhang, G., Zhan, X., Li, Y., Liu, T., Li, G., Li, M., Xiao, Z., Gong, X., et al. (2013). Identification of stromal differentially expressed proteins in the colon carcinoma by quantitative proteomics. Electrophoresis 34, 1679-1692.

Muzumdar, M. D., Tasic, B., Miyamichi, K., Li, L., and Luo, L. (2007). A global double-fluorescent Cre reporter mouse. Genesis 45, 593-605.

Nash, M. A., Deavers, M. T., and Freedman, R. S. (2002). The expression of decorin in human ovarian tumors. Clin Cancer Res 8, 1754-1760.

Neesse, A., Frese, K. K., Bapiro, T. E., Nakagawa, T., Sternlicht, M. D., Seeley, T. W., Pilarsky, C., Jodrell, D. I., Spong, S. M., and Tuveson, D. A. (2013). CTGF antagonism with mAb FG-3019 enhances chemotherapy response without increasing drug delivery in murine ductal pancreas cancer. Proc Natl Acad Sci USA 110, 12325-12330.

Neesse, A., Michl, P., Frese, K. K., Feig, C., Cook, N., Jacobetz, M. A., Lolkema, M. P., Buchholz, M., Olive, K. P., Gress, T. M., et al. (2011). Stromal biology and therapy in pancreatic cancer. Gut 60, 861-868.

Neuzillet, C., Tijeras-Raballand, A., Cros, J., Faivre, S., Hammel, P., and Raymond, E. (2013). Stromal expression of SPARC in pancreatic adenocarcinoma. Cancer metastasis reviews.

Ogino, S., Kawasaki, T., Brahmandam, M., Yan, L., Cantor, M., Namgyal, C., Mino-Kenudson, M., Lauwers, G. Y., Loda, M., and Fuchs, C. S. (2005). Sensitive sequencing method for KRAS mutation detection by Pyrosequencing. The Journal of molecular diagnostics: JMD 7, 413-421.

Ohta, T., Numata, M., Tsukioka, Y., Futagami, F., Kayahara, M., Kitagawa, H., Nagakawa, T., Yamamoto, M., Wakayama, T., Kitamura, Y., et al. (1997). Neurotrophin-3 expression in human pancreatic cancers. The Journal of pathology 181, 405-412.

Olive, K. P., Jacobetz, M. A., Davidson, C. J., Gopinathan, A., McIntyre, D., Honess, D., Madhu, B., Goldgraben, M. A., Caldwell, M. E., Allard, D., et al. (2009). Inhibition of Hedgehog signaling enhances delivery of chemotherapy in a mouse model of pancreatic cancer. Science 324, 1457-1461.

Ozkumur, E., Shah, A. M., Ciciliano, J. C., Emmink, B. L., Miyamoto, D. T., Brachtel, E., Yu, M., Chen, P. I., Morgan, B., Trautwein, J., et al. (2013). Inertial focusing for tumor antigen-dependent and -independent sorting of rare circulating tumor cells. Sci Transl Med 5, 179ra147.

Pantel, K., Brakenhoff, R. H., and Brandt, B. (2008). Detection, clinical relevance and specific biological properties of disseminating tumour cells. Nat Rev Cancer 8, 329-340.

Powell, A. A., Talasaz, A. H., Zhang, H., Coram, M. A., Reddy, A., Deng, G., Telli, M. L., Advani, R. H., Carlson, R. W., Mollick, J. A., et al. (2012). Single cell profiling of circulating tumor cells: transcriptional heterogeneity and diversity from breast cancer cell lines. PLoS One 7, e33788.

Prasad, N. B., Biankin, A. V., Fukushima, N., Maitra, A., Dhara, S., Elkahloun, A. G., Hruban, R. H., Goggins, M., and Leach, S. D. (2005). Gene expression profiles in pancreatic intraepithelial neoplasia reflect the effects of Hedgehog signaling on pancreatic ductal epithelial cells. Cancer Res 65, 1619-1626.

Provenzano, P. P., Cuevas, C., Chang, A. E., Goel, V. K., Von Hoff, D. D., and Hingorani, S. R. (2012). Enzymatic targeting of the stroma ablates physical barriers to treatment of pancreatic ductal adenocarcinoma. Cancer Cell 21, 418-429.

Ramskold, D., Luo, S., Wang, Y. C., Li, R., Deng, Q., Faridani, O. R., Daniels, G. A., Khrebtukova, I., Loring, J. F., Laurent, L. C., et al. (2012). Full-length mRNA-Seq from single-cell levels of RNA and individual circulating tumor cells. Nat Biotechnol 30, 777-782.

Rasheed, Z. A., and Matsui, W. (2012). Biological and clinical relevance of stem cells in pancreatic adenocarcinoma. Journal of gastroenterology and hepatology 27 Suppl 2, 15-18.

Rasheed, Z. A., Matsui, W., and Maitra, A. (2012). Pathology of pancreatic stroma in PDAC. In Pancreatic Cancer and Tumor Microenvironment, P. J. Grippo, and H. G. Munshi, eds. (Trivandrum (India)).

Rasheed, Z. A., Yang, J., Wang, Q., Kowalski, J., Freed, I., Murter, C., Hong, S. M., Koorstra, J. B., Rajeshkumar, N. V., He, X., et al. (2010). Prognostic significance of tumorigenic cells with mesenchymal features in pancreatic adenocarcinoma. J Natl Cancer Inst 102, 340-351.

Rhim, A. D., Mirek, E. T., Aiello, N. M., Maitra, A., Bailey, J. M., McAllister, F., Reichert, M., Beatty, G. L., Rustgi, A. K., Vonderheide, R. H., et al. (2012). EMT and dissemination precede pancreatic tumor formation. Cell 148, 349-361.

Sergeant, G., van Eijsden, R., Roskams, T., Van Duppen, V., and Topal, B. (2012). Pancreatic cancer circulating tumour cells express a cell motility gene signature that predicts survival after surgery. BMC cancer 12, 527.

Siegel, P. M., and Massague, J. (2003). Cytostatic and apoptotic actions of TGF-beta in homeostasis and cancer. Nat Rev Cancer 3, 807-821.

Society, A. C. (2013). Cancer Facts & Figures 2013 (Atlanta: American Cancer Society).

Takahashi, K., and Yamanaka, S. (2006). Induction of pluripotent stem cells from mouse embryonic and adult fibroblast cultures by defined factors. Cell 126, 663-676.

Tang, F., Barbacioru, C., Nordman, E., Li, B., Xu, N., Bashkirov, V. I., Lao, K., and Surani, M. A. (2010). RNA-Seq analysis to capture the transcriptome landscape of a single cell. Nat Protoc 5, 516-535.

Von Hoff, D. D., Ramanathan, R. K., Borad, M. J., Laheru, D. A., Smith, L. S., Wood, T. E., Korn, R. L., Desai, N., Trieu, V., Iglesias, J. L., et al. (2011). Gemcitabine plus nab-paclitaxel is an active regimen in patients with advanced pancreatic cancer: a phase I/II trial. J Clin Oncol 29, 4548-4554.

Wang, W., Zhao, H., Zhang, S., Kang, E., Chen, Y., Ni, C., Zhang, S., and Zhu, M. (2009). Patterns of expression and function of the p75(NGFR) protein in pancreatic cancer cells and tumours. European journal of surgical oncology: the journal of the European Society of Surgical Oncology and the British Association of Surgical Oncology 35, 826-832.

Wei, D., Wang, L., Kanai, M., Jia, Z., Le, X., Li, Q., Wang, H., and Xie, K. (2010). KLF4alpha up-regulation promotes cell cycle progression and reduces survival time of patients with pancreatic cancer. Gastroenterology 139, 2135-2145.

Weigelt, B., Wessels, L. F., Bosma, A. J., Glas, A. M., Nuyten, D. S., He, Y. D., Dai, H., Peterse, J. L., and van't Veer, L. J. (2005). No common denominator for breast cancer lymph node metastasis. Br J Cancer 93, 924-932.

Welty, C. J., Coleman, I., Coleman, R., Lakely, B., Xia, J., Chen, S., Gulati, R., Larson, S. R., Lange, P. H., Montgomery, B., et al. (2013). Single cell transcriptomic analysis of prostate cancer cells. BMC molecular biology 14, 6.

Whitfield, M. L., Sherlock, G., Saldanha, A. J., Murray, J. I., Ball, C. A., Alexander, K. E., Matese, J. C., Perou, C. M., Hurt, M. M., Brown, P. O., et al. (2002). Identification of genes periodically expressed in the human cell cycle and their expression in tumors. Molecular biology of the cell 13, 1977-2000.

Yardley, D. A. (2013). nab-Paclitaxel mechanisms of action and delivery. Journal of controlled release: official journal of the Controlled Release Society 170, 365-372.

Yu, M., Stott, S., Toner, M., Maheswaran, S., and Haber, D. A. (2011). Circulating tumor cells: approaches to isolation and characterization. J Cell Biol 192, 373-382.

Yu, M., Ting, D. T., Stott, S. L., Wittner, B. S., Ozsolak, F., Paul, S., Ciciliano, J. C., Smas, M. E., Winokur, D., Gilman, A. J., et al. (2012). RNA sequencing of pancreatic circulating tumour cells implicates WNT signalling in metastasis. Nature 487, 510-513.

Zhang, Y., Dang, C., Ma, Q., and Shimahara, Y. (2005). Expression of nerve growth factor receptors and their prognostic value in human pancreatic cancer. Oncology reports 14, 161-171.

TABLE 1

Annotation of CTC enriched genes in KEGG defined signaling pathways.
*indicates gene found in multiple pathway gene sets.

| MAPK Pathway | WNT Pathway | Neurotropin Pathway | TGF-beta Pathway | Toll-Like Receptor Pathway | VEGF Pathway |
|---|---|---|---|---|---|
| 1500003o03rik* | Jund | 1500003o03rik* | Akt2* | Amhr2 | Akt2* | 1500003o03rik* |
| Akt2* | Map3k3* | Crebbp* | Braf* | Crebbp* | Fos* | Akt2* |
| B230120h23rik | Mapk1* | Csnk1a1 | Calm1 | Dcn | Ifnar2 | Hspb1* |
| Braf* | Mapkapk3* | Jun* | Calm2 | Id1 | Irak4* | Kdr |
| Dusp1 | Mef2c | Nkd1 | Irak4* | Id2 | Irf7 | Mapk1* |
| Dusp14 | Mras | Ppp3ca* | Irs2 | Mapk1* | Jun* | Mapkapk3* |
| Dusp3 | Nf1 | Rock1* | Jun* | Rock1* | Mapk1* | Pla2g4a* |
| Fas | Nfkb2 | Rock2* | Maged1 | Rock2* | Nfkbia* | Ppp3ca* |
| Fgf1 | Nr4a1 | Siah1a | Map3k3* | Smad4* | Tirap | Src |
| Flnc | Pla2g4a* | Smad4* | Mapk1* | Tgfb2* | Tlr2 | |
| Fos* | Ppp3ca* | Tbl1x | Nfkbia* | Tgfbr2* | | |
| Gadd45b | Rras2 | Tcf7l1 | Shc1 | Thbs1 | | |
| Hspa2 | Tgfb2* | Wnt4 | Ywhaz | | | |
| Hspb1* | Tgfbr2* | | | | | |
| Jun* | | | | | | |

TABLE 2

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 1 | Upk3b | Tff2 | Clec1b | kg:uc007pge.1 |
| 2 | Ier2 | Wfdc2 | AU023871 | kg:uc007pgd.1 |
| 3 | Egr1 | Lamb3 | Alox12 | kg:uc007pgf.1 |
| 4 | Nkain4 | Lad1 | Itga2b | kg:uc007pgg.1 |
| 5 | Igfbp5 | Dmbt1 | Ppbp | Igj |
| 6 | Slc6a4 | Npy | Gng11 | kg:uc012enb.1 |
| 7 | Klf4 | Pmepa1 | Vwf | 2010001M09Rik |
| 8 | Tmem221 | Kcnn4 | Pf4 | kg:uc009cfw.1 |
| 9 | Arl4d | Serinc2 | Fcer1g | kg:uc007pgi.1 |
| 10 | Lrrn4 | 5730559C18Rik | Tmem40 | kg:uc007pgh.1 |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 11 | Cldn15 | Muc1 | Hba-a2 | kg:uc007yos.1 |
| 12 | Gpm6a | Chi3l3 | Stom | Coro1a |
| 13 | Atf3 | Pglyrp1 | Beta-s | Pou2af1 |
| 14 | Ptma | Arl4c | Plek | kg:uc011yvj.1 |
| 15 | Slc9a3r1 | Spp1 | Srgn | Glipr1 |
| 16 | Fos | Col15a1 | Myl9 | Cd52 |
| 17 | Tmem119 | C1qb | Cd84 | Cd79b |
| 18 | Ptgis | Tnnt2 | F5 | Sec11c |
| 19 | Dcn | Gkn3 | Treml1 | Tnfrsf17 |
| 20 | Gbp2 | Onecut2 | Hbb-b1 | Krr1 |
| 21 | Dmkn | Mmp7 | Itgb3 | Gmfg |
| 22 | Sdc4 | Cd74 | Gp9 | Ccr9 |
| 23 | Ildi2 | Ctss | Mpl | Pycard |
| 24 | Akap2 | Lamc2 | Ctla2a | Derl3 |
| 25 | Gfpt2 | Olfml3 | Tubb1 | Rac2 |
| 26 | Klf6 | Lgals4 | Mylk | Srgn |
| 27 | Btg2 | Lcn2 | F13a1 | Cytip |
| 28 | Myl7 | Ly6a | Slamf1 | Edem2 |
| 29 | Igfbp6 | Pak1 | Rgs10 | Itgb7 |
| 30 | Gpr133 | Capn5 | Mkrn1 | Lsp1 |
| 31 | Oasl2 | Ptprn | Laptm5 | Lcp1 |
| 32 | Pfn1 | Reg3b | 1810058I24Rik | Cyfip2 |
| 33 | Cap1 | Fmnl3 | Itgb2 | Nans |
| 34 | Nfkbia | Sdc1 | Slc2a3 | Slamf7 |
| 35 | Malat1 | Prom1 | Pcmt1 | Ell2 |
| 36 | Rarres2 | Ankrd50 | Gp5 | H2-Eb1 |
| 37 | Rspo1 | Ccl6 | Ube2o | Creld2 |
| 38 | Espn | Slc4a11 | 5430417L22Rik | Cd74 |
| 39 | Klf9 | Oraov1 | Ptpn18 | Blnk |
| 40 | Zbtb7c | Aldh1l1 | Lat | Fmnl1 |
| 41 | Brd2 | Slc20a1 | Fermt3 | Snrnp70 |
| 42 | Olfr1033 | Cldn7 | Nrgn | Sec61b |
| 43 | Wt1 | Acsbg1 | Mrvi1 | Edem1 |
| 44 | Esam | Las1l | Lyz2 | Tspan13 |
| 45 | kg:uc009igb.1 | C1qc | Epb4.1 | Psmb8 |
| 46 | Tmem151a | Lama5 | Rasgrp2 | Pim1 |
| 47 | Mgll | Mgat4a | Treml2 | Sept1 |
| 48 | Csrnp1 | Cldn2 | Hist1h4i | Cd48 |
| 49 | Cd9 | Mcpt2 | March2 | Sub1 |
| 50 | Gjb5 | Fxyd3 | Ltbp1 | Lims1 |
| 51 | Lrrc61 | Il4ra | Nptn | Ncoa2 |
| 52 | Wasf2 | Itga5 | Abtb1 | Ctnnbl1 |
| 53 | Pdpn | Porcn | Ctla2b | Fdps |
| 54 | kg:uc009ogv.1 | Mast3 | Prkab2 | Ube2j1 |
| 55 | Sdpr | Scara3 | Arhgdib | Mettl1 |
| 56 | Gpr64 | Atox1 | Alas2 | Lax1 |
| 57 | Flnc | Arrdc1 | Odc1 | Rilpl2 |
| 58 | Add3 | Mmp2 | Ptpn11 | Ctse |
| 59 | Gata6 | Saa3 | Dhcr24 | Glrx |
| 60 | Wfdc1 | Serpinf1 | Mfsd2b | Fut8 |
| 61 | A130040M12Rik | Sox11 | Gp1bb | AI662270 |
| 62 | Ankrd12 | Prpsap1 | Rbpms2 | Gramd3 |
| 63 | Adamtsl1 | Mcpt1 | Fyb | Il2rg |
| 64 | C2 | Mfge8 | Smox | Rasgrp3 |
| 65 | Prss23 | Col18a1 | P2rx1 | Impdh1 |
| 66 | Ube2v1 | Lyz2 | Otud7b | Plek |
| 67 | Cryab | C1qa | kg:uc007ttx.1 | Ints5 |
| 68 | Pkhd1l1 | Acp5 | Samd14 | Blmh |
| 69 | Rtn1 | Angptl4 | Clca1 | Dnmt1 |
| 70 | Birc6 | Ccnd1 | kg:uc007tty.1 | Galk1 |
| 71 | Xdh | Asl | Gpr56 | kg:uc007hxv.1 |
| 72 | Cd34 | Ctxn1 | Sh3bgrl2 | Ccdc88b |
| 73 | Rab6b | Pgs1 | Pttg1ip | Selplg |
| 74 | Dusp1 | Anapc2 | Nomo1 | Sar1b |
| 75 | Clic4 | Cp | Gnaz | Lat2 |
| 76 | C3 | Gpx3 | Mmrn1 | Slc16a6 |
| 77 | Rhob | Lama3 | Gp1ba | Mki67 |
| 78 | Mir3064 | Rbp1 | Sh3bgrl3 | Dnajc3 |
| 79 | Thbd | Cotl1 | Slc24a3 | H2-Ab1 |
| 80 | Dpysl2 | Nek6 | Sord | Ndufs6 |
| 81 | Cob1 | Cpxm1 | Nfe2 | Actr3 |
| 82 | Npr1 | Sfrp1 | Tuba4a | Etnk1 |
| 83 | Dnajb9 | Ttr | Zyx | Herpud1 |
| 84 | Arhgap29 | Gsto1 | Cnn2 | Ptpn7 |
| 85 | Cav1 | Npepl1 | Itgb5 | Ctss |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 86 | Gbp7 | Usmg5 | Gata1 | Cs |
| 87 | Hes1 | Polr2l | Hist1h1c | Fbxw7 |
| 88 | Gm16897 | Sphk1 | Tbxas1 | Ppp2r5c |
| 89 | Ppp1r12a | Asxl1 | Ptplad2 | Znrd1 |
| 90 | Sv2a | Ctsh | Bpgm | Rfc2 |
| 91 | Ang | Egfl7 | Pdlim7 | Preb |
| 92 | Aldh1a2 | C1qtnf6 | Mmd | Fcer1g |
| 93 | Cryl1 | Rras | G6b | Dnajb11 |
| 94 | Kank1 | Lgi4 | kg:uc009duo.1 | Slc35b1 |
| 95 | 2210403K04Rik | Hmga2 | Lyz1 | Sin3b |
| 96 | kg:uc009okn.1 | Cep250 | Tacc1 | Nktr |
| 97 | Osr1 | B4galt3 | Dap | |
| 98 | kg:uc008ewj.2 | Tmem223 | Mast2 | |
| 99 | kg:uc009tuw.1 | Ltbp2 | Atp2a3 | |
| 100 | Gadd45b | Tnfrsf23 | Snca | |
| 101 | Ablim3 | Col7a1 | Stx11 | |
| 102 | Clec3b | Ggct | C030046I01Rik | |
| 103 | Usp25 | Rab25 | Trpt1 | |
| 104 | Sntb2 | Nedd8 | Tsc22d1 | |
| 105 | Rock2 | 9430023L20Rik | Prkar2b | |
| 106 | Col14a1 | Arl2 | Cd9 | |
| 107 | Cd200 | Wbp1 | Pgm2l1 | |
| 108 | kg:uc008ehr.1 | H2-Ab1 | Gp6 | |
| 109 | Atp2b1 | Preb | Pde5a | |
| 110 | Exoc4 | Sgsm3 | Itga6 | |
| 111 | Abcb1b | Sfn | Itga1 | |
| 112 | Nrgn | Prrx2 | Edem1 | |
| 113 | kg:uc009cvm.1 | Ptprk | Isg20 | |
| 114 | Ncoa4 | Reg1 | Cdc42ep5 | |
| 115 | Ndufa4 | Sdcbp2 | Nipal3 | |
| 116 | Upk1b | Pcbd1 | Ccdc92 | |
| 117 | Jun | Slc25a1 | Sort1 | |
| 118 | Syne2 | Vamp5 | Ly6g6c | |
| 119 | kg:uc007bvx.1 | Crlf1 | Ubash3b | |
| 120 | Ap4e1 | Avil | Inf2 | |
| 121 | Spock2 | 2700094K13Rik | Asap1 | |
| 122 | Efemp1 | Ctse | Sec11c | |
| 123 | Prpf40a | Penk | Gas2l1 | |
| 124 | Tspan5 | Tmc4 | Parvb | |
| 125 | Lgals7 | Dhrs3 | Tmsb4x | |
| 126 | Kif5b | Ap1s1 | kg:uc007xrw.1 | |
| 127 | Psip1 | Arl6ip4 | Nudt3 | |
| 128 | kg:uc008oki.1 | 9430008C03Rik | Bcl2l1 | |
| 129 | 1810014B01Rik | Fcer1g | B230312A22Rik | |
| 130 | Ptges3 | Uqcr11 | Cnp | |
| 131 | Limch1 | Nhp2 | Plp1 | |
| 132 | Bicd1 | Plbd2 | Cnst | |
| 133 | Rdx | Capg | Rgs18 | |
| 134 | Pcdh15 | Pnpla6 | Lsm12 | |
| 135 | Foxn3 | Ppdpf | Alox5ap | |
| 136 | Morf4l2 | Hgfac | Ppif | |
| 137 | Ppp1r15a | Apoe | Spnb1 | |
| 138 | Cdc42ep3 | Fam40a | Ormdl3 | |
| 139 | Pard3b | Lyz1 | Hpse | |
| 140 | Bicc1 | 2200002D01Rik | Srxn1 | |
| 141 | Amhr2 | Laptm5 | 2010002N04Rik | |
| 142 | Gucy1a3 | Qars | Hist1h2bc | |
| 143 | Psmb2 | Tmx2 | Cyba | |
| 144 | Mapkapk3 | Fkbp4 | Chst12 | |
| 145 | Ube2l6 | Plin2 | kg:uc009sps.1 | |
| 146 | kg:uc007pff.1 | Fcgr3 | Max | |
| 147 | kg:uc007ctp.1 | Gkn1 | Was | |
| 148 | Nedd4 | Snhg1 | Isca1 | |
| 149 | Plxna4 | Lsp1 | Pdzk1ip1 | |
| 150 | 2010107G12Rik | Gm20605 | Lyn | |
| 151 | Ifhgr1 | Ly6c1 | Mob3a | |
| 152 | Bcam | Aim1 | H2-T24 | |
| 153 | Ccnl1 | 2310007B03Rik | Slc44a1 | |
| 154 | Hoxa5 | Tgfbi | Derl1 | |
| 155 | Fhl1 | Tsta3 | Gclm | |
| 156 | 1810041L15Rik | Pafah1b3 | Fech | |
| 157 | 2900002K06Rik | Chid1 | Ywhah | |
| 158 | Hspb1 | Smox | Igtp | |
| 159 | Podn | 1500012F01Rik | Myl6 | |
| 160 | Fam63b | Tspan4 | Thbs1 | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 161 | Hsp90b1 | Agrn | Tln1 | |
| 162 | Dpp4 | Cfp | kg:uc009apq.1 | |
| 163 | Gas1 | Cdh1 | Bcap31 | |
| 164 | kg:uc007zak.1 | Rasgrf1 | Ilk | |
| 165 | Zc3h13 | Nxf1 | Epha1 | |
| 166 | Sox6 | Pdrg1 | 2810453I06Rik | |
| 167 | Arid4a | Polr2j | Rnf19b | |
| 168 | Tnxb | Suds3 | Gsn | |
| 169 | Tsix | D0H4S114 | Flna | |
| 170 | Scd1 | Ccl9 | Arrb1 | |
| 171 | Jund | Neat1 | kg:uc007pum.1 | |
| 172 | Crls1 | Ccdc12 | Mbnl1 | |
| 173 | 1110003E01Rik | Prr24 | Ccnd3 | |
| 174 | Rnase4 | Impdh1 | Pdlim1 | |
| 175 | Arhgef12 | Card10 | Ctse | |
| 176 | Irf7 | Cpsf1 | Tspan17 | |
| 177 | Bbx | Sema4g | Gpx4 | |
| 178 | Sema5a | Hes6 | Bnip3l | |
| 179 | Mau2 | C130074G19Rik | P2ry12 | |
| 180 | Abi3bp | Ctrb1 | kg:uc009vev.1 | |
| 181 | Dag1 | Rnaseh2a | Prkab1 | |
| 182 | Cyp2s1 | Golm1 | F2rl2 | |
| 183 | Sfrs18 | Ctsz | Stk4 | |
| 184 | Hspb8 | Cyb561 | Fhl1 | |
| 185 | Cnot6l | Ndufs8 | Rnf10 | |
| 186 | Twsg1 | Atp6ap1 | Rasa3 | |
| 187 | Gpc3 | Srd5a1 | Taldo1 | |
| 188 | Lrrn4cl | Carkd | Bysl | |
| 189 | Cdh3 | Cd24a | Esd | |
| 190 | Cyr61 | Eng | Aldh2 | |
| 191 | Cyp2d22 | Tcirg1 | Rhog | |
| 192 | Hist1h1c | Slc9a3r2 | kg:uc009ecr.1 | |
| 193 | Aplp1 | 0910001L09Rik | Cald1 | |
| 194 | Tbl1x | Cox5b | Wbp2 | |
| 195 | Pcm1 | Adipor2 | Ptprj | |
| 196 | Ifi204 | Scarf2 | Tpm4 | |
| 197 | Nfix | Myo7a | Mxi1 | |
| 198 | Flrt2 | Ppap2c | Ly6g6f | |
| 199 | Heg1 | Pea15a | Sla | |
| 200 | Il6ra | Sh3pxd2b | Slpi | |
| 201 | Ralbp1 | H19 | Bicd2 | |
| 202 | Rhoj | Tpd52 | Clu | |
| 203 | Ktn1 | 2610203C20Rik | Mtmr14 | |
| 204 | Arl6ip5 | Naa10 | Abca7 | |
| 205 | Crebbp | Fermt1 | Ppp1r18 | |
| 206 | Ppig | Sap30l | Kif2a | |
| 207 | Akap13 | Bgn | Prdx6 | |
| 208 | Rab7 | Timm13 | kg:uc009ize.1 | |
| 209 | Plxdc2 | Krt20 | Calm3 | |
| 210 | Aldh1a1 | Itga3 | Dhrs1 | |
| 211 | Bnc2 | Pfkl | Cfl1 | |
| 212 | Slc4a4 | Agpat6 | Glipr2 | |
| 213 | Tbx18 | Mrpl11 | Slc25a37 | |
| 214 | Zbtb16 | Ramp1 | Atox1 | |
| 215 | Arid4b | Hmga1 | BC057079 | |
| 216 | Enpp2 | Gpx2 | Pla2g16 | |
| 217 | Ptplad2 | 0610012G03Rik | Rnf44b | |
| 218 | Akr1b3 | 9130017N09Rik | Stk16 | |
| 219 | Gm6644 | Cygb | Rsad2 | |
| 220 | Arf5 | Tmprss4 | Paip2 | |
| 221 | Chi3l1 | Paox | Capzb | |
| 222 | Gpr116 | Endod1 | Ppp1r12c | |
| 223 | Cd82 | Cndp2 | 4930412F15Rik | |
| 224 | Srrm1 | Suv39h1 | Ninj1 | |
| 225 | Fmo2 | Cog4 | 2510009E07Rik | |
| 226 | Tgfb1i1 | Trim27 | kg:uc007vsr.1 | |
| 227 | Qrich1 | Cyhr1 | Pygb | |
| 228 | Nfia | Trmt1 | Tlk1 | |
| 229 | Pmp22 | Zfyve19 | Myct1 | |
| 230 | Cdh11 | Esrp1 | Rnasek | |
| 231 | Arid5b | kg:uc008oow.1 | Ctsd | |
| 232 | Rbm3 | Dync1h1 | 0610010K14Rik | |
| 233 | Prelp | Tab1 | Bcas3 | |
| 234 | kg:uc007qse.1 | Pla2g6 | Atpif1 | |
| 235 | Ddx3x | Timp1 | Serf2 | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 236 | Sulf1 | Eif3f | Becn1 | |
| 237 | Spnb2 | Abhd11 | Tspan9 | |
| 238 | Tspan31 | Pmm2 | Acer2 | |
| 239 | Prr13 | Tyrobp | Vdac3 | |
| 240 | Ppp1cb | Farsb | kg:uc008kbg.1 | |
| 241 | Fbln1 | Plod3 | Oaz2 | |
| 242 | Gm6548 | Abtb1 | Serpine2 | |
| 243 | Uap1 | Brf1 | Ccdc90a | |
| 244 | Mpdz | Tnk2 | Ndufa1 | |
| 245 | Sat1 | Rfc2 | Tssc1 | |
| 246 | Stim1 | Stxbp2 | Mboat7 | |
| 247 | Mll3 | Pdlim7 | Cd44 | |
| 248 | Slurp1 | A430105I19Rik | Cxx1c | |
| 249 | Cd81 | Vill | Ecm1 | |
| 250 | Emp2 | Bmp1 | Mff | |
| 251 | Trpm7 | Mpzl1 | Ptpn12 | |
| 252 | Crym | Thy1 | Mgmt | |
| 253 | Enpp4 | Stab1 | Cox4i1 | |
| 254 | Raly | Aldh16a1 | Tollip | |
| 255 | Celf2 | Eif4ebp3 | Cds2 | |
| 256 | Ap3s1 | Itpripl2 | Ybx1 | |
| 257 | C1s | Mrpl52 | Gypc | |
| 258 | Frmd4b | 2310002L13Rik | Dgkd | |
| 259 | Nr4a1 | Mcm6 | Pecam1 | |
| 260 | Acin1 | Kcnk1 | Ftl2 | |
| 261 | Plod2 | Pmf1 | Nt5c3 | |
| 262 | Id1 | Cuta | 1700037H04Rik | |
| 263 | Creg1 | Nt5dc2 | Cd151 | |
| 264 | Zfp318 | Rmnd5b | Lpin2 | |
| 265 | Tmem140 | Araf | 6430548M08Rik | |
| 266 | Mras | Wwp2 | Pon2 | |
| 267 | Vwa5a | Lamb1 | Ndufa3 | |
| 268 | Esyt3 | Kcne3 | 6330578E17Rik | |
| 269 | Hexb | Uqcrq | Mfap31 | |
| 270 | Nckap1 | Gps1 | Mink1 | |
| 271 | Nipal3 | Rexo4 | Ston2 | |
| 272 | Ubxn4 | Coro1c | Rac2 | |
| 273 | Zfp36 | Hras1 | Fyn | |
| 274 | Hnrnpl | Spint1 | Serinc3 | |
| 275 | C1ra | Cblc | Maged2 | |
| 276 | Nnmt | Fhod1 | Ap2m1 | |
| 277 | Mut | Atp13a1 | Pacsin2 | |
| 278 | kg:uc008jup.1 | Man2c1 | Ftl1 | |
| 279 | Pnrc1 | Vsig2 | Adipor1 | |
| 280 | Usp8 | Bpgm | kg:uc009qdo.1 | |
| 281 | Pgcp | Bap1 | Snap23 | |
| 282 | Junb | Smpd2 | Tagln2 | |
| 283 | C1rl | Ubqln4 | Cox6c | |
| 284 | Slc6a6 | Sirt7 | Creg1 | |
| 285 | kg:uc008znh.1 | Krt23 | Bsg | |
| 286 | Aqp1 | D8Ertd738e | Cmtm6 | |
| 287 | Myh10 | Mapk13 | Cntd1 | |
| 288 | Slc43a3 | kg:uc008bcq.1 | Plekho2 | |
| 289 | Spint2 | Polr2g | Arrb2 | |
| 290 | Hnrnph1 | Ndufs2 | Pard3b | |
| 291 | Arhgap28 | Dad1 | Mlec | |
| 292 | Cfh | Wnt7b | Taf10 | |
| 293 | Brd4 | Fam20c | Gabarapl2 | |
| 294 | Fndc1 | Cxxc5 | Bag1 | |
| 295 | Star | Polr2f | Galnt2 | |
| 296 | Nfkbiz | Ltf | Hk1 | |
| 297 | Arsb | 2210407C18Rik | Fbxo9 | |
| 298 | Rnd3 | Cdipt | kg:uc009izd.1 | |
| 299 | Stard5 | Glrx5 | Pnpo | |
| 300 | Thbs1 | Gemin7 | Fam46c | |
| 301 | kg:uc008wkn.1 | Man1b1 | Pkm | |
| 302 | Slc26a3 | Heatr7a | Ap1b1 | |
| 303 | Phip | Arid5a | Rap1b | |
| 304 | Usp2 | Sumo3 | Itgb1 | |
| 305 | Golgb1 | Srm | St7 | |
| 306 | Rock1 | Plscr3 | Smap1 | |
| 307 | Rgma | 2210010C17Rik | Rabgap1l | |
| 308 | Actg1 | Fam102a | Tmbim4 | |
| 309 | BC013529 | Dlst | H3f3a | |
| 310 | kg:uc007zwh.1 | Vps37c | Frmd8 | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 311 | 3110062M04Rik | Ngfrap1 | Nlrx1 | |
| 312 | Cast | Pold4 | Oaz1 | |
| 313 | Mob3c | Grcc10 | Fam125b | |
| 314 | Slc16a1 | Wnt7a | Hexa | |
| 315 | Fam117a | 2010111I01Rik | Tspo | |
| 316 | Pdia3 | Pxdn | Dcaf12 | |
| 317 | Trim8 | Coasy | Nav1 | |
| 318 | kg:uc009mng.1 | Dctn1 | Cd24a | |
| 319 | eg:245190:chr7:m | Ncor2 | Uqcr11 | |
| 320 | Sbsn | Postn | Wipf1 | |
| 321 | Serpinb6b | Col4a2 | F10 | |
| 322 | Daglb | Cib1 | Erlec1 | |
| 323 | Smarca2 | Tbc1d13 | Map2k3 | |
| 324 | Mef2c | Ccnl2 | Stk24 | |
| 325 | Prrc2c | Dcakd | Ldlrap1 | |
| 326 | BC005537 | Cdc34 | Ehd4 | |
| 327 | Hsp90ab1 | Atp6v0b | Atp6v1f | |
| 328 | Snrnp70 | Abhd12 | Gnas | |
| 329 | Ppl | Flot2 | Arhgap18 | |
| 330 | Serpinh1 | Sla2 | Arhgap10 | |
| 331 | Sorbs3 | Rhbdf1 | Pitpnm1 | |
| 332 | Golga4 | Cdh17 | S100a1 | |
| 333 | Acbd3 | Psmb5 | Bin1 | |
| 334 | Hook3 | Serf1 | Ttyh3 | |
| 335 | Map3k3 | Slc15a3 | Selp | |
| 336 | Rhou | Sftpd | Trappc9 | |
| 337 | Smc2 | Pop5 | Aes | |
| 338 | C1d | Nudc | Taok3 | |
| 339 | kg:uc008dzh.1 | Sh2d5 | Zfand3 | |
| 340 | Psmd7 | kg:uc007fwp.1 | Stim1 | |
| 341 | Dab2 | Mrpl37 | Rnf11 | |
| 342 | Cep164 | Rin1 | Sep15 | |
| 343 | Crim1 | Podxl | kg:uc012hdk.1 | |
| 344 | Rtf1 | Paqr5 | Lgals9 | |
| 345 | Fxyd1 | Sepx1 | Cox6b1 | |
| 346 | H2-D1 | Agr2 | Riok3 | |
| 347 | Zfp704 | Bax | Slc38a10 | |
| 348 | Mtap1a | Rxrb | Rtn3 | |
| 349 | Ascc3 | Tes | B3gat2 | |
| 350 | Med13l | Hdac6 | Ccndbp1 | |
| 351 | Jup | 1110008F13Rik | Rsu1 | |
| 352 | Nid2 | Mpnd | kg:uc007upr.1 | |
| 353 | Kdr | Gmppa | Itm2b | |
| 354 | Ifnar2 | Gramd1a | St3gal1 | |
| 355 | 5430435G22Rik | Wars | Sec61g | |
| 356 | Col4a6 | Mtap | Ptpn1 | |
| 357 | Il17re | C1qtnf5 | kg:uc012bhf.1 | |
| 358 | Gbp3 | Mrpl28 | B2m | |
| 359 | Slc39a8 | Mfrp | Rasgrp3 | |
| 360 | Cfl2 | Kars | Memo1 | |
| 361 | Slc38a1 | Lbp | Slc39a4 | |
| 362 | Cuedc1 | Plxnb1 | Sdcbp | |
| 363 | Fgf1 | 2700081O15Rik | Tspan14 | |
| 364 | Gas6 | Mrps24 | Ubl7 | |
| 365 | Cldn25 | Klc4 | Nras | |
| 366 | Sorbs1 | Dctn3 | Ssx2ip | |
| 367 | Hspa12a | Kcnq1 | kg:uc007zbz.1 | |
| 368 | kg:uc007zts.1 | Smurf1 | Wbp1 | |
| 369 | Slc1a5 | Fam162a | 1110003E01Rik | |
| 370 | Nr3c1 | Hip1r | Clip2 | |
| 371 | Adamts5 | kg:uc007hyr.2 | Gapdh | |
| 372 | Gpcpd1 | Gys1 | Gm6578 | |
| 373 | Dpysl3 | Sac3d1 | Actn1 | |
| 374 | Colec12 | Ndufs6 | St3gal2 | |
| 375 | Pdcd6ip | Rgl2 | 3110001D03Rik | |
| 376 | Dst | Atp5g1 | Ctsz | |
| 377 | Ifit4 | Itgb4 | kg:uc007vdl.1 | |
| 378 | Chst4 | Sars | Fam73a | |
| 379 | Xist | 2310003F16Rik | Vcl | |
| 380 | Ifi27l2a | Nhp2l1 | Lims1 | |
| 381 | Fkbp5 | D19Wsu162e | Lars2 | |
| 382 | Agap1 | Cd320 | Birc2 | |
| 383 | Ankrd11 | Pigq | Lamp2 | |
| 384 | kg:uc007qca.1 | Chd3 | Rasl10a | |
| 385 | Syt11 | Zdhhc4 | Mif | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 386 | Ptrf | Eif3l | Rab10 | |
| 387 | Krcc1 | St8sia3 | Pabpc1 | |
| 388 | Zfp488 | Rcan3 | Wwp2 | |
| 389 | Lama4 | Meg3 | Nqo2 | |
| 390 | Aebp1 | Nudt4 | kg:uc007fte.1 | |
| 391 | Fam134b | Gss | Plxna4 | |
| 392 | Tppp3 | Pih1d1 | Gm1821 | |
| 393 | Maf | Limd2 | Gadd45a | |
| 394 | Peli1 | Ap1s2 | Slc25a39 | |
| 395 | Zfp353 | BC056474 | kg:uc009pet.1 | |
| 396 | Cdon | Mms19 | Ubb | |
| 397 | Sarnp | Clip2 | Ppp1r2 | |
| 398 | Atxn7l3b | 2310016M24Rik | Rab27b | |
| 399 | Pef1 | Itpa | Cap1 | |
| 400 | App | Slc25a10 | Jarid2 | |
| 401 | Mtdh | Fibp | Rnf11 | |
| 402 | Lrrc20 | Higd2a | Tmem50b | |
| 403 | Btbd2 | Snrpd2 | Myh9 | |
| 404 | Gnb2 | Eri3 | Tmem128 | |
| 405 | Pigt | Nbeal2 | Stradb | |
| 406 | Efna5 | Trim28 | Cela1 | |
| 407 | Tm4sf1 | S100a4 | Ndrg2 | |
| 408 | Coq10b | Ivns1abp | Dhrs3 | |
| 409 | Eif2s3x | Ppp1r18 | Hipk1 | |
| 410 | Cmah | Efemp2 | Atg9a | |
| 411 | Sf3b1 | Med22 | | |
| 412 | Eea1 | Nelf | | |
| 413 | Slpi | 2810428I15Rik | | |
| 414 | Tmod3 | D2Wsu81e | | |
| 415 | Ppp3ca | Trappc6a | | |
| 416 | Tceal8 | Trappc2l | | |
| 417 | Anp32a | Antxr2 | | |
| 418 | Actb | Rab11fip5 | | |
| 419 | Ddx5 | Ldhd | | |
| 420 | Cobll1 | Npnt | | |
| 421 | Cish | Acrbp | | |
| 422 | Nod1 | Pafah1b2 | | |
| 423 | Psd | Angptl2 | | |
| 424 | Gm10052 | Fzr1 | | |
| 425 | Lims2 | Aaas | | |
| 426 | Stra6 | Eif2b2 | | |
| 427 | kg:uc007bgn.1 | 1190003J15Rik | | |
| 428 | Plxdc1 | 5730403B10Rik | | |
| 429 | Nfe2l1 | Adamts13 | | |
| 430 | Smpd3 | Eif3b | | |
| 431 | Bcl10 | Znrf1 | | |
| 432 | Ilf3 | Pkp3 | | |
| 433 | Fam76a | Lemd2 | | |
| 434 | Cybrd1 | Rab34 | | |
| 435 | Gm3893 | Mpv17l2 | | |
| 436 | Siae | Cdkn2b | | |
| 437 | Ssh2 | Snrpe | | |
| 438 | Nfic | Gm14005 | | |
| 439 | Btf3 | Prdx4 | | |
| 440 | Sp100 | Xab2 | | |
| 441 | Ndn | Dpp3 | | |
| 442 | Matr3 | Tyms | | |
| 443 | Gm13251 | Leprotl1 | | |
| 444 | Arhgap5 | Uqcr10 | | |
| 445 | Zbtb4 | Cdk5rap3 | | |
| 446 | Pgrmc1 | Gorasp2 | | |
| 447 | 4930402H24Rik | Wbp7 | | |
| 448 | Bptf | Sort1 | | |
| 449 | Dusp3 | Ddx41 | | |
| 450 | Pla2g4a | Cct3 | | |
| 451 | Brp44l | Mrps33 | | |
| 452 | Oxct1 | Frmd8 | | |
| 453 | Stk40 | 1110049F12Rik | | |
| 454 | Ddr1 | Fscn1 | | |
| 455 | Ifi205 | Ndufa2 | | |
| 456 | Col3a1 | Dpcd | | |
| 457 | Nipbl | Unc13a | | |
| 458 | Plk1s1 | Eif1ad | | |
| 459 | Bdp1 | Sgta | | |
| 460 | Smc3 | Chaf1a | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 461 | Ifitm3 | Plxna1 | | |
| 462 | Ndst1 | Hspa9 | | |
| 463 | Zbed6 | 1110014N23Rik | | |
| 464 | Rest | Cd9l2 | | |
| 465 | kg:uc007vnc.1 | Snrpa | | |
| 466 | Ccdc88a | Mcm7 | | |
| 467 | Stat3 | Tars2 | | |
| 468 | Arf2 | Gon4l | | |
| 469 | Trib1 | Stk38 | | |
| 470 | Gcap14 | C1qtnf1 | | |
| 471 | Tbc1d15 | Tbrg4 | | |
| 472 | Igf1r | Tmem132a | | |
| 473 | Ppbp | Cox6c | | |
| 474 | kg:uc008tky.1 | Alcam | | |
| 475 | Rab1b | Phka2 | | |
| 476 | Krt14 | Trim3 | | |
| 477 | Med21 | Ppp1r14b | | |
| 478 | Gja1 | Gpaa1 | | |
| 479 | Klf10 | Ctps2 | | |
| 480 | Id2 | Ptpn23 | | |
| 481 | Mfap1a | Endog | | |
| 482 | Ogn | Mrto4 | | |
| 483 | Gpc4 | Mrps6 | | |
| 484 | Bst2 | Pvr | | |
| 485 | Dtx2 | Phgdh | | |
| 486 | Wac | Itpr3 | | |
| 487 | Kpna3 | Polr2e | | |
| 488 | Kcnab1 | Sec16a | | |
| 489 | Orai3 | Mdp1 | | |
| 490 | Gcsh | Fbf1 | | |
| 491 | Wdr92 | Mcpt8 | | |
| 492 | Olfr613 | Rps6ka4 | | |
| 493 | Tcf7l1 | Mical1 | | |
| 494 | Tgfb2 | Mrpl34 | | |
| 495 | Il16 | Agpat3 | | |
| 496 | Manf | 2310044H10Rik | | |
| 497 | Mgst1 | Myo9b | | |
| 498 | kg:uc008tkz.1 | Ndufb10 | | |
| 499 | Creb3l1 | Apex1 | | |
| 500 | Txndc5 | Elk3 | | |
| 501 | Klf2 | Cpsf3l | | |
| 502 | Slu7 | Tnk1 | | |
| 503 | Ttc28 | Pmvk | | |
| 504 | 1110002B05Rik | Ppp1r16a | | |
| 505 | Zcchc11 | Arhgef5 | | |
| 506 | Ptp4a2 | Lonp1 | | |
| 507 | Pbx1 | Pla2g7 | | |
| 508 | Clcn3 | Pip5k1c | | |
| 509 | Tmco7 | Inf2 | | |
| 510 | Lrrc58 | Pgk1 | | |
| 511 | Eif3a | Parp6 | | |
| 512 | Cldn10 | Urm1 | | |
| 513 | H2-Q6 | Mad2l2 | | |
| 514 | Ccdc80 | Ing4 | | |
| 515 | kg:uc009iln.1 | Rbck1 | | |
| 516 | Rab5c | Cant1 | | |
| 517 | Tsc22d3 | Sgpl1 | | |
| 518 | Tm4sf5 | Ehbp1l1 | | |
| 519 | Hmgb1 | Runx1 | | |
| 520 | Sec62 | Slc27a4 | | |
| 521 | Maoa | Ndufa7 | | |
| 522 | Clec1b | Mcm3ap | | |
| 523 | Mphosph8 | 1110008P14Rik | | |
| 524 | Oat | Rassf7 | | |
| 525 | Ncor1 | Ptpmt1 | | |
| 526 | Cyb5 | Arfgap1 | | |
| 527 | Trafd1 | Sec61a1 | | |
| 528 | Rpp25 | Rps6ka1 | | |
| 529 | kg:uc007ded.1 | Ints1 | | |
| 530 | 2610101N10Rik | Tpcn1 | | |
| 531 | Il6st | Iffo2 | | |
| 532 | Evpl | Trim44 | | |
| 533 | Psmd11 | kg:uc012ctw.1 | | |
| 534 | Dync1i2 | Golga2 | | |
| 535 | Lars2 | Msto1 | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 536 | Pdia4 | Ppp6r3 | | |
| 537 | Cd55 | Trmt2a | | |
| 538 | Amfr | Appl2 | | |
| 539 | Zcchc3 | Sparcl1 | | |
| 540 | Herpud2 | Rapgef1 | | |
| 541 | Txnrd1 | Zfpl1 | | |
| 542 | Vat1 | Psmc4 | | |
| 543 | Diap1 | Mosc2 | | |
| 544 | Tmed2 | Fam101b | | |
| 545 | Arf3 | 1500010J02Rik | | |
| 546 | Arap2 | Ccdc124 | | |
| 547 | St3gal1 | Ptges | | |
| 548 | Man1a | Fam189b | | |
| 549 | Rgs10 | Thl1 | | |
| 550 | Tmsb4x | Kctd2 | | |
| 551 | Uba7 | Olfr1372-ps1 | | |
| 552 | C4b | Hexa | | |
| 553 | Tmem98 | Anapc5 | | |
| 554 | Lpar2 | Serpina3n | | |
| 555 | Gabarapl1 | 1810046J19Rik | | |
| 556 | Cmtm7 | Tmem167 | | |
| 557 | Spon2 | Gm11428 | | |
| 558 | Smarca5 | Gcn1l1 | | |
| 559 | Mxd4 | Kansl3 | | |
| 560 | Smc4 | Fasn | | |
| 561 | Thsd4 | Slc50a1 | | |
| 562 | Gsr | Smad3 | | |
| 563 | Ptprd | Trip6 | | |
| 564 | Clip1 | Atp6v1e1 | | |
| 565 | Cln8 | Chchd5 | | |
| 566 | Rbm27 | Adssl1 | | |
| 567 | Zmat1 | Nes | | |
| 568 | Smc6 | Ap1b1 | | |
| 569 | B2m | Fcgrt | | |
| 570 | Irf2bp2 | Ltbp3 | | |
| 571 | Ppap2a | Csf2rb | | |
| 572 | Zfhx4 | Ssna1 | | |
| 573 | Tob2 | Mrps16 | | |
| 574 | Rabgap1l | Cyba | | |
| 575 | Nfkb2 | Cyth2 | | |
| 576 | Nfyc | Igf2 | | |
| 577 | Ube2d1 | Pisd-ps1 | | |
| 578 | Creb5 | Atp13a2 | | |
| 579 | Opa3 | Mlph | | |
| 580 | Csnk1a1 | Cyp4f16 | | |
| 581 | Fam84b | 2010107E04Rik | | |
| 582 | Ddr2 | Gas5 | | |
| 583 | Usp54 | Eif3k | | |
| 584 | Akt2 | Fam149a | | |
| 585 | Strn3 | Mif | | |
| 586 | Hnrnpm | B230312A22Rik | | |
| 587 | eg:497210:chr14:m | Ppp1r12c | | |
| 588 | Tpt1 | Tfip11 | | |
| 589 | Naa25 | Tex 10 | | |
| 590 | Eef1a1 | Slc16a3 | | |
| 591 | Parp4 | Stk16 | | |
| 592 | Msn | Epn1 | | |
| 593 | Zbtb20 | Noc4l | | |
| 594 | Fermt2 | Rcc2 | | |
| 595 | Bod1l | Rgs12 | | |
| 596 | Sltm | Shkbp1 | | |
| 597 | Dapk1 | Got2 | | |
| 598 | Hnrnpr | Plek2 | | |
| 599 | Baz2a | Lilrb3 | | |
| 600 | Rnf167 | Ndufb5 | | |
| 601 | Mapk1 | Tesk1 | | |
| 602 | eg:320169:chr9:p | Rab24 | | |
| 603 | 4930523C07Rik | Atp5j2 | | |
| 604 | Nf1 | Commd9 | | |
| 605 | Fam53b | Rtkn | | |
| 606 | Faim2 | Prpf19 | | |
| 607 | Tgm2 | 6720401G13Rik | | |
| 608 | Calm2 | Ppa1 | | |
| 609 | AI848100 | Pgp | | |
| 610 | Slc10a3 | Hps1 | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 611 | Ogdh | Puf60 | | |
| 612 | Arl3 | Mdm2 | | |
| 613 | Timp2 | kg:uc012cgd.1 | | |
| 614 | Atxn2 | kg:uc009uim.1 | | |
| 615 | Mll1 | Pyy | | |
| 616 | Ces2g | Zfp358 | | |
| 617 | Mat2a | Timm8b | | |
| 618 | Esf1 | Ddx39 | | |
| 619 | Hsp90aa1 | Pgm2 | | |
| 620 | Zfp385a | kg:uc008gbp.1 | | |
| 621 | Zfp672 | Sipa1 | | |
| 622 | Csda | Mgat1 | | |
| 623 | Pf4 | Tmem208 | | |
| 624 | Arsa | Ruvbl2 | | |
| 625 | F11r | 8430410A17Rik | | |
| 626 | C4a | Bad | | |
| 627 | Kpna1 | Pfdn5 | | |
| 628 | Rbbp8 | Eme1 | | |
| 629 | Oxnad1 | kg:uc009mzj.1 | | |
| 630 | Rb1cc1 | Igf1 | | |
| 631 | Setd2 | Prkag1 | | |
| 632 | Kif1b | kg:uc009sua.1 | | |
| 633 | 2510002D24Rik | Uap1l1 | | |
| 634 | Cep57 | Trappc4 | | |
| 635 | Chd2 | Bola2 | | |
| 636 | Serinc5 | Usp5 | | |
| 637 | Marcksl1 | Ear2 | | |
| 638 | Shfm1 | Cars | | |
| 639 | Bbs4 | 1810027O10Rik | | |
| 640 | Impad1 | Amdhd2 | | |
| 641 | Tbcel | Phb | | |
| 642 | Kdelr1 | Kcmf1 | | |
| 643 | Ninl | Lsmd1 | | |
| 644 | Sytl1 | Sec11c | | |
| 645 | Tpm3 | Pcbp4 | | |
| 646 | Rbbp6 | Mepce | | |
| 647 | Lman1 | Tpd52l2 | | |
| 648 | Ankrd17 | Trf | | |
| 649 | Naga | Hsd17b11 | | |
| 650 | Rbpms | Pilra | | |
| 651 | Magt1 | Atn1 | | |
| 652 | Tfdp2 | Pgf | | |
| 653 | Gem | Nxn | | |
| 654 | Pde4dip | Inpp5k | | |
| 655 | Mrgprf | Actr1a | | |
| 656 | kg:uc008ajk.1 | Cd68 | | |
| 657 | Itch | Eef1g | | |
| 658 | Elf1 | Fbn1 | | |
| 659 | Meis2 | Hint1 | | |
| 660 | Arid1a | March5 | | |
| 661 | Serping1 | Usp48 | | |
| 662 | Slc27a3 | Hnf1b | | |
| 663 | Thoc2 | Gga3 | | |
| 664 | Gsta3 | Drosha | | |
| 665 | Hnrnph2 | Ubp1 | | |
| 666 | Socs3 | Pkn3 | | |
| 667 | Armcx3 | Tmem192 | | |
| 668 | Siah1a | Prpf31 | | |
| 669 | kg:uc009ize.1 | Hspd1 | | |
| 670 | Irs2 | Otub1 | | |
| 671 | Mettl7a1 | Mrpl20 | | |
| 672 | Ppfibp2 | Tead2 | | |
| 673 | Blvrb | Phpt1 | | |
| 674 | Yipf5 | Neu1 | | |
| 675 | Plat | Pygo2 | | |
| 676 | Gm6578 | Myeov2 | | |
| 677 | Mat2b | Cdk5 | | |
| 678 | Tmpo | Ndor1 | | |
| 679 | Metap2 | Rbp4 | | |
| 680 | Zfp277 | Psat1 | | |
| 681 | Wls | Mrpl41 | | |
| 682 | Mesdc1 | Snrpg | | |
| 683 | kg:uc009acs.1 | Acot7 | | |
| 684 | Col1a2 | Vars | | |
| 685 | Csf1 | Nono | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 686 | Sulf2 | Gtf2i | | |
| 687 | Ifrd1 | Traf3 | | |
| 688 | Wrnip1 | Ppp2r4 | | |
| 689 | Flii | Actg2 | | |
| 690 | 2810474O19Rik | Pi4k2a | | |
| 691 | Sep15 | Slc35b2 | | |
| 692 | 2310030G06Rik | Ubqln1 | | |
| 693 | Cmtm3 | Ppox | | |
| 694 | Mylip | Bud31 | | |
| 695 | Slc8a1 | Man2b1 | | |
| 696 | Btbd7 | Nat15 | | |
| 697 | Hdac5 | Spon1 | | |
| 698 | Zfand6 | Cyc1 | | |
| 699 | Tapbp | Mpeg1 | | |
| 700 | Keap1 | Nsun2 | | |
| 701 | Ube2n | Rab4a | | |
| 702 | Ssr3 | Mtmr11 | | |
| 703 | H3f3a | BC004004 | | |
| 704 | Myst4 | B4galnt1 | | |
| 705 | G3bp1 | Atp5k | | |
| 706 | Ugdh | Lin37 | | |
| 707 | Lamp2 | D330041H03Rik | | |
| 708 | Zrsr1 | Tbc1d17 | | |
| 709 | Pim1 | March6 | | |
| 710 | Gm9199 | 2410015M20Rik | | |
| 711 | Supt16h | 1810013D10Rik | | |
| 712 | Ano6 | Eif2s1 | | |
| 713 | Soat1 | Traf7 | | |
| 714 | Eci1 | Rpl36al | | |
| 715 | Plce1 | Psenen | | |
| 716 | Atg3 | Aip | | |
| 717 | Bnc1 | Cmas | | |
| 718 | Pik3c2a | Rpia | | |
| 719 | Pqlc3 | Ncbp1 | | |
| 720 | Thrap3 | Mea1 | | |
| 721 | Irak4 | Timm50 | | |
| 722 | Kdm6b | Ear12 | | |
| 723 | Apol9a | Fkbp1a | | |
| 724 | Wnt4 | Commd4 | | |
| 725 | 1500003O03Rik | Col5a3 | | |
| 726 | Phf3 | Fblim1 | | |
| 727 | 1110004F10Rik | Cwh43 | | |
| 728 | Kansl1 | Arl2bp | | |
| 729 | Fth1 | Mrpl46 | | |
| 730 | Tmem50a | Tcn2 | | |
| 731 | Utp20 | Add2 | | |
| 732 | Smad4 | Specc1l | | |
| 733 | Stmn2 | Ppcs | | |
| 734 | Gstm1 | Vrk3 | | |
| 735 | Senp6 | Trim25 | | |
| 736 | Gda | Nfatc1 | | |
| 737 | Nucks1 | Rap1gap | | |
| 738 | Ints10 | Hsd17b12 | | |
| 739 | Syne1 | Epas1 | | |
| 740 | Itga6 | Ddx1 | | |
| 741 | Acad9 | Prdx6 | | |
| 742 | Maged1 | Mmp24 | | |
| 743 | Spen | Ndufb9 | | |
| 744 | Chd1 | Phf23 | | |
| 745 | Taf3 | Rpa2 | | |
| 746 | Ptgs1 | 5031439G07Rik | | |
| 747 | Spare | Rrp7a | | |
| 748 | R74862 | Arfip2 | | |
| 749 | B230120H23Rik | Efna1 | | |
| 750 | Tmem234 | Agps | | |
| 751 | Ryk | Sephs1 | | |
| 752 | Dlgap4 | Apoc2 | | |
| 753 | Atp1b1 | Mrps27 | | |
| 754 | Parp14 | Snn | | |
| 755 | Tgfbr2 | Serinc3 | | |
| 756 | Ccdc90a | Pdcd5 | | |
| 757 | Ncoa1 | AA986860 | | |
| 758 | Pppde1 | Pitpna | | |
| 759 | Luc7l3 | Vac14 | | |
| 760 | Prg4 | 2810025M15Rik | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 761 | Rab11fip1 | Def8 | | |
| 762 | Plk2 | Hilpda | | |
| 763 | Ifi35 | Eif6 | | |
| 764 | Pdap1 | Brd7 | | |
| 765 | Cd248 | Fes | | |
| 766 | Sesn1 | Sbf1 | | |
| 767 | Ecd | Ak2 | | |
| 768 | Ap1s3 | 1810035L17Rik | | |
| 769 | H2-K1 | Lime1 | | |
| 770 | Spag9 | Hspe1 | | |
| 771 | Tshz1 | Csrp2bp | | |
| 772 | Dennd5a | Uba5 | | |
| 773 | Stag1 | Gsta4 | | |
| 774 | Gpx8 | 2900092E17Rik | | |
| 775 | Sod3 | | | |
| 776 | BC005561 | | | |
| 777 | kg:uc009vev.1 | | | |
| 778 | Ywhaz | | | |
| 779 | Ganab | | | |
| 780 | Rras2 | | | |
| 781 | Dusp14 | | | |
| 782 | kg:uc012hdk.1 | | | |
| 783 | Nr1d1 | | | |
| 784 | Wwc2 | | | |
| 785 | Ubxn2a | | | |
| 786 | Iqsec1 | | | |
| 787 | kg:uc007vsr.1 | | | |
| 788 | Cfl1 | | | |
| 789 | Csrp1 | | | |
| 790 | Smchd1 | | | |
| 791 | Myl12a | | | |
| 792 | Ubqln2 | | | |
| 793 | Tmcc3 | | | |
| 794 | Kdm5a | | | |
| 795 | Rbm25 | | | |
| 796 | Wdr26 | | | |
| 797 | Vim | | | |
| 798 | Arpc2 | | | |
| 799 | Calm1 | | | |
| 800 | Dnaja2 | | | |
| 801 | Shc1 | | | |
| 802 | Vps13a | | | |
| 803 | Klf7 | | | |
| 804 | 1810074P20Rik | | | |
| 805 | BC003331 | | | |
| 806 | Itpr2 | | | |
| 807 | Jmjd1c | | | |
| 808 | Pcdhgb5 | | | |
| 809 | Tubb2a | | | |
| 810 | Ehd2 | | | |
| 811 | Ift74 | | | |
| 812 | Per1 | | | |
| 813 | Pitpnm2 | | | |
| 814 | Gstm4 | | | |
| 815 | Dnmt1 | | | |
| 816 | Tmco1 | | | |
| 817 | Lass4 | | | |
| 818 | Ptprf | | | |
| 819 | Sirt2 | | | |
| 820 | Gfm2 | | | |
| 821 | Taf7 | | | |
| 822 | Spop | | | |
| 823 | Zzef1 | | | |
| 824 | Ccdc34 | | | |
| 825 | Zfp281 | | | |
| 826 | Tuba1a | | | |
| 827 | Ccdc109b | | | |
| 828 | Cdk13 | | | |
| 829 | Dhx15 | | | |
| 830 | Src | | | |
| 831 | Braf | | | |
| 832 | Mapre2 | | | |
| 833 | Anxa7 | | | |
| 834 | Sept9 | | | |
| 835 | Alox12 | | | |

TABLE 2-continued

Significantly Expressed Genes by Rank Product (FDR < 0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 836 | Pknox1 | | | |
| 837 | 2610034B18Rik | | | |
| 838 | Topors | | | |
| 839 | Phf21a | | | |
| 840 | Qser1 | | | |
| 841 | Tirap | | | |
| 842 | Fas | | | |
| 843 | Lass2 | | | |
| 844 | 6330406I15Rik | | | |
| 845 | Parvb | | | |
| 846 | Atp1a1 | | | |
| 847 | Mtmr6 | | | |
| 848 | Cd109 | | | |
| 849 | Dnajc1 | | | |
| 850 | Hp1bp3 | | | |
| 851 | 1600029D21Rik | | | |
| 852 | Ttc38 | | | |
| 853 | Mfhas1 | | | |
| 854 | Filip1l | | | |
| 855 | Zfp148 | | | |
| 856 | Nkd1 | | | |
| 857 | Usp16 | | | |
| 858 | Tlr2 | | | |
| 859 | Zc3h18 | | | |
| 860 | Stk10 | | | |
| 861 | Ltbp4 | | | |
| 862 | Hdac3 | | | |
| 863 | Efhd2 | | | |
| 864 | Prkar2a | | | |
| 865 | Atp6v1a | | | |
| 866 | Sf3b4 | | | |
| 867 | Gprc5b | | | |
| 868 | Clip3 | | | |
| 869 | Mettl2 | | | |
| 870 | Secisbp2 | | | |
| 871 | Fmod | | | |
| 872 | kg:uc0091xf.1 | | | |
| 873 | Elovl6 | | | |
| 874 | Bzw1 | | | |
| 875 | Etfa | | | |
| 876 | Hspa2 | | | |
| 877 | kg:uc007won.1 | | | |
| 878 | Rnf20 | | | |

TABLE 3

Most Significant Gene Ontology Terms in CTC-c enriched genes using BP_FAT and CC_FAT Datasets
q-value < 0.01

| Source | Term | Count | Odds Ratio | Benjamini (q-value) |
|---|---|---|---|---|
| GOTERM_BP_FAT | GO: 0060429~epithelium development | 35 | 2.92 | 8.72E−05 |
| GOTERM_BP_FAT | GO: 0030029~actin filament-based process | 27 | 3.47 | 6.85E−05 |
| GOTERM_BP_FAT | GO: 0030036~actin cytoskeleton organization | 26 | 3.57 | 4.95E−05 |
| GOTERM_BP_FAT | GO: 0007010~cytoskeleton organization | 36 | 2.50 | 6.27E−04 |
| GOTERM_BP_FAT | GO: 0051173~positive regulation of nitrogen compound metabolic process | 49 | 2.11 | 6.62E−04 |
| GOTERM_BP_FAT | GO: 0035295~tube development | 31 | 2.66 | 7.80E−04 |
| GOTERM_BP_FAT | GO: 0010604~positive regulation of macromolecule metabolic process | 54 | 1.93 | 0.001727 |
| GOTERM_BP_FAT | GO: 0031328~positive regulation of cellular biosynthetic process | 49 | 2.01 | 0.0015751 |
| GOTERM_BP_FAT | GO: 0051789~response to protein stimulus | 16 | 4.16 | 0.0014484 |
| GOTERM_BP_FAT | GO: 0035239~tube morphogenesis | 23 | 3.05 | 0.0015064 |
| GOTERM_BP_FAT | GO: 0045449~regulation of transcription | 140 | 1.42 | 0.0014097 |
| GOTERM_BP_FAT | GO: 0048729~tissue morphogenesis | 28 | 2.66 | 0.0013058 |
| GOTERM_BP_FAT | GO: 0009891~positive regulation of biosynthetic process | 49 | 1.99 | 0.0012408 |

TABLE 3-continued

Most Significant Gene Ontology Terms in CTC-c enriched genes using
BP_FAT and CC_FAT Datasets
q-value < 0.01

| Source | Term | Count | Odds Ratio | Benjamini (q-value) |
|---|---|---|---|---|
| GOTERM_BP_FAT | GO: 0045935~positive regulation of nucleobase, nucleoside, nucleotide and nucleic acid metabolic process | 46 | 2.04 | 0.0012061 |
| GOTERM_BP_FAT | GO: 0002009~morphogenesis of an epithelium | 23 | 3.01 | 0.0012149 |
| GOTERM_BP_FAT | GO: 0048584~positive regulation of response to stimulus | 24 | 2.92 | 0.0011396 |
| GOTERM_BP_FAT | GO: 0051276~chromosome organization | 39 | 2.19 | 0.0012619 |
| GOTERM_BP_FAT | GO: 0045637~regulation of myeloid cell differentiation | 12 | 5.33 | 0.0014358 |
| GOTERM_BP_FAT | GO: 0045785~positive regulation of cell adhesion | 11 | 5.79 | 0.0016889 |
| GOTERM_BP_FAT | GO: 0045941~positive regulation of transcription | 43 | 2.05 | 0.0016795 |
| GOTERM_BP_FAT | GO: 0045893~positive regulation of transcription, DNA-dependent | 39 | 2.12 | 0.0019852 |
| GOTERM_BP_FAT | GO: 0051254~positive regulation of RNA metabolic process | 39 | 2.11 | 0.0022107 |
| GOTERM_BP_FAT | GO: 0006357~regulation of transcription from RNA polymerase II promoter | 51 | 1.87 | 0.0022801 |
| GOTERM_BP_FAT | GO: 0006325~chromatin organization | 32 | 2.30 | 0.0025187 |
| GOTERM_BP_FAT | GO: 0010628~positive regulation of gene expression | 43 | 2.00 | 0.0025252 |
| GOTERM_BP_FAT | GO: 0060562~epithelial tube morphogenesis | 17 | 3.47 | 0.0025847 |
| GOTERM_BP_FAT | GO: 0042127~regulation of cell proliferation | 45 | 1.89 | 0.0051485 |
| GOTERM_BP_FAT | GO: 0010557~positive regulation of macromolecule biosynthetic process | 44 | 1.88 | 0.0071937 |
| GOTERM_BP_FAT | GO: 0002253~activation of immune response | 14 | 3.69 | 0.0078441 |
| GOTERM_BP_FAT | GO: 0050778~positive regulation of immune response | 18 | 3.00 | 0.0080458 |
| GOTERM_BP_FAT | GO: 0002684~positive regulation of immune system process | 23 | 2.53 | 0.0088166 |
| GOTERM_BP_FAT | GO: 0045944~positive regulation of transcription from RNA polymerase II promoter | 33 | 2.09 | 0.0090124 |
| GOTERM_CC_FAT | GO: 0005578~proteinaceous extracellular matrix | 32 | 2.38 | 0.0047511 |
| GOTERM_CC_FAT | GO: 0031012~extracellular matrix | 32 | 2.28 | 0.0051923 |
| GOTERM_CC_FAT | GO: 0044421~extracellular region part | 60 | 1.71 | 0.0064365 |
| GOTERM_CC_FAT | GO: 0031981~nuclear lumen | 65 | 1.62 | 0.0102413 |
| GOTERM_CC_FAT | GO: 0043233~organelle lumen | 79 | 1.53 | 0.0085938 |
| GOTERM_CC_FAT | GO: 0005829~cytosol | 45 | 1.81 | 0.0100772 |
| GOTERM_CC_FAT | GO: 0070013~intracellular organelle lumen | 78 | 1.52 | 0.0093866 |
| GOTERM_CC_FAT | GO: 0031982~vesicle | 43 | 1.83 | 0.0087123 |
| GOTERM_CC_FAT | GO: 0031974~membrane-enclosed lumen | 80 | 1.50 | 0.0082696 |

TABLE 4

Most Significant Gene Sets Enriched in CTC-plt vs CTC-c
q-value < 0.01

| Source | Term | Count | Odds Ratio | Benjamini (q-value) |
|---|---|---|---|---|
| GOTERM_BP_FAT | GO: 0042060~wound healing | 18 | 7.8 | 1.86E-07 |
| GOTERM_BP_FAT | GO: 0007596~blood coagulation | 15 | 10.4 | 9.31E-08 |
| GOTERM_BP_FAT | GO: 0050817~coagulation | 15 | 10.4 | 9.31E-08 |
| GOTERM_BP_FAT | GO: 0007599~hemostasis | 15 | 10.3 | 7.59E-08 |
| GOTERM_BP_FAT | GO: 0050878~regulation of body fluid levels | 15 | 8.2 | 1.30E-06 |
| GOTERM_BP_FAT | GO: 0030029~actin filament-based process | 20 | 5.5 | 1.14E-06 |
| GOTERM_BP_FAT | GO: 0007010~cytoskeleton organization | 26 | 3.9 | 3.95E-06 |
| GOTERM_BP_FAT | GO: 0030036~actin cytoskeleton organization | 18 | 5.3 | 1.11E-05 |
| GOTERM_BP_FAT | GO: 0009611~response to wounding | 26 | 3.6 | 1.02E-05 |
| GOTERM_BP_FAT | GO: 0007155~cell adhesion | 33 | 2.9 | 2.86E-05 |
| GOTERM_BP_FAT | GO: 0022610~biological adhesion | 33 | 2.8 | 2.70E-05 |

TABLE 4-continued

Most Significant Gene Sets Enriched in CTC-plt vs CTC-c
q-value < 0.01

| Source | Term | Count | Odds Ratio | Benjamini (q-value) |
|---|---|---|---|---|
| GOTERM_BP_FAT | GO: 0001775~cell activation | 19 | 3.7 | 4.70E−04 |
| GOTERM_BP_FAT | GO: 0030168~platelet activation | 6 | 18.2 | 1.68E−03 |
| GOTERM_BP_FAT | GO: 0007229~integrin-mediated signaling pathway | 10 | 6.4 | 2.95E−03 |
| GOTERM_BP_FAT | GO: 0016192~vesicle-mediated transport | 25 | 2.6 | 3.81E−03 |
| MSigDBv3.1 CGP | GNATENKO PLATELET SIGNATURE | 20 | 55.1 | 3.91E−24 |
| MSigDBv3.1 CGP | TENEDINI MEGAKARYOCYTE MARKERS | 14 | 15.3 | 1.35E−11 |
| MSigDBv3.1 CP:REACTOME | REACTOME FACTORS INVOLVED IN MEGAKARYOCYTE DEVELOPMENT AND PLATELET PRODUCTION | 6 | 2.9 | 2.25E−02 |

TABLE 5

Most Significant Gene Sets Enriched in CTC-pro vs CTC-c
q-value < 0.01

| Source | Term | Count | Odds Ratio | Benjamini (q-value) |
|---|---|---|---|---|
| GOTERM_BP_FAT | GO: 0002495~antigen processing and presentation of peptide antigen via MHC class II | 5 | 59.81 | 6.97E−04 |
| GOTERM_BP_FAT | GO: 0019886~antigen processing and presentation of exogenous peptide antigen via MHC class II | 5 | 59.81 | 6.97E−04 |
| GOTERM_BP_FAT | GO: 0002504~antigen processing and presentation of peptide or polysaccharide antigen via MHC class II | 5 | 50.36 | 7.34E−04 |
| GOTERM_BP_FAT | GO: 0002478~antigen processing and presentation of exogenous peptide antigen | 5 | 41.60 | 1.10E−03 |
| GOTERM_BP_FAT | GO: 0019884~antigen processing and presentation of exogenous antigen | 5 | 34.18 | 1.87E−03 |
| GOTERM_BP_FAT | GO: 0048002~antigen processing and presentation of peptide antigen | 5 | 27.34 | 3.72E−03 |
| GOTERM_BP_FAT | GO: 0001775~cell activation | 9 | 7.00 | 3.82E−03 |
| GOTERM_BP_FAT | GO: 0019882~antigen processing and presentation | 6 | 13.20 | 7.40E−03 |

Example 2

Supplemental Methods

Mice and cell lines. Mice with pancreatic cancer used in these experiments express Cre driven by Pdx1, LSL-Kras$^{G12D}$, and Trp53$^{lox/+}$ or Trp53$^{lox/lox}$ (otherwise referred to as KPC) as previously described (Bardeesy et al., 2006). EGFP pancreatic lineage tagged KPC mice were generated by breeding the mT/mG mouse (Purchased from the Jackson Laboratory—Gt(ROSA)26Sortm4(ACTB-tdTomato,-EGFP)Luo/J) into the breeder pairs used for KPC mouse generation. Normal FVB mice were purchased from Jackson Laboratory. All mice care and procedures were done under MGH SRAC approved protocols.

For cardiocentesis, animals were sedated with isoflurane, the chest wall was sterilized with ethanol and a skin incision was made above the rib cage to expose the thoracic cavity and eliminate normal skin epithelial cell contamination. A 23-gauge needle was used to draw approximately 1 mL of blood into a 1 mL syringe primed with 100 μL of PBS-10 mM EDTA pH 7.4 (Gibco). Blood EDTA concentration was raised to 5 mM by either the addition of a concentrated bolus of 500 mM EDTA or 1:1 dilution with 10 mM EDTA. Animals were then euthanized per animal protocol guidelines.

A mouse pancreatic cell line NB508 (Pdx1-Cre/Kras$^{G12D}$/Trp53$^{lox/+}$) previously generated from primary tumors developed in this endogenous model was GFP transfected by lentivirus (NB508-GFP). This cell line was used for spiked cell experiments and orthotopic tumor formation.

NB508-GFP Cell lines were maintained in standard culture conditions using RPMI-1640 medium+10% FBS+1% Pen/Strep (Gibco/Invitrogen).

For orthotopic experiments, NB508-GFP cells were orthotopically injected into the pancreas of healthy syngeneic (FVB background) mice. Briefly, mice were anesthesized with isofluorane and the left abdominal wall was treated with Nair® hair removal product, and sterilized with 70% ethanol. A small incision was made on the upper left lateral abdominal wall and the pancreas was mobilized. Approximately 1 million NB508-GFP cells in PBS in a total volume of 0.1 mL was injected into the pancreas. The peritoneum and abdominal wall was closed by sterile surgical staples. The tumors were allowed to grow for 2 weeks, at which time blood was obtained by cardiocentesis for CTC-iChip processing.

Adaptation of CTC Enrichment Technology.

Given the desire for an unbiased enrichment system, the negative depletion technology was selected for this application. All processing protocols were identical to those previously identified, except a rat anti-mouse CD45 antibody (BAM114, R&D Systems, USA) was conjugated to MyOne beads.

Spiked cell experiments were conducted to validate the system by spiking ~1000 GFP expressing NB508 cells into 1 mL of healthy mouse blood and processing to determine recovery efficiency. Orthotopic models were used to validate recovery efficiency as well as initially determine expected depletion efficiency from tumor-bearing mice. In these experiments, enriched samples were evaluated for the number of GFP+ cells observed in the product.

Immunostaining of CTCs Isolated from the Endogenous Model.

Isolated CTCs were spun onto glass slides and immunostained using a primary-secondary approach. Primary antibodies were rabbit anti-wide spectrum cytokeratin (1:50, Abcam ab9377), and goat anti-mouse CD45 (1:500, R&D systems AF114). Secondary immunofluorescent-tagged antibodies were used for signal amplification. These were donkey anti-rabbit Alexa Fluor 594 (1:500, Invitrogen A-21207), and donkey anti-goat Alexa Fluor 488 (1:500, Invitrogen A-11055). Nuclei were then counterstained with DAPI and the slides were rinsed with PBS, cover slipped and stored at 4° C. They were imaged under 10× magnification using the BioView™ Ltd. automated imaging system (Billerica, Mass.) as well as an automated upright fluorescence microscope (Eclipse 90i™, Nikon, Melville, N.Y.). Positive staining for CK, without CD45 staining, was required for scoring potential CTCs, which were then manually reviewed. Threshold and baseline signals were established using specimens from non-tumor bearing mice.

Single Cell Micromanipulation.

After whole blood anti-CD45 negative depletion, the product containing enriched cells was collected in a 35 mm petri dish and viewed using a Nikon Eclipse Ti™ inverted fluorescent microscope. Cells of interest were identified based on intact cellular morphology and lack of labeling with anti-CD45 magnetic beads. These target cells were individually micromanipulated with a 10 μm transfer tip on an Eppendorf TransferMan® NK 2 micromanipulator and ejected into PCR tubes containing RNA protective lysis buffer (10×PCR Buffer II, 25 mM MgCl2, 10% NP40, 0.1 M DTT, SUPERase-In, Rnase Inhibitor, 0.5 uM UP1 Primer, 10 mM dNTP and Nuclease-free water) and immediately flash frozen in liquid nitrogen.

Single Cell Amplification and Sequencing.

Single cell amplification and sequencing were done as previously described (Tang et al., 2010) with slight modifications underlined below. RNA samples from extracted single circulating tumor cells were thawed on ice and incubated at 70° C. for 90 seconds. To generate cDNA, samples were treated with reverse transcription master mix (0.05 uL RNase inhibitor, 0.07 uL T4 gene 32 protein, and 0.33 uL SuperScript™ III Reverse Transcriptase per 1× volume) and incubated on thermocycler at 50° C. for 30 minutes and 70° C. for 15 minutes. To remove free primer, 1.0 uL of EXOSAP mix was added to each sample, which was incubated at 37° C. for 30 minutes and inactivated at 80° C. for 25 minutes. Next, a 3'-poly-A tail was added to the cDNA in each sample by incubating in master mix (0.6 uL 10×PCR Buffer II, 0.36 uL 25 mM MgCl$_2$, 0.18 uL 100 mM dATP, 0.3 uL Terminal Transferase, 0.3 uL RNase H, and 4.26 uL H$_2$O per 1× volume) at 37° C. for 15 minutes and inactivated at 70° C. for 10 minutes. A second strand cDNA was synthesis by dividing each sample into 4 and incubating in master mix (2.2 uL 10× High Fidelity PCR Buffer, 1.76 uL 2.5 mM each dNTP, 0.066 uL UP2 Primer at 100 uM, 0.88 uL 50 mM MgSO$_4$, 0.44 uL Platinum Taq DNA Polymerase, and 13.654 uL H$_2$O per 1× volume) at 95° C. for 3 minutes, 50° C. for 2 minutes, and 72° C. for 10 minutes.

PCR amplification (95° C. for 3 minutes, 20 cycles of 95° C. for 30 seconds, 67° C. for 1 minute, and 72° C. for 6 minutes 6 seconds) was performed with master mix (4.1 uL 10× High Fidelity PCR Buffer, 1.64 uL 50 mM MgSO$_4$, 4.1 uL 2.5 mM each dNTP, 0.82 uL AUP1 Primer at 100 uM, 0.82 uL AUP2 Primer at 100 uM, 0.82 uL Platinum Taq DNA Polymerase, and 6.7 uL H$_2$O per 1× volume). The 4 reactions of each sample were pooled and purified using the QIAGEN PCR Purification Kit (Cat. No 28106) and eluted in 50 uL EB buffer. Samples were selected by testing for genes Gapdh, ActB, Ptprc (CD45), Krt8, Krt18, Krt19, and Pdx1 using qPCR. Each sample was again divided in 4 and a second round of PCR amplification (9 cycles of 98° C. for 3 minutes, 67° C. for 1 minute, and 72° C. for 6 minutes 6 seconds) was performed with master mix (9 uL 10× High Fidelity PCR Buffer, 3.6 uL 50 mM MgSO$_4$, 13.5 uL 2.5 mM each dNTP, 0.9 uL AUP1 Primer at 100 uM, 0.9 uL AUP2 Primer at 100 uM, 1.8 uL Platinum Taq DNA Polymerase, and 59.1 uL H$_2$O per 1× volume). Samples were pooled and purified using Agencourt AMPure XP beads and eluted in 40 uL 1× low TE buffer.

Sequencing Library Construction.

To shear the DNA using the Covaris S2™ System, 1× low TE buffer and 1.2 uL shear buffer were added to each sample. Conditions of the shearing program include: 6 cycles, 5° C. bath temperature, 15° C. bath temperature limit, 10% duty cycle, intensity of 5, 100 cycles/burst, and 60 seconds. Then, samples were end-polished at room temperature for 30 minutes with master mix (40 uL 5× Reaction Buffer, 8 uL 10 mM dNTP, 8 uL End Polish Enzyme1, 10 uL End Polish Enzyme2, and 14 uL H$_2$O per 1× volume). DNA fragments larger than 500 bp were removed with 0.5× volumes of Agencourt AMPure XP™ beads. Supernatant was transferred to separate tubes. To size-select 200-500 bp DNA products, 0.3× volumes of beads were added and samples were washed 2× with 70% EtOH. The products were eluted in 36 uL low TE buffer. A dA-tail was added to each size-selected DNA by treating with master mix (10 uL 5× Reaction Buffer, 1 uL 10 mM dATP, and 5 uL A-Tailing Enzyme I per 1× volume) and incubated at 68° C. for 30 minutes and cooled to room temperature. To label and distinguish each DNA sample for sequencing, barcode adaptors (5500 SOLiD 4464405) were ligated to DNA using the 5500 SOLiD Fragment Library Enzyme Module™ (4464413). Following barcoding, samples were purified twice using the Agencourt AMPure XP™ beads and eluted in 22 uL low TE buffer. Following a round of PCR Amplification (95° C. for 5 minutes, 12 cycles of 95° C. for 15 seconds, 62° C. for 15 seconds, and 70° C. for 1 minute, and 70° C. for 5 minutes), the libraries were purified with AMPure XP beads. Finally, to quantify the amount of ligated DNA, SOLiD Library TaqMan Quantitation Kit™ was used to perform qPCR. Completed barcoded libraries were then subjected to emulsion PCR with template beads preparation and sequenced on the ABI 5500XL™.

RNA In Situ Hybridization (RNA-ISH).

Paraffin-embedded tissue blocks were freshly cut and frozen at −80° C. Upon removal from the freezer, slides were baked for 1 hr at 60° C. and fixed in %10 formaldehyde for 1 hr at room temperature (RT). Paraffin was removed using Histo-Clear™ and RNA-ISH™ was performed according to the Affymetrix QuantiGene ViewRNA ISH Tissue-2 Plex Assay™. Tissue sections were permeabilized by pretreating in buffer solution for 10 min at 95° C. and digested with protease for 10 min, before being fixed at RT in 5% formaldehyde. Target probe sets were applied and hybridized to the tissue by incubating for 2 hr at 40° C. Type 1 probes were used at a dilution of 1:50 and included Aldh1a2 (VB1-14197), Dcn (VB1-14962), Klf4 (VB1-14988), Igfbp5 (VB1-14987), and Sparc (VB1-14196). Type 6 probes included EGFP (VF6-13336) at 1:50 and pooled Krt8 (VB6-11060) and Krt18 (VB6-11059) at 1:100 each. Signal was amplified through the sequential hybridization of PreAmplifier and Amplifer QT mixes to the target probe set. Target mRNA molecules were detected by applying Type 6 Label Probe with Fast Blue substrate and Type 1 Label Probe with Fast Red substrate. Tissue was counterstained with Gill's Hemotoxylin for 10 sec at RT. DAPI (Invitrogen, D3571; 3.0 μg/ml) staining was performed for 1 min. Fluorescence microscopy using a Nikon 90i was used to visualize target mRNAs. Type 1 probes were detected in the Cy3 channel and Type 6 probes in the Cy5 channel. Merged images were generated using NIS-Elements™ software.

Determination of Reads-Per-Million (rpm)

Color space reads were aligned using Tophat™ version 2.0.4 (Trapnell et al., 2009) and Bowtie1™ version 0.12.7 with the no-novel-juncs argument set with mouse genome version mm9 and transcriptome defined by the mm9 knownGene table from genome.ucsc.edu. Reads that did not align or aligned to multiple locations in the genome were discarded. The mm9 table knownToLocusLink from genome.ucsc.edu was used to map, if possible, each aligned read to the gene who's exons the read had aligned to. The reads count for each gene was the number of reads that were so mapped to that gene. This count was divided by the total number of reads that were mapped to any gene and multiplied by one million to form the reads-per-million (rpm) count. Rpm rather than rpkm was used because a 3' bias was noted in the alignments.

Unsupervised Hierarchical Clustering and Principal Components Analysis.

The minimum of 1 and the smallest positive value of the rpm matrix was added to the rpm matrix to eliminate zeros. The result was then log 10 transformed, yielding what is termed the log 10 (rpm) matrix. The rows (corresponding to genes) of the log 10 (rpm) matrix with the top 2000 standard deviations were retained and the rest of the rows discarded. The result was then median polished. The result was clustered using agglomerative hierarchical clustering with average linkage with distance metric equal to 1 minus the Pearson correlation coefficient. The principal components of the log 10 (rpm) matrix were computed and the coordinates of the samples with respect to the first three principal components were plotted.

Measures of Cellular Heterogeneity.

For a collection of clusters of samples, a statistic, M, was defined as the mean over the clusters of the mean over all the pairs of samples in the cluster of the a tan h of the correlation coefficient between the two columns of the rpm matrix corresponding to the pair. The "mean intra-cluster correlation coefficient" was defined as tan h(M). The jackknife estimator was used with respect to the samples to estimate a standard deviation, s, of the statistic. The 95% CI was defined as tan h ($M \pm s\phi^{-1}(0.975)$), where 4 is the cumulative distribution function of the standard normal distribution. To compute a p-value for the null hypothesis that the mean of the distribution of the M statistic for a cluster is the same as the mean of the distribution of the M statistic for a collection of clusters, we let $p=2(1-\phi(|M1-M2|/\sqrt{s^2_1+s^2_2}))$. Of note, bootstrap was performed on the same data as an alternative to jackknife and similar results obtained (data not shown).

Supervised Differential Gene Expression Using Rank Product.

To find differentially expressed genes between two sets of samples, analysis was begin with the log 10 (rpm) matrix defined above. Columns corresponding to samples not in either set of samples were removed. Then removed rows for which the 90$^{th}$ percentile of the values was less than log 10(10) were removed. The RP function of the Bioconductor (Gentleman et al., 2004) RankProd™ package (version 2.28.0) was used to get FDR estimates for both up and down differential expression. Genes were considered to be differentially expressed if their FDR estimate was less than 0.01, but discarded if they were both up and down differentially expressed, if there were any.

Gene Set Enrichment.

Enrichment was considered in four gene set collections: (1) all of KEGG™, as found in DAVID™ 6.7 (Huang da et al., 2009), (2) Gene Ontology (GO) using GO_BP as found in DAVID 6.7, and (3) GO_CC as found in DAVID 6.7. Sets of genes found to be differentially expressed were tested for enrichment in the gene set collections using a hypergeometric test for each gene set in the collection. The resulting p-values for each collection were converted to FDR estimates using the Benjamini-Hochberg method (Benjamini and Hochberg, 1995).

Digital Removal of all Annotated Platelet Transcripts

The 446 genes whose expression in the log 10 (rpm) matrix had an absolute value of correlation coefficient greater than 0.6 with the expression of any of the genes in the gene sets named GNATENKO_PLATELET_SIGNATURE and TENEDINI_MEGAKARYOCYTE_MARKERS in MSigDB v3.1 were removed from the log 10 (rpm) matrix (defined above). Clustering was then performed as described above.

SUPPLEMENTAL METHODS REFERENCES

Bardeesy, N., Aguirre, A. J., Chu, G. C., Cheng, K. H., Lopez, L. V., Hezel, A. F., Feng, B., Brennan, C., Weissleder, R., Mahmood, U., et al. (2006). Both p16 (Ink4a) and the p19(Arf)-p53 pathway constrain progression of pancreatic adenocarcinoma in the mouse. Proc Natl Acad Sci USA 103, 5947-5952.

Benjamini, Y., and Hochberg, Y. (1995). Controlling the False Discovery Rate: A Practical and Powerful Approach to Multiple Testing. Journal of the Royal Statistical Society Series B (Methodological) 57, 289-300.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome biology 5, R80.

Huang da, W., Sherman, B. T., and Lempicki, R. A. (2009). Systematic and integrative analysis of large gene lists using DAVID bioinformatics resources. Nat Protoc 4, 44-57.

Tang, F., Barbacioru, C., Nordman, E., Li, B., Xu, N., Bashkirov, V. I., Lao, K., and Surani, M. A. (2010). RNA-Seq analysis to capture the transcriptome landscape of a single cell. Nat Protoc 5, 516-535.

Trapnell, C., Pachter, L., and Salzberg, S. L. (2009). TopHat: discovering splice junctions with RNA-Seq. Bioinformatics 25, 1105-1111.

Example 3

A comparative analysis of mouse pancreatic CTCs indicated an enrichment of 60 extracellular proteins (Table 6).

Evaluation of these particular biomarkers and therapeutic targets was undertaken in human pancreatic circulating tumor cells and the most abundant targets in human pancreatic CTCs are shown (FIG. 7). These not only represent potential biomarkers, but given their nature as proteins on the external surface of tumor cells, they are therapeutic targets. The extracellular proteins of Table 6 can be targeted, e.g. by antibody-based therapeutics (e.g. as in the cases of trastuzumab for HER2, cetuximab for EGFR, and bevacizumab for VEGF) to treat cancer.

TABLE 6

List of Pancreatic CTC enriched Extracellular Proteins.

| OFFICIAL GENE SYMBOL | Gene Name |
| --- | --- |
| Abi3bp | ABI gene family, member 3 (NESH) binding protein |
| Adamts5 | similar to a disintegrin-like and metalloprotease (reprolysin type) with thrombospondin type 1 motif, 5 (aggrecanase-2); a disintegrin-like and metallopeptidase (reprolysin type) with thrombospondin type 1 motif, 5 (aggrecanase-2) |
| Adamtsl1 | ADAMTS-like 1 |
| Ang | angiogenin, ribonuclease, RNase A family, 5 |
| Arsa | arylsulfatase A |
| C1rl | complement component 1, r subcomponent-like |
| C3 | complement component 3; similar to complement component C3 prepropeptide, last |
| C4a | similar to Complement C4 precursor; complement component 4A (Rodgers blood group); similar to complement C4; complement component 4B (Childo blood group) |
| C4b | similar to Complement C4 precursor; complement component 4A (Rodgers blood group); similar to complement C4; complement component 4B (Childo blood group) |
| Ccdc80 | coiled-coil domain containing 80 |
| Cd109 | CD109 antigen |
| Chi3l1 | chitinase 3-like 1 |
| Clec3b | C-type lectin domain family 3, member b |
| Cmtm3 | CKLF-like MARVEL transmembrane domain containing 3 |
| Cmtm7 | CKLF-like MARVEL transmembrane domain containing 7 |
| Col14a1 | collagen, type XIV, alpha 1 |
| Col1a2 | collagen, type I, alpha 2 |
| Col3a1 | collagen, type III, alpha 1 |
| Col4a6 | collagen, type IV, alpha 6 |
| Csf1 | colony stimulating factor 1 (macrophage) |
| Dag1 | dystroglycan 1 |
| Dcn | decorin |
| Dmkn | dermokine |
| Fbln1 | fibulin 1 |
| Fgf1 | fibroblast growth factor 1 |
| Fmod | fibromodulin |
| Gpc3 | glypican 3 |
| Gpc4 | glypican 4; similar to Glypican 4 |
| Hmgb1 | high mobility group box 1 |
| Ifnar2 | interferon (alpha and beta) receptor 2 |
| Igfbp5 | insulin-like growth factor binding protein 5 |
| Il16 | interleukin 16 |
| Lama4 | laminin, alpha 4 |
| Ltbp4 | latent transforming growth factor beta binding protein 4 |
| Mfap1a | similar to microfibrillar-associated protein 1A; microfibrillar-associated protein 1A; microfibrillar-associated protein 1B |
| Nid2 | nidogen 2 |
| Ogn | osteoglycin |
| Pdap1 | PDGFA associated protein 1 |
| Pf4 | platelet factor 4 |
| Plat | plasminogen activator, tissue |
| Podn | podocan |
| Prelp | proline arginine-rich end leucine-rich repeat |
| Rspo1 | R-spondin homolog (Xenopus laevis) |
| Serping1 | serine (or cysteine) peptidase inhibitor, clade G, member 1 |
| Slurp1 | secreted Ly6/Plaur domain containing 1 |
| Sod3 | superoxide dismutase 3, extracellular |
| Sparc | secreted acidic cysteine rich glycoprotein; similar to Secreted acidic cysteine rich glycoprotein |
| Spock2 | sparc/osteonectin, cwcv and kazal-like domains proteoglycan 2 |
| Spon2 | spondin 2, extracellular matrix protein |
| Sulf1 | sulfatase 1 |
| Sulf2 | sulfatase 2 |
| Tgfb2 | transforming growth factor, beta 2 |
| Tgm2 | transglutaminase 2, C polypeptide |
| Thbd | thrombomodulin |
| Thbs1 | thrombospondin 1; similar to thrombospondin 1 |
| Thsd4 | thrombospondin, type I, domain containing 4 |
| Timp2 | tissue inhibitor of metalloproteinase 2 |
| Tnxb | tenascin XB |

TABLE 6-continued

List of Pancreatic CTC enriched Extracellular Proteins.

| OFFICIAL GENE SYMBOL | Gene Name |
|---|---|
| Tpt1 | predicted gene 1974; tumor protein, translationally-controlled 1 pseudogene; tumor protein, translationally-controlled 1; predicted gene 14456 |
| Twsg1 | twisted gastrulation homolog 1 (*Drosophila*) |
| Wnt4 | wingless-related MMTV integration site 4 |

Extending these CTC enriched genes to human pancreatic, breast, and prostate single cell CTC data identified 5 candidate genes shown in Table 9.

TABLE 9

Percent of human single CTCs with high expression by RNA-seq

| | Percent of Single CTCs >50 RPM of Expression | | | |
|---|---|---|---|---|
| Cancer Type | Pancreas (N = 7) | Breast (N = 29) | Prostate (N = 77) | ALL (N = 113) |
| TPT1 | 86% | 90% | 90% | 89% |
| HMGB1 | 43% | 62% | 44% | 49% |
| SPON2 | 43% | 7% | 45% | 35% |
| SPARC | 100% | 41% | 9% | 23% |
| ARSA | 71% | 17% | 5% | 12% |

Focusing on pancreatic cancer, SPARC was selected as an initial gene to evaluate. SPARC RNA-ISH in mouse and human primary tumors (data not shown) demonstrated significant expression in the stromal cells of the tumor that provides essential microenvironmental signals to tumors. Much effort in the field focuses on targeting the stroma of PDAC for therapeutic efficacy [1-4] making SPARC a CTC therapeutic target as well as a stromal directed target. A total of 196/198 (99%) of human pancreatic tumors were positive for SPARC and 36% with clear epithelial tumor cell expression.

Figure 8:
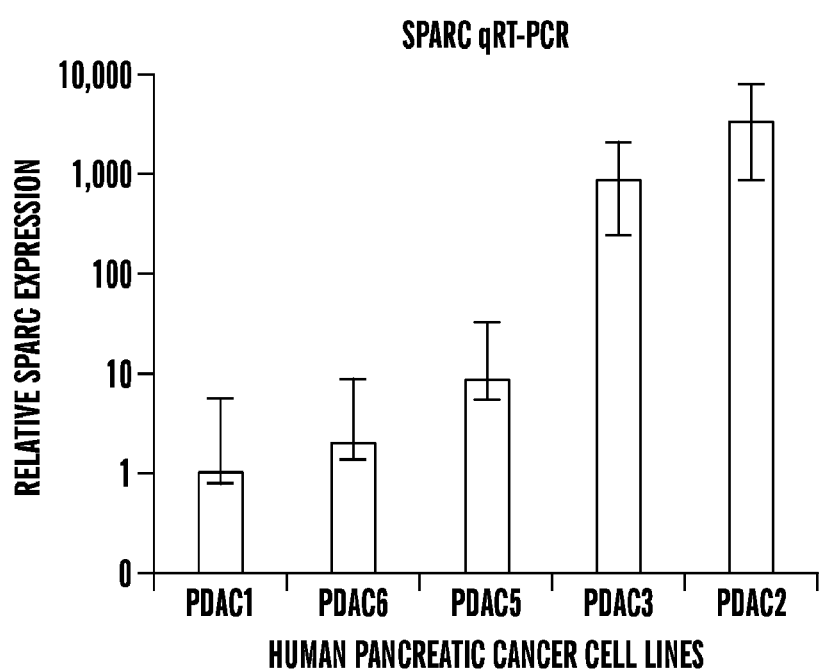
FIG. 8 depicts a graph of quantitative RT-PCR of SPARC expression in human pancreatic cancer cell lines.

Evaluation of human pancreatic cancer cell lines identified 3 of 5 cell lines with elevated SPARC expression which correlates to increased migratory behavior, a surrogate in vitro assay that correlates with metastatic behavior (FIG. 8).

Figure 9:
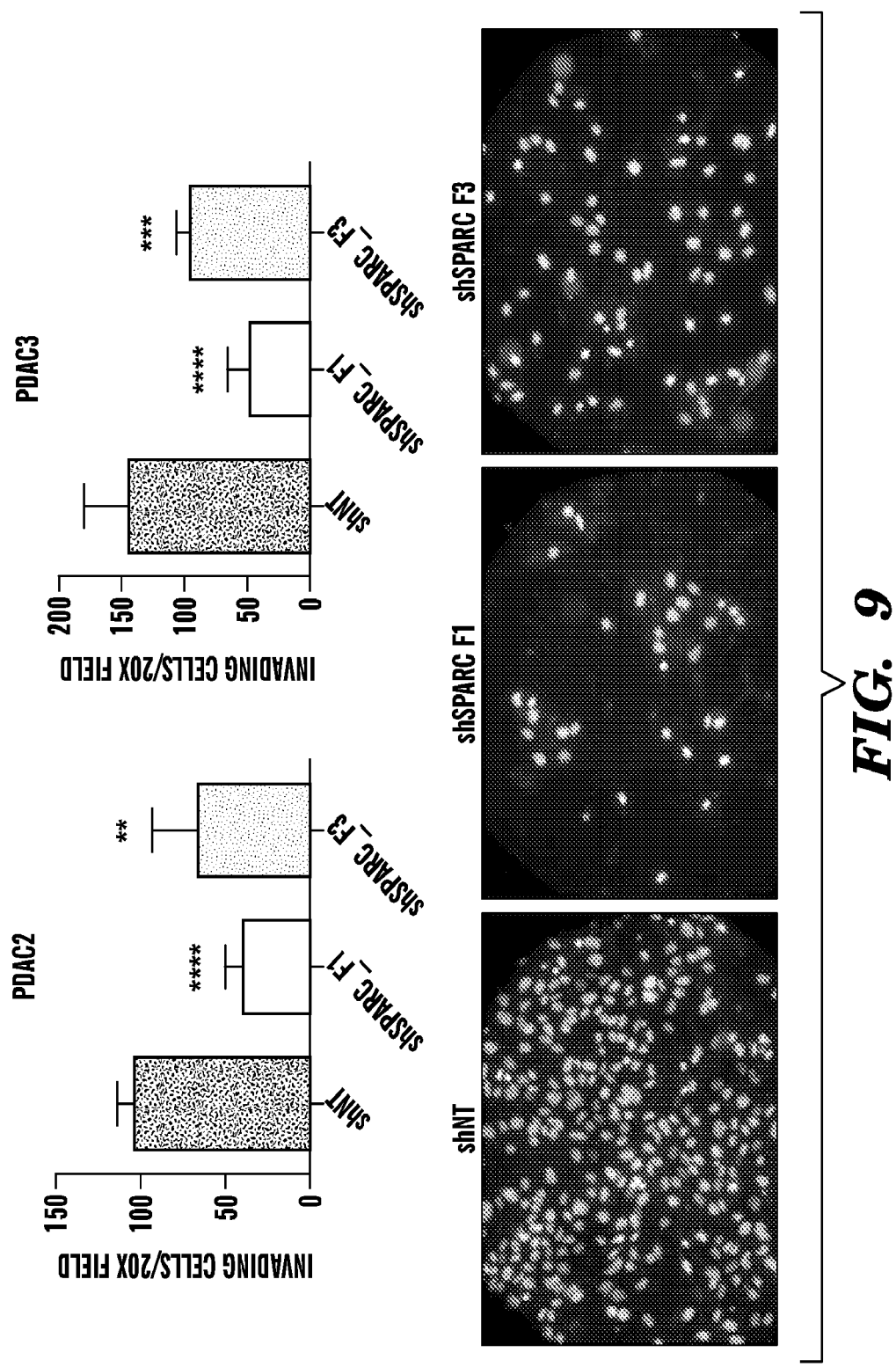
FIG. 9 depicts invasion assays. Decreases in invasion through Matrigel of PDAC2 and PDAC 3 cell lines with shRNA against SPARC (ShF1 and ShF3) were observed. shNT=Non-target shRNA

Evaluation of SPARC function in human pancreatic cancer was done using short hairpin RNA interferences (shRNA) on the two cell lines with highest SPARC expression (PDAC2 and PDAC3). Multiple in vitro assays were done including proliferation, migration, invasion, scratch, and soft agar. The most profound effects of suppressing SPARC expression was on migratory behavior (FIG. 9 and data not shown), indicating SPARC is not only present in many CTCs, but has functional consequences when inhibited in cell line models.

Figure 10:
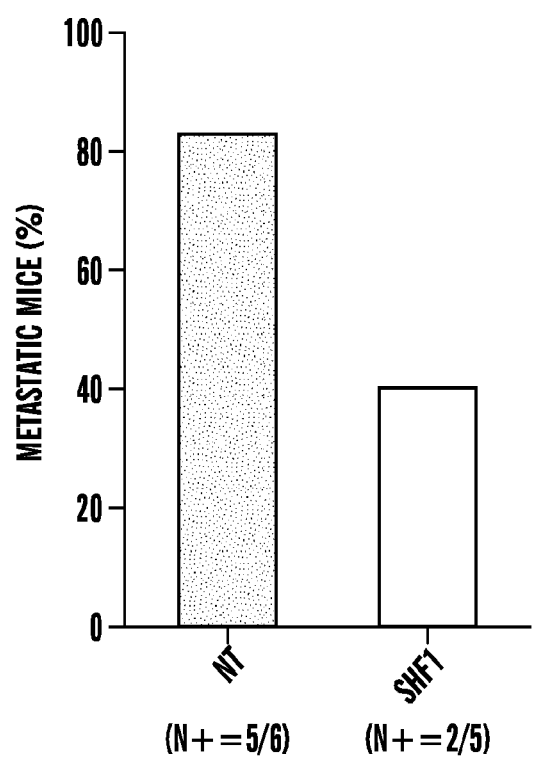
FIG. 10 depicts a graph of the number of mice with detectable metastases by in vivo luciferase imaging in non-target shRNA (NT) and SPARC shRNA (SHF1).
Figure 11:
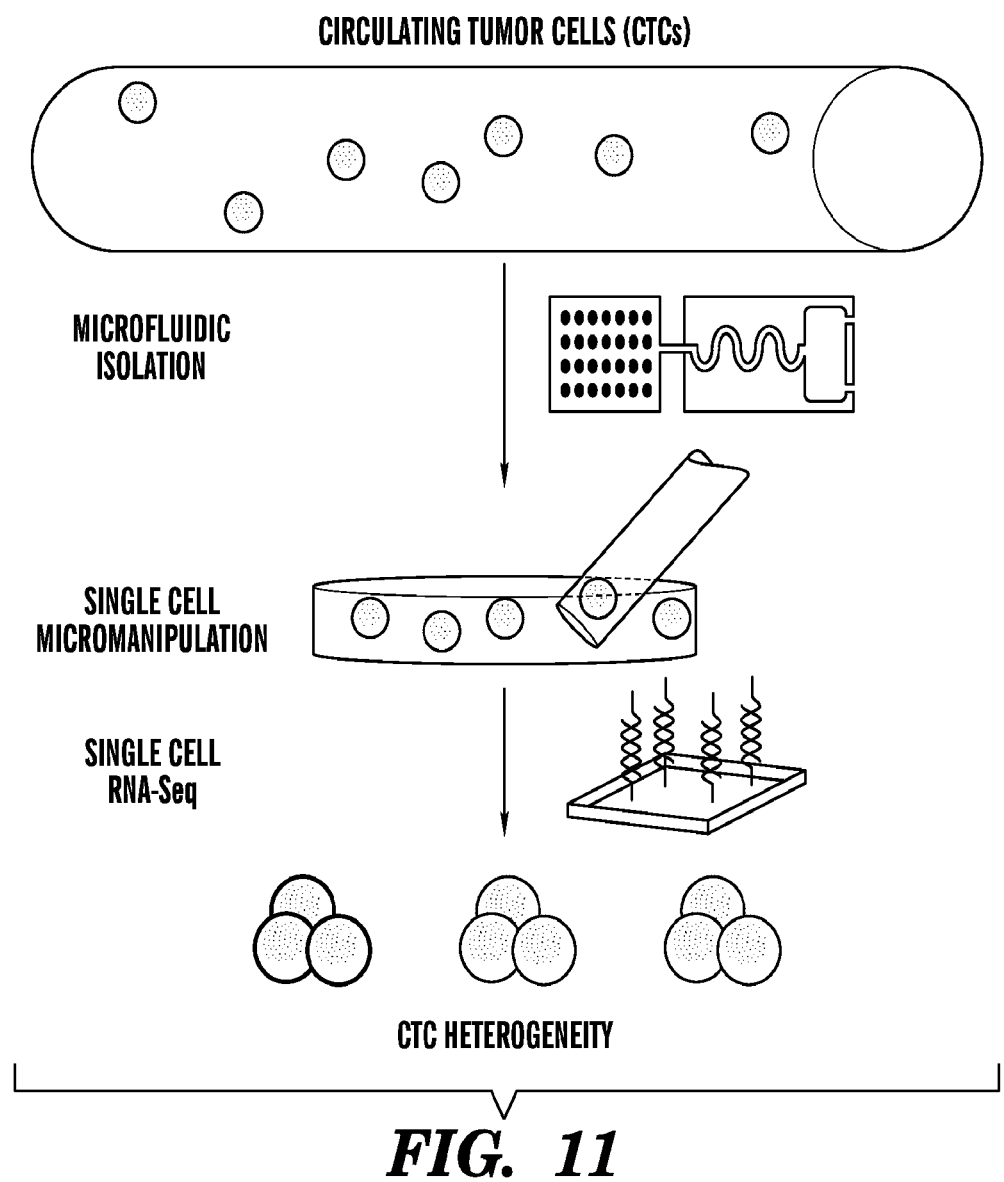
FIG. 11 depicts a schematic of the process of determining CTC heterogeneity.

Given these data, in vivo tail vein inoculation was performed using PDAC-3 to determine if SPARC knockdown affected metastasis. Initial data at 2 weeks post tail vein injection indicates there is reduced metastatic potential when SPARC is inhibited by shRNA with 83% of control mice with metastases compared to 40% in cell lines with shRNA against SPARC (FIG. 10).

Surface Protein Targets

Most of the targets identified in Table 9 are secreted factors and analysis of genes annotated as cell surface proteins are summarized in Table 14.

TABLE 14

Percent of human single CTCs with high expression of surface protein genes

| | Percent of Single CTCs >50 RPM of Expression | | | |
|---|---|---|---|---|
| Cancer type | Pancreas (N = 7) | Breast (N = 29) | Prostate (N = 77) | ALL (N = 113) |
| IL6ST | 0% | 38% | 8% | 15% |
| ARSA | 71% | 17% | 5% | 12% |
| TIMP2 | 0% | 21% | 4% | 8% |
| CD55 | 0% | 17% | 4% | 7% |
| SULF2 | 0% | 24% | 0% | 6% |
| ITGA6 | 0% | 14% | 3% | 5% |
| SDC4 | 0% | 14% | 3% | 5% |
| CDON | 0% | 7% | 5% | 5% |
| SV2A | 14% | 3% | 1% | 3% |

It is contemplated herein that these genes are targets given they would be integrated into the plasma membrane of CTCs. In general, RNA expression of cell surface markers tend to be lower than actual protein levels on cells.

Contemplated herein are antibodies to IL6ST, SULF2, and SV2A for therapeutic utility.

1. IL6ST—signal transducer for IL6, LIF, CNTF, and oncostatin M.
    a. Important for STAT3 activation downstream
    b. Antibodies against IL6 receptor and IL6 have been developed for human disease including cancer
2. SULF2—sulfatase modifies heparin sulfate by removing 6-O-sulfate groups
    a. Expression enriched in cancer progression and metastasis
    b. Drugs have been developed against sulfatase activity and tested with activity in liver cancer models
3. SV2A—synaptic vesicle glycoprotein elevated in neuroendocrine cells
    a. A marker of neuroendocrine cells, which appear at the epithelial stromal border of human pancreatic cancer
    b. Neuroendocrine differentiation common feature in cancers and portends to more aggressive disease

REFERENCES

1. Olive, K. P., M. A. Jacobetz, C. J. Davidson, A. Gopinathan, D. McIntyre, D. Honess, B. Madhu, M. A. Goldgraben, M. E. Caldwell, D. Allard, K. K. Frese, G. Denicola, C. Feig, C. Combs, S. P. Winter, H. Ireland-Zecchini, S. Reichelt, W. J. Howat, A. Chang, M. Dhara, L. Wang, F. Ruckert, R. Grutzmann, C. Pilarsky, K. Izeradjene, S. R. Hingorani, P. Huang, S. E. Davies, W. Plunkett, M. Egorin, R. H. Hruban, N. Whitebread, K. McGovern, J. Adams, C. Iacobuzio-Donahue, J. Griffiths, and D. A. Tuveson, *Inhibition of Hedgehog signaling enhances delivery of chemotherapy in a mouse model of pancreatic cancer*. Science, 2009. 324(5933): p. 1457-61.

2. Neesse, A., P. Michl, K. K. Frese, C. Feig, N. Cook, M. A. Jacobetz, M. P. Lolkema, M. Buchholz, K. P. Olive, T. M. Gress, and D. A. Tuveson, *Stromal biology and therapy in pancreatic cancer.* Gut, 2011. 60(6): p. 861-8.
3. Rasheed, Z. A., W. Matsui, and A. Maitra, Pathology of pancreatic stroma in PDAC, in *Pancreatic Cancer and Tumor Microenvironment*, P. J. Grippo and H. G. Munshi, Editors. 2012: Trivandrum (India).
4. Provenzano, P. P., C. Cuevas, A. E. Chang, V. K. Goel, D. D. Von Hoff, and S. R. Hingorani, *Enzymatic targeting of the stroma ablates physical barriers to treatment of pancreatic ductal adenocarcinoma.* Cancer Cell, 2012. 21(3): p. 418-29.
5. Nagasaki, T., M. Hara, H. Nakanishi, H. Takahashi, M. Sato, and H. Takeyama, *Interleukin-6 released by colon cancer-associated fibroblasts is critical for tumour angiogenesis: anti-interleukin-6 receptor antibody suppressed angiogenesis and inhibited tumour-stroma interaction.* Br J Cancer, 2014. 110(2): p. 469-78.
6. Zarogoulidis, P., L. Yarmus, and K. Zarogoulidis, *New insights for IL-6 targeted therapy as an adjuvant treatment for non-small-cell lung cancer.* Ther Deliv, 2013. 4(10): p. 1221-3.
7. Voorhees, P. M., R. F. Manges, P. Sonneveld, S. Jagannath, G. Somlo, A. Krishnan, S. Lentzsch, R. C. Frank, S. Zweegman, P. W. Wijermans, R. Z. Orlowski, B. Kranenburg, B. Hall, T. Casneuf, X. Qin, H. van de Velde, H. Xie, and S. K. Thomas, *A phase 2 multicentre study of siltuximab, an anti-interleukin-6 monoclonal antibody, in patients with relapsed or refractory multiple myeloma.* Br J Haematol, 2013. 161(3): p. 357-66.
8. Betts, B. C., E. T. St Angelo, M. Kennedy, and J. W. Young, *Anti-IL6-receptor-alpha (tocilizumab) does not inhibit human monocyte-derived dendritic cell maturation or alloreactive T-cell responses.* Blood, 2011. 118(19): p. 5340-3.
9. Bayliss, T. J., J. T. Smith, M. Schuster, K. H. Dragnev, and J. R. Rigas, *A humanized anti-IL-6 antibody (ALD518) in non-small cell lung cancer.* Expert Opin Biol Ther, 2011. 11(12): p. 1663-8.
10. Khurana, A., D. Jung-Beom, X. He, S. H. Kim, R. C. Busby, L. Lorenzon, M. Villa, A. Baldi, J. Molina, M. P. Goetz, and V. Shridhar, *Matrix detachment and proteasomal inhibitors diminish Sulf-2 expression in breast cancer cell lines and mouse xenografts.* Clin Exp Metastasis, 2013. 30(4): p. 407-15.
11. Lui, N. S., A. van Zante, S. D. Rosen, D. M. Jablons, and H. Lemjabbar-Alaoui, *SULF2 expression by immunohistochemistry and overall survival in oesophageal cancer: a cohort study.* BMJ Open, 2012. 2(6).
12. Hur, K., T. S. Han, E. J. Jung, J. Yu, H. J. Lee, W. H. Kim, A. Goel, and H. K. Yang, *Up-regulated expression of sulfatases (SULF1 and SULF2) as prognostic and metastasis predictive markers in human gastric cancer.* J Pathol, 2012. 228(1): p. 88-98.
13. Phillips, J. J., E. Huillard, A. E. Robinson, A. Ward, D. H. Lum, M. Y. Polley, S. D. Rosen, D. H. Rowitch, and Z. Werb, *Heparan sulfate sulfatase SULF2 regulates PDGFRalpha signaling and growth in human and mouse malignant glioma.* J Clin Invest, 2012. 122(3): p. 911-22.
14. Zheng, X., X. Gai, S. Han, C. D. Moser, C. Hu, A. M. Shire, R. A. Floyd, and L. R. Roberts, *The human sulfatase 2 inhibitor 2,4-disulfonylphenyl-tert-butylnitrone (OKN-007) has an antitumor effect in hepatocellular carcinoma mediated via suppression of TGFB1/SMAD2 and Hedgehog/GLI1 signaling.* Genes Chromosomes Cancer, 2013. 52(3): p. 225-36.
15. Bandala, C., A. Miliar-Garcia, C. M. Mejia-Barradas, M. Anaya-Ruiz, J. P. Luna-Arias, C. I. Bazan-Mendez, M. Gomez-Lopez, S. Juarez-Mendez, and E. Lara-Padilla, *Synaptic vesicle protein 2 (SV2) isoforms.* Asian Pac J Cancer Prev, 2012. 13(10): p. 5063-7.
16. Ting, D. T., D. Lipson, S. Paul, B. W. Brannigan, S. Akhavanfard, E. J. Coffman, G. Contino, V. Deshpande, A. J. Iafrate, S. Letovsky, M. N. Rivera, N. Bardeesy, S. Maheswaran, and D. A. Haber, *Aberrant overexpression of satellite repeats in pancreatic and other epithelial cancers.* Science, 2011. 331(6017): p. 593-6.
17. Zeng, Y. J., W. Lai, L. Liu, H. Wu, X. X. Luo, J. Wang, and Z. H. Chu, *Prognostic Significance of Neuroendocrine Differentiation in Colorectal Adenocarcinoma After Radical Operation: a Meta-analysis.* J Gastrointest Surg, 2014.
18. Wang, J., B. Wei, C. T. Albarracin, J. Hu, S. C. Abraham, and Y. Wu, *Invasive neuroendocrine carcinoma of the breast: a population-based Study from the Surveillance, Epidemiology and End Results (SEER) database.* BMC Cancer, 2014. 14(1): p. 147.
19. Lipianskaya, J., A. Cohen, C. J. Chen, E. Hsia, J. Squires, Z. Li, Y. Zhang, W. Li, X. Chen, H. Xu, and J. Huang, *Androgen-deprivation therapy-induced aggressive prostate cancer with neuroendocrine differentiation.* Asian J Androl, 2014.
20. Chen, Y., I. Nowak, J. Huang, P. C. Keng, H. Sun, H. Xu, G. Wei, and S. O. Lee, *Erk/MAP kinase signaling pathway and neuroendocrine differentiation of non-small-cell lung cancer.* J Thorac Oncol, 2014. 9(1): p. 50-8.
21. Chang, P. C., T. Y. Wang, Y. T. Chang, C. Y. Chu, C. L. Lee, H. W. Hsu, T. A. Zhou, Z. Wu, R. H. Kim, S. J. Desai, S. Liu, and H. J. Kung, *Autophagy Pathway Is Required for IL-6 Induced Neuroendocrine Differentiation and Chemoresistance of Prostate Cancer LNCaP Cells.* PLoS One, 2014. 9(2): p. e88556.
22. Debes, J. D. and D. J. Tindall, *Mechanisms of androgen-refractory prostate cancer.* N Engl J Med, 2004. 351(15): p. 1488-90.

Example 5

Circulating tumor cells (CTCs) are shed from primary tumors into the bloodstream, mediating the hematogenous spread of cancer to distant organs. To define their composition, genomewide expression profiles of CTCs were compared with matched primary tumors in a mouse model of pancreatic cancer, isolating individual CTCs using epitope-independent microfluidic capture, followed by single-cell RNA sequencing. CTCs clustered separately from primary tumors and tumor-derived cell lines, showing low proliferative signatures, enrichment for Aldh1a2, biphenotypic expression of epithelial and mesenchymal markers, and expression of Igfbp5, a gene transcript enriched at the epithelial-stromal interface. Mouse as well as human pancreatic CTCs exhibit a very high expression of stromal-derived extracellular matrix (ECM) proteins, including SPARC, whose knockdown in cancer cells suppresses cell migration and invasiveness. The aberrant expression by CTCs of stromal ECM genes points to their contribution of microenvironmental signals for the spread of cancer to distant organs.

Figure 12A:
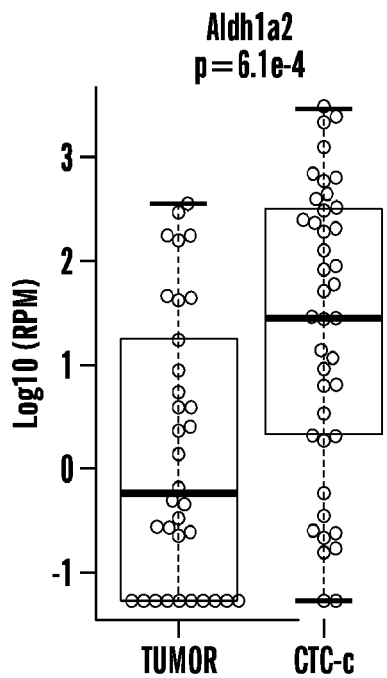
FIGS. 12A-12C demonstrate that CTC-Enriched Genes are Found in Epithelial and Stromal Components of Primary Tumors. Depicted are expression boxplots of (FIG. 12A) Aldh1a2 stem cell and CTC highly enriched genes (FIG. 12B) Klf4 and (FIG. 12C) Igfbp5 genes. Bar=median, box plot=quartiles, scale in log 10 (rpm).

Classical CTCs expressed predominantly the Aldh1a2 isoform, while Aldh1a1 was expressed in a variety of cell types (data not shown). Within single CTCs, there was no correlation between expression of Aldh1 isoforms and either enrichment for the mesenchymal genes (Cdh11, Vim) or loss of epithelial genes (Cdh1, Muc1), indicating that stem cell and EMT markers are not intrinsically linked in CTCs. Analysis of primary pancreatic tumors for Aldh1a2 using RNA in situ hybridization (RNA-ISH) identified rare epithelial tumor cells expressing this stem cell marker, but the majority of expression was present within the cancer associated stromal cells (FIG. 12A), consistent with immunohistochemistry for ALDH protein in human PDAC (Rasheed et al., 2010).

Figure 12B:
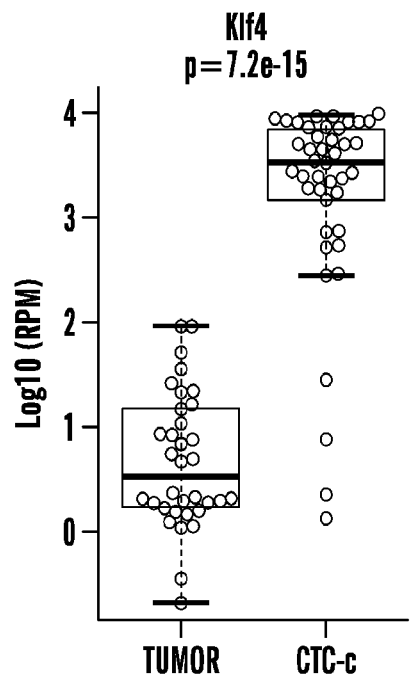
Figure 12C:
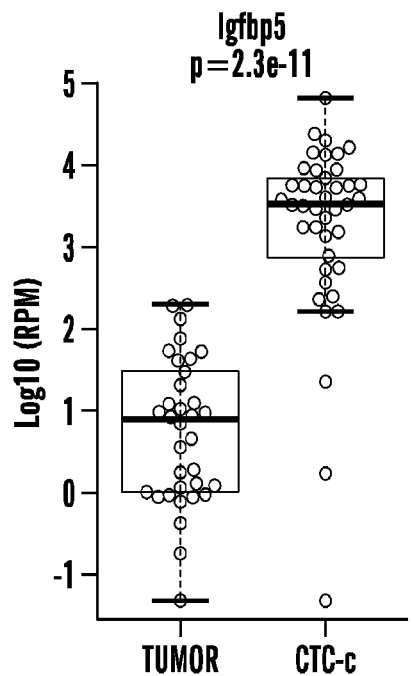

Besides the evident diversity of CTCs, shared transcripts were searched for that could provide further insight into their cell of origin within the primary tumor and the mechanisms by which they invade and survive within the bloodstream and ultimately identify potential CTC-specific therapeutic targets. Rigorous criteria were selected to identify the most highly enriched CTC-c transcripts (RP score<300), expressed at very high levels (>100 rpm) in R90% of all classical CTCs. Three genes met these criteria: Kruppel-like factor 4 (Klf4), one of the key stem cell (iPS) reprogramming factors (Takahashi and Yamanaka, 2006), insulin-like growth factor binding protein 5 (Igfbp5), an extracellular growth factor binding protein and decorin (Dcn). RNA-ISH was utilized in primary tumor specimens to identify the potential colocalization of these three highly enriched CTC genes. In contrast to Aldh1a2, Klf4 is expressed in epithelial components of the primary tumor (FIG. 12B). Igfbp5 is of particular interest, in that it is expressed focally at the tumor epithelial-stromal interface (FIG. 12C). It is contemplated herein that this geographic area is enriched for cancer cells undergoing EMT, contributing to the mixed epithelial/stromal transcriptional programs evident by RNA-seq of single CTCs.

In addition to highly expressing Dcn, CTCs consistently had high levels of multiple ECM gene transcripts. GO analysis of all CTC-enriched genes (Table 3) identified 32 proteinaceous ECM genes (GO:0005578, OR 2.4, q-value 4.8 3 10.3). These genes are normally expressed in reactive stromal cells, rather than in epithelial cancer cells, and while recent studies have highlighted the importance of the stroma in supporting pancreatic cancer pathogenesis and metastasis (Feig et al., 2012; Neesse et al., 2011, 2013; Olive et al., 2009; Provenzano et al., 2012), the expression of these stroma-associated ECM genes within tumor cells in circulation was unexpected. Using RP differential expression analysis, CTCs were compared with purified EGFP-tagged primary tumor single cells (TuGMP3) and bulk tumor samples (tumor cells admixed with reactive stromal cells). Six proteinaceous ECM genes were highly expressed by CTCs and by stromal component, but not by epithelial cells within primary tumors: Dcn, Sparc, Ccdc80, Col1a2, Col3a1, and Timp2 (data not shown). RNA-ISH analysis of both Dcn and Spare confirmed diffuse expression in stromal elements of mouse primary tumors, with rare areas where these transcripts are colocalized with keratin-expressing cells at the epithelial-stromal border (data not shown).

SPARC is a ECM protein gene. RNA-ISH analysis of 198 primary human PDACs demonstrates abundant stromal cell expression of SPARC transcripts in 99% of cases, with up to a third of tumors with rare epithelial cells expressing this ECM gene product (data not shown). Consistent with these observations, RNA-seq of EGFP-tagged single primary tumor cells (data not shown) identified only 1 of 20 cells (5%) with coexpression of high levels (>100 rpm) of Spare and Krt19.

In summary, abundant expression of ECM genes is a common feature of all keratin-rich classical CTCs. This is in marked contrast to the primary tumor, where these gene products are secreted by supporting stromal cells and not by the epithelial cancer cells. However, rare cells at the epithelial-stromal interface of primary tumors do appear to express both keratins and ECM genes, consistent with the pattern observed in CTCs themselves.

Figure 13:
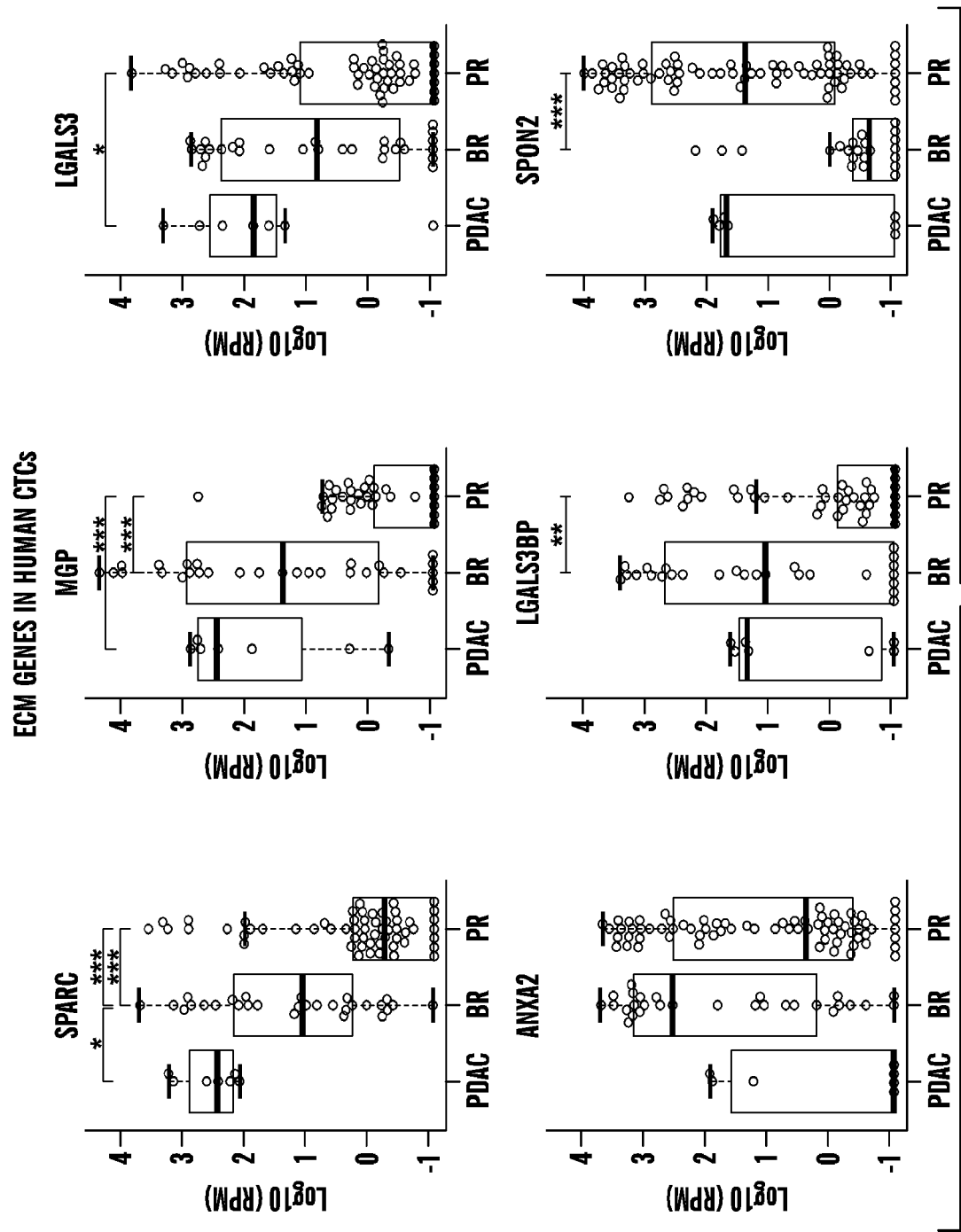
FIG. 13 demonstrates that human and mouse CTCs across different epithelial cancer express high levels of ECM protein genes. Depicted are expression boxplot of highly expressed ecm genes in human pdac, breast (br), and prostate (pr) ctcs. bar, median; boxplot, quartiles; scale in log 10 (rpm). holm-adjusted p value<0.05 (*), 0.01 (), 0.001 (*).

To confirm the expression of proteinaceous ECM genes by human cancer cells circulating in the bloodstream, single CTCs were isolated from patients with pancreatic (n=7), breast (n=29), and prostate (n=77) cancers and subjected these to single-cell RNA-seq. Six ECM protein genes were highly expressed in human CTCs (>100 rpm in >15% of all CTC samples) (FIG. 13; Table 13). Notably, three genes (SPARC, MGP, SPON2) are ECM glycoproteins, defined as part of the core matrisome (Naba et al., 2012). The core matrisome protein SPARC was particularly enriched in pancreatic CTCs being expressed at high levels (>100 rpm) in 100% of pancreatic CTCs compared to 31% of breast and 9% of prostate CTCs. The notable differences in ECM protein gene expression across human epithelial CTCs suggest microenvironment tissue specificity as well as probable redundancies in ECM protein signaling. Together, the consistent expression of ECM gene family members in human CTCs indicates that their upregulation contributes either to the generation of CTCs from primary tumors or to the survival of cancer cells deprived of microenvironmental signals as they circulate in the bloodstream.

In order to define the functional consequences of SPARC expression in pancreatic cancer cells, a panel of patient-derived, low-passage PDAC cell lines was screened for expression. Two human PDAC cell lines with relatively high SPARC expression were identified (PDAC2 and PDAC3), making it possible to test the consequences of small hairpin RNA (shRNA)-mediated knockdown (FIG. 8, 9, FIGS. 16A-16D). Suppression of endogenous SPARC expression in both PDAC2 and PDAC3 cell lines using two independent shRNA constructs did not affect proliferation in 2D cultures or anchorage-independent tumor sphere formation (FIGS. 14A-14B, FIGS. 16A-16D). However, SPARC knockdown by both shRNAs significantly reduced pancreatic cancer cell migration in wound scratch assays and their invasive properties, as measured by in vitro Boyden assays (data not shown).

Figure 14A:
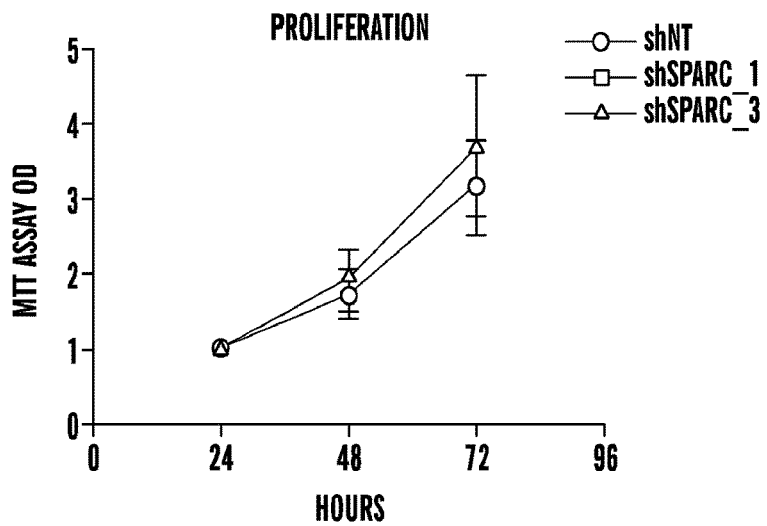
FIGS. 14A-14E demonstrate that SPARC expression in human PDAC enhances invasion and metastasis.
Figure 14B:
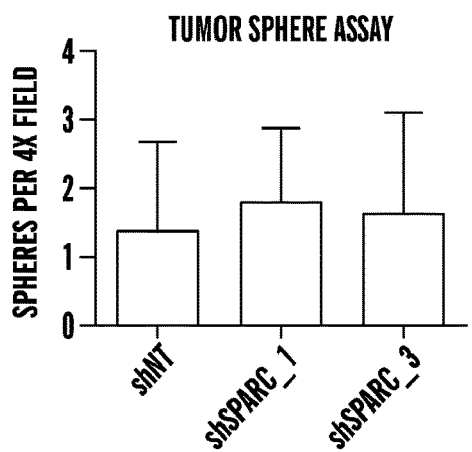
Figure 14C:
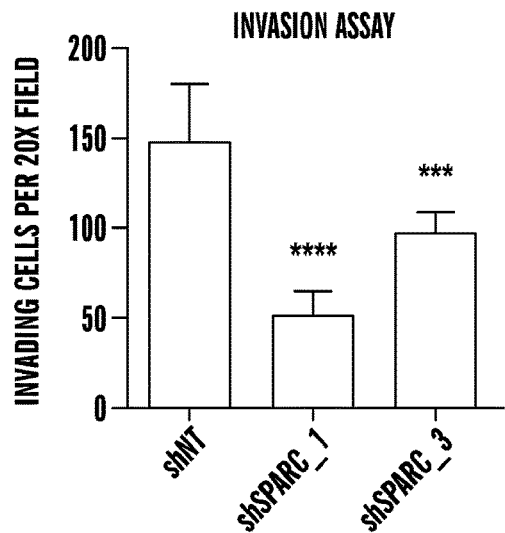
Figure 14D:
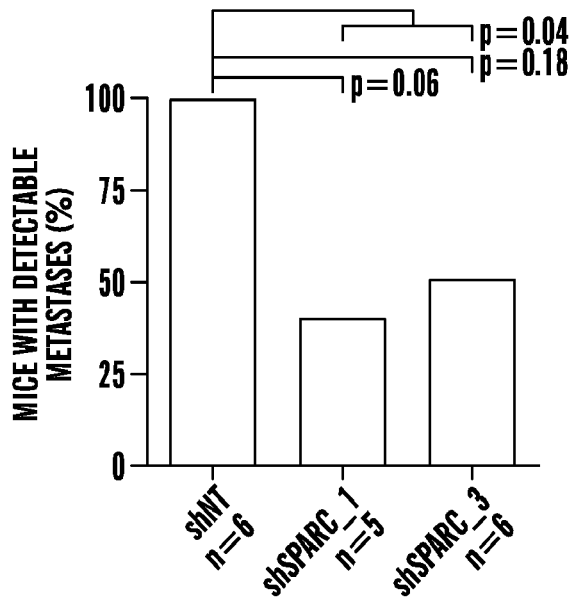
Figure 14E:
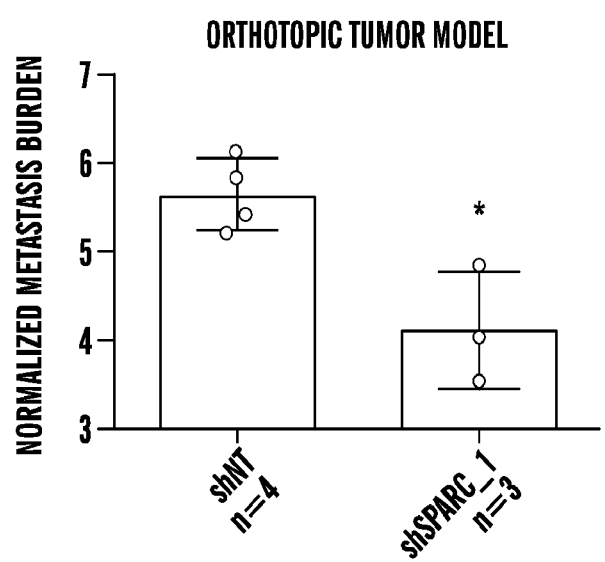

Tail vein injection of SPARC-suppressed PDAC3 cells using both shRNA constructs generated significantly fewer lung metastases than cells expressing nontargeting hairpin (shNT) controls (FIG. 14D). Metastases generated from orthotopic pancreatic xenografts were also significantly reduced for SPARC-suppressed PDAC3 cells, as measured by luciferase imaging and normalized for primary tumor size (FIG. 14E). Thus, SPARC expression by pancreatic cancer cells appears to selectively enhance their invasive and migratory properties to augment metastatic virulence. The high levels of SPARC expression evident in virtually all pancreatic CTCs thus raises the possibility that it contributes significantly to the metastatic spread of pancreatic cancer.

Discussion

Described herein is the detailed analysis of CTC composition and diversity in pancreatic cancer, using single-cell RNA-seq. High-quality transcriptomes were achieved in 93 single mouse pancreatic CTCs, which were compared with bulk and single-cell preparations from matched primary tumors and from an immortalized cell line established from the same mouse pancreatic tumor model. The use of the KPC mouse model made it possible to compare simultaneously isolated primary tumor specimens and CTCs, and it allowed measurements of CTC heterogeneityacross multiple mice sharing the same Kras/Trp53 genetic drivers. The large number of isolated CTCs and the high quality of the isolated RNA from these cells reflect the application of the CTC-iChip technology, which effectively depletes normal blood components, enriching for CTCs that are untagged and accessible for single-cell manipulation. Finally, the purification of CTCs irrespective of their cell-surface epitopes avoids any bias associated with their purification based on expression of common epithelial markers such as EpCAM.

Figure 15:
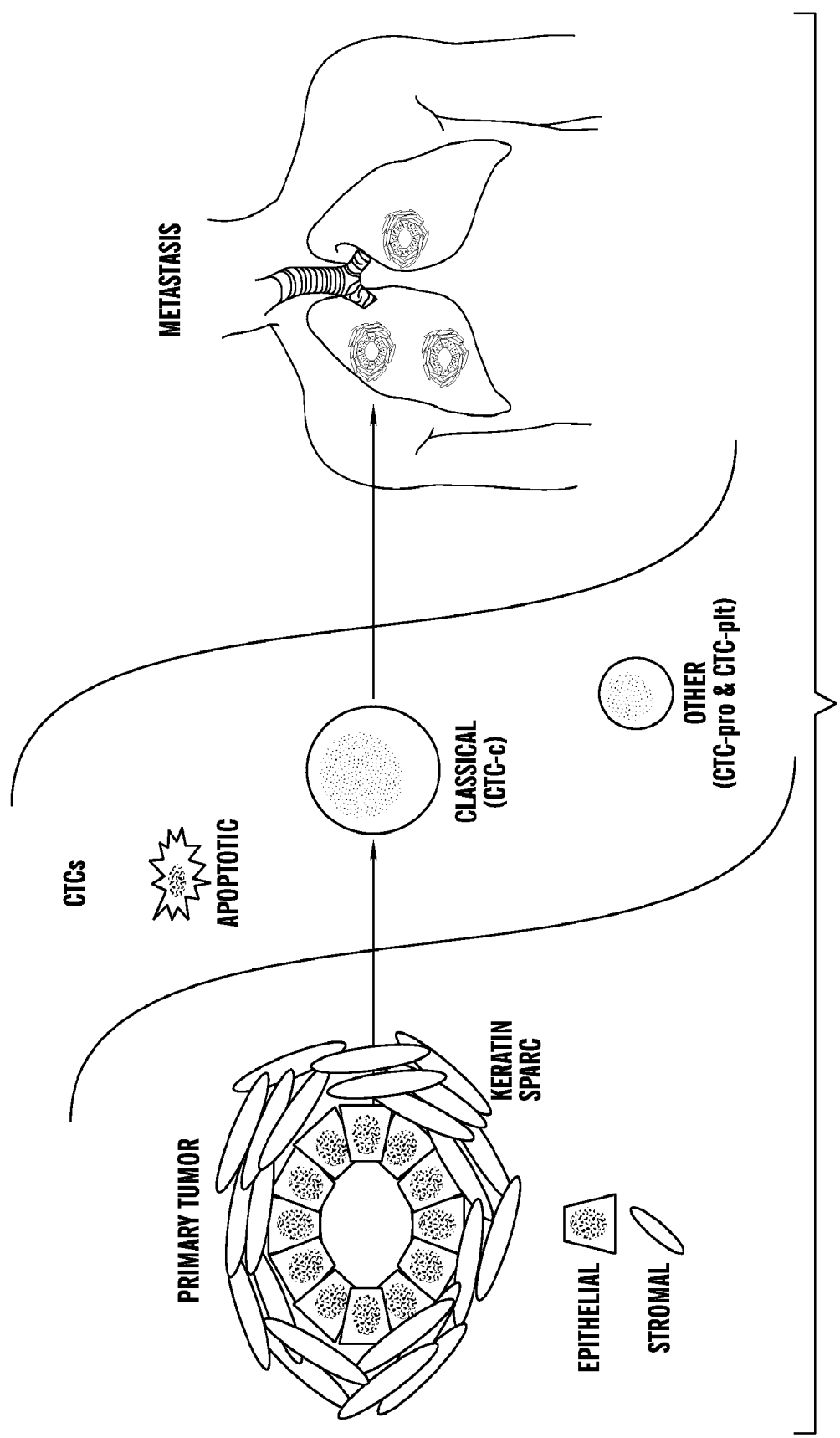
FIG. 15 depicts a Summary Model of the Role of Pancreatic CTCs in the Metastatic Cascade. Shown are the heterogeneous subsets of pancreatic CTCs with a focus on the most prominent classical CTC group, which are enriched for coexpression of epithelial (keratin) and stromal (Sparc) genes.
Figure 16A:
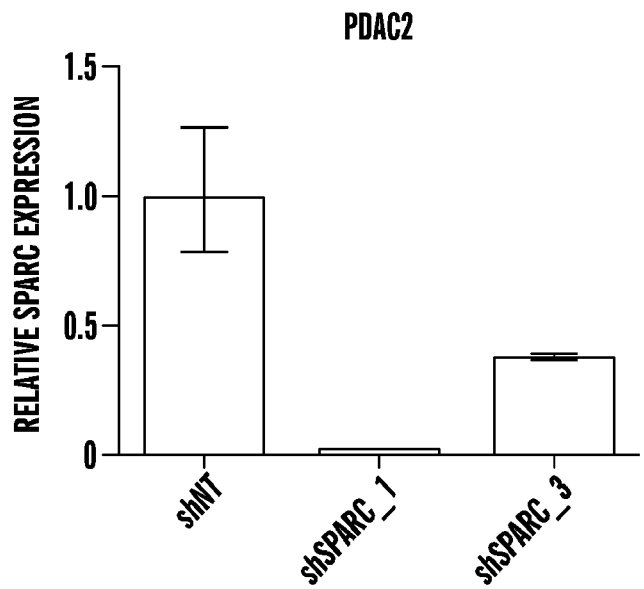
FIG. 16A depicts a graph of PDAC2 shRNA cell lines by qRT-PCR. Average shown with max and min RQ (error bars).
Figure 16B:
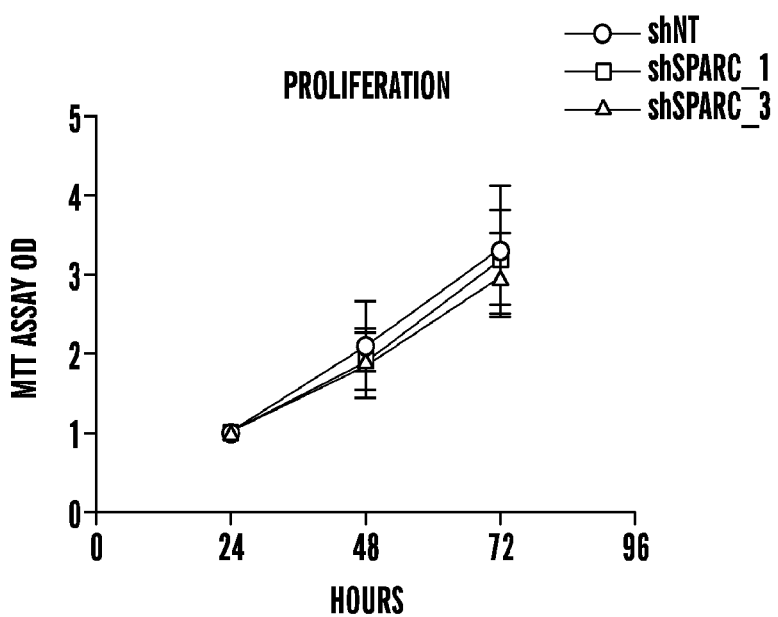
FIG. 16B depicts a graph of proliferation rates by MTT assay similar in PDAC2 cell line between shNT and shSPARC stable lines.
Figure 16C:
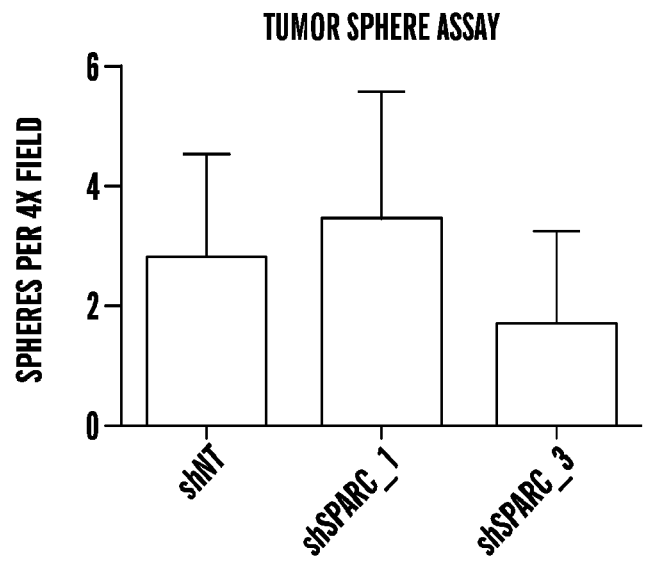
FIG. 16C depicts a graph of tumor sphere invasion assay (error bars=STD) formation at 2 weeks similar between shNT and shSPARC cell lines. Quantiation done per 4× magnification field (Error bars=SD). Migratory behavior reduced by shSPARC_1 & 3 as determined by (FIG. 16D) invasion assay at 48 hours.
Figure 16D:
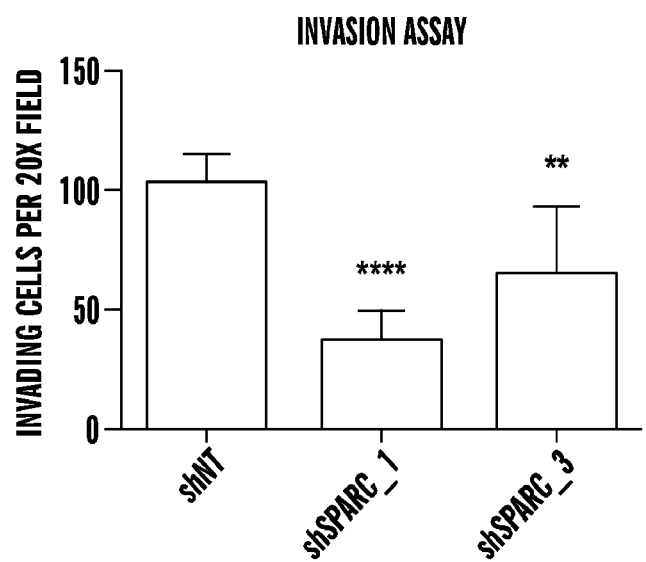

Together, the observations made herein include the following. (1) CTC expression profiles cluster into three classes, including a major "classical CTC" group, and others that are defined by platelet derived markers or proliferative signatures. (2) Common features shared by virtually all classical CTCs include expression of both epithelial and mesenchymal markers, the stem cell-associated gene Aldh1a2, and three highly expressed transcripts, Klf4, Igfbp5, and Dcn. The specific localization of Igfbp5-expressing cells at the epithelial-stromal boundary within primary tumors may point to a region that contributes significantly to CTC generation. (3) The most highly enriched CTC-specific transcripts shared by almost all classical CTCs encode extracellular matrix proteins, such as Sparc. (4) Aberrant expression in CTCs of this ECM gene product, which is normally abundant in the tumor stromal compartment, is observed in both mouse and human pancreatic CTCs, and its knockdown attenuates cancer cell migration and invasion in reconstituted systems. (FIG. 15) Compared with RNA-seq of partially purified, bulk CTC populations, which required digital subtraction of leukocyte-derived reads (Yu et al., 2012, 2013), the single-cell analysis reported here provides considerably more depth of tumor cell-specific transcript reads, and it allows measurements of CTC heterogeneity.

It is contemplated herein that in addition to the initiating mutations, somatically acquired genetic and epigenetic changes may distinguish CTCs derived from different tumors. Multiple mouse tumors contributed to each of the three distinct clusters of CTCs. Despite their atypical expression pattern, the identification of platelet-associated and proliferative CTC subsets as being tumor-derived is established by their inclusion of lineage-tagged tumor cells. The more characteristic expression pattern exhibited by the classical CTC cluster enabled detailed comparison with primary tumor cells, thereby providing further insight into the origin and properties of CTCs.

Mouse pancreatic classical CTCs uniformly lose expression of the epithelial marker E-cadherin (Cdh1), a key feature of epithelial-to-mesenchymal transition. However, the cells do not lose expression of other epithelial markers, such as cytokeratins, nor is there a consistent increase in classical mesenchymal markers such as vimentin. As such, most classical CTCs appear arrested in a biphenotypic state. Despite their expression of cytokeratins, which are present in the epithelial components of the primary tumor, most other highly expressed markers in CTCs are shared with the stromal component of the primary tumor. Among these stromal genes is Aldh1a2 (Rasheed and Matsui, 2012; Rasheed et al., 2010). A provocative observation relating to the shared epithelial and mesenchymal state of classical CTCs is their virtually universal (93%) expression of Igfbp5, which is uniquely expressed in a small subpopulation of cells at the epithelial/stromal interface within primary tumors. This raises the possibility that this critical location within the primary tumor generates a disproportionate fraction of viable CTCs.

The most unexpected observation from the single-CTC RNAseq study is the high abundance of ECM transcripts in the vast majority of classical CTCs. The coexpression of pancreatic cancer-enriched cytokeratins (Krt7 and Krt19) in single cells expressing these ECM gene products excludes the possibility that these represent circulating tumor-derived fibroblasts.

Consistent with the aberrant expression of SPARC in some pancreatic cancer cells, a subset of patient-derived tumor cell lines also coexpress it along with epithelial cytokeratins. The reduction in cell migration and metastatic potential exhibited by these pancreatic cell lines following SPARC knockdown indicates that it contributes to CTC-mediated metastasis. It is contemplated herein that Sparc expression contributes to metastasis, but inherent redundancies in ECM protein expression may mitigate this effect in some embodiments.

Considerable effort has been directed to targeting the pancreatic cancer stroma as a means of improving delivery of chemotherapeutics as well as stripping tumor cells of their supportive microenvironment (Neesse et al., 2011; Olive et al., 2009; Provenzano et al., 2012; Rasheed et al., 2012). The findings described herein, e.g., that these gene products are also expressed by CTCs themselves suggests a remarkable level of cellular plasticity. To the extent that invasive properties of CTCs are mediated in part by expression of such ECM proteins, it also raises the possibility of targeting cancer cells in the blood.

TABLE 13

Human CTC ECM Gene Expression

| | | Percent of Samples >100 RPM | | | |
|---|---|---|---|---|---|
| Count | ECM Gene Symbol | All CTCs | PDAC CTCs | Breast CTCs | Prostate CTCs |
| 1 | ANXA2 | 36.3% | 0.0% | 51.7% | 33.8% |
| 2 | SPON2 | 29.2% | 0.0% | 3.4% | 41.6% |
| 3 | LGALS3 | 22.1% | 42.9% | 37.9% | 14.3% |
| 4 | SPARC | 21.2% | 100.0% | 31.0% | 10.4% |
| 5 | LGALS3BP | 16.8% | 0.0% | 34.5% | 11.7% |
| 6 | MGP | 15.9% | 57.1% | 44.8% | 1.3% |
| 7 | LAMC1 | 15.0% | 0.0% | 6.9% | 19.5% |
| 8 | SMC3 | 15.0% | 42.9% | 17.2% | 11.7% |
| 9 | CALR | 14.2% | 0.0% | 6.9% | 18.2% |
| 10 | TIMP1 | 13.3% | 14.3% | 27.6% | 7.8% |
| 11 | MMP24 | 11.5% | 0.0% | 10.3% | 13.0% |
| 12 | DAG1 | 10.6% | 0.0% | 20.7% | 7.8% |
| 13 | ERBB2IP | 10.6% | 14.3% | 20.7% | 6.5% |
| 14 | MMP19 | 10.6% | 0.0% | 10.3% | 11.7% |
| 15 | AGRN | 8.8% | 0.0% | 6.9% | 10.4% |
| 16 | CRTAP | 8.8% | 0.0% | 6.9% | 10.4% |
| 17 | COL24A1 | 8.0% | 57.1% | 17.2% | 0.0% |
| 18 | ANG | 7.1% | 0.0% | 0.0% | 10.4% |
| 19 | MFAP1 | 7.1% | 0.0% | 6.9% | 7.8% |
| 20 | VWF | 7.1% | 14.3% | 17.2% | 2.6% |
| 21 | VWA1 | 7.1% | 0.0% | 3.4% | 9.1% |
| 22 | TIMP2 | 6.2% | 0.0% | 13.8% | 3.9% |
| 23 | ECM1 | 6.2% | 0.0% | 24.1% | 0.0% |
| 24 | LTBP1 | 6.2% | 28.6% | 10.3% | 2.6% |
| 25 | LGALS1 | 6.2% | 0.0% | 10.3% | 5.2% |
| 26 | SERPINA1 | 6.2% | 0.0% | 20.7% | 1.3% |
| 27 | SPOCK1 | 6.2% | 14.3% | 0.0% | 7.8% |
| 28 | TFF3 | 6.2% | 0.0% | 17.2% | 2.6% |
| 29 | NPNT | 5.3% | 0.0% | 3.4% | 6.5% |
| 30 | TFIP11 | 5.3% | 14.3% | 6.9% | 3.9% |
| 31 | COL9A2 | 4.4% | 0.0% | 0.0% | 6.5% |
| 32 | COL6A1 | 4.4% | 0.0% | 0.0% | 6.5% |
| 33 | FN1 | 4.4% | 14.3% | 10.3% | 1.3% |
| 34 | LAD1 | 4.4% | 0.0% | 10.3% | 2.6% |
| 35 | LAMA1 | 4.4% | 14.3% | 3.4% | 3.9% |
| 36 | LAMB2 | 4.4% | 0.0% | 10.3% | 2.6% |
| 37 | MATN2 | 4.4% | 14.3% | 3.4% | 3.9% |
| 38 | ZP3 | 4.4% | 0.0% | 0.0% | 6.5% |
| 39 | ADAMTSL3 | 3.5% | 28.6% | 3.4% | 1.3% |

TABLE 13-continued

Human CTC ECM Gene Expression

| | | Percent of Samples >100 RPM | | | |
|---|---|---|---|---|---|
| Count | ECM Gene Symbol | All CTCs | PDAC CTCs | Breast CTCs | Prostate CTCs |
| 40 | FRAS1 | 3.5% | 14.3% | 0.0% | 3.9% |
| 41 | TIMP3 | 3.5% | 0.0% | 3.4% | 3.9% |
| 42 | DST | 3.5% | 0.0% | 6.9% | 2.6% |
| 43 | GFOD2 | 3.5% | 14.3% | 0.0% | 3.9% |
| 44 | LAMA3 | 3.5% | 14.3% | 0.0% | 3.9% |
| 45 | LAMB1 | 3.5% | 14.3% | 0.0% | 3.9% |
| 46 | MMP7 | 3.5% | 0.0% | 0.0% | 5.2% |
| 47 | ANGPTL4 | 2.7% | 0.0% | 0.0% | 3.9% |
| 48 | BMP4 | 2.7% | 0.0% | 0.0% | 3.9% |
| 49 | LTBP2 | 2.7% | 28.6% | 3.4% | 0.0% |
| 50 | LEPRE1 | 2.7% | 0.0% | 0.0% | 3.9% |
| 51 | LUM | 2.7% | 0.0% | 0.0% | 3.9% |
| 52 | NID2 | 2.7% | 14.3% | 6.9% | 0.0% |
| 53 | SLC1A3 | 2.7% | 28.6% | 0.0% | 1.3% |
| 54 | TECTA | 2.7% | 14.3% | 3.4% | 1.3% |
| 55 | THSD4 | 2.7% | 0.0% | 6.9% | 1.3% |
| 56 | ADAMTS15 | 1.8% | 0.0% | 6.9% | 0.0% |
| 57 | USH2A | 1.8% | 14.3% | 3.4% | 0.0% |
| 58 | APLP1 | 1.8% | 0.0% | 0.0% | 2.6% |
| 59 | COL4A3 | 1.8% | 14.3% | 3.4% | 0.0% |
| 60 | COL7A1 | 1.8% | 0.0% | 3.4% | 1.3% |
| 61 | COL11A1 | 1.8% | 0.0% | 6.9% | 0.0% |
| 62 | COL11A2 | 1.8% | 0.0% | 0.0% | 2.6% |
| 63 | COL15A1 | 1.8% | 28.6% | 0.0% | 0.0% |
| 64 | CTGF | 1.8% | 0.0% | 0.0% | 2.6% |
| 65 | CRISP3 | 1.8% | 0.0% | 0.0% | 2.6% |
| 66 | DCN | 1.8% | 0.0% | 0.0% | 2.6% |
| 67 | ENTPD2 | 1.8% | 0.0% | 0.0% | 2.6% |
| 68 | FMOD | 1.8% | 0.0% | 3.4% | 1.3% |
| 69 | GPC1 | 1.8% | 0.0% | 0.0% | 2.6% |
| 70 | HSPG2 | 1.8% | 0.0% | 0.0% | 2.6% |
| 71 | LAMA5 | 1.8% | 0.0% | 3.4% | 1.3% |
| 72 | LAMC2 | 1.8% | 14.3% | 0.0% | 1.3% |
| 73 | MMP10 | 1.8% | 0.0% | 3.4% | 1.3% |
| 74 | MMP12 | 1.8% | 0.0% | 0.0% | 2.6% |
| 75 | NTN4 | 1.8% | 0.0% | 6.9% | 0.0% |
| 76 | NAV2 | 1.8% | 0.0% | 6.9% | 0.0% |
| 77 | PAPLN | 1.8% | 0.0% | 3.4% | 1.3% |
| 78 | SFTPA2 | 1.8% | 0.0% | 0.0% | 2.6% |
| 79 | VCAN | 1.8% | 14.3% | 0.0% | 1.3% |
| 80 | ADAMTS13 | 0.9% | 0.0% | 3.4% | 0.0% |
| 81 | ADAMTS3 | 0.9% | 14.3% | 0.0% | 0.0% |
| 82 | ADAMTS5 | 0.9% | 14.3% | 0.0% | 0.0% |
| 83 | ADAMTSL4 | 0.9% | 0.0% | 0.0% | 1.3% |
| 84 | EFEMP1 | 0.9% | 0.0% | 3.4% | 0.0% |
| 85 | EFEMP2 | 0.9% | 0.0% | 3.4% | 0.0% |
| 86 | EGFLAM | 0.9% | 14.3% | 0.0% | 0.0% |
| 87 | KAL1 | 0.9% | 0.0% | 0.0% | 1.3% |
| 88 | KAZALD1 | 0.9% | 0.0% | 0.0% | 1.3% |
| 89 | MAMDC2 | 0.9% | 14.3% | 0.0% | 0.0% |
| 90 | SMOC1 | 0.9% | 0.0% | 0.0% | 1.3% |
| 91 | SMOC2 | 0.9% | 0.0% | 0.0% | 1.3% |
| 92 | ACHE | 0.9% | 0.0% | 0.0% | 1.3% |
| 93 | AMTN | 0.9% | 0.0% | 3.4% | 0.0% |
| 94 | ANXA2P2 | 0.9% | 0.0% | 3.4% | 0.0% |
| 95 | CPZ | 0.9% | 0.0% | 3.4% | 0.0% |
| 96 | CHADL | 0.9% | 0.0% | 0.0% | 1.3% |
| 97 | COCH | 0.9% | 0.0% | 0.0% | 1.3% |
| 98 | COL6A6 | 0.9% | 14.3% | 0.0% | 0.0% |
| 99 | COL1A2 | 0.9% | 0.0% | 3.4% | 0.0% |
| 100 | COL2A1 | 0.9% | 0.0% | 0.0% | 1.3% |
| 101 | COL4A1 | 0.9% | 14.3% | 0.0% | 0.0% |
| 102 | COL4A2 | 0.9% | 0.0% | 0.0% | 1.3% |
| 103 | COL4A6 | 0.9% | 0.0% | 0.0% | 1.3% |
| 104 | COL5A1 | 0.9% | 14.3% | 0.0% | 0.0% |
| 105 | COL6A2 | 0.9% | 0.0% | 0.0% | 1.3% |
| 106 | COL8A1 | 0.9% | 14.3% | 0.0% | 0.0% |
| 107 | COL12A1 | 0.9% | 14.3% | 0.0% | 0.0% |
| 108 | COL14A1 | 0.9% | 14.3% | 0.0% | 0.0% |
| 109 | COL19A1 | 0.9% | 14.3% | 0.0% | 0.0% |
| 110 | COL17A1 | 0.9% | 14.3% | 0.0% | 0.0% |
| 111 | COL22A1 | 0.9% | 14.3% | 0.0% | 0.0% |
| 112 | ENTPD1 | 0.9% | 14.3% | 0.0% | 0.0% |
| 113 | FBN2 | 0.9% | 0.0% | 0.0% | 1.3% |
| 114 | FBN3 | 0.9% | 0.0% | 3.4% | 0.0% |
| 115 | FBLN1 | 0.9% | 14.3% | 0.0% | 0.0% |
| 116 | FBLN7 | 0.9% | 0.0% | 0.0% | 1.3% |
| 117 | GPC4 | 0.9% | 0.0% | 3.4% | 0.0% |
| 118 | HMCN1 | 0.9% | 14.3% | 0.0% | 0.0% |
| 119 | IMPG1 | 0.9% | 14.3% | 0.0% | 0.0% |
| 120 | IMPG2 | 0.9% | 0.0% | 3.4% | 0.0% |
| 121 | LAMA2 | 0.9% | 0.0% | 3.4% | 0.0% |
| 122 | LAMB3 | 0.9% | 14.3% | 0.0% | 0.0% |
| 123 | MEPE | 0.9% | 0.0% | 3.4% | 0.0% |
| 124 | MMP1 | 0.9% | 14.3% | 0.0% | 0.0% |
| 125 | MMP2 | 0.9% | 0.0% | 3.4% | 0.0% |
| 126 | MMP25 | 0.9% | 0.0% | 0.0% | 1.3% |
| 127 | MMP3 | 0.9% | 0.0% | 3.4% | 0.0% |
| 128 | MMP9 | 0.9% | 14.3% | 0.0% | 0.0% |
| 129 | OGN | 0.9% | 14.3% | 0.0% | 0.0% |
| 130 | PI3 | 0.9% | 0.0% | 0.0% | 1.3% |
| 131 | PRELP | 0.9% | 14.3% | 0.0% | 0.0% |
| 132 | PTPRZ1 | 0.9% | 14.3% | 0.0% | 0.0% |
| 133 | RELN | 0.9% | 0.0% | 3.4% | 0.0% |
| 134 | ADAMTSL2 | 0.9% | 0.0% | 0.0% | 1.3% |
| 135 | TGFBI | 0.9% | 0.0% | 3.4% | 0.0% |
| 136 | UCMA | 0.9% | 0.0% | 3.4% | 0.0% |
| 137 | VIT | 0.9% | 0.0% | 3.4% | 0.0% |
| 138 | WNT10A | 0.9% | 14.3% | 0.0% | 0.0% |
| 139 | WNT10B | 0.9% | 0.0% | 0.0% | 1.3% |
| 140 | WNT11 | 0.9% | 0.0% | 3.4% | 0.0% |
| 141 | WNT4 | 0.9% | 0.0% | 0.0% | 1.3% |
| 142 | ZP2 | 0.9% | 14.3% | 0.0% | 0.0% |
| 143 | ADAMTS1 | 0.0% | 0.0% | 0.0% | 0.0% |
| 144 | ADAMTS10 | 0.0% | 0.0% | 0.0% | 0.0% |
| 145 | ADAMTS12 | 0.0% | 0.0% | 0.0% | 0.0% |
| 146 | ADAMTS14 | 0.0% | 0.0% | 0.0% | 0.0% |
| 147 | ADAMTS16 | 0.0% | 0.0% | 0.0% | 0.0% |
| 148 | ADAMTS17 | 0.0% | 0.0% | 0.0% | 0.0% |
| 149 | ADAMTS18 | 0.0% | 0.0% | 0.0% | 0.0% |
| 150 | ADAMTS19 | 0.0% | 0.0% | 0.0% | 0.0% |
| 151 | ADAMTS2 | 0.0% | 0.0% | 0.0% | 0.0% |
| 152 | ADAMTS20 | 0.0% | 0.0% | 0.0% | 0.0% |
| 153 | ADAMTS4 | 0.0% | 0.0% | 0.0% | 0.0% |
| 154 | ADAMTS6 | 0.0% | 0.0% | 0.0% | 0.0% |
| 155 | ADAMTS8 | 0.0% | 0.0% | 0.0% | 0.0% |
| 156 | ADAMTS9 | 0.0% | 0.0% | 0.0% | 0.0% |
| 157 | ADAMTSL1 | 0.0% | 0.0% | 0.0% | 0.0% |
| 158 | ADAMTSL5 | 0.0% | 0.0% | 0.0% | 0.0% |
| 159 | CD248 | 0.0% | 0.0% | 0.0% | 0.0% |
| 160 | DGCR6 | 0.0% | 0.0% | 0.0% | 0.0% |
| 161 | EGFL6 | 0.0% | 0.0% | 0.0% | 0.0% |
| 162 | EMID1 | 0.0% | 0.0% | 0.0% | 0.0% |
| 163 | FREM1 | 0.0% | 0.0% | 0.0% | 0.0% |
| 164 | FREM2 | 0.0% | 0.0% | 0.0% | 0.0% |
| 165 | RELL2 | 0.0% | 0.0% | 0.0% | 0.0% |
| 166 | SPARCL1 | 0.0% | 0.0% | 0.0% | 0.0% |
| 167 | ACAN | 0.0% | 0.0% | 0.0% | 0.0% |
| 168 | AMBN | 0.0% | 0.0% | 0.0% | 0.0% |
| 169 | AMELX | 0.0% | 0.0% | 0.0% | 0.0% |
| 170 | AMELY | 0.0% | 0.0% | 0.0% | 0.0% |
| 171 | ASPN | 0.0% | 0.0% | 0.0% | 0.0% |
| 172 | BGN | 0.0% | 0.0% | 0.0% | 0.0% |
| 173 | BCAN | 0.0% | 0.0% | 0.0% | 0.0% |
| 174 | CRTAC1 | 0.0% | 0.0% | 0.0% | 0.0% |
| 175 | CILP2 | 0.0% | 0.0% | 0.0% | 0.0% |
| 176 | CILP | 0.0% | 0.0% | 0.0% | 0.0% |
| 177 | COMP | 0.0% | 0.0% | 0.0% | 0.0% |
| 178 | CHL1 | 0.0% | 0.0% | 0.0% | 0.0% |
| 179 | CHI3L1 | 0.0% | 0.0% | 0.0% | 0.0% |
| 180 | CHAD | 0.0% | 0.0% | 0.0% | 0.0% |
| 181 | C6orf15 | 0.0% | 0.0% | 0.0% | 0.0% |
| 182 | CCDC80 | 0.0% | 0.0% | 0.0% | 0.0% |
| 183 | CTHRC1 | 0.0% | 0.0% | 0.0% | 0.0% |
| 184 | COL1A1 | 0.0% | 0.0% | 0.0% | 0.0% |
| 185 | COL3A1 | 0.0% | 0.0% | 0.0% | 0.0% |

TABLE 13-continued

Human CTC ECM Gene Expression

| | | Percent of Samples >100 RPM | | | |
|---|---|---|---|---|---|
| Count | ECM Gene Symbol | All CTCs | PDAC CTCs | Breast CTCs | Prostate CTCs |
| 186 | COL4A4 | 0.0% | 0.0% | 0.0% | 0.0% |
| 187 | COL4A5 | 0.0% | 0.0% | 0.0% | 0.0% |
| 188 | COL9A1 | 0.0% | 0.0% | 0.0% | 0.0% |
| 189 | COL9A3 | 0.0% | 0.0% | 0.0% | 0.0% |
| 190 | COL5A2 | 0.0% | 0.0% | 0.0% | 0.0% |
| 191 | COL5A3 | 0.0% | 0.0% | 0.0% | 0.0% |
| 192 | COL6A3 | 0.0% | 0.0% | 0.0% | 0.0% |
| 193 | COL8A2 | 0.0% | 0.0% | 0.0% | 0.0% |
| 194 | COL10A1 | 0.0% | 0.0% | 0.0% | 0.0% |
| 195 | COL16A1 | 0.0% | 0.0% | 0.0% | 0.0% |
| 196 | COL18A1 | 0.0% | 0.0% | 0.0% | 0.0% |
| 197 | COL21A1 | 0.0% | 0.0% | 0.0% | 0.0% |
| 198 | COL27A1 | 0.0% | 0.0% | 0.0% | 0.0% |
| 199 | COL28A1 | 0.0% | 0.0% | 0.0% | 0.0% |
| 200 | COLQ | 0.0% | 0.0% | 0.0% | 0.0% |
| 201 | DMP1 | 0.0% | 0.0% | 0.0% | 0.0% |
| 202 | DSPP | 0.0% | 0.0% | 0.0% | 0.0% |
| 203 | DPT | 0.0% | 0.0% | 0.0% | 0.0% |
| 204 | ELN | 0.0% | 0.0% | 0.0% | 0.0% |
| 205 | EMILIN1 | 0.0% | 0.0% | 0.0% | 0.0% |
| 206 | EMILIN2 | 0.0% | 0.0% | 0.0% | 0.0% |
| 207 | EMILIN3 | 0.0% | 0.0% | 0.0% | 0.0% |
| 208 | ENAM | 0.0% | 0.0% | 0.0% | 0.0% |
| 209 | EPYC | 0.0% | 0.0% | 0.0% | 0.0% |
| 210 | ECM2 | 0.0% | 0.0% | 0.0% | 0.0% |
| 211 | FBN1 | 0.0% | 0.0% | 0.0% | 0.0% |
| 212 | FGF1 | 0.0% | 0.0% | 0.0% | 0.0% |
| 213 | FGF9 | 0.0% | 0.0% | 0.0% | 0.0% |
| 214 | FLRT1 | 0.0% | 0.0% | 0.0% | 0.0% |
| 215 | FLRT2 | 0.0% | 0.0% | 0.0% | 0.0% |
| 216 | FLRT3 | 0.0% | 0.0% | 0.0% | 0.0% |
| 217 | FBLN2 | 0.0% | 0.0% | 0.0% | 0.0% |
| 218 | FBLN5 | 0.0% | 0.0% | 0.0% | 0.0% |
| 219 | GPLD1 | 0.0% | 0.0% | 0.0% | 0.0% |
| 220 | GPC2 | 0.0% | 0.0% | 0.0% | 0.0% |
| 221 | GPC3 | 0.0% | 0.0% | 0.0% | 0.0% |
| 222 | GPC5 | 0.0% | 0.0% | 0.0% | 0.0% |
| 223 | GPC6 | 0.0% | 0.0% | 0.0% | 0.0% |
| 224 | HAPLN1 | 0.0% | 0.0% | 0.0% | 0.0% |
| 225 | HAPLN2 | 0.0% | 0.0% | 0.0% | 0.0% |
| 226 | HAPLN3 | 0.0% | 0.0% | 0.0% | 0.0% |
| 227 | HAPLN4 | 0.0% | 0.0% | 0.0% | 0.0% |
| 228 | KERA | 0.0% | 0.0% | 0.0% | 0.0% |
| 229 | LAMA4 | 0.0% | 0.0% | 0.0% | 0.0% |
| 230 | LAMB4 | 0.0% | 0.0% | 0.0% | 0.0% |
| 231 | LAMC3 | 0.0% | 0.0% | 0.0% | 0.0% |
| 232 | LTBP4 | 0.0% | 0.0% | 0.0% | 0.0% |
| 233 | LOX | 0.0% | 0.0% | 0.0% | 0.0% |
| 234 | LOXL1 | 0.0% | 0.0% | 0.0% | 0.0% |
| 235 | MATN1 | 0.0% | 0.0% | 0.0% | 0.0% |
| 236 | MATN3 | 0.0% | 0.0% | 0.0% | 0.0% |
| 237 | MMP11 | 0.0% | 0.0% | 0.0% | 0.0% |
| 238 | MMP13 | 0.0% | 0.0% | 0.0% | 0.0% |
| 239 | MMP16 | 0.0% | 0.0% | 0.0% | 0.0% |
| 240 | MMP17 | 0.0% | 0.0% | 0.0% | 0.0% |
| 241 | MMP20 | 0.0% | 0.0% | 0.0% | 0.0% |
| 242 | MMP23A | 0.0% | 0.0% | 0.0% | 0.0% |
| 243 | MMP26 | 0.0% | 0.0% | 0.0% | 0.0% |
| 244 | MMP27 | 0.0% | 0.0% | 0.0% | 0.0% |
| 245 | MMP28 | 0.0% | 0.0% | 0.0% | 0.0% |
| 246 | MMP8 | 0.0% | 0.0% | 0.0% | 0.0% |
| 247 | MFAP5 | 0.0% | 0.0% | 0.0% | 0.0% |
| 248 | MFAP2 | 0.0% | 0.0% | 0.0% | 0.0% |
| 249 | MFAP4 | 0.0% | 0.0% | 0.0% | 0.0% |
| 250 | MUC4 | 0.0% | 0.0% | 0.0% | 0.0% |
| 251 | MMRN2 | 0.0% | 0.0% | 0.0% | 0.0% |
| 252 | NTN1 | 0.0% | 0.0% | 0.0% | 0.0% |
| 253 | NTN3 | 0.0% | 0.0% | 0.0% | 0.0% |
| 254 | NID1 | 0.0% | 0.0% | 0.0% | 0.0% |
| 255 | NYX | 0.0% | 0.0% | 0.0% | 0.0% |
| 256 | ODAM | 0.0% | 0.0% | 0.0% | 0.0% |
| 257 | OPTC | 0.0% | 0.0% | 0.0% | 0.0% |
| 258 | OMD | 0.0% | 0.0% | 0.0% | 0.0% |
| 259 | OTOA | 0.0% | 0.0% | 0.0% | 0.0% |
| 260 | POSTN | 0.0% | 0.0% | 0.0% | 0.0% |
| 261 | PODN | 0.0% | 0.0% | 0.0% | 0.0% |
| 262 | PODNL1 | 0.0% | 0.0% | 0.0% | 0.0% |
| 263 | PRSS36 | 0.0% | 0.0% | 0.0% | 0.0% |
| 264 | RPTN | 0.0% | 0.0% | 0.0% | 0.0% |
| 265 | RBP3 | 0.0% | 0.0% | 0.0% | 0.0% |
| 266 | SPN | 0.0% | 0.0% | 0.0% | 0.0% |
| 267 | ADAMTS7 | 0.0% | 0.0% | 0.0% | 0.0% |
| 268 | SPOCK2 | 0.0% | 0.0% | 0.0% | 0.0% |
| 269 | SPOCK3 | 0.0% | 0.0% | 0.0% | 0.0% |
| 270 | SPON1 | 0.0% | 0.0% | 0.0% | 0.0% |
| 271 | SFTPA1 | 0.0% | 0.0% | 0.0% | 0.0% |
| 272 | SFTPD | 0.0% | 0.0% | 0.0% | 0.0% |
| 273 | TECTB | 0.0% | 0.0% | 0.0% | 0.0% |
| 274 | TNC | 0.0% | 0.0% | 0.0% | 0.0% |
| 275 | TNN | 0.0% | 0.0% | 0.0% | 0.0% |
| 276 | TNR | 0.0% | 0.0% | 0.0% | 0.0% |
| 277 | TNXB | 0.0% | 0.0% | 0.0% | 0.0% |
| 278 | THBS4 | 0.0% | 0.0% | 0.0% | 0.0% |
| 279 | TFPI2 | 0.0% | 0.0% | 0.0% | 0.0% |
| 280 | TGFB1 | 0.0% | 0.0% | 0.0% | 0.0% |
| 281 | TINAG | 0.0% | 0.0% | 0.0% | 0.0% |
| 282 | TNFRSF11B | 0.0% | 0.0% | 0.0% | 0.0% |
| 283 | VEGFA | 0.0% | 0.0% | 0.0% | 0.0% |
| 284 | VTN | 0.0% | 0.0% | 0.0% | 0.0% |
| 285 | VWC2 | 0.0% | 0.0% | 0.0% | 0.0% |
| 286 | WNT2 | 0.0% | 0.0% | 0.0% | 0.0% |
| 287 | WNT1 | 0.0% | 0.0% | 0.0% | 0.0% |
| 288 | WNT16 | 0.0% | 0.0% | 0.0% | 0.0% |
| 289 | WNT2B | 0.0% | 0.0% | 0.0% | 0.0% |
| 290 | WNT3 | 0.0% | 0.0% | 0.0% | 0.0% |
| 291 | WNT3A | 0.0% | 0.0% | 0.0% | 0.0% |
| 292 | WNT5A | 0.0% | 0.0% | 0.0% | 0.0% |
| 293 | WNT5B | 0.0% | 0.0% | 0.0% | 0.0% |
| 294 | WNT6 | 0.0% | 0.0% | 0.0% | 0.0% |
| 295 | WNT7A | 0.0% | 0.0% | 0.0% | 0.0% |
| 296 | WNT7B | 0.0% | 0.0% | 0.0% | 0.0% |
| 297 | WNT8A | 0.0% | 0.0% | 0.0% | 0.0% |
| 298 | WNT8B | 0.0% | 0.0% | 0.0% | 0.0% |
| 299 | WNT9A | 0.0% | 0.0% | 0.0% | 0.0% |
| 300 | WNT9B | 0.0% | 0.0% | 0.0% | 0.0% |
| 301 | ZP1 | 0.0% | 0.0% | 0.0% | 0.0% |
| 302 | ZP4 | 0.0% | 0.0% | 0.0% | 0.0% |

TABLE 10

Most significant Gene Sets Enriched in CTC-pro vs. CTC-c
q-value < 0.01

| Source | Term | Count | Odds Ratio | Benjamini (q-value) |
|---|---|---|---|---|
| GOTERM_BP_FAT | GO: 0002495~antigen processing and presentation of peptide antigen via MHC class II | 5 | 59.81 | 6.97E−04 |
| GOTERM_BP_FAT | GO: 0019886~antigen processing and presentation of exogenous peptide antigen via MHC class II | 5 | 59.81 | 6.97E−04 |
| GOTERM_BP_FAT | GO: 0002504~antigen processing and presentation of peptide or polysaccharide antigen via MHC class II | 5 | 50.36 | 7.34E−04 |
| GOTERM_BP_FAT | GO: 0002478~antigen processing and presentation of exogenous peptide antigen | 5 | 41.60 | 1.10E−03 |
| GOTERM_BP_FAT | GO: 0019884~antigen processing and presentation of exogenous antigen | 5 | 34.18 | 1.87E−03 |
| GOTERM_BP_FAT | GO: 0048002~antigen processing and presentation of peptide antigen | 5 | 27.34 | 3.72E−03 |
| GOTERM_BP_FAT | GO: 0001775~cell activation | 9 | 7.00 | 3.82E−03 |
| GOTERM_BP_FAT | GO: 0019882~antigen processing and presentation | 6 | 13.20 | 7.40E−03 |

TABLE 11

Most significant Gene Sets Enriched in CTC-plt vs. CTC-c
q-value < 0.01

| Source | Term | Count | Odds Ratio | Benjamini (q-value) |
|---|---|---|---|---|
| GOTERM_BP_FAT | GO: 0042060~wound healing | 18 | 7.8 | 1.86E−07 |
| GOTERM_BP_FAT | GO: 0007596~blood coagulation | 15 | 10.4 | 9.31E−08 |
| GOTERM_BP_FAT | GO: 0050817~coagulation | 15 | 10.4 | 9.31E−08 |
| GOTERM_BP_FAT | GO: 0007599~hemostasis | 15 | 10.3 | 7.59E−08 |
| GOTERM_BP_FAT | GO: 0050878~regulation of body fluid levels | 15 | 8.2 | 1.30E−06 |
| GOTERM_BP_FAT | GO: 0030029~actin filament-based process | 20 | 5.5 | 1.14E−06 |
| GOTERM_BP_FAT | GO: 0007010~cytoskeleton organization | 26 | 3.9 | 3.95E−06 |
| GOTERM_BP_FAT | GO: 0030036~actin cytoskeleton organization | 18 | 5.3 | 1.11E−05 |
| GOTERM_BP_FAT | GO: 0009611~response to wounding | 26 | 3.6 | 1.02E−05 |
| GOTERM_BP_FAT | GO: 0007155~cell adhesion | 33 | 2.9 | 2.86E−05 |
| GOTERM_BP_FAT | GO: 0022610~biological adhesion | 33 | 2.8 | 2.70E−05 |
| GOTERM_BP_FAT | GO: 0001775~cell activation | 19 | 3.7 | 4.70E−04 |
| GOTERM_BP_FAT | GO: 0030168~platelet activation | 6 | 18.2 | 1.68E−03 |
| GOTERM_BP_FAT | GO: 0007229~integrin-mediated signaling pathway | 10 | 6.4 | 2.95E−03 |
| GOTERM_BP_FAT | GO: 0016192~vesicle-mediated transport | 25 | 2.6 | 3.81E−03 |
| MSigDBv3.1 CGP | GNATENKO PLATELET SIGNATURE | 20 | 55.1 | 3.91E−24 |
| MSigDBv3.1 CGP | TENEDINI MEGAKARYOCYTE MARKERS | 14 | 15.3 | 1.35E−11 |
| MSigDBv3.1 CP: REACTOME | REACTOME FACTORS INVOLVED IN MEGAKARYOCYTE DEVELOPMENT AND PLATELET PRODUCTION | 6 | 2.9 | 2.25E−02 |

TABLE 12

Significantly Expressed Genes by Rank Product (FDR <0.01)

| Count | CTC-c vs Primary Tumor Enriched Gene | Primary Tumor vs CTC-c Enriched Gene | CTC-plt vs CTC-c | CTC-pro vs CTC-c |
|---|---|---|---|---|
| 1 | Upk3b | Tff2 | Clec1b | kg:uc007pge.1 |
| 2 | Ier2 | Wfdc2 | AU023871 | kg:uc007pgd.1 |
| 3 | Egr1 | Lamb3 | Alox12 | kg:uc007pgf.1 |
| 4 | Nkain4 | Lad1 | Itga2b | kg:uc007pgg.1 |
| 5 | Igfbp5 | Dmbt1 | Ppbp | Igj |
| 6 | Slc6a4 | Npy | Gng11 | kg:uc012enb.1 |
| 7 | Klf4 | Pmepa1 | Vwf | 2010001M09Rik |

TABLE 12-continued

Significantly Expressed Genes by Rank Product (FDR <0.01)

| | | | | |
|---|---|---|---|---|
| 8 | Tmem221 | Kcnn4 | Pf4 | kg:uc009cfw.1 |
| 9 | Arl4d | Serinc2 | Fcer1g | kg:uc007pgi.1 |
| 10 | Lrrn4 | 5730559C18Rik | Tmem40 | kg:uc007pgh.1 |
| 11 | Cldn15 | Muc1 | Hba-a2 | kg:uc007yos.1 |
| 12 | Gpm6a | Chi3l3 | Stom | Coro1a |
| 13 | Atf3 | Pglyrp1 | Beta-s | Pou2af1 |
| 14 | Ptma | Arl4c | Plek | kg:uc011yvj.1 |
| 15 | Slc9a3r1 | Spp1 | Srgn | Glipr1 |
| 16 | Fos | Col15a1 | Myl9 | Cd52 |
| 17 | Tmem119 | C1qb | Cd84 | Cd79b |
| 18 | Ptgis | Tnnt2 | F5 | Sec11c |
| 19 | Dcn | Gkn3 | Treml1 | Tnfrsf17 |
| 20 | Gbp2 | Onecut2 | Hbb-b1 | Krr1 |
| 21 | Dmkn | Mmp7 | Itgb3 | Gmfg |
| 22 | Sdc4 | Cd74 | Gp9 | Ccr9 |
| 23 | Ildr2 | Ctss | Mpl | Pycard |
| 24 | Akap2 | Lamc2 | Ctla2a | Derl3 |
| 25 | Gfpt2 | Olfml3 | Tubb1 | Rac2 |
| 26 | Klf6 | Lgals4 | Mylk | Srgn |
| 27 | Btg2 | Lcn2 | F13a1 | Cytip |
| 28 | Myl7 | Ly6a | Slamf1 | Edem2 |
| 29 | Igfbp6 | Pak1 | Rgs10 | Itgb7 |
| 30 | Gpr133 | Capn5 | Mkrn1 | Lsp1 |
| 31 | Oasl2 | Ptprn | Laptm5 | Lcp1 |
| 32 | Pfn1 | Reg3b | 1810058I24Rik | Cyfip2 |
| 33 | Cap1 | Fmnl3 | Itgb2 | Nans |
| 34 | Nfkbia | Sdc1 | Slc2a3 | Slamf7 |
| 35 | Malat1 | Prom1 | Pcmt1 | Ell2 |
| 36 | Rarres2 | Ankrd50 | Gp5 | H2-Eb1 |
| 37 | Rspo1 | Ccl6 | Ube2o | Creld2 |
| 38 | Espn | Slc4a11 | 5430417L22Rik | Cd74 |
| 39 | Klf9 | Oraov1 | Ptpn18 | Blnk |
| 40 | Zbtb7c | Aldh1l1 | Lat | Fmnl1 |
| 41 | Brd2 | Slc20a1 | Fermt3 | Snrnp70 |
| 42 | Olfr1033 | Cldn7 | Nrgn | Sec61b |
| 43 | Wt1 | Acsbg1 | Mrvi1 | Edem1 |
| 44 | Esam | Las1l | Lyz2 | Tspan13 |
| 45 | kg:uc009igb.1 | C1qc | Epb4.1 | Psmb8 |
| 46 | Tmem151a | Lama5 | Rasgrp2 | Pim1 |
| 47 | Mgll | Mgat4a | Treml2 | Sept1 |
| 48 | Csrnp1 | Cldn2 | Hist1h4i | Cd48 |
| 49 | Cd9 | Mcpt2 | March2 | Sub1 |
| 50 | Gjb5 | Fxyd3 | Ltbp1 | Lims1 |
| 51 | Lrrc61 | Il4ra | Nptn | Ncoa2 |
| 52 | Wasf2 | Itga5 | Abtb1 | Ctnnbl1 |
| 53 | Pdpn | Porcn | Ctla2b | Fdps |
| 54 | kg:uc009ogv.1 | Mast3 | Prkab2 | Ube2j1 |
| 55 | Sdpr | Scara3 | Arhgdib | Mettl1 |
| 56 | Gpr64 | Atox1 | Alas2 | Lax1 |
| 57 | Flnc | Arrdc1 | Odc1 | Rilpl2 |
| 58 | Add3 | Mmp2 | Ptpn11 | Ctse |
| 59 | Gata6 | Saa3 | Dhcr24 | Glrx |
| 60 | Wfdc1 | Serpinf1 | Mfsd2b | Fut8 |
| 61 | A130040M12Rik | Sox11 | Gp1bb | AI662270 |
| 62 | Ankrd12 | Prpsap1 | Rbpms2 | Gramd3 |
| 63 | Adamtsl1 | Mcpt1 | Fyb | Il2rg |
| 64 | C2 | Mfge8 | Smox | Rasgrp3 |
| 65 | Prss23 | Col18a1 | P2rx1 | Impdh1 |
| 66 | Ube2v1 | Lyz2 | Otud7b | Plek |
| 67 | Cryab | C1qa | kg:uc007ttx.1 | Ints5 |
| 68 | Pkhd1l1 | Acp5 | Samd14 | Blmh |
| 69 | Rtn1 | Angptl4 | Clca1 | Dnmt1 |
| 70 | Birc6 | Ccnd1 | kg:uc007tty.1 | Galk1 |
| 71 | Xdh | Asl | Gpr56 | kg:uc007hxv.1 |
| 72 | Cd34 | Ctxn1 | Sh3bgrl2 | Ccdc88b |
| 73 | Rab6b | Pgs1 | Pttg1ip | Selplg |
| 74 | Dusp1 | Anapc2 | Nomo1 | Sar1b |
| 75 | Clic4 | Cp | Gnaz | Lat2 |
| 76 | C3 | Gpx3 | Mmrn1 | Slc16a6 |
| 77 | Rhob | Lama3 | Gp1ba | Mki67 |
| 78 | Mir3064 | Rbp1 | Sh3bgrl3 | Dnajc3 |
| 79 | Thbd | Cotl1 | Slc24a3 | H2-Ab1 |
| 80 | Dpysl2 | Nek6 | Sord | Ndufs6 |
| 81 | Cobl | Cpxm1 | Nfe2 | Actr3 |
| 82 | Npr1 | Sfrp1 | Tuba4a | Etnk1 |
| 83 | Dnajb9 | Ttr | Zyx | Herpud1 |
| 84 | Arhgap29 | Gsto1 | Cnn2 | Ptpn7 |
| 85 | Cav1 | Npepl1 | Itgb5 | Ctss |

TABLE 12-continued

Significantly Expressed Genes by Rank Product (FDR <0.01)

| | | | | |
|---|---|---|---|---|
| 86 | Gbp7 | Usmg5 | Gata1 | Cs |
| 87 | Hes1 | Polr2l | Hist1h1c | Fbxw7 |
| 88 | Gm16897 | Sphk1 | Tbxas1 | Ppp2r5c |
| 89 | Ppp1r12a | Asxl1 | Ptplad2 | Znrd1 |
| 90 | Sv2a | Ctsh | Bpgm | Rfc2 |
| 91 | Ang | Egfl7 | Pdlim7 | Preb |
| 92 | Aldh1a2 | C1qtnf6 | Mmd | Fcer1g |
| 93 | Cryl1 | Rras | G6b | Dnajb11 |
| 94 | Kank1 | Lgi4 | kg:uc009duo.1 | Slc35b1 |
| 95 | 2210403K04Rik | Hmga2 | Lyz1 | Sin3b |
| 96 | kg:uc009okn.1 | Cep250 | Tacc1 | Nktr |
| 97 | Osr1 | B4galt3 | Dap | |
| 98 | kg:uc008ewj.2 | Tmem223 | Mast2 | |
| 99 | kg:uc009tuw.1 | Ltbp2 | Atp2a3 | |
| 100 | Gadd45b | Tnfrsf23 | Snca | |
| 101 | Ablim3 | Col7a1 | Stx11 | |
| 102 | Clec3b | Ggct | C030046I01Rik | |
| 103 | Usp25 | Rab25 | Trpt1 | |
| 104 | Sntb2 | Nedd8 | Tsc22d1 | |
| 105 | Rock2 | 9430023L20Rik | Prkar2b | |
| 106 | Col14a1 | Arl2 | Cd9 | |
| 107 | Cd200 | Wbp1 | Pgm2l1 | |
| 108 | kg:uc008ehr.1 | H2-Ab1 | Gp6 | |
| 109 | Atp2b1 | Preb | Pde5a | |
| 110 | Exoc4 | Sgsm3 | Itga6 | |
| 111 | Abcb1b | Sfn | Itgal | |
| 112 | Nrgn | Prrx2 | Edem1 | |
| 113 | kg:uc009cvm.1 | Ptprk | Isg20 | |
| 114 | Ncoa4 | Reg1 | Cdc42ep5 | |
| 115 | Ndufa4 | Sdcbp2 | Nipal3 | |
| 116 | Upk1b | Pcbd1 | Ccdc92 | |
| 117 | Jun | Slc25a1 | Sort1 | |
| 118 | Syne2 | Vamp5 | Ly6g6c | |
| 119 | kg:uc007bvx.1 | Crlf1 | Ubash3b | |
| 120 | Ap4e1 | Avil | Inf2 | |
| 121 | Spock2 | 2700094K13Rik | Asap1 | |
| 122 | Efemp1 | Ctse | Sec11c | |
| 123 | Prpf40a | Penk | Gas2l1 | |
| 124 | Tspan5 | Tmc4 | Parvb | |
| 125 | Lgals7 | Dhrs3 | Tmsb4x | |
| 126 | Kif5b | Ap1s1 | kg:uc007xrw.1 | |
| 127 | Psip1 | Arl6ip4 | Nudt3 | |
| 128 | kg:uc008oki.1 | 9430008C03Rik | Bcl2l1 | |
| 129 | 1810014B01Rik | Fcer1g | B230312A22Rik | |
| 130 | Ptges3 | Uqcr11 | Cnp | |
| 131 | Limch1 | Nhp2 | Plp1 | |
| 132 | Bicd1 | Plbd2 | Cnst | |
| 133 | Rdx | Capg | Rgs18 | |
| 134 | Pcdh15 | Pnpla6 | Lsm12 | |
| 135 | Foxn3 | Ppdpf | Alox5ap | |
| 136 | Morf4l2 | Hgfac | Ppif | |
| 137 | Ppp1r15a | Apoe | Spnb1 | |
| 138 | Cdc42ep3 | Fam40a | Ormdl3 | |
| 139 | Pard3b | Lyz1 | Hpse | |
| 140 | Bicc1 | 2200002D01Rik | Srxn1 | |
| 141 | Amhr2 | Laptm5 | 2010002N04Rik | |
| 142 | Gucy1a3 | Qars | Hist1h2bc | |
| 143 | Psmb2 | Tmx2 | Cyba | |
| 144 | Mapkapk3 | Fkbp4 | Chst12 | |
| 145 | Ube2l6 | Plin2 | kg:uc009sps.1 | |
| 146 | kg:uc007pff.1 | Fcgr3 | Max | |
| 147 | kg:uc007ctp.1 | Gkn1 | Was | |
| 148 | Nedd4 | Snhg1 | Isca1 | |
| 149 | Plxna4 | Lsp1 | Pdzk1ip1 | |
| 150 | 2010107G12Rik | Gm20605 | Lyn | |
| 151 | Ifngr1 | Ly6c1 | Mob3a | |
| 152 | Bcam | Aim1 | H2-T24 | |
| 153 | Ccnl1 | 2310007B03Rik | Slc44a1 | |
| 154 | Hoxa5 | Tgfbi | Derl1 | |
| 155 | Fhl1 | Tsta3 | Gclm | |
| 156 | 1810041L15Rik | Pafah1b3 | Fech | |
| 157 | 2900002K06Rik | Chid1 | Ywhah | |
| 158 | Hspb1 | Smox | Igtp | |
| 159 | Podn | 1500012F01Rik | Myl6 | |
| 160 | Fam63b | Tspan4 | Thbs1 | |
| 161 | Hsp90b1 | Agrn | Tln1 | |
| 162 | Dpp4 | Cfp | kg:uc009apq.1 | |
| 163 | Gas1 | Cdh1 | Bcap31 | |

TABLE 12-continued

Significantly Expressed Genes by Rank Product (FDR <0.01)

| | | | |
|---|---|---|---|
| 164 | kg:uc007zak.1 | Rasgrf1 | Ilk |
| 165 | Zc3h13 | Nxf1 | Epha1 |
| 166 | Sox6 | Pdrg1 | 2810453I06Rik |
| 167 | Arid4a | Polr2j | Rnf19b |
| 168 | Tnxb | Suds3 | Gsn |
| 169 | Tsix | D0H4S114 | Flna |
| 170 | Scd1 | Ccl9 | Arrb1 |
| 171 | Jund | Neat1 | kg:uc007pum.1 |
| 172 | Crls1 | Ccdc12 | Mbnl1 |
| 173 | 1110003E01Rik | Prr24 | Ccnd3 |
| 174 | Rnase4 | Impdh1 | Pdlim1 |
| 175 | Arhgef12 | Card10 | Ctse |
| 176 | Irf7 | Cpsf1 | Tspan17 |
| 177 | Bbx | Sema4g | Gpx4 |
| 178 | Sema5a | Hes6 | Bnip3l |
| 179 | Mau2 | C130074G19Rik | P2ry12 |
| 180 | Abi3bp | Ctrb1 | kg:uc009vev.1 |
| 181 | Dag1 | Rnaseh2a | Prkab1 |
| 182 | Cyp2s1 | Golm1 | F2rl2 |
| 183 | Sfrs18 | Ctsz | Stk4 |
| 184 | Hspb8 | Cyb561 | Fhl1 |
| 185 | Cnot6l | Ndufs8 | Rnf10 |
| 186 | Twsg1 | Atp6ap1 | Rasa3 |
| 187 | Gpc3 | Srd5a1 | Taldo1 |
| 188 | Lrrn4cl | Carkd | Bysl |
| 189 | Cdh3 | Cd24a | Esd |
| 190 | Cyr61 | Eng | Aldh2 |
| 191 | Cyp2d22 | Tcirg1 | Rhog |
| 192 | Hist1h1c | Slc9a3r2 | kg:uc009ecr.1 |
| 193 | Aplp1 | 0910001L09Rik | Cald1 |
| 194 | Tbl1x | Cox5b | Wbp2 |
| 195 | Pcm1 | Adipor2 | Ptprj |
| 196 | Ifi204 | Scarf2 | Tpm4 |
| 197 | Nfix | Myo7a | Mxi1 |
| 198 | Flrt2 | Ppap2c | Ly6g6f |
| 199 | Heg1 | Pea15a | Sla |
| 200 | Il6ra | Sh3pxd2b | Slpi |
| 201 | Ralbp1 | H19 | Bicd2 |
| 202 | Rhoj | Tpd52 | Clu |
| 203 | Ktn1 | 2610203C20Rik | Mtmr14 |
| 204 | Arl6ip5 | Naa10 | Abca7 |
| 205 | Crebbp | Fermt1 | Ppp1r18 |
| 206 | Ppig | Sap30l | Kif2a |
| 207 | Akap13 | Bgn | Prdx6 |
| 208 | Rab7 | Timm13 | kg:uc009ize.1 |
| 209 | Plxdc2 | Krt20 | Calm3 |
| 210 | Aldh1a1 | Itga3 | Dhrs1 |
| 211 | Bnc2 | Pfkl | Cfl1 |
| 212 | Slc4a4 | Agpat6 | Glipr2 |
| 213 | Tbx18 | Mrpl11 | Slc25a37 |
| 214 | Zbtb16 | Ramp1 | Atox1 |
| 215 | Arid4b | Hmga1 | BC057079 |
| 216 | Enpp2 | Gpx2 | Pla2g16 |
| 217 | Ptplad2 | 0610012G03Rik | Rnf144b |
| 218 | Akr1b3 | 9130017N09Rik | Stk16 |
| 219 | Gm6644 | Cygb | Rsad2 |
| 220 | Arf5 | Tmprss4 | Paip2 |
| 221 | Chi3l1 | Paox | Capzb |
| 222 | Gpr116 | Endod1 | Ppp1r12c |
| 223 | Cd82 | Cndp2 | 4930412F15Rik |
| 224 | Srrm1 | Suv39h1 | Ninj1 |
| 225 | Fmo2 | Cog4 | 2510009E07Rik |
| 226 | Tgfb1i1 | Trim27 | kg:uc007vsr.1 |
| 227 | Qrich1 | Cyhr1 | Pygb |
| 228 | Nfia | Trmt1 | Tlk1 |
| 229 | Pmp22 | Zfyve19 | Myct1 |
| 230 | Cdh11 | Esrp1 | Rnasek |
| 231 | Arid5b | kg:uc008oow.1 | Ctsd |
| 232 | Rbm3 | Dync1h1 | 0610010K14Rik |
| 233 | Prelp | Tab1 | Bcas3 |
| 234 | kg:uc007qse.1 | Pla2g6 | Atpif1 |
| 235 | Ddx3x | Timp1 | Serf2 |
| 236 | Sulf1 | Eif3f | Becn1 |
| 237 | Spnb2 | Abhd11 | Tspan9 |
| 238 | Tspan31 | Pmm2 | Acer2 |
| 239 | Prr13 | Tyrobp | Vdac3 |
| 240 | Ppp1cb | Farsb | kg:uc008kbg.1 |
| 241 | Fbln1 | Plod3 | Oaz2 |

TABLE 12-continued

Significantly Expressed Genes by Rank Product (FDR <0.01)

| | | | |
|---|---|---|---|
| 242 | Gm6548 | Abtb1 | Serpine2 |
| 243 | Uap1 | Brf1 | Ccdc90a |
| 244 | Mpdz | Tnk2 | Ndufa1 |
| 245 | Sat1 | Rfc2 | Tssc1 |
| 246 | Stim1 | Stxbp2 | Mboat7 |
| 247 | Mll3 | Pdlim7 | Cd44 |
| 248 | Slurp1 | A430105I19Rik | Cxx1c |
| 249 | Cd81 | Vill | Ecm1 |
| 250 | Emp2 | Bmp1 | Mff |
| 251 | Trpm7 | Mpzl1 | Ptpn12 |
| 252 | Crym | Thy1 | Mgmt |
| 253 | Enpp4 | Stab1 | Cox4i1 |
| 254 | Raly | Aldh16a1 | Tollip |
| 255 | Celf2 | Eif4ebp3 | Cds2 |
| 256 | Ap3s1 | Itpripl2 | Ybx1 |
| 257 | C1s | Mrpl52 | Gypc |
| 258 | Frmd4b | 2310002L13Rik | Dgkd |
| 259 | Nr4a1 | Mcm6 | Pecam1 |
| 260 | Acin1 | Kcnk1 | Ftl2 |
| 261 | Plod2 | Pmf1 | Nt5c3 |
| 262 | Id1 | Cuta | 1700037H04Rik |
| 263 | Creg1 | Nt5dc2 | Cd151 |
| 264 | Zfp318 | Rmnd5b | Lpin2 |
| 265 | Tmem140 | Araf | 6430548M08Rik |
| 266 | Mras | Wwp2 | Pon2 |
| 267 | Vwa5a | Lamb1 | Ndufa3 |
| 268 | Esyt3 | Kcne3 | 6330578E17Rik |
| 269 | Hexb | Uqcrq | Mfap3l |
| 270 | Nckap1 | Gps1 | Mink1 |
| 271 | Nipal3 | Rexo4 | Ston2 |
| 272 | Ubxn4 | Coro1c | Rac2 |
| 273 | Zfp36 | Hras1 | Fyn |
| 274 | Hnrnpl | Spint1 | Serinc3 |
| 275 | C1ra | Cblc | Maged2 |
| 276 | Nnmt | Fhod1 | Ap2m1 |
| 277 | Mut | Atp13a1 | Pacsin2 |
| 278 | kg:uc008jup.1 | Man2c1 | Ftl1 |
| 279 | Pnrc1 | Vsig2 | Adipor1 |
| 280 | Usp8 | Bpgm | kg:uc009qdo.1 |
| 281 | Pgcp | Bap1 | Snap23 |
| 282 | Junb | Smpd2 | Tagln2 |
| 283 | C1rl | Ubqln4 | Cox6c |
| 284 | Slc6a6 | Sirt7 | Creg1 |
| 285 | kg:uc008znh.1 | Krt23 | Bsg |
| 286 | Aqp1 | D8Ertd738e | Cmtm6 |
| 287 | Myh10 | Mapk13 | Cntd1 |
| 288 | Slc43a3 | kg:uc008bcq.1 | Plekho2 |
| 289 | Spint2 | Polr2g | Arrb2 |
| 290 | Hnrnph1 | Ndufs2 | Pard3b |
| 291 | Arhgap28 | Dad1 | Mlec |
| 292 | Cfh | Wnt7b | Taf10 |
| 293 | Brd4 | Fam20c | Gabarapl2 |
| 294 | Fndc1 | Cxxc5 | Bag1 |
| 295 | Star | Polr2f | Galnt2 |
| 296 | Nfkbiz | Ltf | Hk1 |
| 297 | Arsb | 2210407C18Rik | Fbxo9 |
| 298 | Rnd3 | Cdipt | kg:uc009izd.1 |
| 299 | Stard5 | Glrx5 | Pnpo |
| 300 | Thbs1 | Gemin7 | Fam46c |
| 301 | kg:uc008wkn.1 | Man1b1 | Pkm |
| 302 | Slc26a3 | Heatr7a | Ap1b1 |
| 303 | Phip | Arid5a | Rap1b |
| 304 | Usp2 | Sumo3 | Itgb1 |
| 305 | Golgb1 | Srm | St7 |
| 306 | Rock1 | Plscr3 | Smap1 |
| 307 | Rgma | 2210010C17Rik | Rabgap1l |
| 308 | Actg1 | Fam102a | Tmbim4 |
| 309 | BC013529 | Dlst | H3f3a |
| 310 | kg:uc007zwh.1 | Vps37c | Frmd8 |
| 311 | 3110062M04Rik | Ngfrap1 | Nlrx1 |
| 312 | Cast | Pold4 | Oaz1 |
| 313 | Mob3c | Grcc10 | Fam125b |
| 314 | Slc16a1 | Wnt7a | Hexa |
| 315 | Fam117a | 2010111I01Rik | Tspo |
| 316 | Pdia3 | Pxdn | Dcaf12 |
| 317 | Trim8 | Coasy | Nav1 |
| 318 | kg:uc009mng.1 | Dctn1 | Cd24a |
| 319 | eg:245190:chr7:m | Ncor2 | Uqcr11 |

TABLE 12-continued

Significantly Expressed Genes by Rank Product (FDR <0.01)

| | | | |
|---|---|---|---|
| 320 | Sbsn | Postn | Wipf1 |
| 321 | Serpinb6b | Col4a2 | F10 |
| 322 | Daglb | Cib1 | Erlec1 |
| 323 | Smarca2 | Tbc1d13 | Map2k3 |
| 324 | Mef2c | Ccnl2 | Stk24 |
| 325 | Prrc2c | Dcakd | Ldlrap1 |
| 326 | BC005537 | Cdc34 | Ehd4 |
| 327 | Hsp90ab1 | Atp6v0b | Atp6v1f |
| 328 | Snrnp70 | Abhd12 | Gnas |
| 329 | Ppl | Flot2 | Arhgap18 |
| 330 | Serpinh1 | Sla2 | Arhgap10 |
| 331 | Sorbs3 | Rhbdf1 | Pitpnm1 |
| 332 | Golga4 | Cdh17 | S100a1 |
| 333 | Acbd3 | Psmb5 | Bin1 |
| 334 | Hook3 | Serf1 | Ttyh3 |
| 335 | Map3k3 | Slc15a3 | Selp |
| 336 | Rhou | Sftpd | Trappc9 |
| 337 | Smc2 | Pop5 | Aes |
| 338 | C1d | Nudc | Taok3 |
| 339 | kg:uc008dzh.1 | Sh2d5 | Zfand3 |
| 340 | Psmd7 | kg:uc007fwp.1 | Stim1 |
| 341 | Dab2 | Mrpl37 | Rnf114 |
| 342 | Cep164 | Rin1 | Sep15 |
| 343 | Crim1 | Podxl | kg:uc012hdk.1 |
| 344 | Rtf1 | Paqr5 | Lgals9 |
| 345 | Fxyd1 | Sepx1 | Cox6b1 |
| 346 | H2-D1 | Agr2 | Riok3 |
| 347 | Zfp704 | Bax | Slc38a10 |
| 348 | Mtap1a | Rxrb | Rtn3 |
| 349 | Ascc3 | Tes | B3gat2 |
| 350 | Med13l | Hdac6 | Ccndbp1 |
| 351 | Jup | 1110008F13Rik | Rsu1 |
| 352 | Nid2 | Mpnd | kg:uc007upr.1 |
| 353 | Kdr | Gmppa | Itm2b |
| 354 | Ifnar2 | Gramd1a | St3gal1 |
| 355 | 5430435G22Rik | Wars | Sec61g |
| 356 | Col4a6 | Mtap | Ptpn1 |
| 357 | Il17re | C1qtnf5 | kg:uc012bhf.1 |
| 358 | Gbp3 | Mrpl28 | B2m |
| 359 | Slc39a8 | Mfrp | Rasgrp3 |
| 360 | Cfl2 | Kars | Memo1 |
| 361 | Slc38a1 | Lbp | Slc39a4 |
| 362 | Cuedc1 | Plxnb1 | Sdcbp |
| 363 | Fgfl | 2700081O15Rik | Tspan14 |
| 364 | Gas6 | Mrps24 | Ubl7 |
| 365 | Cldn25 | Klc4 | Nras |
| 366 | Sorbs1 | Dctn3 | Ssx2ip |
| 367 | Hspa12a | Kcnq1 | kg:uc007zbz.1 |
| 368 | kg:uc007zts.1 | Smurf1 | Wbp1 |
| 369 | Slc1a5 | Fam162a | 1110003E01Rik |
| 370 | Nr3c1 | Hip1r | Clip2 |
| 371 | Adamts5 | kg:uc007hyr.2 | Gapdh |
| 372 | Gpcpd1 | Gys1 | Gm6578 |
| 373 | Dpysl3 | Sac3d1 | Actn1 |
| 374 | Colec12 | Ndufs6 | St3gal2 |
| 375 | Pdcd6ip | Rgl2 | 3110001D03Rik |
| 376 | Dst | Atp5g1 | Ctsz |
| 377 | Ifit3 | Itgb4 | kg:uc007vdl.1 |
| 378 | Chst4 | Sars | Fam73a |
| 379 | Xist | 2310003F16Rik | Vcl |
| 380 | Ifi27l2a | Nhp2l1 | Lims1 |
| 381 | Fkbp5 | D19Wsu162e | Lars2 |
| 382 | Agap1 | Cd320 | Birc2 |
| 383 | Ankrd11 | Pigq | Lamp2 |
| 384 | kg:uc007qca.1 | Chd3 | Rasl10a |
| 385 | Syt11 | Zdhhc4 | Mif |
| 386 | Ptrf | Eif3l | Rab10 |
| 387 | Krcc1 | St8sia3 | Pabpc1 |
| 388 | Zfp488 | Rcan3 | Wwp2 |
| 389 | Lama4 | Meg3 | Nqo2 |
| 390 | Aebp1 | Nudt4 | kg:uc007fte.1 |
| 391 | Fam134b | Gss | Plxna4 |
| 392 | Tppp3 | Pih1d1 | Gm1821 |
| 393 | Maf | Limd2 | Gadd45a |
| 394 | Peli1 | Ap1s2 | Slc25a39 |
| 395 | Zfp353 | BC056474 | kg:uc009pet.1 |
| 396 | Cdon | Mms19 | Ubb |
| 397 | Sarnp | Clip2 | Ppp1r2 |

TABLE 12-continued

Significantly Expressed Genes by Rank Product (FDR <0.01)

| | | | |
|---|---|---|---|
| 398 | Atxn7l3b | 2310016M24Rik | Rab27b |
| 399 | Pef1 | Itpa | Cap1 |
| 400 | App | Slc25a10 | Jarid2 |
| 401 | Mtdh | Fibp | Rnf11 |
| 402 | Lrrc20 | Higd2a | Tmem50b |
| 403 | Btbd2 | Snrpd2 | Myh9 |
| 404 | Gnb2 | Eri3 | Tmem128 |
| 405 | Pigt | Nbeal2 | Stradb |
| 406 | Efna5 | Trim28 | Cela1 |
| 407 | Tm4sf1 | S100a4 | Ndrg2 |
| 408 | Coq10b | Ivns1abp | Dhrs3 |
| 409 | Eif2s3x | Ppp1r18 | Hipk1 |
| 410 | Cmah | Efemp2 | Atg9a |
| 411 | Sf3b1 | Med22 | |
| 412 | Eea1 | Nelf | |
| 413 | Slpi | 2810428I15Rik | |
| 414 | Tmod3 | D2Wsu81e | |
| 415 | Ppp3ca | Trappc6a | |
| 416 | Tceal8 | Trappc2l | |
| 417 | Anp32a | Antxr2 | |
| 418 | Actb | Rab11fip5 | |
| 419 | Ddx5 | Ldhd | |
| 420 | Cobll1 | Npnt | |
| 421 | Cish | Acrbp | |
| 422 | Nod1 | Pafah1b2 | |
| 423 | Psd | Angptl2 | |
| 424 | Gm10052 | Fzr1 | |
| 425 | Lims2 | Aaas | |
| 426 | Stra6 | Eif2b2 | |
| 427 | kg:uc007bgn.1 | 1190003J15Rik | |
| 428 | Plxdc1 | 5730403B10Rik | |
| 429 | Nfe2l1 | Adamts13 | |
| 430 | Smpd3 | Eif3b | |
| 431 | Bcl10 | Znrf1 | |
| 432 | Ilf3 | Pkp3 | |
| 433 | Fam76a | Lemd2 | |
| 434 | Cybrd1 | Rab34 | |
| 435 | Gm3893 | Mpv17l2 | |
| 436 | Siae | Cdkn2b | |
| 437 | Ssh2 | Snrpe | |
| 438 | Nfic | Gm14005 | |
| 439 | Btf3 | Prdx4 | |
| 440 | Sp100 | Xab2 | |
| 441 | Ndn | Dpp3 | |
| 442 | Matr3 | Tyms | |
| 443 | Gm13251 | Leprotl1 | |
| 444 | Arhgap5 | Uqcr10 | |
| 445 | Zbtb4 | Cdk5rap3 | |
| 446 | Pgrmc1 | Gorasp2 | |
| 447 | 4930402H24Rik | Wbp7 | |
| 448 | Bptf | Sort1 | |
| 449 | Dusp3 | Ddx41 | |
| 450 | Pla2g4a | Cct3 | |
| 451 | Brp44l | Mrps33 | |
| 452 | Oxct1 | Frmd8 | |
| 453 | Stk40 | 1110049F12Rik | |
| 454 | Ddr1 | Fscn1 | |
| 455 | Ifi205 | Ndufa2 | |
| 456 | Col3a1 | Dpcd | |
| 457 | Nipbl | Unc13a | |
| 458 | Plk1s1 | Eif1ad | |
| 459 | Bdp1 | Sgta | |
| 460 | Smc3 | Chaf1a | |
| 461 | Ifitm3 | Plxna1 | |
| 462 | Ndst1 | Hspa9 | |
| 463 | Zbed6 | 1110014N23Rik | |
| 464 | Rest | Cd99l2 | |
| 465 | kg:uc007vnc.1 | Snrpa | |
| 466 | Ccdc88a | Mcm7 | |
| 467 | Stat3 | Tars2 | |
| 468 | Arf2 | Gon4l | |
| 469 | Trib1 | Stk38 | |
| 470 | Gcap14 | C1qtnf1 | |
| 471 | Tbc1d15 | Tbrg4 | |
| 472 | Igf1r | Tmem132a | |
| 473 | Ppbp | Cox6c | |
| 474 | kg:uc008tky.1 | Alcam | |
| 475 | Rab1b | Phka2 | |

TABLE 12-continued

Significantly Expressed Genes by Rank Product (FDR <0.01)

| | | |
|---|---|---|
| 476 | Krt14 | Trim3 |
| 477 | Med21 | Ppp1r14b |
| 478 | Gja1 | Gpaa1 |
| 479 | Klf10 | Ctps2 |
| 480 | Id2 | Ptpn23 |
| 481 | Mfap1a | Endog |
| 482 | Ogn | Mrto4 |
| 483 | Gpc4 | Mrps6 |
| 484 | Bst2 | Pvr |
| 485 | Dtx2 | Phgdh |
| 486 | Wac | Itpr3 |
| 487 | Kpna3 | Polr2e |
| 488 | Kcnab1 | Sec16a |
| 489 | Orai3 | Mdp1 |
| 490 | Gcsh | Fbf1 |
| 491 | Wdr92 | Mcpt8 |
| 492 | Olfr613 | Rps6ka4 |
| 493 | Tcf7l1 | Mical1 |
| 494 | Tgfb2 | Mrpl34 |
| 495 | Il16 | Agpat3 |
| 496 | Manf | 2310044H10Rik |
| 497 | Mgst1 | Myo9b |
| 498 | kg:uc008tkz.1 | Ndufb10 |
| 499 | Creb3l1 | Apex1 |
| 500 | Txndc5 | Elk3 |
| 501 | Klf2 | Cpsf3l |
| 502 | Slu7 | Tnk1 |
| 503 | Ttc28 | Pmvk |
| 504 | 1110002B05Rik | Ppp1r16a |
| 505 | Zcchc11 | Arhgef5 |
| 506 | Ptp4a2 | Lonp1 |
| 507 | Pbx1 | Pla2g7 |
| 508 | Clcn3 | Pip5k1c |
| 509 | Tmco7 | Inf2 |
| 510 | Lrrc58 | Pgk1 |
| 511 | Eif3a | Parp6 |
| 512 | Cldn10 | Urm1 |
| 513 | H2-Q6 | Mad2l2 |
| 514 | Ccdc80 | Ing4 |
| 515 | kg:uc009iln.1 | Rbck1 |
| 516 | Rab5c | Cant1 |
| 517 | Tsc22d3 | Sgpl1 |
| 518 | Tm4sf5 | Ehbp1l1 |
| 519 | Hmgb1 | Runx1 |
| 520 | Sec62 | Slc27a4 |
| 521 | Maoa | Ndufa7 |
| 522 | Clec1b | Mcm3ap |
| 523 | Mphosph8 | 1110008P14Rik |
| 524 | Oat | Rassf7 |
| 525 | Ncor1 | Ptpmt1 |
| 526 | Cyb5 | Arfgap1 |
| 527 | Trafd1 | Sec61a1 |
| 528 | Rpp25 | Rps6ka1 |
| 529 | kg:uc007ded.1 | Ints1 |
| 530 | 2610101N10Rik | Tpcn1 |
| 531 | Il6st | Iffo2 |
| 532 | Evpl | Trim44 |
| 533 | Psmd11 | kg:uc012ctw.1 |
| 534 | Dync1i2 | Golga2 |
| 535 | Lars2 | Msto1 |
| 536 | Pdia4 | Ppp6r3 |
| 537 | Cd55 | Trmt2a |
| 538 | Amfr | Appl2 |
| 539 | Zcchc3 | Sparcl1 |
| 540 | Herpud2 | Rapgef1 |
| 541 | Txnrd1 | Zfpl1 |
| 542 | Vat1 | Psmc4 |
| 543 | Diap1 | Mosc2 |
| 544 | Tmed2 | Fam101b |
| 545 | Arf3 | 1500010J02Rik |
| 546 | Arap2 | Ccdc124 |
| 547 | St3gal1 | Ptges |
| 548 | Man1a | Fam189b |
| 549 | Rgs10 | Th1l |
| 550 | Tmsb4x | Kctd2 |
| 551 | Uba7 | Olfr1372-ps1 |
| 552 | C4b | Hexa |
| 553 | Tmem98 | Anapc5 |

TABLE 12-continued

Significantly Expressed Genes by Rank Product (FDR <0.01)

| | | |
|---|---|---|
| 554 | Lpar2 | Serpina3n |
| 555 | Gabarapl1 | 1810046J19Rik |
| 556 | Cmtm7 | Tmem167 |
| 557 | Spon2 | Gm11428 |
| 558 | Smarca5 | Gcn1l1 |
| 559 | Mxd4 | Kansl3 |
| 560 | Smc4 | Fasn |
| 561 | Thsd4 | Slc50a1 |
| 562 | Gsr | Smad3 |
| 563 | Ptprd | Trip6 |
| 564 | Clip1 | Atp6v1e1 |
| 565 | Cln8 | Chchd5 |
| 566 | Rbm27 | Adssl1 |
| 567 | Zmat1 | Nes |
| 568 | Smc6 | Ap1b1 |
| 569 | B2m | Fcgrt |
| 570 | Irf2bp2 | Ltbp3 |
| 571 | Ppap2a | Csf2rb |
| 572 | Zfhx4 | Ssna1 |
| 573 | Tob2 | Mrps16 |
| 574 | Rabgap1l | Cyba |
| 575 | Nfkb2 | Cyth2 |
| 576 | Nfyc | Igf2 |
| 577 | Ube2d1 | Pisd-ps1 |
| 578 | Creb5 | Atp13a2 |
| 579 | Opa3 | Mlph |
| 580 | Csnk1a1 | Cyp4f16 |
| 581 | Fam84b | 2010107E04Rik |
| 582 | Ddr2 | Gas5 |
| 583 | Usp54 | Eif3k |
| 584 | Akt2 | Fam149a |
| 585 | Strn3 | Mif |
| 586 | Hnrnpm | B230312A22Rik |
| 587 | eg:497210:chr14:m | Ppp1r12c |
| 588 | Tpt1 | Tfip11 |
| 589 | Naa25 | Tex10 |
| 590 | Eef1a1 | Slc16a3 |
| 591 | Parp4 | Stk16 |
| 592 | Msn | Epn1 |
| 593 | Zbtb20 | Noc4l |
| 594 | Fermt2 | Rcc2 |
| 595 | Bod1l | Rgs12 |
| 596 | Sltm | Shkbp1 |
| 597 | Dapk1 | Got2 |
| 598 | Hnrnpr | Plek2 |
| 599 | Baz2a | Lilrb3 |
| 600 | Rnf167 | Ndufb5 |
| 601 | Mapk1 | Tesk1 |
| 602 | eg:320169:chr9:p | Rab24 |
| 603 | 4930523C07Rik | Atp5j2 |
| 604 | Nf1 | Commd9 |
| 605 | Fam53b | Rtkn |
| 606 | Faim2 | Prpf19 |
| 607 | Tgm2 | 6720401G13Rik |
| 608 | Calm2 | Ppa1 |
| 609 | AI848100 | Pgp |
| 610 | Slc10a3 | Hps1 |
| 611 | Ogdh | Puf60 |
| 612 | Arl3 | Mdm2 |
| 613 | Timp2 | kg:uc012cgd.1 |
| 614 | Atxn2 | kg:uc009uim.1 |
| 615 | Mll1 | Pyy |
| 616 | Ces2g | Zfp358 |
| 617 | Mat2a | Timm8b |
| 618 | Esf1 | Ddx39 |
| 619 | Hsp90aa1 | Pgm2 |
| 620 | Zfp385a | kg:uc008gbp.1 |
| 621 | Zfp672 | Sipa1 |
| 622 | Csda | Mgat1 |
| 623 | Pf4 | Tmem208 |
| 624 | Arsa | Ruvbl2 |
| 625 | F11r | 8430410A17Rik |
| 626 | C4a | Bad |
| 627 | Kpna1 | Pfdn5 |
| 628 | Rbbp8 | Eme1 |
| 629 | Oxnad1 | kg:uc009mzj.1 |
| 630 | Rb1cc1 | Igf1 |
| 631 | Setd2 | Prkag1 |

TABLE 12-continued

Significantly Expressed Genes by Rank Product (FDR <0.01)

| | | |
|---|---|---|
| 632 | Kif1b | kg:uc009sua.1 |
| 633 | 2510002D24Rik | Uap1l1 |
| 634 | Cep57 | Trappc4 |
| 635 | Chd2 | Bola2 |
| 636 | Serinc5 | Usp5 |
| 637 | Marcksl1 | Ear2 |
| 638 | Shfm1 | Cars |
| 639 | Bbs4 | 1810027O10Rik |
| 640 | Impad1 | Amdhd2 |
| 641 | Tbcel | Phb |
| 642 | Kdelr1 | Kcmf1 |
| 643 | Ninl | Lsmd1 |
| 644 | Sytl1 | Sec11c |
| 645 | Tpm3 | Pcbp4 |
| 646 | Rbbp6 | Mepce |
| 647 | Lman1 | Tpd52l2 |
| 648 | Ankrd17 | Trf |
| 649 | Naga | Hsd17b11 |
| 650 | Rbpms | Pilra |
| 651 | Magt1 | Atn1 |
| 652 | Tfdp2 | Pgf |
| 653 | Gem | Nxn |
| 654 | Pde4dip | Inpp5k |
| 655 | Mrgprf | Actr1a |
| 656 | kg:uc008ajk.1 | Cd68 |
| 657 | Itch | Eef1g |
| 658 | Elf1 | Fbn1 |
| 659 | Meis2 | Hint1 |
| 660 | Arid1a | March5 |
| 661 | Serping1 | Usp48 |
| 662 | Slc27a3 | Hnf1b |
| 663 | Thoc2 | Gga3 |
| 664 | Gsta3 | Drosha |
| 665 | Hnrnph2 | Ubp1 |
| 666 | Socs3 | Pkn3 |
| 667 | Armcx3 | Tmem192 |
| 668 | Siah1a | Prpf31 |
| 669 | kg:uc009ize.1 | Hspd1 |
| 670 | Irs2 | Otub1 |
| 671 | Mettl7a1 | Mrpl20 |
| 672 | Ppfibp2 | Tead2 |
| 673 | Blvrb | Phpt1 |
| 674 | Yipf5 | Neu1 |
| 675 | Plat | Pygo2 |
| 676 | Gm6578 | Myeov2 |
| 677 | Mat2b | Cdk5 |
| 678 | Tmpo | Ndor1 |
| 679 | Metap2 | Rbp4 |
| 680 | Zfp277 | Psat1 |
| 681 | Wls | Mrpl41 |
| 682 | Mesdc1 | Snrpg |
| 683 | kg:uc009acs.1 | Acot7 |
| 684 | Col1a2 | Vars |
| 685 | Csf1 | Nono |
| 686 | Sulf2 | Gtf2i |
| 687 | Ifrd1 | Traf3 |
| 688 | Wrnip1 | Ppp2r4 |
| 689 | Flii | Actg2 |
| 690 | 2810474O19Rik | Pi4k2a |
| 691 | Sep15 | Slc35b2 |
| 692 | 2310030G06Rik | Ubqln1 |
| 693 | Cmtm3 | Ppox |
| 694 | Mylip | Bud31 |
| 695 | Slc8a1 | Man2b1 |
| 696 | Btbd7 | Nat15 |
| 697 | Hdac5 | Spon1 |
| 698 | Zfand6 | Cyc1 |
| 699 | Tapbp | Mpeg1 |
| 700 | Keap1 | Nsun2 |
| 701 | Ube2n | Rab4a |
| 702 | Ssr3 | Mtmr11 |
| 703 | H3f3a | BC004004 |
| 704 | Myst4 | B4galnt1 |
| 705 | G3bp1 | Atp5k |
| 706 | Ugdh | Lin37 |
| 707 | Lamp2 | D330041H03Rik |
| 708 | Zrsr1 | Tbc1d17 |
| 709 | Pim1 | March6 |

TABLE 12-continued

Significantly Expressed Genes by Rank Product (FDR <0.01)

| | | |
|---|---|---|
| 710 | Gm9199 | 2410015M20Rik |
| 711 | Supt16h | 1810013D10Rik |
| 712 | Ano6 | Eif2s1 |
| 713 | Soat1 | Traf7 |
| 714 | Eci1 | Rpl36al |
| 715 | Plce1 | Psenen |
| 716 | Atg3 | Aip |
| 717 | Bnc1 | Cmas |
| 718 | Pik3c2a | Rpia |
| 719 | Pqlc3 | Ncbp1 |
| 720 | Thrap3 | Mea1 |
| 721 | Irak4 | Timm50 |
| 722 | Kdm6b | Ear12 |
| 723 | Apol9a | Fkbp1a |
| 724 | Wnt4 | Commd4 |
| 725 | 1500003O03Rik | Col5a3 |
| 726 | Phf3 | Fblim1 |
| 727 | 1110004F10Rik | Cwh43 |
| 728 | Kansl1 | Arl2bp |
| 729 | Fth1 | Mrpl46 |
| 730 | Tmem50a | Tcn2 |
| 731 | Utp20 | Add2 |
| 732 | Smad4 | Specc1l |
| 733 | Stmn2 | Ppcs |
| 734 | Gstm1 | Vrk3 |
| 735 | Senp6 | Trim25 |
| 736 | Gda | Nfatc1 |
| 737 | Nucks1 | Rap1gap |
| 738 | Ints10 | Hsd17b12 |
| 739 | Syne1 | Epas1 |
| 740 | Itga6 | Ddx1 |
| 741 | Acad9 | Prdx6 |
| 742 | Maged1 | Mmp24 |
| 743 | Spen | Ndufb9 |
| 744 | Chd1 | Phf23 |
| 745 | Taf3 | Rpa2 |
| 746 | Ptgs1 | 5031439G07Rik |
| 747 | Sparc | Rrp7a |
| 748 | R74862 | Arfip2 |
| 749 | B230120H23Rik | Efna1 |
| 750 | Tmem234 | Agps |
| 751 | Ryk | Sephs1 |
| 752 | Dlgap4 | Apoc2 |
| 753 | Atp1b1 | Mrps27 |
| 754 | Parp14 | Snn |
| 755 | Tgfbr2 | Serinc3 |
| 756 | Ccdc90a | Pdcd5 |
| 757 | Ncoa1 | AA986860 |
| 758 | Pppde1 | Pitpna |
| 759 | Luc7l3 | Vac14 |
| 760 | Prg4 | 2810025M15Rik |
| 761 | Rab11fip1 | Def8 |
| 762 | Plk2 | Hilpda |
| 763 | Ifi35 | Eif6 |
| 764 | Pdap1 | Brd7 |
| 765 | Cd248 | Fes |
| 766 | Sesn1 | Sbf1 |
| 767 | Ecd | Ak2 |
| 768 | Ap1s3 | 1810035L17Rik |
| 769 | H2-K1 | Lime1 |
| 770 | Spag9 | Hspe1 |
| 771 | Tshz1 | Csrp2bp |
| 772 | Dennd5a | Uba5 |
| 773 | Stag1 | Gsta4 |
| 774 | Gpx8 | 2900092E17Rik |
| 775 | Sod3 | |
| 776 | BC005561 | |
| 777 | kg:uc009vev.1 | |
| 778 | Ywhaz | |
| 779 | Ganab | |
| 780 | Rras2 | |
| 781 | Dusp14 | |
| 782 | kg:uc012hdk.1 | |
| 783 | Nr1d1 | |
| 784 | Wwc2 | |
| 785 | Ubxn2a | |
| 786 | Iqsec1 | |
| 787 | kg:uc007vsr.1 | |

TABLE 12-continued

Significantly Expressed Genes by Rank Product (FDR <0.01)

| | |
|---|---|
| 788 | Cfl1 |
| 789 | Csrp1 |
| 790 | Smchd1 |
| 791 | Myl12a |
| 792 | Ubqln2 |
| 793 | Tmcc3 |
| 794 | Kdm5a |
| 795 | Rbm25 |
| 796 | Wdr26 |
| 797 | Vim |
| 798 | Arpc2 |
| 799 | Calm1 |
| 800 | Dnaja2 |
| 801 | Shc1 |
| 802 | Vps13a |
| 803 | Klf7 |
| 804 | 1810074P20Rik |
| 805 | BC003331 |
| 806 | Itpr2 |
| 807 | Jmjd1c |
| 808 | Pcdhgb5 |
| 809 | Tubb2a |
| 810 | Ehd2 |
| 811 | Ift74 |
| 812 | Per1 |
| 813 | Pitpnm2 |
| 814 | Gstm4 |
| 815 | Dnmt1 |
| 816 | Tmco1 |
| 817 | Lass4 |
| 818 | Ptprf |
| 819 | Sirt2 |
| 820 | Gfm2 |
| 821 | Taf7 |
| 822 | Spop |
| 823 | Zzef1 |
| 824 | Ccdc34 |
| 825 | Zfp281 |
| 826 | Tuba1a |
| 827 | Ccdc109b |
| 828 | Cdk13 |
| 829 | Dhx15 |
| 830 | Src |
| 831 | Braf |
| 832 | Mapre2 |
| 833 | Anxa7 |
| 834 | Sept9 |
| 835 | Alox12 |
| 836 | Pknox1 |
| 837 | 2610034B18Rik |
| 838 | Topors |
| 839 | Phf21a |
| 840 | Qser1 |
| 841 | Tirap |
| 842 | Fas |
| 843 | Lass2 |
| 844 | 6330406I15Rik |
| 845 | Parvb |
| 846 | Atp1a1 |
| 847 | Mtmr6 |
| 848 | Cd109 |
| 849 | Dnajc1 |
| 850 | Hp1bp3 |
| 851 | 1600029D21Rik |
| 852 | Ttc38 |
| 853 | Mfhas1 |
| 854 | Filip1l |
| 855 | Zfp148 |
| 856 | Nkd1 |
| 857 | Usp16 |
| 858 | Tlr2 |
| 859 | Zc3h18 |
| 860 | Stk10 |
| 861 | Ltbp4 |
| 862 | Hdac3 |
| 863 | Efhd2 |
| 864 | Prkar2a |
| 865 | Atp6v1a |

TABLE 12-continued

Significantly Expressed Genes by Rank Product (FDR <0.01)

| | |
|---|---|
| 866 | Sf3b4 |
| 867 | Gprc5b |
| 868 | Clip3 |
| 869 | Mettl2 |
| 870 | Secisbp2 |
| 871 | Fmod |
| 872 | kg:uc009lxf.1 |
| 873 | Elovl6 |
| 874 | Bzw1 |
| 875 | Etfa |
| 876 | Hspa2 |
| 877 | kg:uc007won.1 |
| 878 | Rnf20 |
| 879 | |
| 880 | |
| 881 | |
| 882 | |
| 883 | |
| 884 | |
| 885 | |
| 886 | |
| 887 | |
| 888 | |
| 889 | |
| 890 | |
| 891 | |
| 892 | |
| 893 | |
| 894 | |
| 895 | |
| 896 | |
| 897 | |
| 898 | |
| 899 | |
| 900 | |
| 901 | |
| 902 | |
| 903 | |
| 904 | |
| 905 | |
| 906 | |
| 907 | |
| 908 | |
| 909 | |
| 910 | |
| 911 | |
| 912 | |
| 913 | |
| 914 | |
| 915 | |
| 916 | |
| 917 | |
| 918 | |
| 919 | |
| 920 | |
| 921 | |
| 922 | |
| 923 | |
| 924 | |
| 925 | |
| 926 | |
| 927 | |

| Count | Primary Tumor vs WBC | WBC vs Primary Tumor | CTC-c vs WBC | WBC vs CTC |
|---|---|---|---|---|
| 1 | Wfdc2 | Ppbp | Olfr1033 | Beta-s |
| 2 | Spp1 | Alas2 | Crip1 | Alas2 |
| 3 | Cct3 | Nrgn | Ppp1r12a | Hbb-b1 |
| 4 | Itga3 | Cd9 | Vcp | Il1b |
| 5 | Gsto1 | Csf3r | Klf9 | Ppbp |
| 6 | Mmp2 | Il1b | Mprip | Hba-a2 |
| 7 | Mfge8 | Gdpd3 | Sdc4 | kg:uc007pgs.1 |
| 8 | Capg | Ms4a1 | Gpc5a | kg:uc011yvj.1 |
| 9 | Cd63 | Hbb-b1 | Vat1 | Coro1a |
| 10 | Stub1 | Beta-s | Wdr92 | Cd74 |
| 11 | Lad1 | kg:uc007pgs.1 | S100a11 | Gdpd3 |

TABLE 12-continued

Significantly Expressed Genes by Rank Product (FDR <0.01)

| | | | | |
|---|---|---|---|---|
| 12 | Myo1h | kg:uc011yvj.1 | Clic4 | Ccndbp1 |
| 13 | Igfbp7 | Rprl1 | Dync1i2 | kg:uc009cfw.1 |
| 14 | Kcnn4 | Pfn1 | Nfkbiz | kg:uc012enb.1 |
| 15 | D8Ertd738e | Clec1b | Cyp2s1 | Ptprc |
| 16 | Lamb3 | Ptprc | Esam | Csf3r |
| 17 | Chi3l3 | Stim1 | Surf4 | Rac2 |
| 18 | Arl4c | Ccndbp1 | Krt19 | Rprl1 |
| 19 | Col18a1 | Cap1 | Bsg | H2-Ab1 |
| 20 | Atox1 | Cd79b | Tm4sf1 | Epb4.1 |
| 21 | Ly6a | Alox12 | Lgals3 | Lyz2 |
| 22 | Dmbt1 | Hba-a2 | Clic1 | Ctla2b |
| 23 | Dync1h1 | Ube2l6 | Capns1 | Pld4 |
| 24 | Adipor2 | Cat | Igfbp6 | kg:uc007pgt.1 |
| 25 | Rpl37 | Faim3 | Rrbp1 | Gng11 |
| 26 | Kctd10 | Dusp1 | Calr | Mepce |
| 27 | Col15a1 | kg:uc007pgt.1 | Rtf1 | Tyrobp |
| 28 | Surf4 | E2f2 | Ildr2 | Isca1 |
| 29 | Dad1 | Phospho1 | Mark2 | 2810453I06Rik |
| 30 | Col4a1 | Abi3 | Mt1 | Slc30a9 |
| 31 | Ap2s1 | Sorl1 | Akr1b3 | Treml2 |
| 32 | Sdc1 | Treml2 | Gm6644 | Srgn |
| 33 | Rpl35 | Cytip | Nkain4 | Dcaf12 |
| 34 | Sec61a1 | B2m | Ppp2ca | Plek |
| 35 | Rras | Fyb | Akap2 | Cat |
| 36 | Oraov1 | Peli1 | Hspb1 | Alox12 |
| 37 | Ndufa2 | Plek | Ptgis | Fech |
| 38 | Anapc2 | N4bp3 | Msln | Rbm5 |
| 39 | Pitpna | Fam117a | Emp2 | Cd97 |
| 40 | Psap | Srgn | Capn2 | March8 |
| 41 | Atp5j2 | Sept9 | Rhoc | Pnpo |
| 42 | Onecut2 | kg:uc012hdk.1 | Ptprf | Phospho1 |
| 43 | Hmga1 | kg:uc009vev.1 | Bcam | Isg20 |
| 44 | Pmepa1 | Ptprcap | Ogdh | March2 |
| 45 | S100a11 | kg:uc007pgq.1 | Sparc | Lsp1 |
| 46 | Rbp1 | kg:uc007pgr.1 | Ahnak | 1810058I24Rik |
| 47 | Rpl36al | kg:uc007vdl.1 | Oasl2 | Clec1b |
| 48 | S100a4 | Ctla2b | Wt1 | Btg1 |
| 49 | Atp6ap1 | Myl9 | Klf4 | Laptm5 |
| 50 | Ndufs2 | Itpr2 | Cdkn1a | Nrgn |
| 51 | Anapc5 | kg:uc012enb.1 | Myl7 | H2-Aa |
| 52 | Cox6b1 | Isg20 | Col1a2 | Fyb |
| 53 | Krtcap2 | Rasal3 | Eif4a1 | Cd24a |
| 54 | Atn1 | Gng11 | Rbpms | Fnbp4 |
| 55 | 5730559C18Rik | kg:uc009cfw.1 | Emp3 | Ehbp1l1 |
| 56 | Pea15a | Tmsb4x | Scaf11 | Ctla2a |
| 57 | Grcc10 | Trem1 | Col14a1 | Sgk1 |
| 58 | Lama5 | Fech | Ptrf | Glyr1 |
| 59 | Krt18 | Epb4.1 | Crip2 | Myl9 |
| 60 | Ccnd1 | Sgk1 | Ubxn4 | Il2rg |
| 61 | Arhgef5 | Dgkq | Eif2s2 | Mrps17 |
| 62 | Golm1 | Snap23 | S100a6 | Cdr2 |
| 63 | Tff2 | Usp25 | Hectd1 | Mkrn1 |
| 64 | Plin2 | Kif21b | Zc3h15 | Gart |
| 65 | H13 | Irs2 | Ube2d3 | Lyz1 |
| 66 | Rpl29 | Pxk | A130040M12Rik | Vwf |
| 67 | 1110034A24Rik | Cyp4f18 | Cd34 | Gadd45a |
| 68 | Trim28 | Map4k1 | Igfbp5 | Mpp1 |
| 69 | Ltbp3 | Isca1 | C1s | Stim1 |
| 70 | Fkbp1a | Itga4 | Upk3b | Psme3 |
| 71 | Erp29 | Dock2 | Gpr133 | Ets1 |
| 72 | Muc1 | Spib | Dab2 | Snap23 |
| 73 | Lamc2 | 2810453I06Rik | Serpinh1 | Arhgdib |
| 74 | Plscr3 | Cdr2 | Upk1b | Hmha1 |
| 75 | Agrn | Naa16 | Sdf4 | Itpr2 |
| 76 | Park7 | Arhgdib | Ctbp2 | Ubl7 |
| 77 | Ctnnb1 | Cd79a | Psap | Ddx58 |
| 78 | Atp5g1 | Rbm27 | Arhgef12 | Nfkbie |
| 79 | Eef1g | Lmnb1 | Copb2 | Setd7 |
| 80 | Nhp2 | Slc25a37 | Ctsl | Stk24 |
| 81 | Rrbp1 | Klf6 | Aldh1a2 | Hvcn1 |
| 82 | Sumo3 | Hist1h1c | Dcn | Plekha2 |
| 83 | Scyl1 | Phip | Timp3 | Psme4 |
| 84 | Cox6a1 | Qrfp | Xdh | Ankrd44 |
| 85 | Krt8 | Fermt3 | Irf7 | B4galt5 |
| 86 | Gsta4 | Ptma | Tmem151a | Phf20 |
| 87 | Ppp1r14b | Etv3 | Aebp1 | Zc3hav1 |
| 88 | Tnk1 | Apobr | C2 | Rnf11 |
| 89 | D19Wsu162e | kg:uc008ewj.2 | Spen | Plk3 |

TABLE 12-continued

Significantly Expressed Genes by Rank Product (FDR <0.01)

| | | | | |
|---|---|---|---|---|
| 90 | Ctsl | Malat1 | kg:uc007pfe.1 | Fbxw5 |
| 91 | Timp1 | March8 | Krt18 | Emb |
| 92 | S100a6 | Coro1a | Arf4 | kg:uc007vdl.1 |
| 93 | Rps15 | Rac2 | Rab14 | Taok2 |
| 94 | Polr2j | Glyr1 | Tmem98 | Dhrs11 |
| 95 | Hspe1 | Btg2 | Prss23 | Slc25a39 |
| 96 | Lgals4 | Mtf2 | Egr1 | Csk |
| 97 | Edf1 | Nfkbie | Perp | Bcl2 |
| 98 | Mtch1 | Cd84 | Csrp1 | kg:uc009vev.1 |
| 99 | Rnf187 | AW549877 | Pdpn | Wipf1 |
| 100 | Npy | March2 | Pdcd6ip | Sept9 |
| 101 | Cox5b | Add3 | Rpl37 | Rnf10 |
| 102 | Pak1 | Ddx50 | F11r | Pml |
| 103 | Mmp7 | Prkcb | Gpm6a | Cd9 |
| 104 | Fxyd3 | Klf2 | Tuba1a | D4Wsu53e |
| 105 | Cuta | Dcaf12 | Ctnna1 | Traf7 |
| 106 | Ndufb8 | Il2rg | Anxa8 | Pitpnc1 |
| 107 | Gps1 | Selplg | Tpm1 | Mms19 |
| 108 | Bud31 | Cd37 | S100a16 | Naa16 |
| 109 | Ppap2c | Fastkd2 | Chmp4b | Sharpin |
| 110 | Dap | Rsad2 | Tbrg1 | Capza1 |
| 111 | Slc25a1 | Msn | C3 | Rsad2 |
| 112 | Chaf1a | 2010321M09Rik | Ptgs1 | kg:uc012hdk.1 |
| 113 | Asxl1 | Kif2a | Rhou | Ghitm |
| 114 | Jmjd8 | Cd97 | Cdc42 | Csnk1g1 |
| 115 | Tecr | Hvcn1 | Gpx4 | Dgkz |
| 116 | Mgp | Nipsnap3b | Ppib | B2m |
| 117 | Uqcrh | Uba7 | Stub1 | Irs2 |
| 118 | Wdr38 | 1810058I24Rik | Dmkn | Emg1 |
| 119 | Col4a2 | Nfrkb | Rnh1 | Impact |
| 120 | Tnnt2 | Pabpc1 | Pdgfa | Mylip |
| 121 | Ndufs8 | Usp16 | Rpl37a | Psmb8 |
| 122 | Tspan4 | Pde1b | Rabac1 | Rfk |
| 123 | Agpat6 | Ncoa4 | Timp2 | Map3k5 |
| 124 | Timp3 | Irf8 | Serping1 | Odc1 |
| 125 | Ankrd50 | Ppp1cb | Rbm39 | Slc11a2 |
| 126 | Ube2d3 | Rgs2 | Tgoln1 | Eif2b1 |
| 127 | Sf1 | Smyd4 | Nfix | kg:uc008wjd.1 |
| 128 | Csnk1d | Arid3b | Brd4 | Rexo1 |
| 129 | Reg3b | Sh3bgrl2 | Tmem234 | Ddx50 |
| 130 | Flot2 | Lyl1 | Wbp5 | Nipsnap3b |
| 131 | Lmna | Prr13 | Ppig | Sp100 |
| 132 | 2310044H10Rik | Plagl2 | Cd63 | Uggt1 |
| 133 | H19 | Nfkbia | Col1a1 | kg:uc007czl.1 |
| 134 | Slc20a1 | Eef1a1 | Mt2 | Arpc5 |
| 135 | 6720456B07Rik | Brd2 | Zbtb7c | Nfrkb |
| 136 | Mdh2 | Egr1 | Npr1 | Nap1l4 |
| 137 | Eif6 | Mkrn1 | Tmem119 | Fam117a |
| 138 | Phf5a | Pld4 | Atf3 | Sipa1l1 |
| 139 | Vps28 | Aldh1a1 | Ankhd1 | Ttc1 |
| 140 | Bag1 | Dnajb9 | Tmed10 | kg:uc009vew.1 |
| 141 | Cyc1 | Gjb5 | Slc6a4 | |
| 142 | Angptl4 | Mtif2 | Atxn7l3b | |
| 143 | Lgals3 | H2-DMb2 | Rpl29 | |
| 144 | Farsb | Sdpr | Ccar1 | |
| 145 | Mbd3 | 4932438A13Rik | Ltbp4 | |
| 146 | Timm13 | Trem l1 | Scyl1 | |
| 147 | Tpd52l2 | Nup153 | Ap3d1 | |
| 148 | Ptprn | Mpp1 | Iqgap1 | |
| 149 | Crip2 | Dhrs11 | Cldn15 | |
| 150 | Raver1 | Lrmp | Spnb2 | |
| 151 | Eif2b2 | Manf | Ano1 | |
| 152 | Psma7 | Mll3 | Lrrn4 | |
| 153 | Rps6ka4 | Fam116b | Id3 | |
| 154 | Mgat4a | B4galt5 | Eif3a | |
| 155 | Ifitm2 | kg:uc009vew.1 | Prkcdbp | |
| 156 | Wars | Ly6d | Atp1a1 | |
| 157 | Capn5 | Dguok | Dnaja2 | |
| 158 | Bsg | Pnpo | Tubb4b | |
| 159 | Sec16a | Tmem175 | Hnrnpab | |
| 160 | Cldn7 | Gm6548 | Mmp14 | |
| 161 | Cox7a2 | Rsrc2 | Atp1b1 | |
| 162 | Nek6 | Ccdc88b | Psip1 | |
| 163 | Rpl39 | Akna | Mgll | |
| 164 | Itpr3 | Tsc22d3 | Rnase4 | |
| 165 | Ctnna1 | Txndc5 | Ywhab | |
| 166 | Tpd52 | Tubb4a | Clip1 | |

TABLE 12-continued

| Significantly Expressed Genes by Rank Product (FDR <0.01) | | |
|---|---|---|
| 167 | Mlf2 | Stx11 | Syn3 |
| 168 | Crip1 | D4Wsu53e | Myl12a |
| 169 | Fkbp4 | Amfr | Rbm25 |
| 170 | Gprc5a | Tti1 | Arf2 |
| 171 | Slc4a11 | Fam175b | Cav1 |
| 172 | Syn3 | Zfp36 | Hnrnpc |
| 173 | Npc2 | Ddx5 | Syne2 |
| 174 | Rpl32 | Tlr7 | Dst |
| 175 | Inf2 | Rfk | |
| 176 | Rps10 | kg:uc007ded.1 | |
| 177 | Rps26 | Gnb2 | |
| 178 | Rpl37a | Tmed5 | |
| 179 | Ctxn1 | Thbs1 | |
| 180 | Lrrc59 | eg:320169:chr9:p | |
| 181 | Dctn1 | Zfp335 | |
| 182 | Mtap4 | Emg1 | |
| 183 | Uqcr10 | Trmt61a | |
| 184 | Suds3 | Adipor1 | |
| 185 | Ap1s1 | Vwf | |
| 186 | S100a1 | Aatf | |
| 187 | Atp5j | Trib1 | |
| 188 | Aim1 | Pcyt1a | |
| 189 | Plec | Stx18 | |
| 190 | Prom1 | Trp53bp2 | |
| 191 | Rhoc | Stk40 | |
| 192 | Mast3 | Il18 | |
| 193 | Olfml3 | 1810014B01Rik | |
| 194 | Uqcr11 | Lcp2 | |
| 195 | Plp2 | Gimap4 | |
| 196 | Spna2 | Rabl2 | |
| 197 | 1700017B05Rik | Ncf2 | |
| 198 | Anxa4 | eg:497210:chr14:m | |
| 199 | Nudc | Tpt1 | |
| 200 | Asl | Mll5 | |
| 201 | Prkcsh | H3f3a | |
| 202 | Plod3 | Tspan13 | |
| 203 | Ndufa9 | Il10ra | |
| 204 | Impdh2 | Mdc1 | |
| 205 | Ccnl2 | Stk24 | |
| 206 | Nedd8 | Myst4 | |
| 207 | Atp6v1f | Zdhhc20 | |
| 208 | Mt1 | Eif2b1 | |
| 209 | Il4ra | Exoc4 | |
| 210 | Cndp2 | Wipf1 | |
| 211 | Aprt | Impa1 | |
| 212 | Preb | Tmem119 | |
| 213 | Ap3d1 | Pml | |
| 214 | Mcm6 | Ubb | |
| 215 | Ubr4 | Zmat3 | |
| 216 | Pvrl2 | Slc30a9 | |
| 217 | Snrpg | Lat | |
| 218 | Cycs | Tgfb2 | |
| 219 | Efemp2 | Ube2o | |
| 220 | Cct4 | Igfbp5 | |
| 221 | Gm20605 | Tspan5 | |
| 222 | Smad3 | Fmnl1 | |
| 223 | Card10 | Fnbp4 | |
| 224 | Krt7 | Extl3 | |
| 225 | Cct2 | Adcy7 | |
| 226 | Coro1c | Enpp4 | |
| 227 | Ltbr | Sep15 | |
| 228 | Ric8 | H2-Ab1 | |
| 229 | Ndufs6 | Bnip3l | |
| 230 | Fibp | Slc11a2 | |
| 231 | Pold4 | Stom | |
| 232 | Rpl34 | Mfhas1 | |
| 233 | Rpl34-ps1 | Mettl1 | |
| 234 | Clic1 | Rnf10 | |
| 235 | Eri3 | kg:uc009cfd.1 | |
| 236 | Ets2 | Klf4 | |
| 237 | Unc13a | Psme4 | |
| 238 | Usmg5 | Sema4a | |
| 239 | Sh3pxd2b | Ftl2 | |
| 240 | Wdr6 | Atad1 | |
| 241 | Las1l | Tspan31 | |
| 242 | Polr2f | Srrm2 | |
| 243 | Vamp5 | Rab5c | |
| 244 | Endod1 | Capza1 | |

TABLE 12-continued

| Significantly Expressed Genes by Rank Product (FDR <0.01) | | |
|---|---|---|
| 245 | Snrpd2 | H2-Aa |
| 246 | Tpi1 | Fhl1 |
| 247 | Wwp2 | Cryab |
| 248 | Dalrd3 | Arid4b |
| 249 | Iqgap1 | Gart |
| 250 | Ahsa1 | 1110004F10Rik |
| 251 | Trim27 | Rnf11 |
| 252 | Serpinf1 | Zc3hav1 |
| 253 | D330041H03Rik | kg:uc008btl.1 |
| 254 | Ppp2r5d | Rnf34 |
| 255 | Minos1 | Dmkn |
| 256 | Tsta3 | Btg1 |
| 257 | Prpsap1 | Syt11 |
| 258 | Sphk1 | Mtdh |
| 259 | Ldha | Med21 |
| 260 | Abca3 | Rnf2 |
| 261 | B4galt3 | Tcf12 |
| 262 | Porcn | Tacstd2 |
| 263 | Tmc4 | Madd |
| 264 | Serinc2 | D16Ertd472e |
| 265 | Akr1b8 | Pias1 |
| 266 | Nudt4 | Taok2 |
| 267 | Atp5l | Pold1 |
| 268 | Psmc3 | Cep110 |
| 269 | Hint1 | A930013F10Rik |
| 270 | Rpl41 | Tcof1 |
| 271 | Xpnpep1 | kg:uc009bpd.1 |
| 272 | Nav1 | kg:u009bpr.2 |
| 273 | Parva | Capza2 |
| 274 | Immt | Ptp4a2 |
| 275 | Pafah1b3 | Fth1 |
| 276 | Chid1 | Mepce |
| 277 | Aldh1l1 | Rexo1 |
| 278 | Rpl31 | Prg4 |
| 279 | Wbp1 | Ctla2a |
| 280 | Zfp622 | Smarca5 |
| 281 | 2700060E02Rik | Icam2 |
| 282 | Hspa9 | Pbx1 |
| 283 | Tceb2 | Gnl3l |
| 284 | Rpl36a | Slc2a3 |
| 285 | Pgs1 | Nnmt |
| 286 | Mpnd | Rb1cc1 |
| 287 | Cdc42 | Bpgm |
| 288 | Dhrs3 | Lcp1 |
| 289 | Hexa | Sipa1l1 |
| 290 | Cpsf1 | Lilrb4 |
| 291 | Mea1 | Ankrd44 |
| 292 | Polr2e | Specc1 |
| 293 | Ddb1 | Rif1 |
| 294 | Ptcd1 | |
| 295 | Atp5f1 | |
| 296 | Sec61b | |
| 297 | Psmc5 | |
| 298 | Fam89b | |
| 299 | Lama3 | |
| 300 | Tomm6 | |
| 301 | Mrpl28 | |
| 302 | Syngr2 | |
| 303 | Ngfrap1 | |
| 304 | Kcmf1 | |
| 305 | Tubb4b | |
| 306 | Anapc11 | |
| 307 | Vcp | |
| 308 | Arpp19 | |
| 309 | Pglyrp1 | |
| 310 | Rrp1 | |
| 311 | Gkn3 | |
| 312 | Atpif1 | |
| 313 | Prickle3 | |
| 314 | Map4k4 | |
| 315 | Arrdc1 | |
| 316 | C1qtnf6 | |
| 317 | Hras1 | |
| 318 | Lamb1 | |
| 319 | Eif3d | |
| 320 | Snrpa | |
| 321 | Tbrg1 | |
| 322 | Nxf1 | |

TABLE 12-continued

Significantly Expressed Genes by Rank Product (FDR <0.01)

| | |
|---|---|
| 323 | Pdlim7 |
| 324 | Add1 |
| 325 | Pfdn5 |
| 326 | Stk16 |
| 327 | Gm17821 |
| 328 | Csnk1e |
| 329 | Rrp7a |
| 330 | Psmb6 |
| 331 | Snhg1 |
| 332 | Ssr4 |
| 333 | Ergic3 |
| 334 | Rnaseh2a |
| 335 | kg:uc009cut.1 |
| 336 | Bgn |
| 337 | Gm5506 |
| 338 | Uqcrq |
| 339 | Tmem167 |
| 340 | Nasp |
| 341 | Mif |
| 342 | Acaa2 |
| 343 | Fam162a |
| 344 | Eif4ebp3 |
| 345 | Nhp2l1 |
| 346 | Prelid1 |
| 347 | Gss |
| 348 | Lonp1 |
| 349 | Srsf2 |
| 350 | Igsf8 |
| 351 | Ndufa7 |
| 352 | Neat1 |
| 353 | S100a13 |
| 354 | Apoa1bp |
| 355 | Fam40a |
| 356 | Rps25 |
| 357 | Eno1 |
| 358 | Cldn2 |
| 359 | Capn2 |
| 360 | Glo1 |
| 361 | Atp5c1 |
| 362 | Rab2a |
| 363 | Rab25 |
| 364 | Ncor2 |
| 365 | Lgi4 |
| 366 | Ier3 |
| 367 | Tmem223 |
| 368 | Slc9a3r2 |
| 369 | Atp13a1 |
| 370 | Rpn2 |
| 371 | Acp5 |
| 372 | Cct5 |
| 373 | Sdf4 |
| 374 | Mprip |
| 375 | Pmm2 |
| 376 | Snx22 |
| 377 | Arl2 |
| 378 | 1110008F13Rik |
| 379 | Polr1d |
| 380 | Dpm2 |
| 381 | Cela1 |
| 382 | 2310016M24Rik |
| 383 | Cep250 |
| 384 | Mybbp1a |
| 385 | Polr2g |
| 386 | Bag6 |
| 387 | Cpxm1 |
| 388 | Eif3m |
| 389 | Prr24 |
| 390 | Sra1 |
| 391 | Scara3 |
| 392 | Reg1 |
| 393 | Gas5 |
| 394 | Hnrnpab |
| 395 | Mcpt2 |
| 396 | Tgfbi |
| 397 | Capns1 |
| 398 | Fdx1l |
| 399 | S100a16 |
| 400 | Nap1l1 |

TABLE 12-continued

Significantly Expressed Genes by Rank Product (FDR <0.01)

| | |
|---|---|
| 401 | Swi5 |
| 402 | Rpl38 |
| 403 | Dctn2 |
| 404 | Pdlim1 |
| 405 | Gemin7 |
| 406 | Pnpla6 |
| 407 | Nono |
| 408 | Sla2 |
| 409 | Idh3b |
| 410 | Ppp2r4 |
| 411 | Map2k2 |
| 412 | Ndufb10 |
| 413 | Atp5d |
| 414 | Arfgap1 |
| 415 | Tmbim1 |
| 416 | Ergic1 |
| 417 | Pdgfa |
| 418 | Ppp2ca |
| 419 | Hk1 |
| 420 | Ltbp2 |
| 421 | Trim35 |
| 422 | Gtf2i |
| 423 | C1qb |
| 424 | Ankhd1 |
| 425 | Podxl |
| 426 | Rps21 |
| 427 | Huwe1 |
| 428 | Pomp |
| 429 | Dpp3 |
| 430 | Fkbp8 |
| 431 | Itga5 |
| 432 | Hes6 |
| 433 | Mrpl11 |
| 434 | Poldip3 |
| 435 | Scd2 |
| 436 | Tmem55b |
| 437 | Ndufa13 |
| 438 | Dcakd |
| 439 | Ubqln1 |
| 440 | Gpx4 |
| 441 | Cyb561 |
| 442 | Gmppa |
| 443 | Ncaph2 |
| 444 | Pdha1 |
| 445 | Ndufs4 |
| 446 | Fcer1g |
| 447 | Myof |
| 448 | Ppib |
| 449 | Mrpl52 |
| 450 | Tes |
| 451 | Emp3 |
| 452 | Ndufa11 |
| 453 | Tor1aip2 |
| 454 | Anp32b |
| 455 | Tnk2 |
| 456 | Mcpt1 |
| 457 | Ssr2 |
| 458 | Psmb3 |
| 459 | 2700081O15Rik |
| 460 | Pcbd1 |
| 461 | Eif1ax |
| 462 | Pmm1 |
| 463 | Ptprk |
| 464 | Hadha |
| 465 | Calu |
| 466 | Fam73a |
| 467 | Atp5e |
| 468 | Hsd17b10 |
| 469 | Rbm39 |
| 470 | Egfl7 |
| 471 | Psmc1 |
| 472 | Perp |
| 473 | Lman2 |
| 474 | Galnt1 |
| 475 | Rbx1 |
| 476 | Lemd2 |
| 477 | Zglp1 |
| 478 | Ing4 |

TABLE 12-continued

Significantly Expressed Genes by Rank Product (FDR <0.01)

| | |
|---|---|
| 479 | kg:uc008oow.1 |
| 480 | 1500012F01Rik |
| 481 | Cox4i1 |
| 482 | kg:uc008bcq.1 |
| 483 | Ubap2l |
| 484 | Pafah1b2 |
| 485 | Mrpl13 |
| 486 | Nucb1 |
| 487 | Fbn1 |
| 488 | Adrm1 |
| 489 | Itgb4 |
| 490 | Ctss |
| 491 | Plbd2 |
| 492 | Ptpmt1 |
| 493 | Sap30l |
| 494 | Ppp1r12c |
| 495 | Sgta |
| 496 | Acrbp |
| 497 | Higd2a |
| 498 | Higd1a |
| 499 | Tmem208 |
| 500 | Cdh1 |
| 501 | Ube2d2a |
| 502 | Suv39h1 |
| 503 | Rabac1 |
| 504 | Anxa5 |
| 505 | Ubxn6 |
| 506 | Tpm1 |
| 507 | Hmga2 |
| 508 | Cnbp |
| 509 | Rpl21 |
| 510 | Ndufb5 |
| 511 | Sec31a |
| 512 | Znhit1 |
| 513 | Cyb5b |
| 514 | Sfn |
| 515 | Ccdc12 |
| 516 | Elovl1 |
| 517 | Psmb5 |
| 518 | Slc25a11 |
| 519 | Psmd2 |
| 520 | Nsun2 |
| 521 | Slc50a1 |
| 522 | Eme1 |
| 523 | Bnip2 |
| 524 | Pxdn |
| 525 | Mad2l2 |
| 526 | Pdcd6 |
| 527 | 2010107E04Rik |
| 528 | Abhd11 |
| 529 | Carkd |
| 530 | Polr2l |
| 531 | Ppdpf |
| 532 | Cib1 |
| 533 | Dgcr2 |
| 534 | Timm50 |
| 535 | Mrps24 |
| 536 | Abhd12 |
| 537 | Brf1 |
| 538 | Man1b1 |
| 539 | kg:uc012cgd.1 |
| 540 | Gpaa1 |
| 541 | Fmnl3 |
| 542 | Mapk3 |
| 543 | C1qc |
| 544 | Pgls |
| 545 | Cp |
| 546 | Serh1 |
| 547 | 2610203C20Rik |
| 548 | Hsbp1 |
| 549 | Tmem214 |
| 550 | Akt1 |
| 551 | kg:uc007pfe.1 |
| 552 | Tmed10 |
| 553 | Ttll3 |
| 554 | 2200002D01Rik |
| 555 | Tnfrsf23 |
| 556 | Sgsm3 |

TABLE 12-continued

Significantly Expressed Genes by Rank Product (FDR <0.01)

| | |
|---|---|
| 557 | Atp9a |
| 558 | Lcn2 |
| 559 | Pdrg1 |
| 560 | Tspan9 |
| 561 | Nrd1 |
| 562 | Rin1 |
| 563 | Ndufv1 |
| 564 | Naa10 |
| 565 | Wnk1 |
| 566 | Heatr7a |
| 567 | Slc4a2 |
| 568 | Ggct |
| 569 | 5730403B10Rik |
| 570 | Sh3glb2 |
| 571 | Pfkl |
| 572 | Tspan3 |
| 573 | Gns |
| 574 | Sdcbp2 |
| 575 | C130074G19Rik |
| 576 | Cotl1 |
| 577 | Tubb5 |
| 578 | Sec11c |
| 579 | Pigq |
| 580 | Zc3h15 |
| 581 | Lsmd1 |
| 582 | Ppa1 |
| 583 | Chmp4b |
| 584 | Sepn1 |
| 585 | Angptl2 |
| 586 | Itpripl2 |
| 587 | Ddx1 |
| 588 | Hbxip |
| 589 | Cdk2ap1 |
| 590 | Clta |
| 591 | Cpsf3l |
| 592 | Apoe |
| 593 | Ift46 |
| 594 | Sae1 |
| 595 | Gpi1 |
| 596 | Gorasp2 |
| 597 | 1500032L24Rik |
| 598 | Nsmce4a |
| 599 | Dlst |
| 600 | Bap1 |
| 601 | Pitpnb |
| 602 | Meg3 |
| 603 | Cyth2 |
| 604 | Atp5o |
| 605 | Gon4l |
| 606 | Sox11 |
| 607 | Cxxc5 |
| 608 | Avil |
| 609 | Alcam |
| 610 | Eif3f |
| 611 | Cygb |
| 612 | Eif1ad |
| 613 | Polr3h |
| 614 | Araf |
| 615 | Gkn1 |
| 616 | Rhog |
| 617 | Mtap |
| 618 | Eif4ebp1 |
| 619 | Akr1a1 |
| 620 | Trip6 |
| 621 | Prdx6 |
| 622 | 2410015M20Rik |
| 623 | Rps6 |
| 624 | Rps23 |
| 625 | Stxbp2 |
| 626 | Rps19 |
| 627 | Ykt6 |
| 628 | Atp5g2 |
| 629 | Serpinb1a |
| 630 | Col7a1 |
| 631 | Mrps6 |
| 632 | Lgals9 |
| 633 | Rcn3 |
| 634 | Trim44 |

TABLE 12-continued

Significantly Expressed Genes by Rank Product (FDR <0.01)

| | |
|---|---|
| 635 | Surf2 |
| 636 | Rps29 |
| 637 | Cdipt |
| 638 | Lmf2 |
| 639 | Psenen |
| 640 | Ltf |
| 641 | Mpzl1 |
| 642 | Psmd6 |
| 643 | Cttn |
| 644 | Tmc6 |
| 645 | 2500003M10Rik |
| 646 | Atp6v0a1 |
| 647 | Med8 |
| 648 | Prrx2 |
| 649 | Atp5b |
| 650 | Smurf1 |
| 651 | Carhsp1 |
| 652 | Tpcn1 |
| 653 | Ndufb9 |
| 654 | Pih1d1 |
| 655 | Hnrnpa0 |
| 656 | Fn1 |
| 657 | 2810428I15Rik |
| 658 | 0610012G03Rik |
| 659 | Ube2i |
| 660 | Anxa3 |
| 661 | Msto1 |
| 662 | Eng |
| 663 | 0910001L09Rik |
| 664 | Rpl10 |
| 665 | kg:uc007xxx.1 |
| 666 | Mosc2 |
| 667 | Vps37c |
| 668 | Sgpl1 |
| 669 | Fam166a |
| 670 | Polr2b |
| 671 | Fam101b |
| 672 | Nupr1 |
| 673 | Lsm4 |
| 674 | Rpl36 |
| 675 | 0610007C21Rik |
| 676 | Psmc2 |
| 677 | Supt6h |
| 678 | Rps13 |
| 679 | 5430437P03Rik |
| 680 | Dsp |
| 681 | Ddx56 |
| 682 | Tsc2 |
| 683 | Trmt2a |
| 684 | Vdac2 |
| 685 | Cant1 |
| 686 | Eif4h |
| 687 | Puf60 |
| 688 | A430105I19Rik |
| 689 | Cacnb3 |
| 690 | Prdx4 |
| 691 | March5 |
| 692 | Ccar1 |
| 693 | Npepl1 |
| 694 | Fermt1 |
| 695 | Use1 |
| 696 | Axl |
| 697 | Slc39a4 |
| 698 | 1110008P14Rik |
| 699 | Sema4g |
| 700 | Timm8b |
| 701 | Krt23 |
| 702 | Rpl28 |
| 703 | Lgals3bp |
| 704 | Hdgf |
| 705 | 1110005A03Rik |
| 706 | Impdh1 |
| 707 | Mtmr11 |
| 708 | Msln |
| 709 | Zdhhc3 |
| 710 | Znrf1 |
| 711 | Aldh16a1 |
| 712 | Bloc1s1 |

TABLE 12-continued

Significantly Expressed Genes by Rank Product (FDR <0.01)

| | |
|---|---|
| 713 | Prkag1 |
| 714 | Plxnb1 |
| 715 | Crat |
| 716 | Phpt1 |
| 717 | 5930434B04Rik |
| 718 | Kpnb1 |
| 719 | Nme2 |
| 720 | E430025E21Rik |
| 721 | Smyd2 |
| 722 | Cyhr1 |
| 723 | Mvp |
| 724 | Rps27l |
| 725 | Rbp4 |
| 726 | Cars |
| 727 | kg:uc012ctw.1 |
| 728 | Ssr1 |
| 729 | Ssu72 |
| 730 | Usp48 |
| 731 | Atp5k |
| 732 | Lrrk1 |
| 733 | BC056474 |
| 734 | Epn1 |
| 735 | Trappc1 |
| 736 | Clk2 |
| 737 | Sugt1 |
| 738 | Nenf |
| 739 | kg:uc009cuu.1 |
| 740 | Ubap2 |
| 741 | Rps20 |
| 742 | Atp5h |
| 743 | 9430008C03Rik |
| 744 | Kars |
| 745 | Mrpl37 |
| 746 | Aimp1 |
| 747 | Trmt1 |
| 748 | Hspa4 |
| 749 | Cd164 |
| 750 | 9430023L20Rik |
| 751 | Rnf4 |
| 752 | H1f0 |
| 753 | C1qtnf1 |
| 754 | Srd5a1 |
| 755 | 1500010J02Rik |
| 756 | Rpl35a |
| 757 | Cand2 |
| 758 | C630004H02Rik |
| 759 | Acsbg1 |
| 760 | Derl1 |
| 761 | Cbx5 |
| 762 | Tmem63a |
| 763 | Hgfac |
| 764 | Stx5a |
| 765 | Bri3 |
| 766 | Tomm20 |
| 767 | Fam20c |
| 768 | Cox6c |
| 769 | Tm2d2 |
| 770 | Plekhb2 |
| 771 | Ramp1 |
| 772 | 2410001C21Rik |
| 773 | Tardbp |
| 774 | Pebp1 |
| 775 | kg:uc008gbp.1 |
| 776 | Eif3b |
| 777 | Ccna2 |
| 778 | Ptges |
| 779 | kg:uc007hyr.2 |
| 780 | Wbp5 |
| 781 | Chchd2 |
| 782 | Fdft1 |
| 783 | Srm |
| 784 | Gtf3a |
| 785 | D0H4S114 |
| 786 | 1810009A15Rik |
| 787 | Rps27 |
| 788 | Tmem176b |
| 789 | Ndufc1 |
| 790 | Lasp1 |

TABLE 12-continued

Significantly Expressed Genes by Rank Product (FDR <0.01)

| | |
|---|---|
| 791 | Fam108a |
| 792 | Mapk8ip3 |
| 793 | Copa |
| 794 | Serpina3n |
| 795 | Rps17 |
| 796 | Dnpep |
| 797 | Lbp |
| 798 | Krt19 |
| 799 | Ei24 |
| 800 | Ap1b1 |
| 801 | Mogs |
| 802 | Uba1 |
| 803 | Postn |
| 804 | Phf23 |
| 805 | Paox |
| 806 | Nploc4 |
| 807 | Ndufv2 |
| 808 | Actr1a |
| 809 | Mxd3 |
| 810 | Pfdn1 |
| 811 | Ide |
| 812 | Foxp4 |
| 813 | 1810013D10Rik |
| 814 | 2310007B03Rik |
| 815 | Xab2 |
| 816 | Agr2 |
| 817 | Dctn3 |
| 818 | Urm1 |
| 819 | H2-Ke2 |
| 820 | Spint1 |
| 821 | Slc38a2 |
| 822 | Ube2z |
| 823 | Ctrb1 |
| 824 | Fam195b |
| 825 | Suclg1 |
| 826 | Ube2l3 |
| 827 | Rpn1 |
| 828 | Mrps7 |
| 829 | Tsg101 |
| 830 | Drosha |
| 831 | Arfip2 |
| 832 | Mrto4 |
| 833 | Grlf1 |
| 834 | Sort1 |
| 835 | Oaf |
| 836 | Ints1 |
| 837 | Slc44a2 |
| 838 | Dph3 |
| 839 | Gramd1a |
| 840 | Fkbp9 |
| 841 | Fam149a |
| 842 | 1810035L17Rik |
| 843 | kg:uc007fte.1 |
| 844 | Eif2s1 |
| 845 | Smpd1 |
| 846 | Eef1b2 |
| 847 | Actr10 |
| 848 | Rab11fip5 |
| 849 | Ypel3 |
| 850 | Flnb |
| 851 | Tcn2 |
| 852 | Crlf1 |
| 853 | Map3k15 |
| 854 | Cul7 |
| 855 | Atp6v1g1 |
| 856 | Ncbp1 |
| 857 | Atp1b3 |
| 858 | Mtif3 |
| 859 | Aldoa |
| 860 | Htra1 |
| 861 | Rab14 |
| 862 | Ppm1a |
| 863 | Ndufb11 |
| 864 | Kansl3 |
| 865 | Rab24 |
| 866 | Bcl2l1 |
| 867 | Lgals1 |
| 868 | Samm50 |

TABLE 12-continued

Significantly Expressed Genes by Rank Product (FDR <0.01)

| | |
|---|---|
| 869 | Mrps33 |
| 870 | Anxa1 |
| 871 | Chchd1 |
| 872 | Mapre1 |
| 873 | Ctbp2 |
| 874 | Rnps1 |
| 875 | Spg7 |
| 876 | Tnfrsf12a |
| 877 | H6pd |
| 878 | Myo7a |
| 879 | Mcm7 |
| 880 | Psmd13 |
| 881 | Mrpl54 |
| 882 | Atp6v0b |
| 883 | Prdx1 |
| 884 | Elof1 |
| 885 | Rexo4 |
| 886 | Mrps18a |
| 887 | Dpcd |
| 888 | D2Wsu81e |
| 889 | Cd99l2 |
| 890 | Synpo |
| 891 | Atp2a2 |
| 892 | Cdc5l |
| 893 | Stard7 |
| 894 | Atp13a2 |
| 895 | Sdha |
| 896 | Hdac6 |
| 897 | Krt20 |
| 898 | Ppp6r3 |
| 899 | 1700037H04Rik |
| 900 | Napa |
| 901 | PgP |
| 902 | Cnih |
| 903 | Atg4b |
| 904 | Cox8a |
| 905 | Srp68 |
| 906 | St13 |
| 907 | Gng12 |
| 908 | Cfdp1 |
| 909 | Rcc2 |
| 910 | Pisd-ps1 |
| 911 | Ivns1abp |
| 912 | Mpv17l2 |
| 913 | Ssna1 |
| 914 | Gnl1 |
| 915 | Tmem111 |
| 916 | Hbs1l |
| 917 | Agpat3 |
| 918 | Col6a2 |
| 919 | March6 |
| 920 | Usp39 |
| 921 | Rps11 |
| 922 | Ahnak |
| 923 | Lcmt1 |
| 924 | Ddx41 |
| 925 | H2afv |
| 926 | Fau |
| 927 | Tuba1c |

The gene names listed in Table 13 and 12 are common names. NCBI Gene ID numbers for each of the genes listed in Table 13 and 12 can be obtained by searching the "Gene" Database of the NCBI (available on the World Wide Web at http://www.ncbi.nlm.nih.gov/) using the common name as the query and selecting the first returned *Homo sapiens* gene. Other genes may be obtained using the UCSC genome browser (available on the World Wide Web at http://genome.ucsc.edu) using the Gene Sorter function. In certain embodiments, the marker gene(s) are selected from the genes listed in Table 13 and/or 12.

In some embodiments, the marker gene(s) is selected from a marker gene indicated to be upregulated in at least one type of CTC in Table 13, e.g. marker genes 1-142. In some embodiments, the marker gene(s) is selected from a marker gene indicated to be upregulated in at least one type of CTC in Table 12, e.g. marker genes listed in the columns labeled "CTC-c vs. Primary Tumor Enriched Gene" or "CTC-c vs. WBC".

In a CTC, the marker genes listed in Table 13 or 12 can be upregulated, e.g. for marker genes listed in Table 13 and/or 12, if the measured marker gene expression in a cell or sample is higher as compared to a reference level of that marker gene's expression, then the cell is identified as a CTC and/or the sample is identified as comprising CTCs. Preferably, once looks at a statistically significant change.

However, even if a few genes in a group do not differ from normal, a sample can be identified as comprising CTCs if the overall change of the group shows a significant change, preferably a statistically significant change. All possible combinations of 2 or more of the indicated markers are contemplated herein.

What is claimed herein is:

1. A method of processing a sample to specifically detect classical circulating tumor cells (CTC-cs), comprising:
   obtaining a blood sample from a subject;
   isolating circulating tumor cells (CTCs) from the blood sample by hydrodynamic size-based separation or immunodepletion; and
   measuring the expression of insulin-like growth factor binding protein 5 (IGFBP5) and Decorin (DCN) in the CTCs by:
   i) amplification of IGFBP5 and DCN mRNA with primers that hybridize specifically to IGFBP5 and DCN mRNA; or
   ii) detection of IGFBP5 and DCN mRNA with probes that hybridize specifically to IGFBP5 and DCN mRNA.

2. The method of claim 1, wherein the CTC-cs are pancreatic cancer CTC-cs.

3. The method of claim 1, wherein the method further comprises measuring the level of one or more additional genes selected from the group consisting of:
   ABI gene family, member 3 (NESH) binding protein (ABI3BP); a disintegrin-like and metallopeptidase (reprolysin type) with thrombospondin type 1 motif 5 (ADAMTS5); a disintegrin-like and metallopeptidase (reprolysin type) with thrombospondin type 1-like 1 (ADAMTSL); Angiogenin, ribonuclease, RNase A family, 5 (ANG); Arylsulfatase A (ARSA); Complement component 1, r subcomponent-like (C1RL); Complement component 3 (C3); Complement component 4A (C4A); Complement component 4B (C4B); Coiled-coil domain containing 80 (CCDC80); CD109 antigen (CD109); Chitinase 3-like 1 (CHI3L1); C-type lectin domain family 3, member b (CLEC3B); CKLF-like MARVEL transmembrane domain containing 3 (CMTM3); CKLF-like MARVEL transmembrane domain containing 7 (CMTM7); collagen, type XIV, alpha 1(COL14A1); collagen, type I, alpha 2 (COL1A2); collagen, type III, alpha 1 (COL3A1); collagen, type IV, alpha 6 (COL4A6); Colony stimulating factor 1 (CSF1); dystroglycan 1 (DAG1); dermokine (DMKN); fibulin 1 (FBLN1); fibroblast growth factor 1 (FGF1); fibromodulin (FMOD); guanylate binding protein 3 (GPC3); guanylate binding protein 4 (GPC4); High mobility group protein B1 (HMGB1); Interferon (alpha and beta) receptor 2 (IFNAR2); interleukin 16 (IL16); laminin, alpha 4 (LAMA4); Latent transforming growth factor beta binding protein 4 (LTBP4); microfibrillar-associated protein 1A (MFAP1A); nidogen 2 (NID2); osteoglycin (OGN); PDGFA associated protein 1 (PDAP1); platelet factor 4 (PF4); plasminogen activator, tissue (PLAT); podocan (PODN); proline arginine-rich end leucine-rich repeat (PRELP); R-spondin homolog (RSPO1); serine (or cysteine) peptidase inhibitor, clade G, member 1 (SERPING1); secreted Ly6/Plaur domain containing 1 (SLURP1); superoxide dismutase 3 (SOD3); secreted acidic cysteine rich glycoprotein (SPARC); sparc/osteonectin, cwcv and kazal-like domains proteoglycan 2 (SPOCK2); spondin 2 (SPON2); sulfatase 1 (SULF1); sulfatase 2 (SULF2); transforming growth factor, beta 2(TGFB2); transglutaminase 2 (TGM2); thrombomodulin (THBD); thrombospondin 1 (THBS1); thrombospondin, type I, domain containing 4 (THSD4); tissue inhibitor of metalloproteinase 2 (TIMP2); tenascin XB (TNXB); tumor protein, translationally-controlled 1(TPT1); twisted gastrulation homolog 1 (TWSG1); and wingless-related MMTV integration site 4 (WNT4).

4. The method of claim 1, wherein the method further comprises measuring the level of one or more additional genes selected from the group consisting of:
   aldehyde dehydrogenase 1 family, member A1 (ALDH1A1); aldehyde dehydrogenase 1 family, member A2 (ALDH1A2); Kruppel-like factor 4 (KLF4); SPARC; Wingless-related integration site (WNT); TGFB2; vascular endothelial growth factor (VEGF); COL1A2; collagen, type III, alpha 1 (COL3A1); and TIMP2.

5. The method of claim 1, wherein the method further comprises measuring the level of one or more additional genes selected from the group consisting of:
   ALDH1A2; KLF4; and SPARC.

6. The method of claim 1, wherein the method further comprises measuring the level of one or more additional genes selected from the group consisting of:
   ALDH1A2; and KLF4.

7. The method of claim 1, wherein the method further comprises measuring the level of one or more additional genes selected from the group consisting of:
   TPT1; HMGB1; SPON2; SPARC; and ARSA.

8. The method of claim 1, wherein the method further comprises measuring the level of one or more additional genes selected from the group consisting of:
   interleukin 6 signal transducer (IL6ST); ARSA; TIMP2; CD55 antigen (CD55); SULF2; integrin alpha 6 (ITGA6); syndecan 4 (SDC4); cell adhesion molecule-related/down-regulated by oncogenes (CDON); and synaptic vesicle glycoprotein 2 a (SV2A).

9. A method of processing a sample to specifically detect classical circulating tumor cells (CTC-cs), comprising:
   obtaining a blood sample from a subject;
   isolating circulating tumor cells (CTCs) from the blood sample by hydrodynamic size-based separation or immunodepletion; and
   specifically detecting CTC-cs by detecting CTCs that express both insulin-like growth factor binding protein 5 (IGFBP5) and Decorin (DCN) by:
   i) amplification of IGFBP5 and DCN mRNA with primers that hybridize specifically to IGFBP5 and DCN mRNA; or
   ii) detection of IGFBP5 and DCN mRNA with probes that hybridize specifically to IGFBP5 and DCN mRNA.

* * * * *